(12) United States Patent
Widschwendter et al.

(10) Patent No.: US 11,920,200 B2
(45) Date of Patent: *Mar. 5, 2024

(54) EPIGENETIC MARKERS AND RELATED METHODS AND MEANS FOR THE DETECTION AND MANAGEMENT OF CERTAIN CANCERS

(71) Applicants: EUROFINS GENOMICS EUROPE SEQUENCING GMBH, Constance (DE); GENEDATA AG, Basel (CH); UCL BUSINESS LTD., London (GB)

(72) Inventors: Martin Widschwendter, Wildermieming (AT); Allison Jones, London (GB); Iona Evans, London (GB); Harri Lempiäinen, Binningen (CH); Johannes Eichner, Lörrach (DE); Tamas Rujan, Oberweil (CH); Timo Wittenberger, Constance (DE); Tobias Paprotka, Leipzig (DE); Benjamin Lindner, Leipzig (DE)

(73) Assignees: Eurofins Genomics Europe Sequencing GMBH (DE); Genedata AG (CH); UCL Business LTD. (GB)

( * ) Notice: Subject to any disclaimer, the term of this patent is extended or adjusted under 35 U.S.C. 154(b) by 654 days.

This patent is subject to a terminal disclaimer.

(21) Appl. No.: 16/469,963

(22) PCT Filed: Dec. 15, 2017

(86) PCT No.: PCT/EP2017/083170
§ 371 (c)(1),
(2) Date: Jun. 14, 2019

(87) PCT Pub. No.: WO2018/109217
PCT Pub. Date: Jun. 21, 2018

(65) Prior Publication Data
US 2019/0330703 A1    Oct. 31, 2019

(30) Foreign Application Priority Data

Dec. 16, 2016  (EP) .................................... 16204822

(51) Int. Cl.
*C12Q 1/6886*    (2018.01)
*G16B 20/00*    (2019.01)
*G16B 40/10*    (2019.01)
*G16H 20/00*    (2018.01)
*G16H 50/20*    (2018.01)

(52) U.S. Cl.
CPC .......... *C12Q 1/6886* (2013.01); *G16B 20/00* (2019.02); *G16B 40/10* (2019.02); *G16H 20/00* (2018.01); *G16H 50/20* (2018.01); *C12Q 2600/106* (2013.01); *C12Q 2600/112* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS 6,582,908 B2     6/2003  Fodor et al.
2016/0340740 A1*  11/2016 Zhang .................. C12Q 1/6883

FOREIGN PATENT DOCUMENTS

| WO | WO 2009/153667 | 12/2009 |
| WO | WO 2013/033627 | 3/2013 |
| WO | WO 2016/109712 | 7/2016 |
| WO | WO 2017/048932 | 3/2017 |

OTHER PUBLICATIONS

Warton (Frontiers in Molecular Biosciences 2:13 Apr. 22, 2015).*
Legendre (Clinical Epigenetics 2015 7:100).*
International Search Report and Written Opinion prepared by the European Patent Office dated May 14, 2018, for International Application No. PCT/EP2017/083170.
Human bisulfite-converted genomic DNA plus-strand (control), SEQ: 3801, GENESEQ Aug. 25, 2016, XP002773554, 1 page.

(Continued)

*Primary Examiner* — Amanda Haney
(74) *Attorney, Agent, or Firm* — Sheridan Ross P.C.

(57) ABSTRACT

The present invention relates to methods of determining the presence or absence of certain cancers in a human individual, as well as to related methods to determine the response to therapy against certain cancers in a human individual, in particular ovarian cancer in a woman. Such methods are based on the detection-from (eg cell-free) DNA of said human individual—of one or more methylated (or un-methylated) CpGs being associated with differentially methylated regions (DMRs) of the present invention; such as methylation (or un-methylation) at one or more or all of certain CpGs being associated with such DMRs. Accordingly, such methods have diagnostic, prognostic and/or predictive utility for detecting or managing certain cancers in women or men, in particular ovarian cancer in women. The present invention further relates to nucleic acids comprising certain sequences that may be detected during the method, or nucleic acids (such as probes and/or primers) that are useful to detect such sequences, as wells as compositions, kits, computer program products and other aspects that are useful for or related to the practice or application of such methods.

18 Claims, 38 Drawing Sheets
Specification includes a Sequence Listing.

(56) References Cited

OTHER PUBLICATIONS

"Human bisulfite-converted methylated genomic DNA plus-strand, SEQ: 7909," GENESEQ, Aug. 25, 2016, XP002773556, 2 pages.

Bondurant et al. "Quantitative detection of RASSF1A DNA promoter methylation in tumors and serum of patients with serous epithelial ovarian cancer," Gynecologic Oncology, 2011, vol. 123, No. 3, pp. 581-587.

Gifford et al. "The Acquisition of hMLH1 Methylation in Plasma DNA after Chemotherapy Predicts Poor Survival for Ovarian Cancer Patients," Clinical Cancer Research, Jul. 2004, vol. 10, No. 13, pp. 4420-4426.

Liggett et al. "Distinctive DNA methylation patterns of cell-free plasma DNA in women with malignant ovarian tumors," Gynecologic Oncology, 2011, vol. 120, No. 1, pp. 113-120.

Zhang et al. "A multiplex methylation-specific PCR assay for the detection of early-stage ovarian cancer using cell-free serum DNA," Gynecologic Oncology, 2013, vol. 130, No. 1, pp. 132-139.

International Search Report and Written Opinion prepared by the European Patent Office dated May 14, 2018, for International Application No. PCT/EP2017/083159.

\* cited by examiner

SEQUENCE LISTING

```
<160> NUMBER OF SEQ ID NOS: 159

<210> SEQ ID NO 1
<211> LENGTH: 136
<212> TYPE: DNA
<213> ORGANISM: Homo sapiens

<400> SEQUENCE: 1
catccggagg cccaggggtg aggacttcgc cacgggaagg aggcacacga ttcagcccat    60
gacaccgcca cctcggcgtg gtgctgtagg gggaagctca ggcactcacc gaggacagga   120
cccggggaat ccgctg                                                   136

<210> SEQ ID NO 2
<211> LENGTH: 154
<212> TYPE: DNA
<213> ORGANISM: Homo sapiens

<400> SEQUENCE: 2
gatattcggt ggagagccgc agctgcccgc cgcggggccc caggcgcagc acgctctcgc    60
gcgtgggccg cagctggcag cacaggaagt ccaggtggaa gagcggcggc gtgggcggcc   120
cggcgcggcg cggcgagtgc gggctggtat cggc                               154

<210> SEQ ID NO 3
<211> LENGTH: 111
<212> TYPE: DNA
<213> ORGANISM: Homo sapiens
```

<400> SEQUENCE: 3
gttctatggg cgagctgctg cagtgcggct gccaggcgcc ccgcgggcgg gcccctcccc       60
ggccctccgg cctgcccggc accccggac cccctggccc cgcgggctcc c                111

<210> SEQ ID NO 4
<211> LENGTH: 140
<212> TYPE: DNA
<213> ORGANISM: Homo sapiens

<400> SEQUENCE: 4
cccaggcctg acgtgggtcc cccagggcgg cgtcgccaag gcttagacgc tttcgtgcag       60
gagggacgac gactcccctc acgccttcgt ggccccaact cggcgctctg ctatctctga      120
tccggtgaac acacctcaga                                                  140

<210> SEQ ID NO 5
<211> LENGTH: 120
<212> TYPE: DNA
<213> ORGANISM: Homo sapiens

<400> SEQUENCE: 5
gcgaagcagg agtagctgcc gggccccacg agcctccgtc cgttctggtt cgggtttctc       60
cgagttttgc taccagccga ggctgtgcgg gcaactgggt cagcctcccg tcaggagaga      120

<210> SEQ ID NO 6
<211> LENGTH: 120
<212> TYPE: DNA
<213> ORGANISM: Homo sapiens

<400> SEQUENCE: 6
aactctgctg agtgagctca caaacagggc ataaccgaga cgcgggaatg cctgggtcgc       60
cgcgcagtca ccgggcaggg ccgccctccc ctgtgggtca gcaaaaacgg tgtcaagtga      120

<210> SEQ ID NO 7
<211> LENGTH: 130
<212> TYPE: DNA
<213> ORGANISM: Homo sapiens

<400> SEQUENCE: 7
actccgccac acacacagct gtaccggca caacacgcgg ccacaggtca cctcaggtcg       60
cctcgggtgc tcctcccgca gccccacgta gacagaagac attcctcggg cctgggtgcc      120
cagcctcccg                                                             130

<210> SEQ ID NO 8
<211> LENGTH: 120
<212> TYPE: DNA
<213> ORGANISM: Homo sapiens

<400> SEQUENCE: 8
gaggtaatgg aagcggccat ccttgtcctc gctccgcgcc tggctgaagc gatcggggtc       60
gaacacgttc acgtctttga acacgggcgc tgtgtcatgg gtgtcccgga tgctatacat      120

<210> SEQ ID NO 9
<211> LENGTH: 137
<212> TYPE: DNA
<213> ORGANISM: Homo sapiens

<400> SEQUENCE: 9
gcgggcacct gtagtcccag ctactcggga ggctgaggcg ggagaatggc gtgaacccgg       60

```
gaggcggagc ttgcagcgag ccgagatcgc gccaccgcac tccagcctgg gcgacagagc    120
gagactccgt ctaaaaa                                                   137

<210> SEQ ID NO 10
<211> LENGTH: 137
<212> TYPE: DNA
<213> ORGANISM: Homo sapiens

<400> SEQUENCE: 10
tccccggagt ccggagctca ggccagtggc agtcgaccca gccccgaga ctccctcacg    60 ccgctccaaa accaaaacgg agcccaacac gaagctgggt gaagccgtag cttgcaggag    120
ccagggagat gcgctct                                                   137

<210> SEQ ID NO 11
<211> LENGTH: 136
<212> TYPE: DNA
<213> ORGANISM: Homo sapiens

<400> SEQUENCE: 11
gactctgtct caaaaagaa aaaaataggg ccgggcgcgg tggctcacgc ctgtcatccc    60
agcactttgg gaggccgagg cgggtggatc acgaggtcgg gagatcgata ccatcctggg    120
taacacggtg aaaccc                                                    136

<210> SEQ ID NO 12
<211> LENGTH: 138
<212> TYPE: DNA
<213> ORGANISM: Homo sapiens

<400> SEQUENCE: 12
gactcgcgag gttttccagc agctcattcc gggacggcgg tgtctagtcc agtccagggt    60
aactgggctc tctgagagtc cgacctccat cggtctggga gcgagtggtt cgagttcaga    120
tgctgggaac cgtcgctt                                                  138

<210> SEQ ID NO 13
<211> LENGTH: 138
<212> TYPE: DNA
<213> ORGANISM: Homo sapiens

<400> SEQUENCE: 13
taacccattt ctttattaaa ttgcatgaag aaggccgggc gcggtggctc acgcctgtaa    60
tcccagcact tgggaggcc gaggcgggcg gatcacgagg tcaggagatc gagaccacgg    120
tgaaaccccg tctctact                                                  138

<210> SEQ ID NO 14
<211> LENGTH: 142
<212> TYPE: DNA
<213> ORGANISM: Homo sapiens

<400> SEQUENCE: 14
ggcaggagcg ccccactatg cgcaagcccg tggcctggag agcgctgaag gtgggagggg    60 gaagagggc agaaccccg cgggagcgag cgcacagctg ccgccccgtg gccgcttcgg    120
gaatcgctgg ctccggctct gg                                             142

<210> SEQ ID NO 15
<211> LENGTH: 135
<212> TYPE: DNA
```

<213> ORGANISM: Homo sapiens

<400> SEQUENCE: 15

| ctgcagaagc gcactttgct gaacacccccg aggacgtgcc tctcgcacag ggagcgcccg | 60 |
|---|---|
| tctttgctgg ggctggagcg gcgcttggag gccgacactc ggtcgctgtt ggactccctc | 120 |
| gcctgccgct tctgc | 135 |

<210> SEQ ID NO 16
<211> LENGTH: 146
<212> TYPE: DNA
<213> ORGANISM: Homo sapiens

<400> SEQUENCE: 16

| cgtgttagcc aggatggtct cgacctcctg acctcgtgat cagcccgcct cggcctccca | 60 |
|---|---|
| aagtgctggg attaaaggcg tgagccaccg cgccgggccg agactctgtc ttaaaaaaaa | 120 |
| aaggcctggg ctgtggcact ttggga | 146 |

<210> SEQ ID NO 17
<211> LENGTH: 141
<212> TYPE: DNA
<213> ORGANISM: Homo sapiens

<400> SEQUENCE: 17

| agagttgcac tccgaagact ccagattccg agagttgcgg aaacgctacg aggacctgct | 60 |
|---|---|
| aaccaggctg cgggccaacc agagctggga agattcgaac accgacctcg tcccggcccc | 120 |
| tgcagtccgg atactcacgc c | 141 |

<210> SEQ ID NO 18
<211> LENGTH: 109
<212> TYPE: DNA
<213> ORGANISM: Homo sapiens

<400> SEQUENCE: 18

| gtcagacgag agcctggggt caatgtcgag gtggagcgac gctggcacgg caaccctgag | 60 |
|---|---|
| cctgcgcggc ccggcgctat cccctggctc tccgctgctg gctggaccc | 109 |

<210> SEQ ID NO 19
<211> LENGTH: 144
<212> TYPE: DNA
<213> ORGANISM: Homo sapiens

<400> SEQUENCE: 19

| cggtaggtca tccagcagca gggctccacg tcggtctcgt cgatgcccca gaaggccagc | 60 |
|---|---|
| tcctcctcga agagcggccc gcacacgtct gcggggcagt gcagcttgcc ggtgcggtag | 120 |
| taattgagca cataggcgaa gacg | 144 |

<210> SEQ ID NO 20
<211> LENGTH: 115
<212> TYPE: DNA
<213> ORGANISM: Homo sapiens

<400> SEQUENCE: 20

| aatcagccca gcaaccggcg accccaagcg cggcgaccgc aaagggagtg cttgcccatc | 60 |
|---|---|
| cgcgtttgaa agcagacttt ttctcggcag gaacacagga ctcacctgcc agtgg | 115 |

<210> SEQ ID NO 21
<211> LENGTH: 148

<212> TYPE: DNA
<213> ORGANISM: Homo sapiens

<400> SEQUENCE: 21

```
gtgcgaacaa gaccgggcgt tcgccgccg acgcgaaggg gctgtctgtg cgcggcgttg    60
cgggccctcc gcgcgtgggg tgtgcgtgtg cgtgttcggg ttcggttctg tgtgtgcacc   120
gcgggcctgc tcagagtcgg gaccaccg                                     148
```

<210> SEQ ID NO 22
<211> LENGTH: 121
<212> TYPE: DNA
<213> ORGANISM: Homo sapiens

<400> SEQUENCE: 22

```
atattaatct tgtccgggca cggtggctca cgcctgtaat cccagcactt tgggaggccg    60
aggcgggcgg atcacgaggt caggagatcg agaccatcct ggcgaacatg gtgaaaccte   120
g                                                                   121
```

<210> SEQ ID NO 23
<211> LENGTH: 92
<212> TYPE: DNA
<213> ORGANISM: Homo sapiens

<400> SEQUENCE: 23

```
tgcatacaga ttactgtagg accatttcct gtgccttta aaatttcctt ttctcgtttt    60
atttcacata ttcctttgtt ttttacaact cc                                 92
```

<210> SEQ ID NO 24
<211> LENGTH: 103
<212> TYPE: DNA
<213> ORGANISM: Homo sapiens

<400> SEQUENCE: 24

```
ccgctcggga atgggaatat agctacatat gggaaaacgc ggtgcaggga gaaaaccaat    60
tcagtgagga gcggaggcgc aggactgtgg agtgtgcatc cgg                    103
```

<210> SEQ ID NO 25
<211> LENGTH: 94
<212> TYPE: DNA
<213> ORGANISM: Homo sapiens

<400> SEQUENCE: 25

```
ctgcttaaag gcgcagagga gcagctggga acgagaacaa agcggccagg ccccctcgg    60
aggaaggaag gagagagccc caggaaacag ctga                               94
```

<210> SEQ ID NO 26
<211> LENGTH: 101
<212> TYPE: DNA
<213> ORGANISM: Homo sapiens

<400> SEQUENCE: 26

```
ggatgaagga ttcctgcatc actgtgatgg ccatggcgct gctgtctggg ttcttttct    60
tcggtaggca agggaggagg caggggaagg gacatgtgtc t                      101
```

<210> SEQ ID NO 27
<211> LENGTH: 70
<212> TYPE: DNA
<213> ORGANISM: Homo sapiens

```
<400> SEQUENCE: 27
taggctacag gaagaggcat ttcctataga tgacggctgt aaaattttaa gctgagttcc    60
tccaggaagt                                                          70

<210> SEQ ID NO 28
<211> LENGTH: 84
<212> TYPE: DNA
<213> ORGANISM: Homo sapiens

<400> SEQUENCE: 28
aagagagagt ggttgataat cagtagagag aggtttctaa ctcacggaag tgtttgcaat    60
acaacctctt tgtacatcag ctgt                                          84

<210> SEQ ID NO 29
<211> LENGTH: 97
<212> TYPE: DNA
<213> ORGANISM: Homo sapiens

<400> SEQUENCE: 29
ggtccccctc cccgagccat gaagagctgc ctgcggccat cttggccctc gcaccccgtc    60
tctgtcaccc caggcccctg taacttgctt aacgctt                            97

<210> SEQ ID NO 30
<211> LENGTH: 86
<212> TYPE: DNA
<213> ORGANISM: Homo sapiens

<400> SEQUENCE: 30
gaagcttgac actcctggcc ccaaacactg cctggctaca acacgatatc cagggacaga    60
taccttccat gtacagcaag ctgtgg                                        86

<210> SEQ ID NO 31
<211> LENGTH: 91
<212> TYPE: DNA
<213> ORGANISM: Homo sapiens

<400> SEQUENCE: 31 gggggggactg tcgttaattc actgcctaat gaccgcggcc cgcgcgctcc gagtaatcgg    60
gtgatgtatg tggactgtgc acacctcgtg g                                  91

<210> SEQ ID NO 32
<211> LENGTH: 136
<212> TYPE: DNA
<213> ORGANISM: Artificial Sequence
<220> FEATURE:
<223> OTHER INFORMATION: DMR 141

<400> SEQUENCE: 32
tattyggagg tttaggggtg aggatttygt tayggggaagg aggtatayga tttagtttat    60
gatatygtta tttyggygtg gtgttgtagg gggaagttta ggtatttaty gaggatagga   120 ttygggggaat tygttg                                                  136

<210> SEQ ID NO 33
<211> LENGTH: 154
<212> TYPE: DNA
<213> ORGANISM: Artificial Sequence
<220> FEATURE:
<223> OTHER INFORMATION: DMR 204

<400> SEQUENCE: 33
```

```
gatattyggt ggagagtygt agttgttygt ygygggtttt taggygtagt aygttttygy      60
gygtgggtyg tagttggtag tataggaagt ttaggtggaa gagyggyggy gtgggyggtt     120
yggygyggyg yggygagtgy gggttggtat yggt                                 154

<210> SEQ ID NO 34
<211> LENGTH: 111
<212> TYPE: DNA
<213> ORGANISM: Artificial Sequence
<220> FEATURE:
<223> OTHER INFORMATION: DMR 228

<400> SEQUENCE: 34
gttttatggg ygagttgttg tagtgyggtt gttaggygtt tygygggygg gttttttttty     60 ggttttttygg tttgttyggt attttyggat tttttggttt ygygggtttt t             111

<210> SEQ ID NO 35
<211> LENGTH: 140
<212> TYPE: DNA
<213> ORGANISM: Artificial Sequence
<220> FEATURE:
<223> OTHER INFORMATION: DMR 144

<400> SEQUENCE: 35
tttaggtttg aygtgggttt tttagggygg ygtygttaag gtttagaygt tttygtgtag      60
gagggaygay gattttttt aygttttygt ggttttaatt yggygttttg ttattttttga    120 ttyggtgaat atattttaga                                                 140

<210> SEQ ID NO 36
<211> LENGTH: 120
<212> TYPE: DNA
<213> ORGANISM: Artificial Sequence
<220> FEATURE:
<223> OTHER INFORMATION: DMR 123

<400> SEQUENCE: 36
gygaagtagg agtagttgty gggttttayg agttttygtt ygttttggtt ygggtttttt      60
ygagttttgt tattagtyga ggttgtgygg gtaattgggt tagttttttyg ttaggagaga   120

<210> SEQ ID NO 37
<211> LENGTH: 120
<212> TYPE: DNA
<213> ORGANISM: Artificial Sequence
<220> FEATURE:
<223> OTHER INFORMATION: DMR 129

<400> SEQUENCE: 37
aattttgttg agtgagttta taaatagggt ataatygaga ygygggaatg tttgggtygt      60
ygygtagtta tygggtaggg tygttttttt ttgtgggtta gtaaaaaygg tgttaagtga    120

<210> SEQ ID NO 38
<211> LENGTH: 130
<212> TYPE: DNA
<213> ORGANISM: Artificial Sequence
<220> FEATURE:
<223> OTHER INFORMATION: DMR 137

<400> SEQUENCE: 38
atttygttat atatatagtt gtattyggta taatayygygg ttataggtta ttttaggtyg     60
tttygggtgt tttttttygta gttttaygta gatagaagat attttttyggg tttggtgtt    120
```

-continued tagttttttyg 130

<210> SEQ ID NO 39
<211> LENGTH: 120
<212> TYPE: DNA
<213> ORGANISM: Artificial Sequence
<220> FEATURE:
<223> OTHER INFORMATION: DMR 148

<400> SEQUENCE: 39
gaggtaatgg aagyggttat ttttgttttty gtttygygtt tggttgaagy gatygggggty 60 gaataygttt aygtttttga atayggggygt tgtgttatgg gtgtttyggga tgttatatat 120

<210> SEQ ID NO 40
<211> LENGTH: 137
<212> TYPE: DNA
<213> ORGANISM: Artificial Sequence
<220> FEATURE:
<223> OTHER INFORMATION: DMR 150

<400> SEQUENCE: 40 gygggtatttt gtagttttag ttattyggga ggttgaggyg ggagaatggy gtgaattygg 60
gaggyggagt ttgtagygag tygagatygy gttatygtat tttagtttgg gygatagagy 120
gagatttygt ttaaaaa 137

<210> SEQ ID NO 41
<211> LENGTH: 137
<212> TYPE: DNA
<213> ORGANISM: Artificial Sequence
<220> FEATURE:
<223> OTHER INFORMATION: DMR 154

<400> SEQUENCE: 41 tttttyggagt tyggagttta ggttagtggt agtygattta gttttygaga ttttttttayg 60 tygttttaaa attaaaaygg agtttaatay gaagttgggt gaagtygtag tttgtaggag 120
ttagggagat gygtttt 137

<210> SEQ ID NO 42
<211> LENGTH: 136
<212> TYPE: DNA
<213> ORGANISM: Artificial Sequence
<220> FEATURE:
<223> OTHER INFORMATION: DMR 158

<400> SEQUENCE: 42
gattttgttt taaaaaagaa aaaaataggg tygggygygg tggtttaygt ttgttatttt 60
agtattttgg gaggtygagg ygggtggatt aygaggtygg gagatygata ttattttggg 120 taataygggtg aaattt 136

<210> SEQ ID NO 43
<211> LENGTH: 138
<212> TYPE: DNA
<213> ORGANISM: Artificial Sequence
<220> FEATURE:
<223> OTHER INFORMATION: DMR 164

<400> SEQUENCE: 43
gattygygag gttttttagt agtttattty gggayggygg tgtttagttt agtttagggt 60
aattgggttt tttgagagtt ygatttttat yggtttggga gygagtggtt ygagtttaga 120
tgttgggaat ygtygttt 138

<210> SEQ ID NO 44
<211> LENGTH: 138
<212> TYPE: DNA
<213> ORGANISM: Artificial Sequence
<220> FEATURE:
<223> OTHER INFORMATION: DMR 176

<400> SEQUENCE: 44
taatttattt ttttattaaa ttgtatgaag aaggtygggy gyggtggttt aygtttgtaa      60
ttttagtatt ttgggaggty gaggygggyg gattaygagg ttaggagaty gagattaygg     120
tgaaatttyg ttttttatt                                                  138

<210> SEQ ID NO 45
<211> LENGTH: 142
<212> TYPE: DNA
<213> ORGANISM: Artificial Sequence
<220> FEATURE:
<223> OTHER INFORMATION: DMR 178

<400> SEQUENCE: 45
ggtaggagyg ttttattatg ygtaagttyg tggtttggag agygttgaag gtgggagggg      60 gaagagggt agaattttyg ygggagygag ygtatagttg tygtttygtg gtygtttygg     120
gaatygttgg tttyggtttt gg                                              142

<210> SEQ ID NO 46
<211> LENGTH: 135
<212> TYPE: DNA
<213> ORGANISM: Artificial Sequence
<220> FEATURE:
<223> OTHER INFORMATION: DMR 180

<400> SEQUENCE: 46
ttgtagaagy gtattttgtt gaatatttyg aggaygtgtt tttygtatag ggagygttyg      60
tttttgttgg ggttggagyg gygtttggag gtygatatty ggtygttgtt ggattttttty    120 gtttgtygtt tttgt                                                      135

<210> SEQ ID NO 47
<211> LENGTH: 146
<212> TYPE: DNA
<213> ORGANISM: Artificial Sequence
<220> FEATURE:
<223> OTHER INFORMATION: DMR 186

<400> SEQUENCE: 47
ygtgttagtt aggatggttt ygattttttg atttygtgat tagttygttt yggtttttta      60 aagtgtggg attaaaggyg tgagttatyg ygtygggtyg agattttgtt ttaaaaaaaa     120
aaggtttggg ttgtggtatt ttggga                                          146

<210> SEQ ID NO 48
<211> LENGTH: 141
<212> TYPE: DNA
<213> ORGANISM: Artificial Sequence
<220> FEATURE:
<223> OTHER INFORMATION: DMR 188

<400> SEQUENCE: 48
agagttgtat ttygaagatt ttagattyyg agagttgygg aaaygttayg aggatttgtt      60
aattaggttg ygggttaatt agagttggga agattygaat atygatttyg tttyggtttt    120

```
<210> SEQ ID NO 49
<211> LENGTH: 109
<212> TYPE: DNA
<213> ORGANISM: Artificial Sequence
<220> FEATURE:
<223> OTHER INFORMATION: DMR 190

<400> SEQUENCE: 49
gttagaygag agtttggggt taatgtygag gtggagygay gttggtaygg taattttgag      60
tttgygyggt tyggygttat tttttggttt ttygttgttg gttggattt                 109

<210> SEQ ID NO 50
<211> LENGTH: 144
<212> TYPE: DNA
<213> ORGANISM: Artificial Sequence
<220> FEATURE:
<223> OTHER INFORMATION: DMR 192

<400> SEQUENCE: 50
yggtaggtta tttagtagta gggttttayg tyggtttygt ygatgtttta gaaggttagt      60 ttttttttyga agagyggtty gtataygttt gyggggtagt gtagtttgty ggtgyggtag   120
taattgagta tataggygaa gayg                                           144

<210> SEQ ID NO 51
<211> LENGTH: 115
<212> TYPE: DNA
<213> ORGANISM: Artificial Sequence
<220> FEATURE:
<223> OTHER INFORMATION: DMR 200

<400> SEQUENCE: 51
aattagttta gtaatyggyg attttaagyg yggygatygt aaagggagtg tttgtttatt      60
ygygtttgaa agtagatttt ttttyggtag gaatatagga tttatttgtt agtgg         115

<210> SEQ ID NO 52
<211> LENGTH: 148
<212> TYPE: DNA
<213> ORGANISM: Artificial Sequence
<220> FEATURE:
<223> OTHER INFORMATION: DMR 202

<400> SEQUENCE: 52
gtgygaataa gatygggygt ttygtygtyg aygygaaggg gttgtttgtg ygyggygttg      60 yggttttty gygygtgggg tgtgygtgtg ygtgttyggg ttyggttttg tgtgtgtaty     120
gygggtttgt ttagagtygg gattatyg                                       148

<210> SEQ ID NO 53
<211> LENGTH: 121
<212> TYPE: DNA
<213> ORGANISM: Artificial Sequence
<220> FEATURE:
<223> OTHER INFORMATION: DMR 208

<400> SEQUENCE: 53
atattaattt tgttygggta yggtggttta ygtttgtaat tttagtattt tgggaggtyg      60
aggygggygg attaygaggt taggagatyg agattatttt ggygaatatg gtgaaattty   120
g                                                                    121
```

```
<210> SEQ ID NO 54
<211> LENGTH: 92
<212> TYPE: DNA
<213> ORGANISM: Artificial Sequence
<220> FEATURE:
<223> OTHER INFORMATION: DMR 210

<400> SEQUENCE: 54
tgtatataga ttattgtagg attattttt gtgttttta aaattttttt ttttygtttt        60
attttatata ttttttgtt ttttataatt tt                                     92

<210> SEQ ID NO 55
<211> LENGTH: 103
<212> TYPE: DNA
<213> ORGANISM: Artificial Sequence
<220> FEATURE:
<223> OTHER INFORMATION: DMR 213

<400> SEQUENCE: 55
tygttyggga atgggaatat agttatatat gggaaaaygy ggtgtaggga gaaaattaat      60
ttagtgagga gyggaggygt aggattgtgg agtgtgtatt ygg                        103

<210> SEQ ID NO 56
<211> LENGTH: 94
<212> TYPE: DNA
<213> ORGANISM: Artificial Sequence
<220> FEATURE:
<223> OTHER INFORMATION: DMR 214

<400> SEQUENCE: 56
ttgtttaaag gygtagagga gtagttggga aygagaataa agyggttagg tttttttygg      60
aggaaggaag gagagagttt taggaaatag ttga                                  94

<210> SEQ ID NO 57
<211> LENGTH: 101
<212> TYPE: DNA
<213> ORGANISM: Artificial Sequence
<220> FEATURE:
<223> OTHER INFORMATION: DMR 219

<400> SEQUENCE: 57
ggatgaagga ttttgtatt attgtgatgg ttatggygtt gttgtttggg tttttttttt       60
tyggtaggta agggaggagg taggggaagg gatatgtgtt t                          101

<210> SEQ ID NO 58
<211> LENGTH: 70
<212> TYPE: DNA
<213> ORGANISM: Artificial Sequence
<220> FEATURE:
<223> OTHER INFORMATION: DMR 222

<400> SEQUENCE: 58
taggttatag gaagaggtat tttttataga tgayggttgt aaaattttaa gttgagtttt      60
tttaggaagt                                                             70

<210> SEQ ID NO 59
<211> LENGTH: 84
<212> TYPE: DNA
<213> ORGANISM: Artificial Sequence
<220> FEATURE:
<223> OTHER INFORMATION: DMR 223

<400> SEQUENCE: 59
```

```
aagagagagt ggttgataat tagtagagag aggttttaa tttayggaag tgtttgtaat      60
ataatttttt tgtatattag ttgt                                            84

<210> SEQ ID NO 60
<211> LENGTH: 97
<212> TYPE: DNA
<213> ORGANISM: Artificial Sequence
<220> FEATURE:
<223> OTHER INFORMATION: DMR 224

<400> SEQUENCE: 60 ggttttttt ttygagttat gaagagttgt tgyggttat tttggttty gtatttygtt        60 tttgttattt taggttttg taatttgttt aaygttt                               97

<210> SEQ ID NO 61
<211> LENGTH: 86
<212> TYPE: DNA
<213> ORGANISM: Artificial Sequence
<220> FEATURE:
<223> OTHER INFORMATION: DMR 225

<400> SEQUENCE: 61
gaagtttgat attttggtt ttaaatattg tttggttata ataygatatt tagggataga      60 tatttttat gtatagtaag ttgtgg                                           86

<210> SEQ ID NO 62
<211> LENGTH: 91
<212> TYPE: DNA
<213> ORGANISM: Artificial Sequence
<220> FEATURE:
<223> OTHER INFORMATION: DMR 226

<400> SEQUENCE: 62 gggggattg tygttaattt attgtttaat gatygyggtt ygygygttty gagtaatygg      60
gtgatgtatg tggattgtgt atatttygtg g                                    91

<210> SEQ ID NO 63
<211> LENGTH: 84
<212> TYPE: DNA
<213> ORGANISM: Artificial Sequence
<220> FEATURE:
<223> OTHER INFORMATION: DMR 141

<400> SEQUENCE: 63
cgttacggga aggaggtata cgatttagtt tatgatatcg ttatttcggc gtggtgttgt     60
agggggaagt ttaggtattt atcg                                            84

<210> SEQ ID NO 64
<211> LENGTH: 107
<212> TYPE: DNA
<213> ORGANISM: Artificial Sequence
<220> FEATURE:
<223> OTHER INFORMATION: DMR 204

<400> SEQUENCE: 64
cgtcgcgggg ttttaggcgt agtacgtttt cgcgcgtggg tcgtagttgg tagtatagga     60
agtttaggtg gaagagcggc ggcgtgggcg gttcggcgcg gygyggt                   107

<210> SEQ ID NO 65
<211> LENGTH: 62
<212> TYPE: DNA
<213> ORGANISM: Artificial Sequence
```

```
<220> FEATURE:
<223> OTHER INFORMATION: DMR 228

<400> SEQUENCE: 65
yggttgttag gcgtttcgcg ggygggtttt ttttcggttt ttcggtttgt tcggtatttt    60
cg                                                                   62

<210> SEQ ID NO 66
<211> LENGTH: 80
<212> TYPE: DNA
<213> ORGANISM: Artificial Sequence
<220> FEATURE:
<223> OTHER INFORMATION: DMR 144

<400> SEQUENCE: 66
ggcggcgtcg ttaaggttta dacgttttcg tgtaggaggg acgacgattt tttttacgtt    60
ttcgtggttt taattcggcg                                                80

<210> SEQ ID NO 67
<211> LENGTH: 61
<212> TYPE: DNA
<213> ORGANISM: Artificial Sequence
<220> FEATURE:
<223> OTHER INFORMATION: DMR 123

<400> SEQUENCE: 67
tgagtttttg tttgttttgg tttgggtttt tttgagtttt gttattagtt gaggttgtgt    60
g                                                                    61

<210> SEQ ID NO 68
<211> LENGTH: 61
<212> TYPE: DNA
<213> ORGANISM: Artificial Sequence
<220> FEATURE:
<223> OTHER INFORMATION: DMR 129

<400> SEQUENCE: 68
tygagatgtg ggaatgtttg ggtygtygtg tagttattgg gtagggtygt ttttttttgt    60
g                                                                    61

<210> SEQ ID NO 69
<211> LENGTH: 73
<212> TYPE: DNA
<213> ORGANISM: Artificial Sequence
<220> FEATURE:
<223> OTHER INFORMATION: DMR 137

<400> SEQUENCE: 69
tgtggttata ggttatttta ggttgttttg ggtgtttttt ttgtagtttt atgtagatag    60
aagatatttt ttg                                                       73

<210> SEQ ID NO 70
<211> LENGTH: 64
<212> TYPE: DNA
<213> ORGANISM: Artificial Sequence
<220> FEATURE:
<223> OTHER INFORMATION: DMR 148

<400> SEQUENCE: 70
ttttygtttt gtgtttggtt gaagtgattg gggtygaata ygtttaygtt tttgaatatg    60 ggyg                                                                 64
```

```
<210> SEQ ID NO 71
<211> LENGTH: 88
<212> TYPE: DNA
<213> ORGANISM: Artificial Sequence
<220> FEATURE:
<223> OTHER INFORMATION: DMR 150

<400> SEQUENCE: 71
tgggaggttg aggtgggaga atggtgtgaa tttgggaggt ggagtttgta gtgagttgag    60
attgtgttat tgtattttag tttgggtg                                       88

<210> SEQ ID NO 72
<211> LENGTH: 76
<212> TYPE: DNA
<213> ORGANISM: Artificial Sequence
<220> FEATURE:
<223> OTHER INFORMATION: DMR 154

<400> SEQUENCE: 72
gtygatttag ttttcgagat tttttacgt cgttttaaaa ttaaaacgga gtttaatacg     60
aagttgggtg aagtcg                                                    76

<210> SEQ ID NO 73
<211> LENGTH: 76
<212> TYPE: DNA
<213> ORGANISM: Artificial Sequence
<220> FEATURE:
<223> OTHER INFORMATION: DMR 158

<400> SEQUENCE: 73
ygggygtggt ggtttatgtt tgttatttta gtattttggg aggttgaggt gggtggatta    60
tgaggttggg agattg                                                    76

<210> SEQ ID NO 74
<211> LENGTH: 83
<212> TYPE: DNA
<213> ORGANISM: Artificial Sequence
<220> FEATURE:
<223> OTHER INFORMATION: DMR 164

<400> SEQUENCE: 74
ygggayggyg gtgtttagtt tagtttaggg taattgggtt ttttgagagt tcgatttta    60 tcggtttggg agcgagtggt tcg                                            83

<210> SEQ ID NO 75
<211> LENGTH: 76
<212> TYPE: DNA
<213> ORGANISM: Artificial Sequence
<220> FEATURE:
<223> OTHER INFORMATION: DMR 176

<400> SEQUENCE: 75
ygggtgtggt ggtttaygtt tgtaattta gtattttggg aggttgaggt gggyggatta    60
ygaggttagg agatyg                                                    76

<210> SEQ ID NO 76
<211> LENGTH: 91
<212> TYPE: DNA
<213> ORGANISM: Artificial Sequence
<220> FEATURE:
<223> OTHER INFORMATION: DMR 178

<400> SEQUENCE: 76
```

```
ygtggtttgg agagygttga aggtgggagg gggaagaggg gtagaatttt ygcgggagcg    60
agcgtatagt tgtcgtttyg tggtcgttty g                                  91
```

<210> SEQ ID NO 77
<211> LENGTH: 71
<212> TYPE: DNA
<213> ORGANISM: Artificial Sequence
<220> FEATURE:
<223> OTHER INFORMATION: DMR 180

<400> SEQUENCE: 77

```
ygtgttttty gtatagggag cgttygtttt tgttggggtt ggagcggcgt ttggaggtcg    60
atattcggtc g                                                        71
```

<210> SEQ ID NO 78
<211> LENGTH: 88
<212> TYPE: DNA
<213> ORGANISM: Artificial Sequence
<220> FEATURE:
<223> OTHER INFORMATION: DMR 186

<400> SEQUENCE: 78

```
ygtgattagt tygttttggt tttttaaagt gttgggatta aaggtgtgag ttattgtgtt    60
gggttgagat tttgttttaa aaaaaaaa                                      88
```

<210> SEQ ID NO 79
<211> LENGTH: 87
<212> TYPE: DNA
<213> ORGANISM: Artificial Sequence
<220> FEATURE:
<223> OTHER INFORMATION: DMR 188

<400> SEQUENCE: 79

```
tgagagttgy ggaaaygtta ygaggatttg ttaattaggt tgygggttaa ttagagttgg    60
gaagatttga atattgattt tgtttyg                                       87
```

<210> SEQ ID NO 80
<211> LENGTH: 56
<212> TYPE: DNA
<213> ORGANISM: Artificial Sequence
<220> FEATURE:
<223> OTHER INFORMATION: DMR 190

<400> SEQUENCE: 80

```
cgaggtggag cgacgttggt acggtaattt tgagtttgcg cggttcggcg ttattt        56
```

<210> SEQ ID NO 81
<211> LENGTH: 88
<212> TYPE: DNA
<213> ORGANISM: Artificial Sequence
<220> FEATURE:
<223> OTHER INFORMATION: DMR 192

<400> SEQUENCE: 81

```
cgtcggtttc gtcgatgttt tagaaggtta gttttttttc gaagagcggt tcgtatacgt    60
ttgcggggta gtgtagtttg tcggtgcg                                      88
```

<210> SEQ ID NO 82
<211> LENGTH: 58
<212> TYPE: DNA
<213> ORGANISM: Artificial Sequence
<220> FEATURE:

<223> OTHER INFORMATION: DMR 200

<400> SEQUENCE: 82
cgcggcgatc gtaaagggag tgtttgttta ttcgcgtttg aaagtagatt ttttttcg         58

<210> SEQ ID NO 83
<211> LENGTH: 101
<212> TYPE: DNA
<213> ORGANISM: Artificial Sequence
<220> FEATURE:
<223> OTHER INFORMATION: DMR 202

<400> SEQUENCE: 83
ygtygtygay gygaaggggt tgtttgtgcg cggygttgyg ggttttttcgc gcgtggggtg       60 tgcgtgtgcg tgttcgggtt cggttttgtg tgtgtatcgc g                           101

<210> SEQ ID NO 84
<211> LENGTH: 61
<212> TYPE: DNA
<213> ORGANISM: Artificial Sequence
<220> FEATURE:
<223> OTHER INFORMATION: DMR 208

<400> SEQUENCE: 84
atgtttgtaa ttttagtatt ttgggaggtt gaggtgggtg gattatgagg ttaggagatt       60
g                                                                       61

<210> SEQ ID NO 85
<211> LENGTH: 30
<212> TYPE: DNA
<213> ORGANISM: Artificial Sequence
<220> FEATURE:
<223> OTHER INFORMATION: DMR 210

<400> SEQUENCE: 85
tttttaaaat ttttttttt cgttttattt                                         30

<210> SEQ ID NO 86
<211> LENGTH: 49
<212> TYPE: DNA
<213> ORGANISM: Artificial Sequence
<220> FEATURE:
<223> OTHER INFORMATION: DMR 213

<400> SEQUENCE: 86
gaaaacgcgg tgtagggaga aaattaattt agtgaggagc ggaggcgta                   49

<210> SEQ ID NO 87
<211> LENGTH: 34
<212> TYPE: DNA
<213> ORGANISM: Artificial Sequence
<220> FEATURE:
<223> OTHER INFORMATION: DMR 214

<400> SEQUENCE: 87
gaacgagaat aaagcggtta ggttttttttc ggag                                  34

<210> SEQ ID NO 88
<211> LENGTH: 41
<212> TYPE: DNA
<213> ORGANISM: Artificial Sequence
<220> FEATURE:
<223> OTHER INFORMATION: DMR 219

<400> SEQUENCE: 88

```
gcgttgttgt ttgggttttt tttttcggt aggtaaggga g                   41
```

<210> SEQ ID NO 89
<211> LENGTH: 10
<212> TYPE: DNA
<213> ORGANISM: Artificial Sequence
<220> FEATURE:
<223> OTHER INFORMATION: DMR 222
<220> FEATURE:
<221> NAME/KEY: misc_feature
<222> LOCATION: 1..2
<223> OTHER INFORMATION: /note="n can be any nucleotide"
<220> FEATURE:
<221> NAME/KEY: misc_feature
<222> LOCATION: 9..10
<223> OTHER INFORMATION: /note="n can be any nucleotide"

<400> SEQUENCE: 89

```
nnacggttnn                                                     10
```

<210> SEQ ID NO 90
<211> LENGTH: 23
<212> TYPE: DNA
<213> ORGANISM: Artificial Sequence
<220> FEATURE:
<223> OTHER INFORMATION: DMR 223

<400> SEQUENCE: 90

```
agagaggttt ttaatttacg gaa                                      23
```

<210> SEQ ID NO 91
<211> LENGTH: 34
<212> TYPE: DNA
<213> ORGANISM: Artificial Sequence
<220> FEATURE:
<223> OTHER INFORMATION: DMR 224

<400> SEQUENCE: 91

```
tttgcggtta ttttggtttt cgtatttcgt tttt                          34
```

<210> SEQ ID NO 92
<211> LENGTH: 19
<212> TYPE: DNA
<213> ORGANISM: Artificial Sequence
<220> FEATURE:
<223> OTHER INFORMATION: DMR 225

<400> SEQUENCE: 92

```
gttataatac gatatttag                                           19
```

<210> SEQ ID NO 93
<211> LENGTH: 29
<212> TYPE: DNA
<213> ORGANISM: Artificial Sequence
<220> FEATURE:
<223> OTHER INFORMATION: DMR 226

<400> SEQUENCE: 93

```
attgtggttt gtgtgttttg agtaattgg                                29
```

<210> SEQ ID NO 94
<211> LENGTH: 27
<212> TYPE: DNA
<213> ORGANISM: Artificial Sequence
<220> FEATURE:
<223> OTHER INFORMATION: DMR 141 for

```
<400> SEQUENCE: 94
tattyggagg tttaggggtg aggattt                                              27

<210> SEQ ID NO 95
<211> LENGTH: 27
<212> TYPE: DNA
<213> ORGANISM: Artificial Sequence
<220> FEATURE:
<223> OTHER INFORMATION: DMR 204 for

<400> SEQUENCE: 95
gatattyggt ggagagtygt agttgtt                                              27

<210> SEQ ID NO 96
<211> LENGTH: 25
<212> TYPE: DNA
<213> ORGANISM: Artificial Sequence
<220> FEATURE:
<223> OTHER INFORMATION: DMR 228 for

<400> SEQUENCE: 96
gttttatggg ygagttgttg tagtg                                                25

<210> SEQ ID NO 97
<211> LENGTH: 25
<212> TYPE: DNA
<213> ORGANISM: Artificial Sequence
<220> FEATURE:
<223> OTHER INFORMATION: DMR 144 for

<400> SEQUENCE: 97
tttaggtttg aygtgggttt tttag                                                25

<210> SEQ ID NO 98
<211> LENGTH: 28
<212> TYPE: DNA
<213> ORGANISM: Artificial Sequence
<220> FEATURE:
<223> OTHER INFORMATION: DMR 123 for

<400> SEQUENCE: 98
gygaagtagg agtagttgty gggtttta                                             28

<210> SEQ ID NO 99
<211> LENGTH: 34
<212> TYPE: DNA
<213> ORGANISM: Artificial Sequence
<220> FEATURE:
<223> OTHER INFORMATION: DMR 129 for

<400> SEQUENCE: 99
aattttgttg agtgagttta taaatagggt ataa                                      34

<210> SEQ ID NO 100
<211> LENGTH: 35
<212> TYPE: DNA
<213> ORGANISM: Artificial Sequence
<220> FEATURE:
<223> OTHER INFORMATION: DMR 137 for

<400> SEQUENCE: 100
atttygttat atatatagtt gtattyggta taata                                     35

<210> SEQ ID NO 101
<211> LENGTH: 25
```

```
<212> TYPE: DNA
<213> ORGANISM: Artificial Sequence
<220> FEATURE:
<223> OTHER INFORMATION: DMR 148 for

<400> SEQUENCE: 101
gaggtaatgg aagyggttat ttttg                                              25

<210> SEQ ID NO 102
<211> LENGTH: 25
<212> TYPE: DNA
<213> ORGANISM: Artificial Sequence
<220> FEATURE:
<223> OTHER INFORMATION: DMR 150 for

<400> SEQUENCE: 102
gygggtattt gtagttttag ttatt                                              25

<210> SEQ ID NO 103
<211> LENGTH: 31
<212> TYPE: DNA
<213> ORGANISM: Artificial Sequence
<220> FEATURE:
<223> OTHER INFORMATION: DMR 154 for

<400> SEQUENCE: 103
ttttyggagt tyggagttta ggttagtggt a                                       31

<210> SEQ ID NO 104
<211> LENGTH: 31
<212> TYPE: DNA
<213> ORGANISM: Artificial Sequence
<220> FEATURE:
<223> OTHER INFORMATION: DMR 158 for

<400> SEQUENCE: 104
gattttgttt taaaaaagaa aaaaatgggg t                                       31

<210> SEQ ID NO 105
<211> LENGTH: 29
<212> TYPE: DNA
<213> ORGANISM: Artificial Sequence
<220> FEATURE:
<223> OTHER INFORMATION: DMR 164 for

<400> SEQUENCE: 105
gattygygag gttttttagt agtttattt                                          29

<210> SEQ ID NO 106
<211> LENGTH: 35
<212> TYPE: DNA
<213> ORGANISM: Artificial Sequence
<220> FEATURE:
<223> OTHER INFORMATION: DMR 176 for

<400> SEQUENCE: 106 taatttatttt ttttattaaa ttgtatgaag aaggt                                  35

<210> SEQ ID NO 107
<211> LENGTH: 28
<212> TYPE: DNA
<213> ORGANISM: Artificial Sequence
<220> FEATURE:
<223> OTHER INFORMATION: DMR 178 for

<400> SEQUENCE: 107
```

```
ggtaggagyg ttttattatg ygtaagtt                                      28

<210> SEQ ID NO 108
<211> LENGTH: 34
<212> TYPE: DNA
<213> ORGANISM: Artificial Sequence
<220> FEATURE:
<223> OTHER INFORMATION: DMR 180 for

<400> SEQUENCE: 108
ttgtagaagy gtattttgtt gaatatttyg agga                               34

<210> SEQ ID NO 109
<211> LENGTH: 34
<212> TYPE: DNA
<213> ORGANISM: Artificial Sequence
<220> FEATURE:
<223> OTHER INFORMATION: DMR 186 for

<400> SEQUENCE: 109
ygtgttagtt aggatggttt ygatttttg attt                                34

<210> SEQ ID NO 110
<211> LENGTH: 28
<212> TYPE: DNA
<213> ORGANISM: Artificial Sequence
<220> FEATURE:
<223> OTHER INFORMATION: DMR 188 for

<400> SEQUENCE: 110
agagttgtat ttygaagatt ttagattt                                      28

<210> SEQ ID NO 111
<211> LENGTH: 26
<212> TYPE: DNA
<213> ORGANISM: Artificial Sequence
<220> FEATURE:
<223> OTHER INFORMATION: DMR 190 for

<400> SEQUENCE: 111
gttagaygag agtttggggt taatgt                                        26

<210> SEQ ID NO 112
<211> LENGTH: 28
<212> TYPE: DNA
<213> ORGANISM: Artificial Sequence
<220> FEATURE:
<223> OTHER INFORMATION: DMR 192 for

<400> SEQUENCE: 112
yggtaggtta tttagtagta gggtttta                                      28

<210> SEQ ID NO 113
<211> LENGTH: 28
<212> TYPE: DNA
<213> ORGANISM: Artificial Sequence
<220> FEATURE:
<223> OTHER INFORMATION: DMR 200 for

<400> SEQUENCE: 113
aattagttta gtaatyggyg attttaag                                      28

<210> SEQ ID NO 114
<211> LENGTH: 22
<212> TYPE: DNA
<213> ORGANISM: Artificial Sequence
```

<220> FEATURE:
<223> OTHER INFORMATION: DMR 202 for

<400> SEQUENCE: 114
gtgygaataa gatygggygt tt					22

<210> SEQ ID NO 115
<211> LENGTH: 29
<212> TYPE: DNA
<213> ORGANISM: Artificial Sequence
<220> FEATURE:
<223> OTHER INFORMATION: DMR 208 for

<400> SEQUENCE: 115
atattaattt tgttygggta yggtggttt					29

<210> SEQ ID NO 116
<211> LENGTH: 28
<212> TYPE: DNA
<213> ORGANISM: Artificial Sequence
<220> FEATURE:
<223> OTHER INFORMATION: DMR 210 for

<400> SEQUENCE: 116
ggagttgtaa aaataaagg aatatgtg					28

<210> SEQ ID NO 117
<211> LENGTH: 32
<212> TYPE: DNA
<213> ORGANISM: Artificial Sequence
<220> FEATURE:
<223> OTHER INFORMATION: DMR 213 for

<400> SEQUENCE: 117
tygttyggga atgggaatat agttatatat gg					32

<210> SEQ ID NO 118
<211> LENGTH: 28
<212> TYPE: DNA
<213> ORGANISM: Artificial Sequence
<220> FEATURE:
<223> OTHER INFORMATION: DMR 214 for

<400> SEQUENCE: 118
ttgtttaaag gygtagagga gtagttgg					28

<210> SEQ ID NO 119
<211> LENGTH: 35
<212> TYPE: DNA
<213> ORGANISM: Artificial Sequence
<220> FEATURE:
<223> OTHER INFORMATION: DMR 219 for

<400> SEQUENCE: 119
ggatgaagga ttttttgtatt attgtgatgg ttatg					35

<210> SEQ ID NO 120
<211> LENGTH: 32
<212> TYPE: DNA
<213> ORGANISM: Artificial Sequence
<220> FEATURE:
<223> OTHER INFORMATION: DMR 222 for

<400> SEQUENCE: 120
taggttatag gaagaggtat tttttataga tg					32

<210> SEQ ID NO 121
<211> LENGTH: 26
<212> TYPE: DNA
<213> ORGANISM: Artificial Sequence
<220> FEATURE:
<223> OTHER INFORMATION: DMR 223 for

<400> SEQUENCE: 121
aagagagagt ggttgataat tagtag                                          26

<210> SEQ ID NO 122
<211> LENGTH: 29
<212> TYPE: DNA
<213> ORGANISM: Artificial Sequence
<220> FEATURE:
<223> OTHER INFORMATION: DMR 224 for

<400> SEQUENCE: 122
ggtttttttt ttygagttat gaagagttg                                       29

<210> SEQ ID NO 123
<211> LENGTH: 34
<212> TYPE: DNA
<213> ORGANISM: Artificial Sequence
<220> FEATURE:
<223> OTHER INFORMATION: DMR 225 for

<400> SEQUENCE: 123
gaagtttgat atttttggtt ttaaatattg tttg                                 34

<210> SEQ ID NO 124
<211> LENGTH: 31
<212> TYPE: DNA
<213> ORGANISM: Artificial Sequence
<220> FEATURE:
<223> OTHER INFORMATION: DMR 226 for

<400> SEQUENCE: 124 gggggggattg tygttaattt attgtttaat g                                   31

<210> SEQ ID NO 125
<211> LENGTH: 25
<212> TYPE: DNA
<213> ORGANISM: Artificial Sequence
<220> FEATURE:
<223> OTHER INFORMATION: DMR 141 rev

<400> SEQUENCE: 125
caacraattc cccraatcct atcct                                           25

<210> SEQ ID NO 126
<211> LENGTH: 20
<212> TYPE: DNA
<213> ORGANISM: Artificial Sequence
<220> FEATURE:
<223> OTHER INFORMATION: DMR 204 rev

<400> SEQUENCE: 126
accratacca acccrcactc                                                 20

<210> SEQ ID NO 127
<211> LENGTH: 24
<212> TYPE: DNA
<213> ORGANISM: Artificial Sequence
<220> FEATURE:
<223> OTHER INFORMATION: DMR 228 rev

<400> SEQUENCE: 127
aaaaacccrc raaaccaaaa aatc                                    24

<210> SEQ ID NO 128
<211> LENGTH: 35
<212> TYPE: DNA
<213> ORGANISM: Artificial Sequence
<220> FEATURE:
<223> OTHER INFORMATION: DMR 144 rev

<400> SEQUENCE: 128
tctaaaatat attcaccraa tcaaaaataa caaaa                        35

<210> SEQ ID NO 129
<211> LENGTH: 31
<212> TYPE: DNA
<213> ORGANISM: Artificial Sequence
<220> FEATURE:
<223> OTHER INFORMATION: DMR 123 rev

<400> SEQUENCE: 129
tctctcctaa craaaaacta acccaattac c                            31

<210> SEQ ID NO 130
<211> LENGTH: 25
<212> TYPE: DNA
<213> ORGANISM: Artificial Sequence
<220> FEATURE:
<223> OTHER INFORMATION: DMR 129 rev

<400> SEQUENCE: 130
tcacttaaca ccrttttac taacc                                    25

<210> SEQ ID NO 131
<211> LENGTH: 22
<212> TYPE: DNA
<213> ORGANISM: Artificial Sequence
<220> FEATURE:
<223> OTHER INFORMATION: DMR 137 rev

<400> SEQUENCE: 131
craaaaacta aacacccaaa cc                                      22

<210> SEQ ID NO 132
<211> LENGTH: 31
<212> TYPE: DNA
<213> ORGANISM: Artificial Sequence
<220> FEATURE:
<223> OTHER INFORMATION: DMR 148 rev

<400> SEQUENCE: 132
atatataaca tccraaacac ccataacaca a                            31

<210> SEQ ID NO 133
<211> LENGTH: 24
<212> TYPE: DNA
<213> ORGANISM: Artificial Sequence
<220> FEATURE:
<223> OTHER INFORMATION: DMR 150 rev

<400> SEQUENCE: 133
tttttaaacr aaatctcrct ctat                                    24

<210> SEQ ID NO 134

```
<211> LENGTH: 30
<212> TYPE: DNA
<213> ORGANISM: Artificial Sequence
<220> FEATURE:
<223> OTHER INFORMATION: DMR 154 rev

<400> SEQUENCE: 134
aaaacrcatc tccctaactc ctacaaacta                              30

<210> SEQ ID NO 135
<211> LENGTH: 29
<212> TYPE: DNA
<213> ORGANISM: Artificial Sequence
<220> FEATURE:
<223> OTHER INFORMATION: DMR 158 rev

<400> SEQUENCE: 135
aaatttcacc rtattaccca aaataatat                               29

<210> SEQ ID NO 136
<211> LENGTH: 26
<212> TYPE: DNA
<213> ORGANISM: Artificial Sequence
<220> FEATURE:
<223> OTHER INFORMATION: DMR 164 rev

<400> SEQUENCE: 136
aaacracrat tcccaacatc taaact                                  26

<210> SEQ ID NO 137
<211> LENGTH: 27
<212> TYPE: DNA
<213> ORGANISM: Artificial Sequence
<220> FEATURE:
<223> OTHER INFORMATION: DMR 176 rev

<400> SEQUENCE: 137
aataaaaacr aaatttcacc rtaatct                                 27

<210> SEQ ID NO 138
<211> LENGTH: 23
<212> TYPE: DNA
<213> ORGANISM: Artificial Sequence
<220> FEATURE:
<223> OTHER INFORMATION: DMR 178 rev

<400> SEQUENCE: 138
ccaaaaccra aaccaacrat tcc                                     23

<210> SEQ ID NO 139
<211> LENGTH: 30
<212> TYPE: DNA
<213> ORGANISM: Artificial Sequence
<220> FEATURE:
<223> OTHER INFORMATION: DMR 180 rev

<400> SEQUENCE: 139
acaaaaacra caaacraaaa aatccaacaa                              30

<210> SEQ ID NO 140
<211> LENGTH: 24
<212> TYPE: DNA
<213> ORGANISM: Artificial Sequence
<220> FEATURE:
<223> OTHER INFORMATION: DMR 186 rev

<400> SEQUENCE: 140
```
tcccaaaata ccacaaccca aacc                                          24

<210> SEQ ID NO 141
<211> LENGTH: 26
<212> TYPE: DNA
<213> ORGANISM: Artificial Sequence
<220> FEATURE:
<223> OTHER INFORMATION: DMR 188 rev

<400> SEQUENCE: 141 aacrtaaaata tccraactac aaaaac                                       26

<210> SEQ ID NO 142
<211> LENGTH: 27
<212> TYPE: DNA
<213> ORGANISM: Artificial Sequence
<220> FEATURE:
<223> OTHER INFORMATION: DMR 190 rev

<400> SEQUENCE: 142
aaatccaacc aacaacraaa aaccaaa                                       27

<210> SEQ ID NO 143
<211> LENGTH: 28
<212> TYPE: DNA
<213> ORGANISM: Artificial Sequence
<220> FEATURE:
<223> OTHER INFORMATION: DMR 192 rev

<400> SEQUENCE: 143
crtcttcrcc tatatactca attactac                                      28

<210> SEQ ID NO 144
<211> LENGTH: 29
<212> TYPE: DNA
<213> ORGANISM: Artificial Sequence
<220> FEATURE:
<223> OTHER INFORMATION: DMR 200 rev

<400> SEQUENCE: 144
ccactaacaa ataaatccta tattcctac                                     29

<210> SEQ ID NO 145
<211> LENGTH: 25
<212> TYPE: DNA
<213> ORGANISM: Artificial Sequence
<220> FEATURE:
<223> OTHER INFORMATION: DMR 202 rev

<400> SEQUENCE: 145
crataatccc ractctaaac aaacc                                         25

<210> SEQ ID NO 146
<211> LENGTH: 31
<212> TYPE: DNA
<213> ORGANISM: Artificial Sequence
<220> FEATURE:
<223> OTHER INFORMATION: DMR 208 rev

<400> SEQUENCE: 146
craaatttca ccatattcrc caaaataatc t                                  31

<210> SEQ ID NO 147
<211> LENGTH: 34
<212> TYPE: DNA

<213> ORGANISM: Artificial Sequence
<220> FEATURE:
<223> OTHER INFORMATION: DMR 210 rev

<400> SEQUENCE: 147
tacatacaaa ttactataaa accatttcct atac      34

<210> SEQ ID NO 148
<211> LENGTH: 22
<212> TYPE: DNA
<213> ORGANISM: Artificial Sequence
<220> FEATURE:
<223> OTHER INFORMATION: DMR 213 rev

<400> SEQUENCE: 148
ccraatacac actccacaat cc      22

<210> SEQ ID NO 149
<211> LENGTH: 32
<212> TYPE: DNA
<213> ORGANISM: Artificial Sequence
<220> FEATURE:
<223> OTHER INFORMATION: DMR 214 rev

<400> SEQUENCE: 149
tcaactattt cctaaaactc tctccttcct tc      32

<210> SEQ ID NO 150
<211> LENGTH: 25
<212> TYPE: DNA
<213> ORGANISM: Artificial Sequence
<220> FEATURE:
<223> OTHER INFORMATION: DMR 219 rev

<400> SEQUENCE: 150
aaacacatat cccttcccct acctc      25

<210> SEQ ID NO 151
<211> LENGTH: 32
<212> TYPE: DNA
<213> ORGANISM: Artificial Sequence
<220> FEATURE:
<223> OTHER INFORMATION: DMR 222 rev

<400> SEQUENCE: 151
acttcctaaa aaaactcaac ttaaaatttt ac      32

<210> SEQ ID NO 152
<211> LENGTH: 35
<212> TYPE: DNA
<213> ORGANISM: Artificial Sequence
<220> FEATURE:
<223> OTHER INFORMATION: DMR 223 rev

<400> SEQUENCE: 152
acaactaata tacaaaaaaa ttatattaca aacac      35

<210> SEQ ID NO 153
<211> LENGTH: 34
<212> TYPE: DNA
<213> ORGANISM: Artificial Sequence
<220> FEATURE:
<223> OTHER INFORMATION: DMR 224 rev

<400> SEQUENCE: 153
aaacrttaaa caaattacaa aaacctaaaa taac      34

<210> SEQ ID NO 154
<211> LENGTH: 33
<212> TYPE: DNA
<213> ORGANISM: Artificial Sequence
<220> FEATURE:
<223> OTHER INFORMATION: DMR 225 rev

<400> SEQUENCE: 154
ccacaactta ctatacataa aaaatatcta tcc                              33

<210> SEQ ID NO 155
<211> LENGTH: 31
<212> TYPE: DNA
<213> ORGANISM: Artificial Sequence
<220> FEATURE:
<223> OTHER INFORMATION: DMR 226 rev

<400> SEQUENCE: 155
ccacraaata tacacaatcc acatacatca c                                31

<210> SEQ ID NO 156
<211> LENGTH: 84
<212> TYPE: DNA
<213> ORGANISM: Homo sapiens

<400> SEQUENCE: 156
cgccacggga aggaggcaca cgattcagcc catgacaccg ccacctcggc gtggtgctgt    60 aggggggaagc tcaggcactc accg                                         84

<210> SEQ ID NO 157
<211> LENGTH: 107
<212> TYPE: DNA
<213> ORGANISM: Homo sapiens

<400> SEQUENCE: 157
cgccgcgggg ccccaggcgc agcacgctct cgcgcgtggg ccgcagctgg cagcacagga    60
agtccaggtg gaagagcggc ggcgtgggcg gcccggcgcg gcgcggc                 107

<210> SEQ ID NO 158
<211> LENGTH: 62
<212> TYPE: DNA
<213> ORGANISM: Homo sapiens

<400> SEQUENCE: 158
cggctgccag gcgccccgcg ggcgggcccc tccccggccc tccggcctgc ccggcacccc    60
cg                                                                  62

<210> SEQ ID NO 159
<211> LENGTH: 80
<212> TYPE: DNA
<213> ORGANISM: Homo sapiens

<400> SEQUENCE: 159
ggcggcgtcg ccaaggctta gacgctttcg tgcaggaggg acgacgactc ccctcacgcc    60
ttcgtggccc caactcggcg                                               80

EPIGENETIC MARKERS AND RELATED METHODS AND MEANS FOR THE DETECTION AND MANAGEMENT OF CERTAIN CANCERS

CROSS REFERENCE TO RELATED APPLICATIONS

This application is a national stage application under 35 U.S.C. 371 and claims the benefit of PCT Application No. PCT/EP2017/083170 having an international filing date of 15 Dec. 2017, which designated the United States, which PCT application claimed the benefit of European Patent Application No. 16204822.7 filed 16 Dec. 2016, the disclosures of each of which are incorporated herein by reference in their entireties.

The present invention relates to methods of determining the presence or absence of certain cancers in a human individual, as well as to related methods to determine the response to therapy against certain cancers in a human individual, in particular ovarian cancer in a woman. Such methods are based on the detection—from (eg cell-free) DNA of said human individual—of one or more methylated (or un-methylated) CpGs being associated with differentially methylated regions (DMRs) of the present invention; such as methylation (or un-methylation) at one or more or all of certain CpGs being associated with such DMRs. Accordingly, such methods have diagnostic, prognostic and/or predictive utility for detecting or managing certain cancers in women or men, in particular ovarian cancer in women. The present invention further relates to nucleic acids comprising certain sequences that may be detected during the method, or nucleic acids (such as probes and/or primers) that are useful to detect such sequences, as wells as compositions, kits, computer program products and other aspects that are useful for or related to the practice or application of such methods.

Three quarters of ovarian cancers are diagnosed once the tumour has spread into the abdomen and long-term survival rates of these women are low (10-30%) (Ref. 1). High-grade serous (HGS) ovarian cancer (OC) accounts for 70-80% of OC deaths and the survival figures have not changed significantly over the past few decades (Ref. 2). Early diagnosis and personalised treatment still remain the biggest unmet needs in combatting this devastating disease (Ref. 2).

A number of ovarian cancer biomarkers have been studied in the past. Amongst those, CA125, which was discovered more than 30 years ago (Ref. 3), is still the 'gold standard' despite the relatively low sensitivity for early epithelial ovarian cancer and the modest positive predictive value (Ref. 4). The 35 most promising ovarian cancer biomarkers were evaluated in samples taken up to 6 months prior to OC diagnosis from 118 women and 951 age-matched controls from the Prostate, Lung, Colorectal, and Ovarian (PLCO) Cancer Screening Trial. At a fixed specificity of 95%, CA125 had the best sensitivity (Ref. 5). The performance of CA125 dropped dramatically when samples taken >6 months prior to diagnosis were evaluated (Ref. 5). Recently it was demonstrated that the performance of the Risk of Ovarian Cancer Algorithm (ROCA) demonstrates superior performance characteristics during screening, but this requires serial blood samples that are not available in patients presenting clinically (Refs. 6, 7). In addition, the dynamics of CA125 in women undergoing neoadjuvant chemotherapy (NACT) are of limited use in predicting disease response and outcome (Ref. 8).

According to current cancer statistics for the United States (https://www.cancer.gov/about-cancer/understanding/statistics, accessed 11 Dec. 2017), in 2016, an estimated 1,685,210 new cases of cancer will be diagnosed in the United States and 595,690 people will die from the disease. The most common cancers in 2016 are projected to be breast cancer, lung and bronchus cancer, prostate cancer, colon and rectum cancer, bladder cancer, melanoma of the skin, non-Hodgkin lymphoma, thyroid cancer, kidney and renal pelvis cancer, leukaemia, uterine (endometrial) cancer, and pancreatic cancer. The number of new cases of cancer (cancer incidence) is 454.8 per 100,000 men and women per year (based on 2008-2012 cases), and the number of cancer deaths (cancer mortality) is 171.2 per 100,000 men and women per year (based on 2008-2012 deaths). National expenditures for cancer care in the United States totalled nearly $125 billion in 2010 and could reach $156 billion in 2020.

In terms of gynaecologic cancer statistics for the United States, in 2015, it was estimated that 98,280 women would be diagnosed with a gynaecologic cancer and some 30,440 will die from the disease (http://www.foundationforwomenscancer.org/about-gynecologic-cancerst accessed 11 Dec. 2017), with an estimated number of new cases for 2015 of the three most prevalent gynaecologic cancer being: cervical cancer, 12,340 new cases, ovarian cancer, 21,290 new cases; and uterine cancer 54,8970 new cases.

The vast majority of protein-based tumour markers are produced not only by cancerous but also non-neoplastic normal cells; CA125 is produced by mesothelial cells (i.e. peritoneum and pleura) and hence benign or inflammatory processes can result in aberrant elevations of serum CA125.

Recently, markers based on DNA shed from tumour cells, have shown great promise in monitoring treatment response and predicting prognosis (Refs. 9-13). But efforts to characterise the cancer genome have shown that only a few genes are frequently mutated in most cancers with the gene mutation site differing across individuals for similar tumours. Hence, the detection of somatic mutations is limited to patients that harbour a predefined set of mutations. The necessity of prior knowledge regarding specific genomic composition of tumour tissues is one of the limiting factors when using these 'liquid biopsy' approaches for early detection or differential diagnosis of a pelvic mass. Current technology allows for the detection of a mutant allele fraction of 0.1% (which is one mutant molecule in a background of 1000 wild-type molecules) (Refs. 9, 14).

The development of cell-free DNA based early cancer detection tests poses two major challenges: (1) a very low abundance of cancer-DNA in the blood and (2) an extremely high level of "background DNA" (shed from white blood cells (Ref. 15)) in all population based cohorts which allow for the validation of potential screening markers years in advance of current diagnosis.

Alteration of DNA methylation (DNAme) is (i) an early event in cancer development, (ii) more frequently observed than somatic mutations and (Hi) centred around specific regions, i.e. CpG islands (Ref. 17). Together with its chemical and biological stability, the detection of aberrant DNA methylation patterns in serum or plasma provide a novel strategy for cancer diagnosis as evidenced by several proof of principle studies in the past (Refs. 9, 10, 13, 15, 18-20). The fact that technologies to detect DNA methylation allow for the detection of specific methylation patterns (for example, full methylation or un-methylation) of all of (for example, between 7 and 16) certain linked CpGs in a region of 120-150 base-pairs as opposed to single point mutations (e.g. in the TP53 gene) is likely to improve both the performance characteristics of the test and the detection limit of the assay. Plasma SEPT9 methylation analyses—currently the only cell-free DNA which is available for cancer screening in the clinical setting—demonstrates a specificity of 79% and a sensitivity of 68% for detection of colon cancers (Ref. 21). Maternal plasma cell-free DNA testing for foetal trisomy has already become clinical practice as it has a higher sensitivity and a lower false positive rate compared to imaging-based techniques (Ref. 22).

The inventors have employed two different epigenome-wide approaches to identify the most promising DNAme-based markers, developed serum tests and validated their performance benchmarking against serum ovarian cancer marker CA125, and also demonstrate the utility of these DNAme-based markers in other cancers.

It has been suggested that DNA methylation markers have promise (and challenges) for early detection of women's cancers such as ovarian cancer (Ref. 20). Indeed, there are a number of publications that disclose various epigenetic biomarkers and their association with various cancers, including women's cancers such as ovarian cancer, and the use of such biomarkers (including in certain combinations) for the detection and/or management of one or more of such cancers: WO2002/018631A2; WO2002/018632A2; WO2007/019670A1; EP1862555A1; WO2009/153667A2; WO2012/104642A1; WO2012/138609A2; WO2012/143481A2; US2013/0041047A1; WO2013/09661A1). In particular, single-CpG-resolution methylation analysis (including patterns/signatures) in certain specific markers or genes (such as DNA hypermethylation of the CpG sites on the FAM150A, GRM6, ZNF540, ZFP42, EOMES HOXA9, POU4F2, TWIST1, VIM, ZNF154, RIMS4, PCDHAC1, KHDRBS2, ASCL2, KCNQ1, C2CD4D, PRAC, WNT3A, TRH, FAM78A, ZNF671, SLC13A5, NKX6-2, GP5 and HOTAIR genes) has identified cancers, or aggressive types thereof, such as renal cell carcinomas (Arai et al, 2012; Carcinogenesis 33:1487), bladder cancer (Reinert et al, 2012; PLos ONE 10:e46297), other cancers including breast cancer (Refs. 30, 31. Legendre et al, 2015; Clinical Epigenomics 7:100), ovarian cancer (Teschendorff et al, 2009; PLos ONE 4: e8274) and/or association with chemotherapeutic response in ovarian cancer (Ref. 25).

Hence, there is still a need, from one or more of the above or perspectives, for improved methods to determine the presence or absence of one or more cancers in human individuals (such as ovarian cancer in a woman), preferably in a non-invasive manner, such as by the use of (eg cell-free) DNA of said human individual (eg cell-free DNA isolated from a sample of a circulatory fluid). Preferably, such methods will have improved ability to discriminate ovarian cancer from benign pelvic mass, and/or high-grade serious (HGS) ovarian cancer from less severe or aggressive forms of ovarian cancer, such as by having improved specificity and/or sensitivity for the phenotype/disease to be detected. Such methods would provide a significant shift in the clinical paradigm for early-detection, diagnosis (eg by an in-vitro method) and/or management of cancers (especially ovarian cancer, and in particular of HGS ovarian cancer and or chemotherapy-responsive ovarian cancer), and in particular providing the potential for individualisation of treatment for women of men suffering from cancer (eg women suffering from ovarian cancer).

Accordingly, it is an object of the present invention to provide alternative, improved, simpler, cheaper and/or integrated methods, means, compounds, compositions, kits and other aspects that address one or more of these or other problems (such as those set forth elsewhere herein). Such an object underlying the present invention is solved by the subject matter as disclosed or defined anywhere herein, for example by the subject matter of the numbered itemised embodiments or the claimed embodiments.

Generally, and by way of brief description, the main aspects of the present invention can be described as follows:

In a first aspect, and as may be further described, defined, claimed or otherwise disclosed herein, the invention relates to a method of determining the presence or absence of, or response to therapy against, a cancer in a human individual, said method comprising the steps:

Providing a biological sample from said human individual, said sample comprising (eg cell-free) DNA of said human individual; and Determining, in at least one molecule of said (eg cell-free) DNA, the methylation status at one or more CpGs located within one or more of the nucleotide sequences comprised in one or more of the respective DMRs of the present invention independently selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226, or a nucleotide sequence present within about 2,000 bp (such as within about 200 bp) 5' or 3' thereof, or an allelic variant and/or complementary sequence of any of said nucleotide sequences, wherein, the presence in at least one of said (eg cell-free) DNA molecules of one or more: (i) methylated CpGs associated with one or more of the hyper-methylated DMRs of the present invention; and/or (ii) un-methylated CpGs associated with one or more of the hypo-methylated DMRs of the present invention, indicates the presence of, or a reduced response to therapy against, such cancer in said human individual.

In a second aspect, and as may be further described, defined, claimed or otherwise disclosed herein, the invention relates to a chemotherapeutic agent, such as one selected from the group consisting of: carboplatin, paclitaxel, docetaxel, cisplatin, liposomal doxorubicin, gemcitabine, trabectedin, etoposide, cyclophosphamide, an angiogenesis inhibitor (such as bevacizumab) and a PARP inhibitor (such as olaparib), for use in a method of therapy of a cancer in a human individual, wherein said chemotherapeutic agent is administered to a human individual within about 3 months of said human individual having been predicted and/or determined, using a method of the first aspect, to not respond to a therapy against such cancer.

In a third aspect, and as may be further described, defined, claimed or otherwise disclosed herein, the invention relates to a nucleic acid comprising a nucleic acid sequence consisting of at least about 10 contiguous bases (preferably at least about 15 contiguous bases for any DMR other than DMR #222) comprised in a sequence producible by bisulphite conversion of a sequence comprised within a DMR selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226, or an allelic variant and/or complementary sequence of any of said nucleotide sequences.

In other aspects, the invention also relates to a nucleic acid probe, a nucleic acid PCR primer pair, a population of nucleic acids of the invention, a kit and a computer program product, in each case as may be described, defined, claimed or otherwise disclosed herein, and in each case related to use within or in connection with a method of the invention and/or to detect one or more a nucleic acid of the invention.

The figures show:

FIG. 1 depicts the study design. Using two different epigenome-wide technologies, 711 human tissue samples have been analysed to identify a total of 31 regions whose methylation status has been analysed in two sets consisting of 151 serum samples. Three markers have been validated in two independent settings: (1) Serum Set 3 which consisted of 250 serum samples from women with various benign and malignant conditions of the female genital tract; and (2) NACT (NeoAdjuvant ChemoTherapy) Set consisting of serial samples from women with advanced stage ovarian cancer before and during chemotherapy. Samples obtainable from the UKCTOCS (United Kingdom Collaborative Trial of Ovarian Cancer Screening) sample collection may be included in a third validation set to include serum samples from those women in the control arm who developed ovarian cancer within 2 years; for each case, a number of (such as three) control women who did not develop ovarian cancer within 5 years of sample donation can been matched to those women who did so develop ovarian cancer.

FIG. 2 depicts the principles of methylation pattern discovery in tissue and analyses in serum. Reduced Representation Bisulfite Sequencing (RRBS) was used in tissue samples in order to identify those CpG regions for which methylation patterns discriminate ovarian cancer from other tissues, in particular blood cells which were deemed to be the most abundant source of cell-free DNA. An example of region #141 is provided which is a 136 base-pair long region containing 7 linked CpGs. A cancer pattern may consist of reads in which all linked CpGs are methylated, indicated by "1111111" (Panel A). The tissue RRBS data have been processed through a bioinformatic pipeline in order to identify the most promising markers (Panel B). The principles of the serum DNA methylation assay are demonstrated in Panel C.

FIG. 3 depicts serum DNA methylation analysis in women with benign and malignant conditions of the female genital tract. Pattern frequencies for the different regions and CA125 levels analysed in Serum Set 3 samples are shown and horizontal bars denote the mean (Panels A-C; ns not significant; *p<0.05, p<0.01, *p<0.001; Mann-Whitney U test compared to HGS; H, Healthy; BPM, benign pelvic mass; BOT, borderline tumours; NET, non-epithelial tumours; OCM other cancerous malignancies; NHGS, non-high grade serous ovarian cancers; HGS, high grade serous; OC ovarian cancers). Based on Set 1&2 analyses cut-off thresholds of 0.0008, 0.0001 and 0.0001 for regions #141, #204 and #228, respectively, to discriminate HGS OC from H or BPM women were chosen and validated in Set 3; combining Sets 1-3 the cut-off thresholds have been refined for regions #204 and #228 so that the final cut-offs were 0.0008, 0.00003 and 0.00001, respectively; the sample was called positive if at least one of the three regions showed a pattern frequency above the cut-off; sensitivities and specificities to discriminate HGS from H&BPM are shown in Panel E. The overlap between CA125 positive samples (cut-off >35 IU/mL) and the three DNA methylation (DNAme) marker panel in cases and controls is shown in Panel F.

FIG. 4 depicts the dynamics of serum DNA methylation markers and CA125 as a function of exposure to carboplatin-based chemotherapy. The changes in pattern frequency of the three markers as well as CA125 is shown before compared to after 2 cycles of chemotherapy (Panels A-D). The changes of markers during chemotherapy and whether this can predict response (as described in Supplementary Information) to chemotherapy in all patients and in those who had no macroscopic residual disease after interval-debulking surgery (RO/1) is shown (Panel E). Definitions of CA125 and DNA methylation positivity are provided in FIG. 3.

FIG. 5 depicts the algorithm which first determines sets of consecutive CpG sites of maximum size, from which multiple potentially overlapping subsets are derived, which still meet the selection criteria.

FIG. 6 depicts cancer-specific differentially methylated region (DMR) discovery with Illumina 450K methylation arrays. (A) Schematic illustration of DMRs that are discovered by the single CpG and range approaches. Each horizontal line of lollipops indicates neighbouring CpGs in a single DNA molecule extracted from the indicated tissue. Filled lollipop indicates a methylated CpG, and an unfilled lollipop indicates an unmethylated CpG. 450K methylation arrays measure the ratio (% of methylation) of methylated and unmethylated molecules at a given single CpG location. See Supplementary Information for details on the DMR discovery methods. "up-arrow" (↑) Single CpG DMRs (high scoring); "left/right-arrow" (← →) Range of DMR (high scoring); asterisk (*) Not identified as DMRs because of the methylation in WBCs, "hash" (#) Not identified as high scoring DMRs with single CpG approach because the methylation difference between OC and other control tissues (=colon, lung, liver, rectum, endometrium, fimbriae and benign ovarian tissue) is not large enough. Identified as DMRs with range approach because the pooling of neighbouring CpG information increases statistical robustness. (B) Example of the methylation data for a high scoring DMR. The #228 targeted BS reaction was designed for this DMR.

FIG. 7 depicts a procedure for the isolation of cell-free DNA from a plasma or serum biological sample.

FIG. 8 depicts pattern frequencies for the different regions analysed in Serum Set 1 samples. H, Healthy; BPM, benign pelvic mass; NHGS, non-high grade serous ovarian cancers; HGS, high grade serous ovarian cancers. Horizontal bar denotes mean. ns not significant; *p<0.05, Mann-Whitney U test compared to HGS.

FIG. 9 depicts pattern frequencies for the different regions analysed in Serum Set 2 samples. H, Healthy; BPM, benign pelvic mass; BOT, borderline tumour; NET, non-epithelial tumours; OCM, other cancerous malignancies; NHGS, non-high grade serous ovarian cancers; HGS, high grade serous ovarian cancers. Horizontal bar denotes mean. ns not significant; * p<0.05;  p<0.01; * p<0.001, Mann-Whitney U test compared to HGS.

FIG. 10 depicts coverage (number of reads) for the three different regions analysed in Serum Set 3 samples. H, Healthy; BPM, benign pelvic mass; BOT, borderline tumour; NET, non-epithelial tumours; OCM, other cancerous malignancies; NHGS, non-high grade serous ovarian cancers; HGS, high grade serous ovarian cancers. Horizontal bar denotes mean. ns not significant; * p<0.05; Mann-Whitney U test compared to HGS.

FIG. 11 depicts CA125 levels measured in the NACT (the neoadjuvant chemotherapy) Serum Set samples. Samples taken before chemotherapy, after the first cycle of chemotherapy, and after the second cycle of chemotherapy. ns not significant; ** p<0.01; Mann-Whitney U test compared to before chemotherapy.

FIG. 12 depicts pattern frequencies for the top 3 reactions measured in NACT Serum Set samples. Samples taken before chemotherapy, after the first cycle of chemotherapy, and after the second cycle of chemotherapy. * p<0.05;  p<0.01;  p<0.01; Mann-Whitney U test compared to before chemotherapy.

FIG. 13 depicts coverage (number of reads) for the top 3 reactions measured in NACT Serum Set samples. Samples taken before chemotherapy, after the first cycle of chemotherapy, and after the second cycle of chemotherapy. ns not significant; Mann-Whitney U test compared to before chemotherapy.

Figure 1:
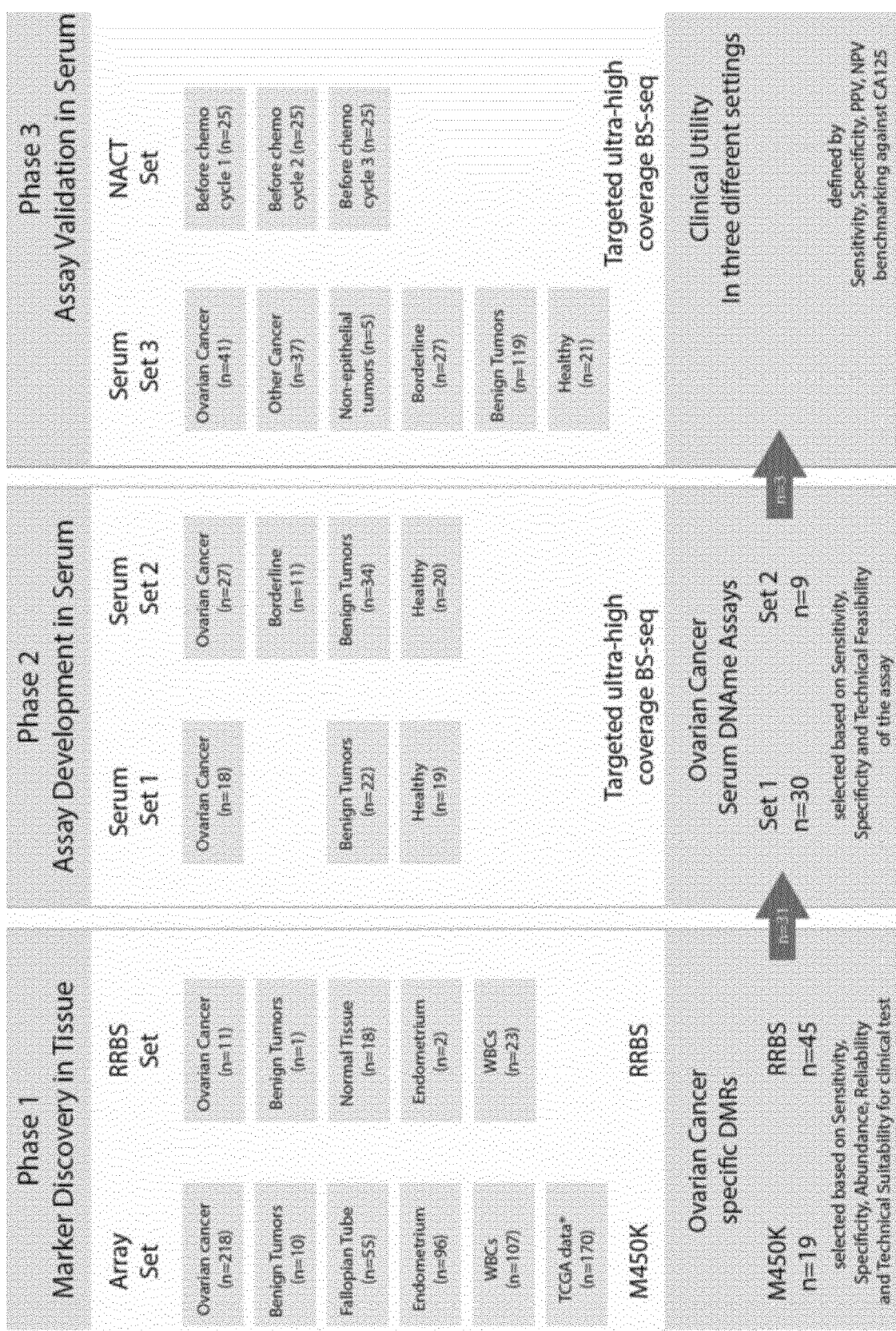

The present invention, and particular non-limiting aspects and/or embodiments thereof, can be described in more detail as follows:

In a first aspect, the invention relates to a method of determining the presence or absence of, or response to therapy against, a cancer in a human individual, said method comprising the steps:

Providing a biological sample from said human individual, said sample comprising DNA of said human individual; and Determining, in at least one molecule of said DNA, the methylation status at one or more CpGs located within one or more of the nucleotide sequences independently selected from the group consisting of: SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and 31 (for example, within one or more of the nucleotide sequences comprised in one or more of the respective DMRs of the present invention independently selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226), or a nucleotide sequence present within about 2,000 bp (such as within about 200 bp) 5' or 3' thereof, or an allelic variant and/or complementary sequence of any of said nucleotide sequences, wherein, the presence in at least one of said DNA molecules of one or more: (i) methylated CpGs associated with (such as located within) one or more of the hyper-methylated DMRs of the present invention (eg, as identified in TABLE 1A), for example associated with (such as located within) one or more of said nucleotide sequences independently selected from: SEQ ID NOs: 1, 2, 3, 4, 10, 12, 14, 15, 18, 19, 20, 21, 23, 24, 25, 26, 27, 28, 29 and 30; and/or (ii) un-methylated CpGs associated with (such as located within) one or more of the hypo-methylated DMRs of the present invention (eg, as identified in TABLE 1B), for example associated with (such as located within) one or more of said nucleotide sequences independently selected from: SEQ ID NOs: 5, 6, 7, 8, 9, 11, 13, 16, 17, 22 and 31, indicates the presence of, or a reduced response to therapy against, such cancer in said human individual.

In certain embodiments of this aspect, the sample comprises cell-free DNA of said human individual, and the determining step comprises determining, in at least one molecule of said cell-free DNA, the methylation status at one or more of such CpGs, and wherein, the presence in at least one of said cell-free DNA molecules of one or more of said methylated (or un-methylated) CpGs indicates the presence of, or a reduced response to therapy against, such cancer in said human individual. In one particular such embodiment, the human individual is a woman and the cancer is ovarian cancer. In another particular such embodiment, the human individual is a woman and the cancer is another gynaecological cancer (such as uterine cancer, vaginal cancer, cervical cancer, and vulvar cancer) or a cancer of the colon or breast. In yet another particular such embodiment, the human individual is not a woman and/or the cancer is not ovarian cancer and/or the cancer is not another gynaecological cancer (such as not uterine cancer, vaginal cancer, cervical cancer, and/or vulvar cancer) and/or is not a cancer of the breast and/or is not a cancer of the colon in a woman.

In alternative embodiments, of this aspect, the sample comprises DNA of said human individual obtained from a tissue sample taken from said human individual, such as a tissue sample (or biopsy) taken from (eg the site of) a suspected cancer.

In a certain particular embodiment of this aspect, the cancer is one selected from the group consisting of: Ovarian cancer (OC), Bladder Urothelial Carcinoma (BLCA), Breast invasive carcinoma (BRCA), Cervical squamous cell carcinoma and endocervical adenocarcinoma (CESC), Colon adenocarcinoma (COAD), Oesophageal carcinoma (ESCA), Head and Neck squamous cell carcinoma (HNSC), Kidney cancer (eg Kidney renal clear cell carcinoma (KIRC) and Kidney renal papillary cell carcinoma (KIRP)), Liver hepatocellular carcinoma (LIHC), Lung cancer (LC) (including Lung squamous cell carcinoma (LSCC) and Lung adenocarcinoma (LUAD)), Pancreatic adenocarcinoma (PAAD), Prostate adenocarcinoma (PRAD), Rectum adenocarcinoma (READ), Sarcoma (SARC), Skin Cutaneous Melanoma (SKCM), Stomach adenocarcinoma (STAD), Thyroid carcinoma (THCA) and Uterine Corpus Endometrial Carcinoma (UCEC).

In a first certain preferred embodiment of this aspect, the human individual is a woman and the cancer is one selected from the list consisting of: breast cancer, lung cancer, colon cancer, pancreatic cancer and ovarian cancer.

In a second certain preferred embodiment of this aspect, the human individual is a man and the cancer is one selected from the list consisting of: lung cancer, colon cancer and pancreatic cancer.

In one particular preferred embodiment of this aspect, the cancer is breast cancer (and the human individual is a woman).

In another particular preferred embodiment of this aspect, the cancer is lung cancer (such as lung adenocarcinoma or lung squamous cell carcinoma) and, for example, the human individual is a woman or a man.

In yet another particular preferred embodiment of this aspect, the cancer is colon cancer and, for example, the human individual is a woman or a man (in particular, a man).

In a yet further particular preferred embodiment of this aspect, the cancer is a pancreatic cancer and, for example, the human individual is a woman or a man.

In one other further particular preferred embodiment of this aspect, the cancer is uterine cancer (and the human individual is a woman).

In another further particular preferred embodiment of this aspect, the cancer is cervical cancer (and the human individual is a woman).

yet another further particular preferred embodiment of this aspect, the cancer is prostate cancer (and the human individual is a man).

The genomic sequence and genome coordinates (hg19) of one class of the regions of the genome used in the present invention as a source of epigenetic markers, ie those where the presence of methylation at one or more CpGs therein (or associated therewith, such as within about 2,000 bp—such as within about 200 bp—5' or 3' thereof), and represent the hyper-methylated cancer-specific differentially methylated regions (DMRs) of the present invention, are set out in TABLE 1A. Any of such CpGs (including those of an allelic variant and/or complementary sequence of any of the respective said nucleotide sequence/s) is one considered "associated with" the respective hyper-methylated cancer-specific DMR of the present invention.

TABLE 1A

Identity, source, genome-coordinates and genomic sequences of the hyper-methylated DMRs of the present invention

| DMR # | Data basis | Amplicon coordinates (hg19) | Amplicon genomic sequence (relevant CpGs are underlined) | Class | SEQ ID NO. |
|---|---|---|---|---|---|
| 141 | RRBS | chr5:178004395-178004530 | CATCCGGAGGCCCAGGGGTGAGGACTTCGCCACGGGAAGG AGGCACACGATTCAGCCCATGACACCGCCACCTCGGCGTG GTGCTGTAGGGGGAAGCTCAGGCACTCACCGAGGACAGGA CCCGGGGAATCCGCTG | Hyper | 1 |
| 204 | RRBS | chr1:151810784-151810937 | GATATTCGGTGGAGAGCCGCAGCTGCCCGCCGCGGGCCC CAGGCGCAGCACGCTCTCGCGCGTGGGCCGCAGCTGGCAG CACAGGAAGTCCAGGTGGAAGAGCGGCGGCGTGGGCGGCC CGGCGCGGCGCGGCGAGTGCGGGCTGGTATCGGC | Hyper | 2 |
| 228 | 450K | chr2:219736276-219736386 | GTTCTATGGGCGAGCTGCTGCAGTGCGGCTGCCAGGCGCC CCGCGGGCGGGCCCCTCCCCGGCCCTCCGGCCTGCCCGGC ACCCCCGGACCCCCTGGCCCCGCGGGCTCCC | Hyper | 3 |
| 144 | RRBS | chr19:58220413-58220552 | CCCAGGCCTGACGTGGGTCCCCCAGGGCGGCGTCGCCAAG GCTTAGACGCTTTCGTGCAGGAGGGACGACGACTCCCCTC ACGCCTTCGTGGCCCCAACTCGGCGCTCTGCTATCTCTGA TCCGGTGAACACACCTCAGA | Hyper | 4 |
| 154 | RRBS | chr17:70112132-70112268 | TCCCCGGAGTCCGGAGCTCAGGCCAGTGGCAGTCGACCCA GCCCCCGAGACTCCCTCACGCCGCTCCAAAACCAAAACGG AGCCCAACACGAAGCTGGGTGAAGCCGTAGCTTGCAGGAG CCAGGGAGATGCGCTCT | Hyper | 10 |
| 164 | RRBS | chr4:174427917-174428054 | GACTCGCGAGGTTTTCCAGCAGCTCATTCCGGGACGGCGG TGTCTAGTCCAGTCCAGGGTAACTGGGCTCTCTGAGAGTC CGACCTCCATCGGTCTGGGAGCGAGTGGTTCGAGTTCAGA TGCTGGGAACCGTCGCTT | Hyper | 12 |

TABLE 1A-continued

Identity, source, genome-coordinates and genomic sequences of the hyper-methylated DMRs of the present invention

| DMR # | Data basis | Amplicon coordinates (hg19) | Amplicon genomic sequence (relevant CpGs are underlined) | Class | SEQ ID NO. |
|---|---|---|---|---|---|
| 178 | RRBS | chr19:13215409-13215550 | GGCAGGAGCGCCCCACTATGCGCAAGCCCGTGGCCTGGAG AGCGCTGAAGGTGGGAGGGGAAGAGGGGcAGAAcccccG CGGGAGCGAGCGCACAGCTGCCGCCCCGTGGCCGCTTCGG GAATCGCTGGCTCCGGCTCTGG | Hyper | 14 |
| 180 | RRBS | chr3:192125846-192125980 | CTGCAGAAGCGCACTTTGCTGAACACCCCGAGGACGTGCC TCTCGCACAGGGAGCGCCCGTCTTTGCTGGGGCTGGAGCG GCGCTTGGAGGCCGACACTCGGTCGCTGTTGGACTCCCTC GCCTGCCGCTTCTGC | Hyper | 15 |
| 190 | RRBS | chr9:79629064-79629172 | GTCAGACGAGAGCCTGGGGTCAATGTCGAGGTGGAGCGAC GCTGGCACGGCAACCCTGAGCCTGCGCGGCCCGGCGCTAT CCCCTGGCTCTCCGCTGCTGGCTGGACCC | Hyper | 18 |
| 192 | RRBS | chr12:75601294-75601437 | CGGTAGGTCATCCAGCAGCAGGGCTCCACGTCGGTCTCGT CGATGCCCCAGAAGGCCAGCTCCTCCTCGAAGAGCGGCCC GCACACGTCTGCGGGGCAGTGCAGCTTGCCGGTGCGGTAG TAATTGAGCACATAGGCGAAGACG | Hyper | 19 |
| 200 | RRBS | chr9: 138999180-138999294 | AATCAGCCCAGCAACCGGCGACCCCAAGCGCGGCGACCGC AAAGGGAGTGCTTGCCCATCCGCGTTTGAAAGCAGACTTT TTCTCGGCAGGAACACAGGACTCACCTGCCAGTGG | Hyper | 20 |
| 202 | RRBS | chr1:2987508-2987655 | GTGCGAACAAGACCGGGCGTTTCGCCGCCGACGCGAAGGG GCTGTCTGTGCGCGGCGTTGCGGGCCCTCCGCGCGTGGGG TGTGCGTGTGCGTGTTCGGGTTCGGTTCTGTGTGTGCACC GCGGGCCTGCTCAGAGTCGGGACCACCG | Hyper | 21 |
| 210 | 450K | chr12:123713499-123713590 | TGCATACAGATTACTGTAGGACCATTTCCTGTGCCTTTTA AAATTTCCTTTTCTCGTTTTATTTCACATATTCCTTTGTT TTTTACAACTCC | Hyper | 23 |
| 213 | 450K | chr2:106776938-106777040 | CCGCTCGGGAATGGGAATATAGCTACATATGGGAAAACGC GGTGCAGGGAGAAAACCAATTCAGTGAGGAGCGGAGGCGC AGGACTGTGGAGTGTGCATCCGG | Hyper | 24 |
| 214 | 450K | chr3:141516260-141516353 | CTGCTTAAAGGCGCAGAGGAGCAGCTGGGAACGAGAACAA AGCGGCCAGGCCCCCCTCGGAGGAAGGAAGGAGAGAGCCC CAGGAAACAGCTGA | Hyper | 25 |
| 219 | 450K | chr16:30484157-30484257 | GGATGAAGGATTCCTGCATCACTGTGATGGCCATGGCGCT GCTGTCTGGGTTCTTTTTCTTCGGTAGGCAAGGGAGGAGG CAGGGGAAGGGACATGTGTCT | Hyper | 26 |
| 222 | 450K | chr3:111809437-111809506 | TAGGCTACAGGAAGAGGCATTTCCTATAGATGACGGCTGT AAAATTTTAAGCTGAGTTCCTCCAGGAAGT | Hyper | 27 |
| 223 | 450K | chr10:120489250-120489333 | AAGAGAGAGTGGTTGATAATCAGTAGAGAGAGGTTTCTAA CTCACGGAAGTGTTTGCAATACAACCTCTTTGTACATCAG CTGT | Hyper | 28 |
| 224 | 450K | chr11:1874037-1874133 | GGTCCCCCTCCCCGAGCCATGAAGAGCTGCCTGCGGCCAT CTTGGCCCTCGCACCCCGTCTCTGTCACCCCAGGCCCCTG TAACTTGCTTAACGCTT | Hyper | 29 |
| 225 | 450K | chr7:142422193-142422278 | GAAGCTTGACACTCCTGGCCCCAAACACTGCCTGGCTACA ACACGATATCCAGGGACAGATACCTTCCATGTACAGCAAG CTGTGG | Hyper | 30 |

The genomic sequence and genome coordinates (hg19) of the other class of the regions of the genome used in the present invention as a source of epigenetic markers, ie those where the absence of methylation at one or more CpGs therein, (or associated therewith, such as within about 2,000 bp—such as within about 200 bp—5' or 3' thereof), and represent the hypo-methylated cancer-specific DMRs of the present invention, are set out in TABLE 1B. Any of such CpGs (including those of an allelic variant and/or complementary sequence of the respective said nucleotide sequence/s) is one considered "associated with" the respective hypo-methylated cancer-specific DMR of the present invention.

TABLE 1B

Identity, source, genome-coordinates and genomic sequences of the hypo-methylated DMRs of the present invention

| DMR # | Data basis | Amplicon coordinates (hg19) | Amplicon genomic sequence (relevant CpGs are underlined) | Class | SEQ ID NO. |
|---|---|---|---|---|---|
| 123 | RRBS | chr16:1271152-1271271 | GCGAAGCAGGAGTAGCTGCCGGGCCCCACGAGCCTCCGTCCGTTCTGGTTCGGGTTTCTCCGAGTTTTGCTACCAGCCGAGGCTGTGCGGGCAACTGGGTCAGCCTCCCGTCAGGAGAGA | Hypo | 5 |
| 129 | RRBS | chr11:69054638-69054757 | AACTCTGCTGAGTGAGCTCACAAACAGGGCATAACCGAGACGCGGGAATGCCTGGGTCGCCGCGCAGTCACCGGGCAGGGCCGCCCTCCCCTGTGGGTCAGCAAAAACGGTGTCAAGTGA | Hypo | 6 |
| 137 | RRBS | chr12:132896275-132896404 | ACTCCGCCACACACACAGCTGTACCCGGCACAACACGCGGCCACAGGTCACCTCAGGTCGCCTCGGGTGCTCCTCCCGCAGCCCCACGTAGACAGAAGACATTCCTCGGGCCTGGGTGCCCAGCCTCCCG | Hypo | 7 |
| 148 | RRBS | chr2:72359599-72359718 | GAGGTAATGGAAGCGGCCATCCTTGTCCTCGCTCCGCGCCTGGCTGAAGCGATCGGGGTCGAACACGTTCACGTCTTTGAACACGGGCGCTGTGTCATGGGTGTCCCGGATGCTATACAT | Hypo | 8 |
| 150 | RRBS | chr7:156735029-156735165 | GCGGGCACCTGTAGTCCCAGCTACTCGGGAGGCTGAGGCGGGAGAATGGCGTGAACCCGGGAGGCGGAGCTTGCAGCGAGCCGAGATCGCGCCACCGCACTCCAGCCTGGGCGACAGAGCGAGACTCCGTCTAAAAA | Hypo | 9 |
| 158 | RRBS | chr16:74441696-74441831 | GACTCTGTCTCAAAAAAGAAAAAAATAGGGCCGGGCGCGGTGGCTCACGCCTGTCATCCCAGCACTTTGGGAGGCCGAGGCGGGTGGATCACGAGGTCGGGAGATCGATACCATCCTGGGTAACACGGTGAAACCC | Hypo | 11 |
| 176 | RRBS | chr6:119107203-119107340 | TAACCCATTTCTTTATTAAATTGCATGAAGAAGGCCGGGCGCGGTGGCTCACGCCTGTAATCCCAGCACTTTGGGAGGCCGAGGCGGGCGGATCACGAGGTCAGGAGATCGAGACCACGGTGAAACCCCGTCTCTACT | Hypo | 13 |
| 186 | RRBS | chr22:21483239-21483384 | CGTGTTAGCCAGGATGGTCTCGACCTCCTGACCTCGTGATCAGCCCGCCTCGGCCTCCCAAAGTGCTGGGATTAAAGGCGTGAGCCACCGCGCCGGGCCGAGACTCTGTCTTAAAAAAAAAAGGCCTGGGCTGTGGCACTTTGGGA | Hypo | 16 |
| 188 | RRBS | chr19:18497131-18497271 | AGAGTTGCACTCCGAAGACTCCAGATTCCGAGAGTTGCGGAAACGCTACGAGGACCTGCTAACCAGGCTGCGGGCCAACCAGAGCTGGGAAGATTCGAACACCGACCTCGTCCCGGCCCCTGCAGTCCGGATACTCACGCC | Hypo | 17 |
| 208 | RRBS | chr8:55467518-55467638 | ATATTAATCTTGTCCGGGCACGGTGGCTCACGCCTGTAATCCCAGCACTTTGGGAGGCCGAGGCGGGCGGATCACGAGGTCAGGAGATCGAGACCATCCTGGCGAACATGGTGAAACCTCG | Hypo | 22 |
| 226 | 450K | chr1:3086452-3086542 | GGGGGGACTGTCGTTAATTCACTGCCTAATGACCGCGGCCCGCGCGCTCCGAGTAATCGGGTGATGTATGTGGACTGTGCACACCTCGTGG | Hypo | 31 |

In particular embodiments, the present invention may not include (or not include the use of) one or more of the specific epigenetic markers (eg the presence of absence of methylation at one or more CpGs therein, that are within (or associated therewith, such as within about 2,000 bp—such as within about 200 bp—5' or 3' of) one or more of the DMRs set forth in TABLE 1A or TABLE 1B), for example, the present invention may not encompass one, two, three, four, five, six, seven, eight, nine, ten, or about 12, 15, 20, 25 28, 29, or 30 of the DMRs independently selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226. In certain of such embodiments, the present invention may not encompass DMR #144 (SEQ ID NO. 4).

As set out herein, the epigenetic marker (eg the presence/absence of methylation at a CpG) may be within the nucleotide sequence of a DMR of the present invention, or may be present within about 2,000 bp (such as within about 200 bp) 5' or 3' of such DMR sequence; ie is upstream or downstream of the DMR sequence disclosed herein. This is because (CpG) "islands" are present throughout the genome and the cancer-specific pattern of methylation/un-methylation described herein may equally be detectable elsewhere in such "island" such at one or more CpGs located within about 2,000 bp (eg about 200 bp) 5' or 3' of the DMR sequence disclosed herein. Following the disclosure herein, the person of ordinary skill will readily recognise that inspection of the human genome sequence can identify other CpGs potentially useful epigenomic markers within any of such "islands" such as around or associated with any of the DMRs of the present invention, and hence such other epigenomic markers (eg other CpGs within about 2,000 bp—such as within about 200 bp—5' or 3' of such DMR sequence) are specifically envisioned as being within the scope of the present invention. In certain embodiments, one or more of said CpGs is located within about 1,750, 1,500, 1,250, 1,000, 750, 500, 250, 200, 150, 125, 100, 75, 60, 50, 40, 30, 25, 20, 15, 10 or 5 base pairs 5' of a DMR described herein; or within about 1,750, 1,500, 1,250, 1,000, 750, 500, 250, 200, 150, 125, 100, 75, 60, 50, 40, 30, 25, 20, 15, 10 or 5 base pairs 3' of a DMR described herein.

In further embodiment, the DMR of the present invention may be a variant of the respective sequence given herein. For example, by the deletion, addition or substitution of one or more (such as 2, 3, 4, 5 or more than 5) base pairs compared to the respective sequences. As will be understood by the person of ordinary skill, such variants can exist in any population of women, such as by being an allelic variant or a SNP.

As will also be appreciated by the person of ordinary skill, any of such sequences may be represented by (or analysed as) a complementary sequence to any of the sequences set out herein.

The term "human individual" (or "[said/the/such] individual") will be readily understood by the person of ordinary skill in the field of the present invention (eg, a clinical oncologist), and for the purposes herein such term is used interchangeably with "woman or man" (and "women and/or men", or the like, when used in the plural). Given the types and nature of the cancers analysed herein, a human individual in the context of the present invention is, typically, an adult human; that is one older than about 18, 20, 30, 40, 50, 60, 70 or 80 years (or even older). For example, and in particular, the human individual may be middle-aged (eg, about 45 to 65) or elderly (eg, older than about 65). More particularly, the human individual can, in certain embodiments, be older than about 50 years, for example for prostate cancer. However, certain of the cancers analysed herein may occur in younger human individuals, such as young adults (eg about 18 to 40-45). Indeed, whilst rare, such "adult" cancers may occur in humans under the age of 18, such as in adolescent, pubescent or yet younger humans. For example, the most common types of cancer diagnosed in the United States in 15 to 19 year-olds after lymphomas, brain and other central nervous system tumours, and leukaemia, are gonadal (testicular and ovarian) germ cell tumours, thyroid cancer, and melanoma (Siegel et al, 2017; A Cancer Journal for Clinicians 2017; 67:7). Accordingly, the term "human individual" should also be understood to apply to any human under the age of 18 having, suffering from or suspected to suffer from one of the ("adult") cancers analysed herein, and such younger human, despite being under 18, would still be considered a "woman" or a "man" (as applicable) for the purposes of the present invention. Furthermore, a human that is classified as "intersexual" (or "transsexual") would also be considered as a "human individual", and depending on the cancer such a human has, suffers from, or is suspected of suffering from, would still be considered—for the purposes of the present invention—as a "woman" or a "man". For example, an intersex (or transsexual) human having a gynaecological cancer (such as ovarian cancer) would, for the purposes of the present invention, be considered a "woman", and an intersex (or transsexual) human having prostate cancer would, for the purposes of the present invention, be considered a "man". In the event an intersex (or transsexual) human has, is suffering from or is suspect of suffering from a cancer such as lung, colon or pancreatic cancer, then such human can be considered as a "human individual", or either as a "woman" or a "man", as applicable to the degree of intersex, prevalence of sexual phenotypes, the professional judgment of the clinical oncologist or the personal preference of the specific human. An intersex human individual suffering from breast cancer, would, for the purposes of the present invention, typically be considered a "woman"; although cases of breast cancer in males are known.

As used herein, "determining" may be understood in the broadest sense as any recognition, including detection, localisation, diagnosis, classifying, staging or quantification of a (eg ovarian, breast, lung, colon, pancreatic, uterine, cervical or prostate, or any other cancer analysed herein) cancer. Determining may be performed as set out herein. In the context of the present invention, determining is, preferably, performed in respect of the human individual (eg, woman or man, as applicable) in-vitro, for example as an in vitro method of diagnosis. That is, the biological sample comprising (eg cell-free) DNA is obtained from the human individual, and the method of determining (or, eg diagnosis) is conducted on such sample that is isolated and separated from said human individual. For example, the biological sample is processed in a laboratory and/or in plastic or glass receptacles to analyses that the (eg cell-free) DNA of said human individual by a method of the present invention.

As will be appreciated, a method that determines the response to therapy against a (eg ovarian, breast, lung, colon, pancreatic, uterine, cervical or prostate, or any other cancer analysed herein) cancer in a human individual (eg, a woman or man, as applicable) can be understood as a method of monitoring the increase (or reduction) of the cancer in a human individual previously diagnosed (eg by other methods or tests) with the cancer; in particular providing a method of monitoring—in an individual-specific manner—the success of (chemo)therapy administered to said human individual in reducing or otherwise treating the cancer, or other symptoms thereof.

It will be understood by the person of ordinary skill that "determining" the presence or absence of (or response to therapy against) a (eg ovarian, breast, lung, colon, pancreatic, uterine, cervical or prostate, or any other cancer analysed herein) cancer may not be, in every and all circumstance, 100% accurate. Such determination (or diagnoses) may be reported as a likelihood of the present or absence of the cancer, and/or interpreted in the context of the false-positive and/or false-negative rates of such a method or test. As is conventional in diagnostic tests, such rates can also be represented by the sensitivity and/or specificity of the test.

Accordingly, in particular embodiments of the present invention, the tests or methods hereof provide a test for the determination of ovarian cancer that has a sensitivity and/or specificity that is superior to that provided by a CA125 test, and/or has non-overlapping false-positives and/or false-negatives with a CA125 test. Also envisioned are embodiments of the present invention wherein a methods or test (for, eg ovarian, breast, lung, colon, pancreatic, uterine, cervical or prostate cancer, or any other cancer analysed herein) may be provided having: (i) a sensitivity (ie true-positive rate) of greater than about 30%, 40%, 50%, 55%, 60%, 65%, 70%, 75%, 80%, 85%, 88%, 90%, 92%, 94%, 95%, 96%, 97%, 98%, 99% or 99.5%, in particular greater than about 90%, 95% or 98%; and/or (ii) a specificity (ie, true-negative rate) of greater than about 30%, 40%, 50%, 55%, 60%, 65%, 70%, 75%, 80%, 85%, 88%, 90%, 92%, 94%, 95%, 96%, 97%, 98%, 99% or 99.5%, in particular greater than about 55%, 60%, 70% or 80%. For example, in one embodiment, a test or method of the present invention may have a specificity of greater than about 95% (such as about 98%) and a sensitivity of greater than about 60% (such as about 63%). In another embodiment, a test or method of the present invention may have a specificity of greater than about 85% (such as about 90%) and a sensitivity of greater than about 55% (such as about 58%). In yet another embodiment, a test or method of the present invention may have a specificity of greater than about 98% (such as greater than about 99.5%) and a sensitivity of greater than about 70% (such as greater than about 75%), for example if applied to a general population. As will be appreciated, such test parameters can depend on the population of human individuals (eg women and/or men, as applicable) being screened, and in particular the prevalence of the cancer (eg OC, or breast, lung, colon, pancreatic, uterine, cervical or prostate cancer, or any other cancer analysed herein) in such population. In this regard are presented two examples: (1) in a population which has a dramatically increased prevalence of OC (eg BRCA mutation carriers who have an OC lifetime risk of up to 60%), a lower specificity may be applicable as the rate of false positives will be substantially lower and a false-positive result would have substantial less impact in such women—who may eventually opt for risk reducing surgery anyway; and (2) in a general population setting, the prevalence of OC in those women actually tested using the present invention may be "artificially increased" by conducting a pre-screen for OC (eg, by using ROCA or other diagnostic tests/methods as described elsewhere herein) and then conducting a test of the present invention only in the sub-population of women who have an intermediate or elevated OC risk as determined by such pre-screen (which may be about 8% of general female population), and in this sub-population of women, a lower specificity may also be applicable.

The term "ovarian cancer" is art recognised, and encompasses any cancer that forms in tissue associated with the ovary; in particular those that result in abnormal cells that have the ability to invade or spread to other parts of the body. The most common type of ovarian cancer, comprising more than 95% of cases, is ovarian carcinoma. There are five main subtypes of ovarian carcinoma, of which high-grade serous (HGS) is most common. The other main subtypes include: low-grade serous, endometrioid, clear cell and mucinous carcinomas. These tumours are believed to start in the cells covering the ovaries, though some may form at the Fallopian tubes. Other types of ovarian cancer include germ cell tumours and sex cord stromal tumours. For the purpose of the present invention, the term "ovarian cancer" can also include peritoneal cancer and Fallopian tube cancer, in each case in women, as both are high-grade serous, have analogous biology to ovarian cancer and have the same treatment modalities as ovarian cancer.

The various aspects and embodiments of the present invention, may apply to any one (or more) of such specific types/subtypes of ovarian cancer, and in particular the discrimination of one types/subtypes of ovarian cancer from others or from other disorders (such as gynaecological disorders). For example, in certain embodiments, the present invention is used to discriminate ovarian cancer from benign pelvic mass, and/or high-grade serious (HGS) ovarian cancer from less severe or aggressive forms of ovarian cancer, and/or or chemotherapy-resistant from chemotherapy-responsive ovarian cancer.

In other aspects or embodiments of the present invention, the test may determine (or diagnose) the presence or absence of a cancer in a woman other than ovarian cancer (instead of, or as well as, determining the presence or absence of, or the response to therapy against, ovarian cancer). Such other cancer may be another gynaecological cancer (such as uterine cancer, vaginal cancer, cervical cancer, and vulvar cancer) or a cancer of the colon or breast. Such aspects or embodiments are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in DMR #204 [SEQ ID No. 2], optionally where the present invention makes use of one or more further epigenetic markers within one or more other DMRs of the present invention (such as #141, #228 and/or #144 [SEQ ID NOs: 1, 3, and/or 4, respectively]; in particular #141, and #228, or #228 and #144).

In yet other aspects or embodiments of the present invention, the test may determine (or diagnose) the presence or absence of a cancer in a woman other than ovarian cancer (instead of, or as well as, determining the presence or absence of, or the response to therapy against, ovarian cancer). Such other cancer may be breast cancer, lung cancer (eg lung adenocarcinoma, lung squamous carcinoma), colon cancer, pancreatic cancer, uterine cancer or cervical cancer, or it may be bladder cancer, oesophageal cancer, head and neck cancer, kidney clear cell cancer, kidney papillary cell cancer, liver cancer, rectum cancer, sarcoma, skin cutaneous melanoma, stomach cancer or thyroid cancer.

In yet further aspects or embodiments of the present invention, the test may determine (or diagnosis) the presence or absence of a cancer in a man. Such other cancer may be lung cancer (eg lung adenocarcinoma, lung squamous carcinoma), colon cancer, pancreatic cancer or prostate cancer, or it may be bladder cancer, oesophageal cancer, head and neck cancer, kidney clear cell cancer, kidney papillary cell cancer, liver cancer, rectum cancer, sarcoma, skin cutaneous melanoma, stomach cancer or thyroid cancer.

Figure 14:
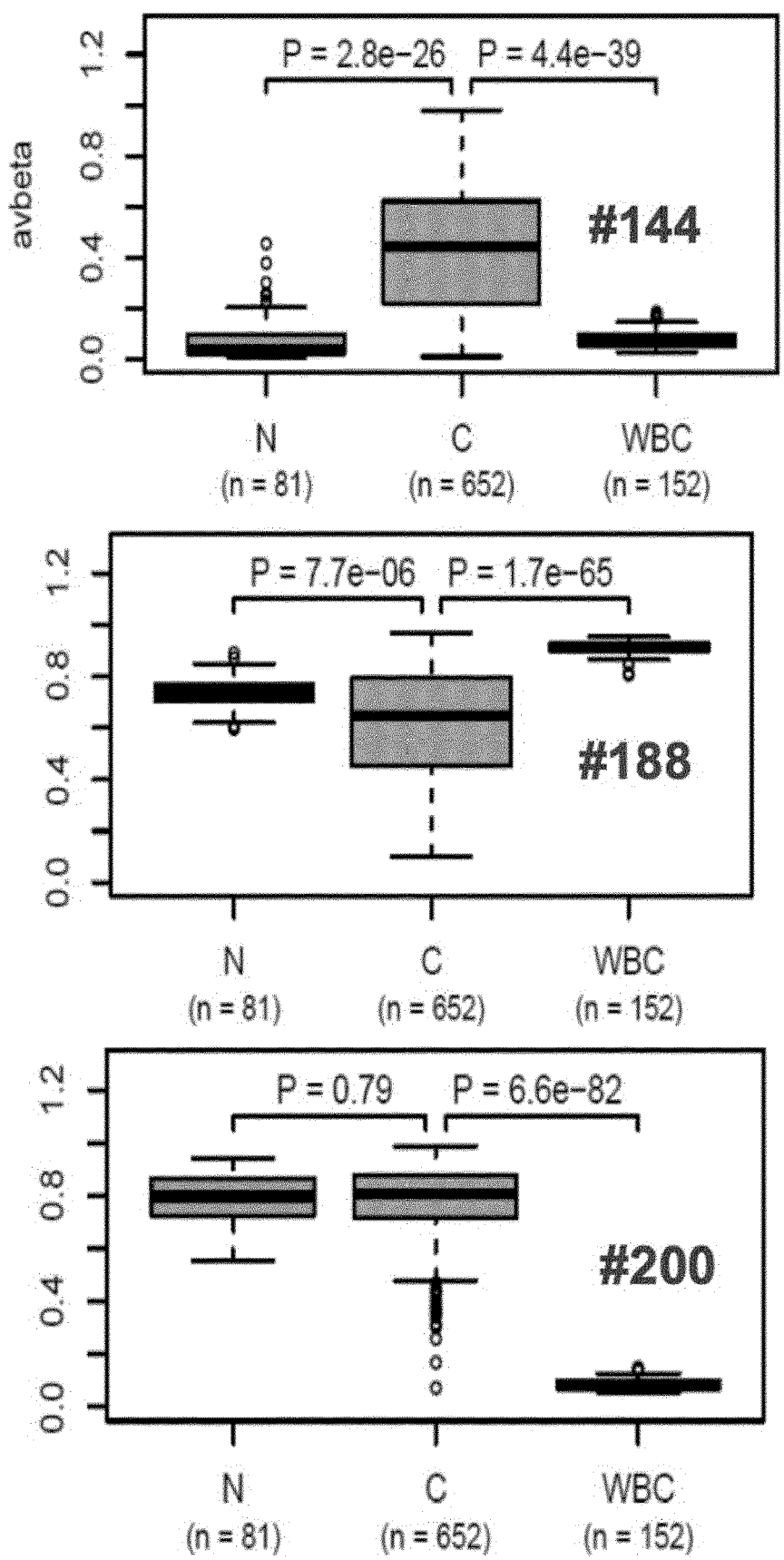
FIG. 14 depicts the magnitude and significance of the association between certain DMRs of the invention and breast cancer. A box-plot of the level of methylation (average beta value "avbeta") for each DMR in DNA isolated from samples of normal (N) tissue, cancerous (C) tissue and white blood cells (WBC) is shown, together with the P-value of a two-tailed Wilcoxon rank sum test.
Figure 14:
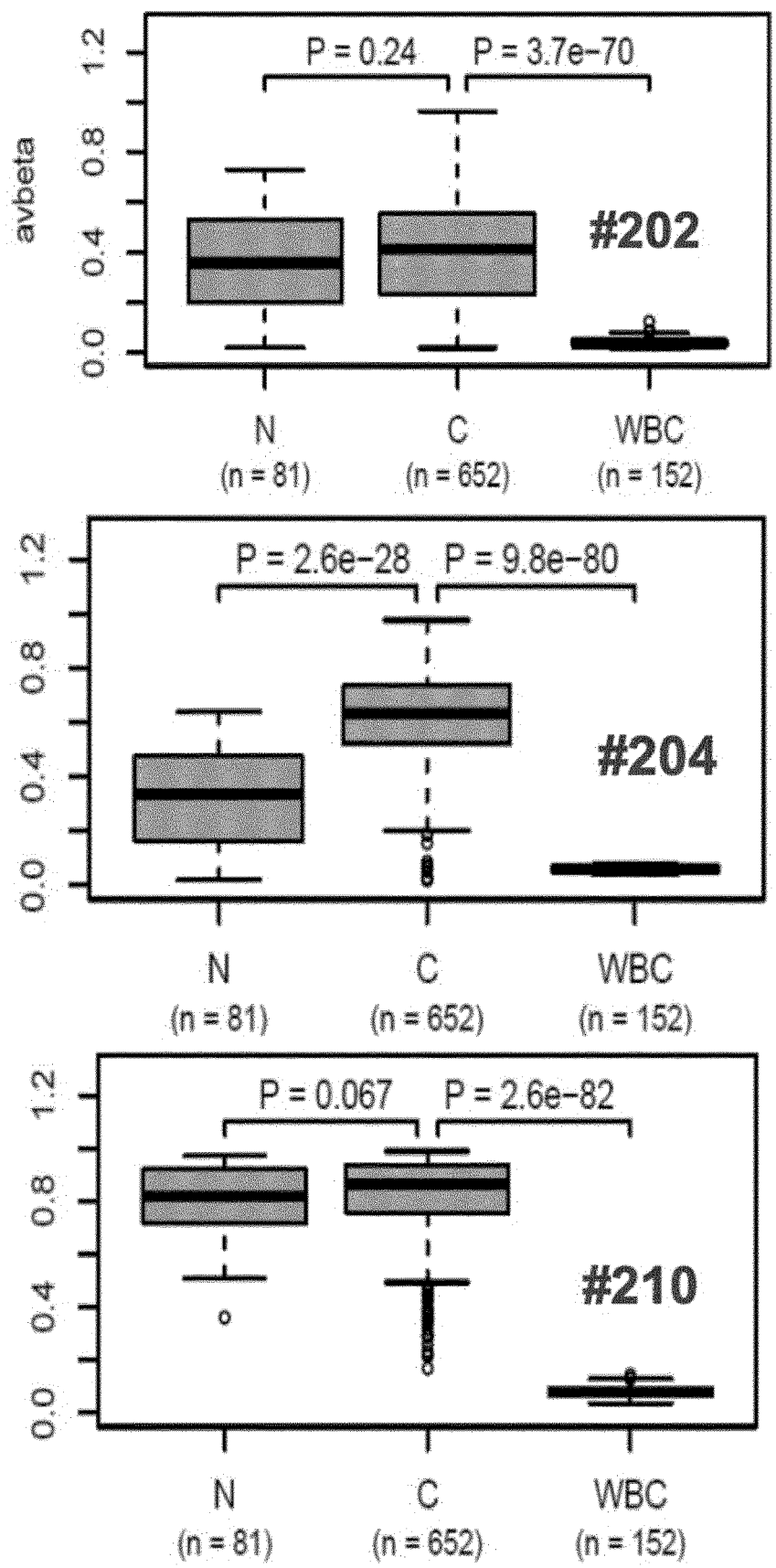
Figure 14:
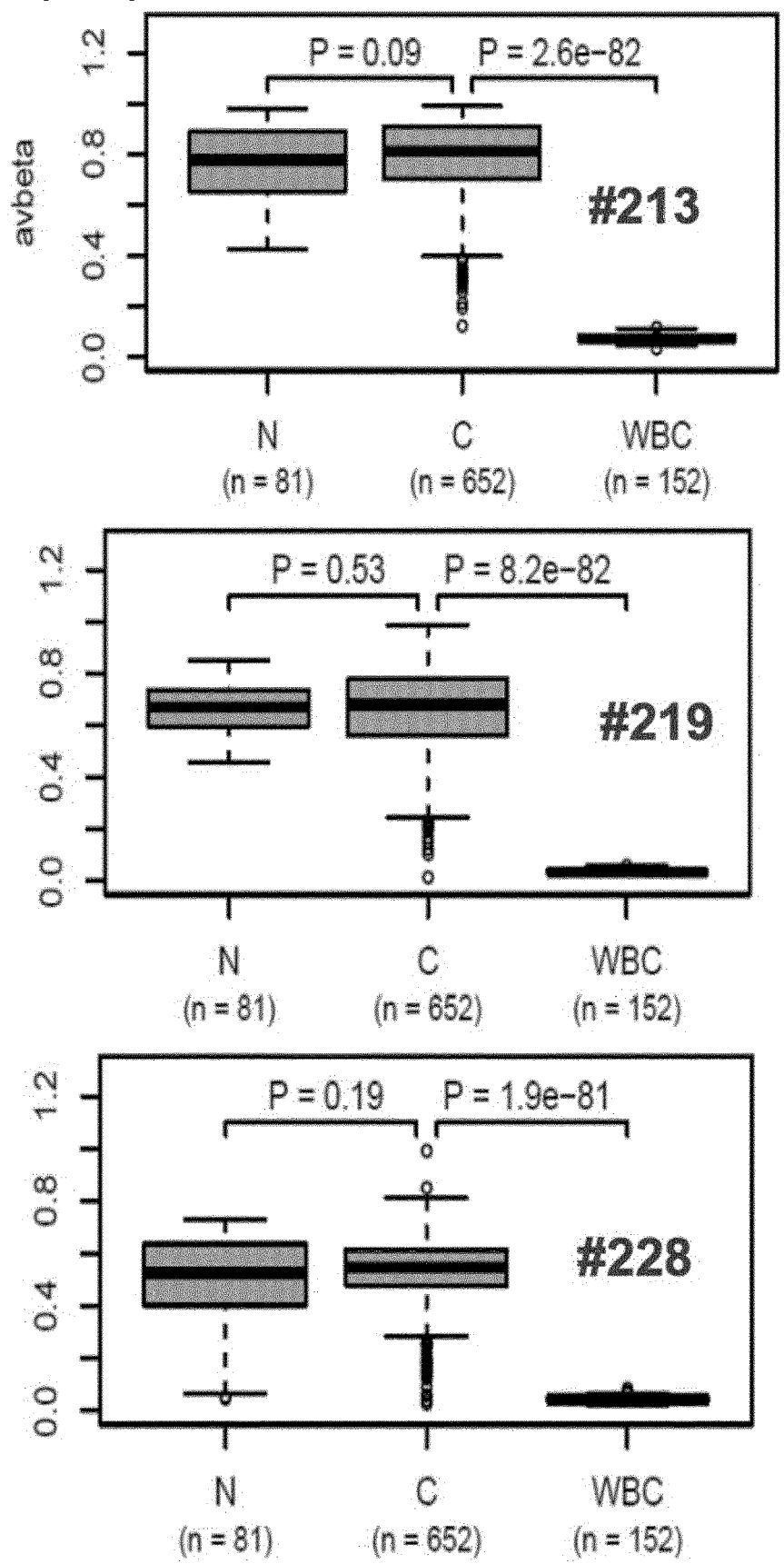

The term "breast cancer" is art recognised, and encompasses any cancer that forms in tissue associated with the breast; in particular those that result in abnormal cells that have the ability to invade or spread to other parts of the body. Aspects or embodiments of the present invention in respect of breast cancer and cell-free DNA are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #144, #188, #200, #202, #204, #210, #213, #219 and #228 (FIG. 14), in particular DMRs selected from the list consisting of: #200, #202, #210, #213, #219 and #228, and preferably a combination that includes at least two of these DMRs, such as a combination of two DMRs as set forth in Table X1. Aspects or embodiments of the present invention in respect of breast cancer and DNA of said human individual obtained from a tissue sample are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #144, #188 and #204, and preferably a combination that includes at least two of these DMRs, such as a combination of two DMRs as set forth in Table X2.

TABLE X1

Preferred pair-combinations of DMRs in respect of breast cancer and cell-free DNA

| #200 & #202 | #200 & #210 | #200 & #213 | #200 & #219 | #200 & #228 |
|---|---|---|---|---|
| | #202 & #210 | #202 & #213 | #202 & #219 | #202 & #228 |
| | | #210 & #213 | #210 & #219 | #210 & #228 |
| | | | #213 & #219 | #213 & #228 |
| | | | | #219 & #228 |

TABLE X2

Preferred pair-combinations of DMRs in respect of breast cancer and DNA from tissue samples

| | |
|---|---|
| #144 & #188 | #144 & #204 |
| | #188 & #204 |

TABLE X3

Preferred pair-combinations of DMRs in respect of lung adenocarcinoma and cell-free DNA

| | |
|---|---|
| #213 & #219 | #213 & #224 |
| | #219 & #224 |

TABLE X4

Preferred pair-combinations of DMRs in respect of lung adenocarcinoma and DNA from tissue samples

| | | | |
|---|---|---|---|
| #188 & #200 | #188 & #210 | #188 & #214 | #188 & #228 |
| | #200 & #210 | #200 & #214 | #200 & #228 |
| | | #210 & #214 | #210 & #228 |
| | | | #214 & #228 |

In one particular preferred embodiment of the invention, the cancer is breast cancer (and the human individual is a woman) and one of the DMRs is #228, and more preferably another DMR is selected from one or more of the other DMRs of the invention, such as one or more DMR selected from the list consisting of: #204, #144 and #141. In particular of such embodiments, the sample comprises cell-free DNA of said woman (eg, cell-free DNA isolated from a plasma or serum sample from such woman), and the determining step comprises determining, in at least one molecule of said cell-free DNA, the methylation status at one or more of the CpGs located associated with such DMR(s), and wherein, the presence in at least one of said cell-free DNA molecules of one or more of said methylated CpGs indicates the presence of, or a reduced response to therapy against, such cancer in said woman.

The term "lung cancer" is art recognised, and encompasses any cancer that forms in tissue associated with the lung; in particular those that result in abnormal cells that have the ability to invade or spread to other parts of the body, and includes lung adenocarcinoma and lung squamous cell carcinoma.

Figure 15:
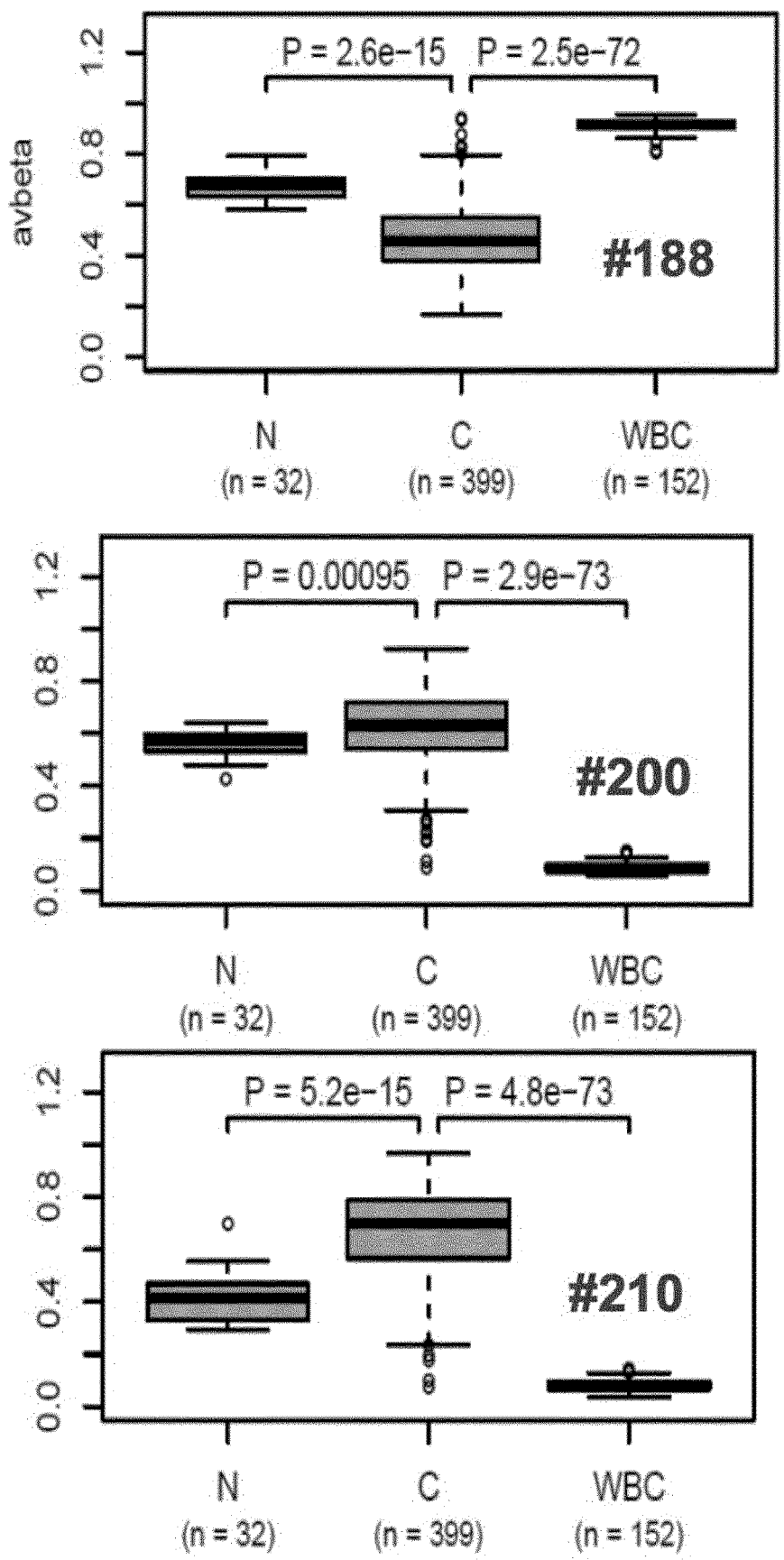
FIG. 15 depicts the magnitude and significance of the association between certain DMRs of the invention and lung adenocarcinoma. A box-plot of the level of methylation (average beta value "avbeta") for each DMR in DNA isolated from samples of normal (N) tissue, cancerous (C) tissue and white blood cells (WBC) is shown, together with the P-value of a two-tailed Wilcoxon rank sum test.
Figure 15:
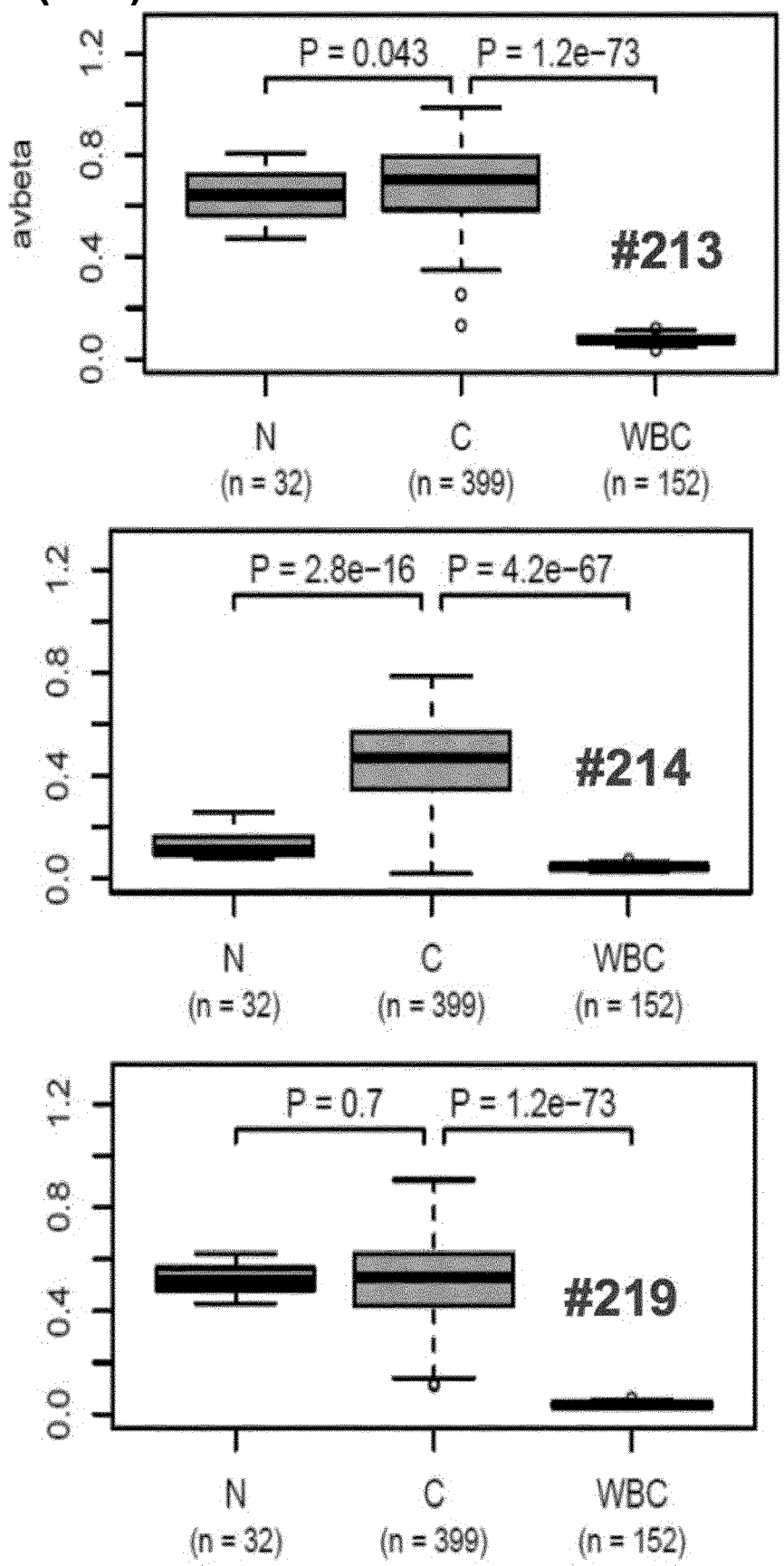
Figure 15:
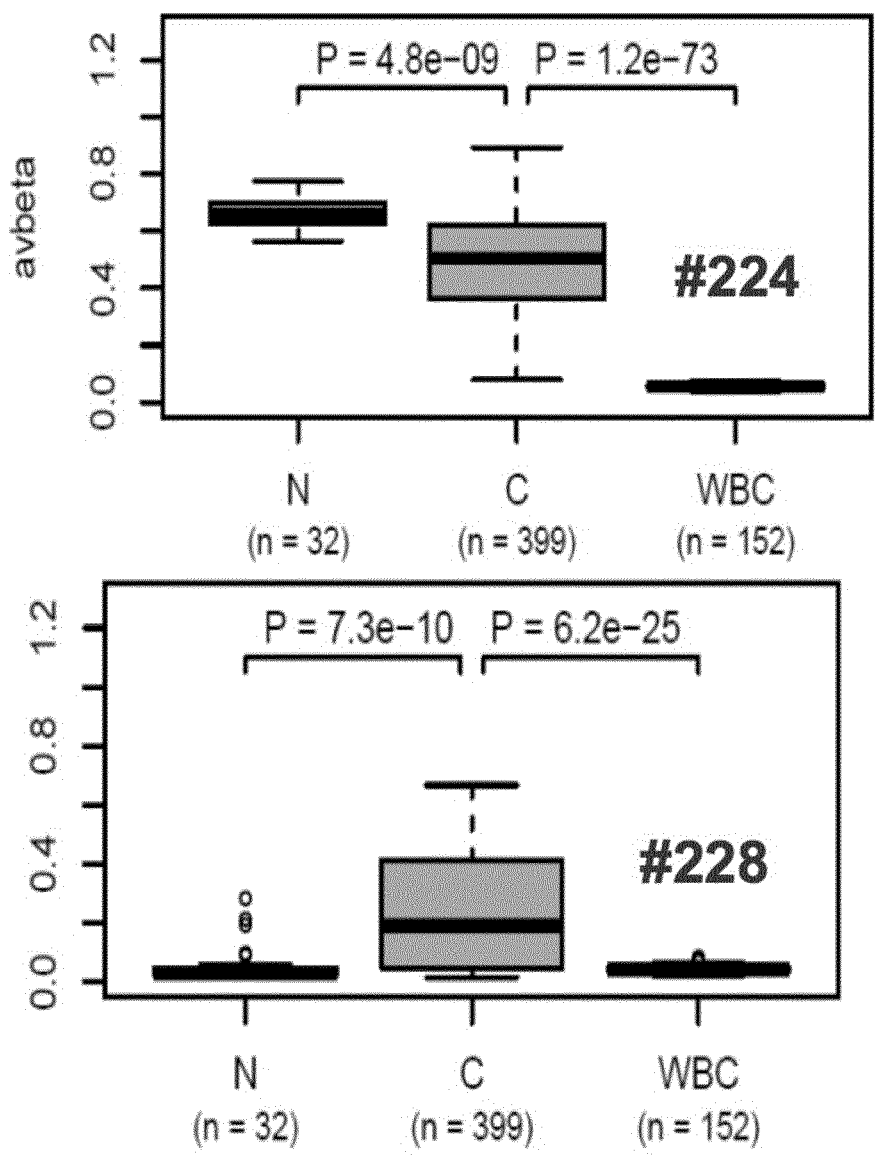

The term "lung adenocarcinoma" (pulmonary adenocarcinoma) is art recognised, and encompasses lung cancer that contains certain distinct malignant tissue architectural, cytological, or molecular features, including gland and/or duct formation and/or production of significant amounts of mucus; in particular those cancers that result in abnormal cells that have the ability to invade or spread to other parts of the body. Lung adenocarcinomas are highly heterogeneous tumours. Several major histological subtypes are currently recognized by the World Health Organisation: Non-invasive or minimally invasive adenocarcinoma, Adenocarcinoma in situ of the lung (Bronchioalveolar carcinoma), Minimally invasive adenocarcinoma of the lung, Invasive adenocarcinoma, Acinar predominant adenocarcinoma, Papillary predominant adenocarcinoma, Micropapillary predominant adenocarcinoma, Solid predominant adenocarcinoma and Invasive mucinous adenocarcinoma. Aspects or embodiments of the present invention in respect of lung adenocarcinoma and cell-free DNA are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #188, #200, #210, #213, #214, #219, #244 and #228 (FIG. 15), in particular DMRs selected from the list consisting of: #213, #219 and #224, and preferably a combination that includes at least two of these DMRs, such as a combination of two DMRs as set forth in Table X3. Aspects or embodiments of the present invention in respect of lung adenocarcinoma and DNA of said human individual obtained from a tissue sample are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #188, #200, #210, #214, and #228, and preferably a combination that includes at least two of these DMRs such a combination of two DMRs as set forth in Table X4.

In one particular preferred embodiment of the invention, the cancer is lung adenocarcinoma (and the human individual is a woman or a man) and one of the DMRs is #228, and more preferably another DMR is selected from one or more of the other DMRs of the invention, such as one or more DMR selected from the list consisting of: #204, #144 and #141. In particular of such embodiments, the sample comprises cell-free DNA of said human individual (eg, cell-free DNA isolated from a plasma or serum sample from such human individual), and the determining step comprises determining, in at least one molecule of said cell-free DNA, the methylation status at one or more of the CpGs located associated with such DMR(s), and wherein, the presence in at least one of said cell-free DNA molecules of one or more of said methylated CpGs indicates the presence of, or a reduced response to therapy against, such cancer in said human individual.

Figure 16:
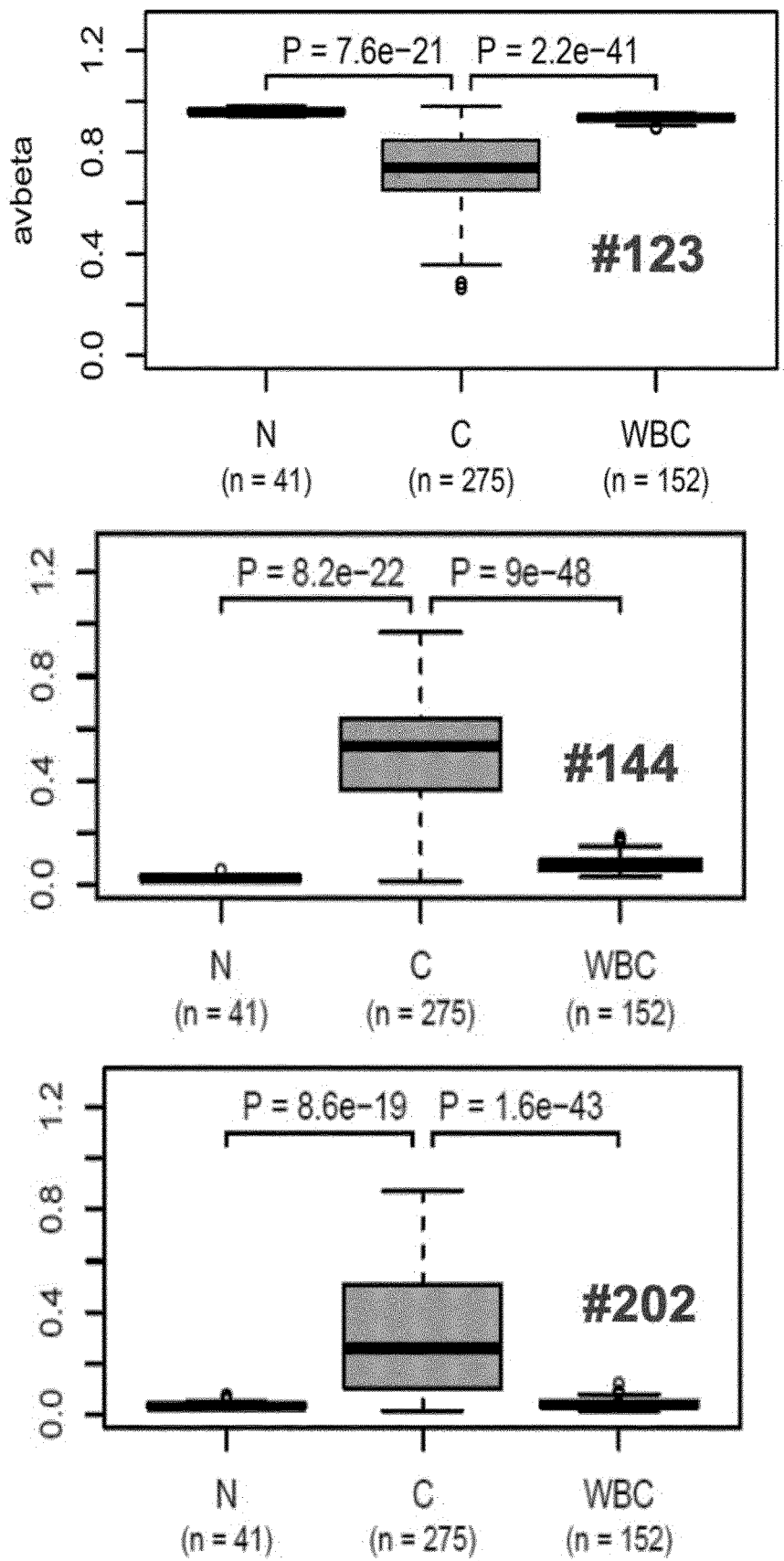
FIG. 16 depicts the magnitude and significance of the association between certain DMRs of the invention and lung squamous cell carcinoma. A box-plot of the level of methylation (average beta value "avbeta") for each DMR in DNA isolated from samples of normal (N) tissue, cancerous (C) tissue and white blood cells (WBC) is shown, together with the P-value of a two-tailed Wilcoxon rank sum test.
Figure 16:
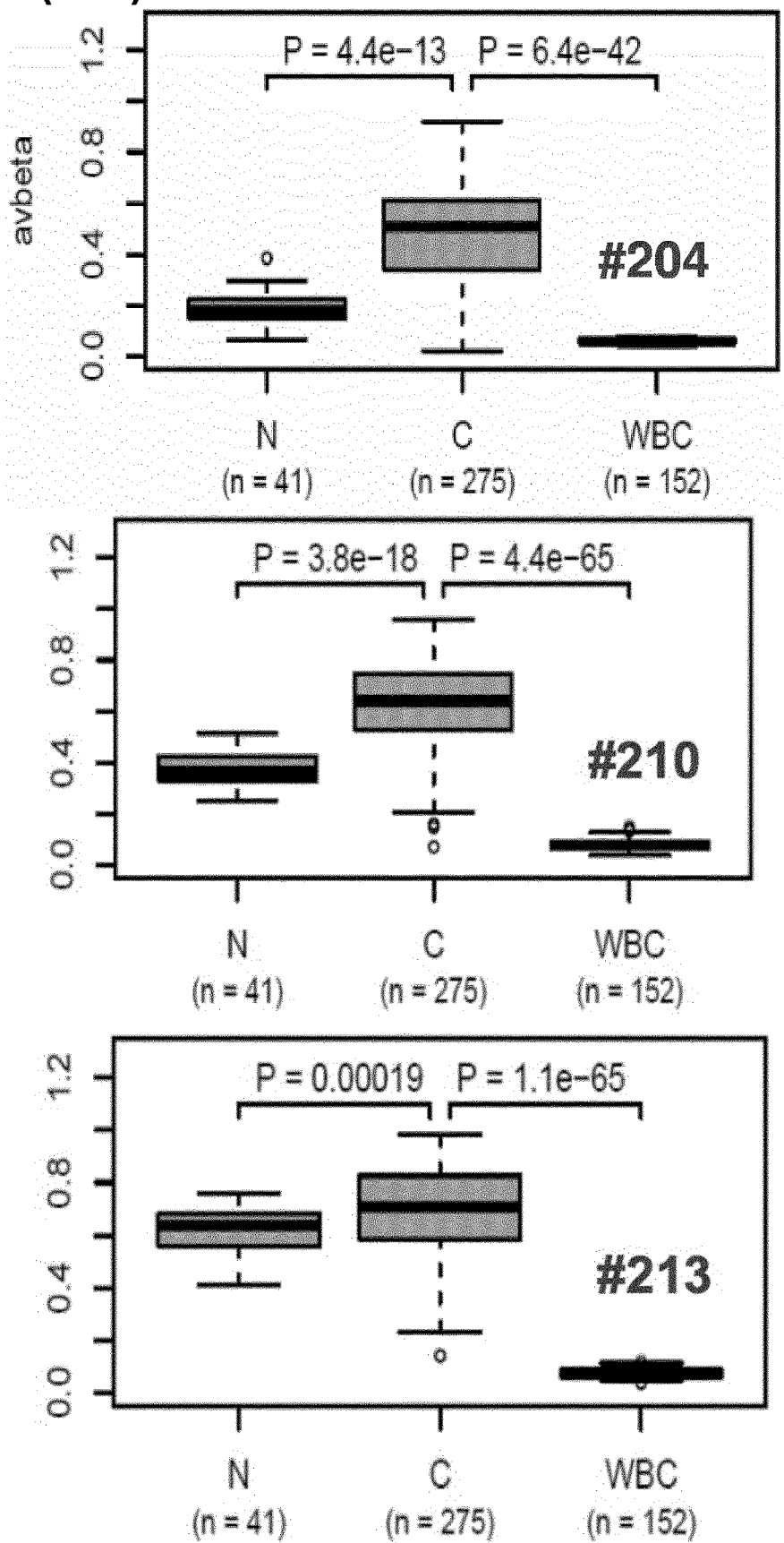
Figure 16:
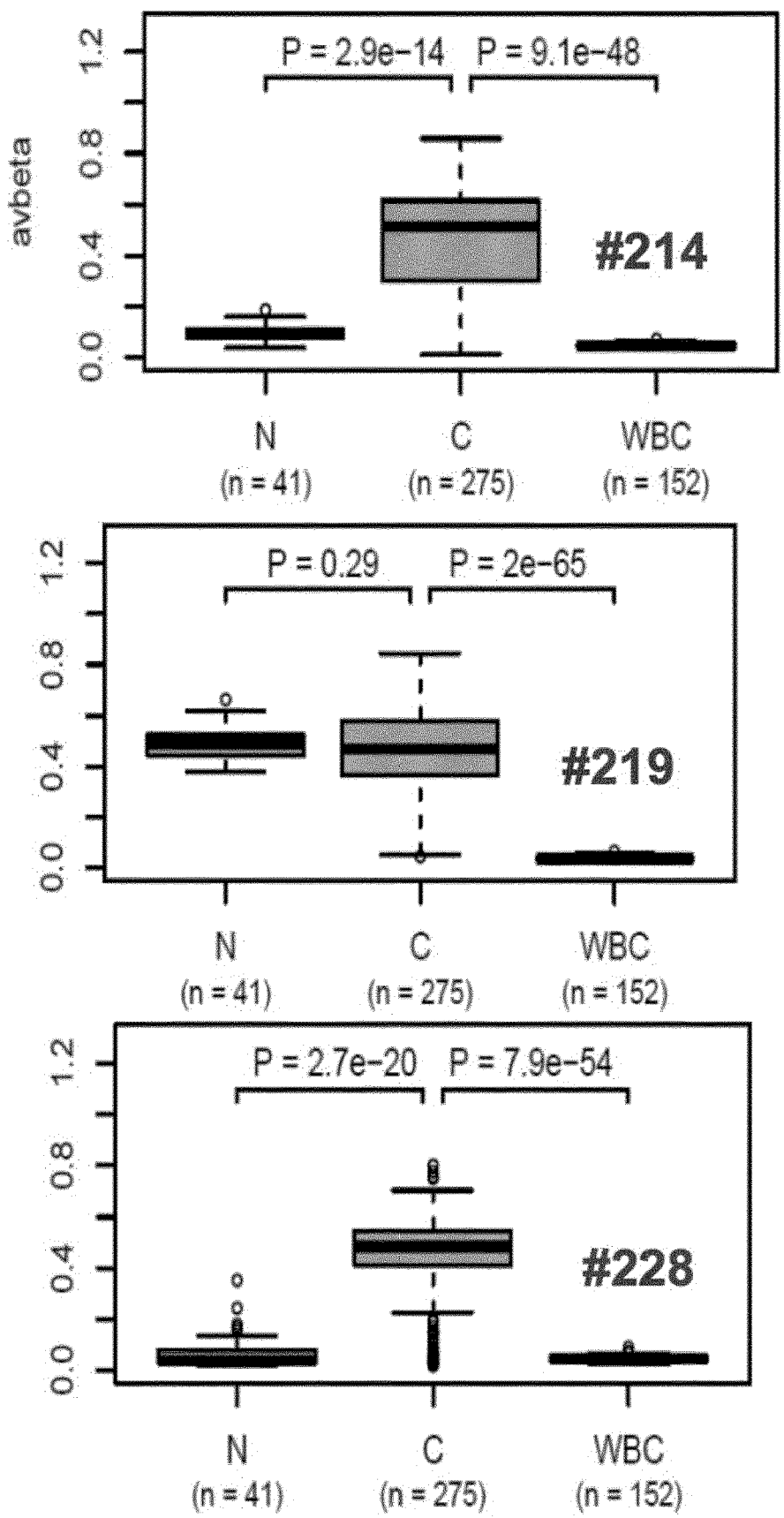

The term "lung squamous cell carcinoma" (squamous-cell carcinoma of the lung) is art recognised, and encompasses a type of non-small-cell lung carcinoma and is more common in men than in women. It is closely correlated with a history of tobacco smoking, more so than most other types of lung cancer. Currently, four variants (papillary, small-cell, clear-cell, and basaloid) of squamous-cell carcinoma of the lung are recognised. Aspects or embodiments of the present invention in respect of lung squamous cell carcinoma and cell-free DNA are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #123, #144, #202, #204, #210, #213, #214, #219 and #228 (FIG. 16), in particular DMRs selected from the list consisting of: #213, #219 and #228, and preferably a combination that includes at least the two DMRs #213 and #219 or #219 and #228. Aspects or embodiments of the present invention in respect of lung squamous cell carcinoma and DNA of said human individual obtained from a tissue sample are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #123, #144, #202, #204, #210, #213 and #214, and preferably a combination that includes at least two of these DMRs, such as a combination of two DMRs as set forth in Table X5.

TABLE X5

Preferred pair-combinations of DMRs in respect of lung
squamous cell carcinoma and DNA from tissue samples

| | | | | | | |
|---|---|---|---|---|---|---|
| #123 & #144 | #123 & #202 | #123 & #204 | #123 & #210 | #123 & #213 | #123 & #214 | |
| | #144 & #202 | #144 & #204 | #144 & #210 | #144 & #213 | #144 & #214 | |
| | | #202 & #204 | #202 & #210 | #202 & #213 | #202 & #214 | |
| | | | #204 & #210 | #204 & #213 | #204 & #214 | |
| | | | | #210 & #213 | #210 & #214 | |
| | | | | | #213 & #214 | |

In one particular preferred embodiment of the invention, the cancer is lung squamous cell carcinoma (and the human individual is a woman or a man) and one of the DMRs is #228, and more preferably another DMR is selected from one or more of the other DMRs of the invention, such as one or more DMRs selected from the list consisting of: #204, #144 and #141. In particular of such embodiments, the sample comprises cell-free DNA of said human individual (eg, cell-free DNA isolated from a plasma or serum sample from such human individual), and the determining step comprises determining, in at least one molecule of said cell-free DNA, the methylation status at one or more of the CpGs located associated with such DMR(s), and wherein, the presence in at least one of said cell-free DNA molecules of one or more of said methylated CpGs indicates the presence of, or a reduced response to therapy against, such cancer in said human individual.

Figure 17:
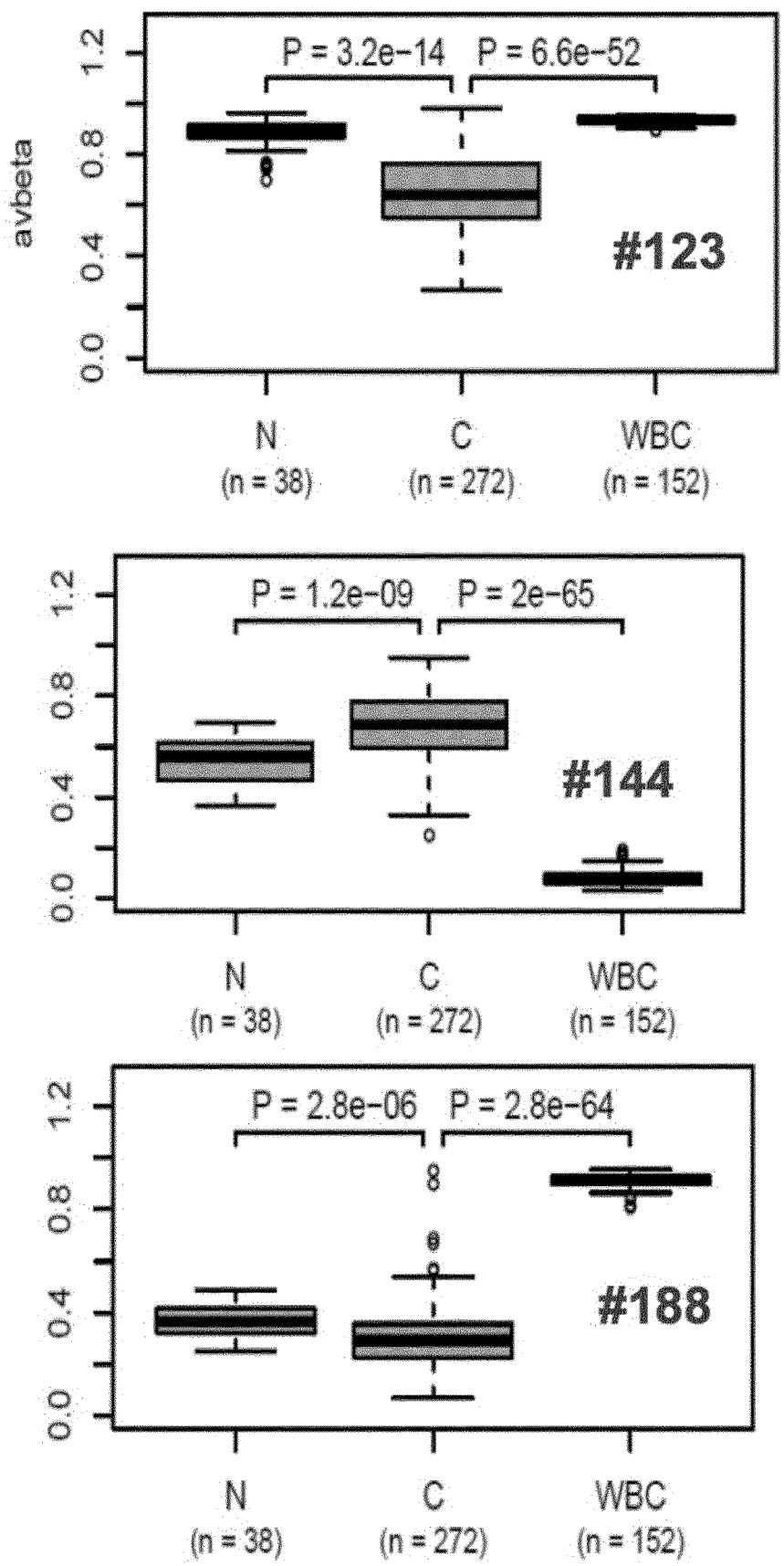
FIG. 17 depicts the magnitude and significance of the association between certain DMRs of the invention and colon cancer. A box-plot of the level of methylation (average beta value "avbeta") for each DMR in DNA isolated from samples of normal (N) tissue, cancerous (C) tissue and white blood cells (WBC) is shown, together with the P-value of a two-tailed Wilcoxon rank sum test.
Figure 17:
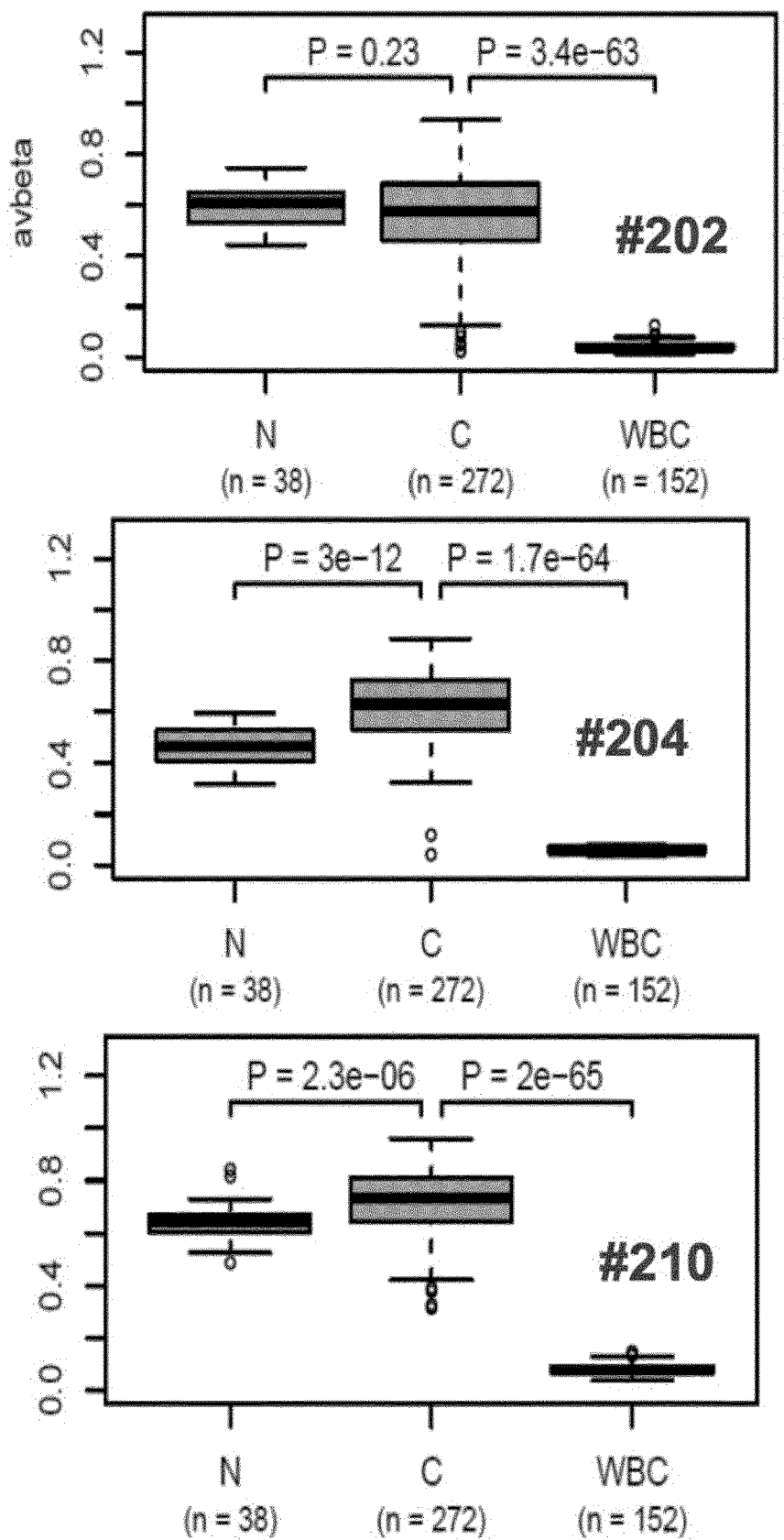
Figure 17:
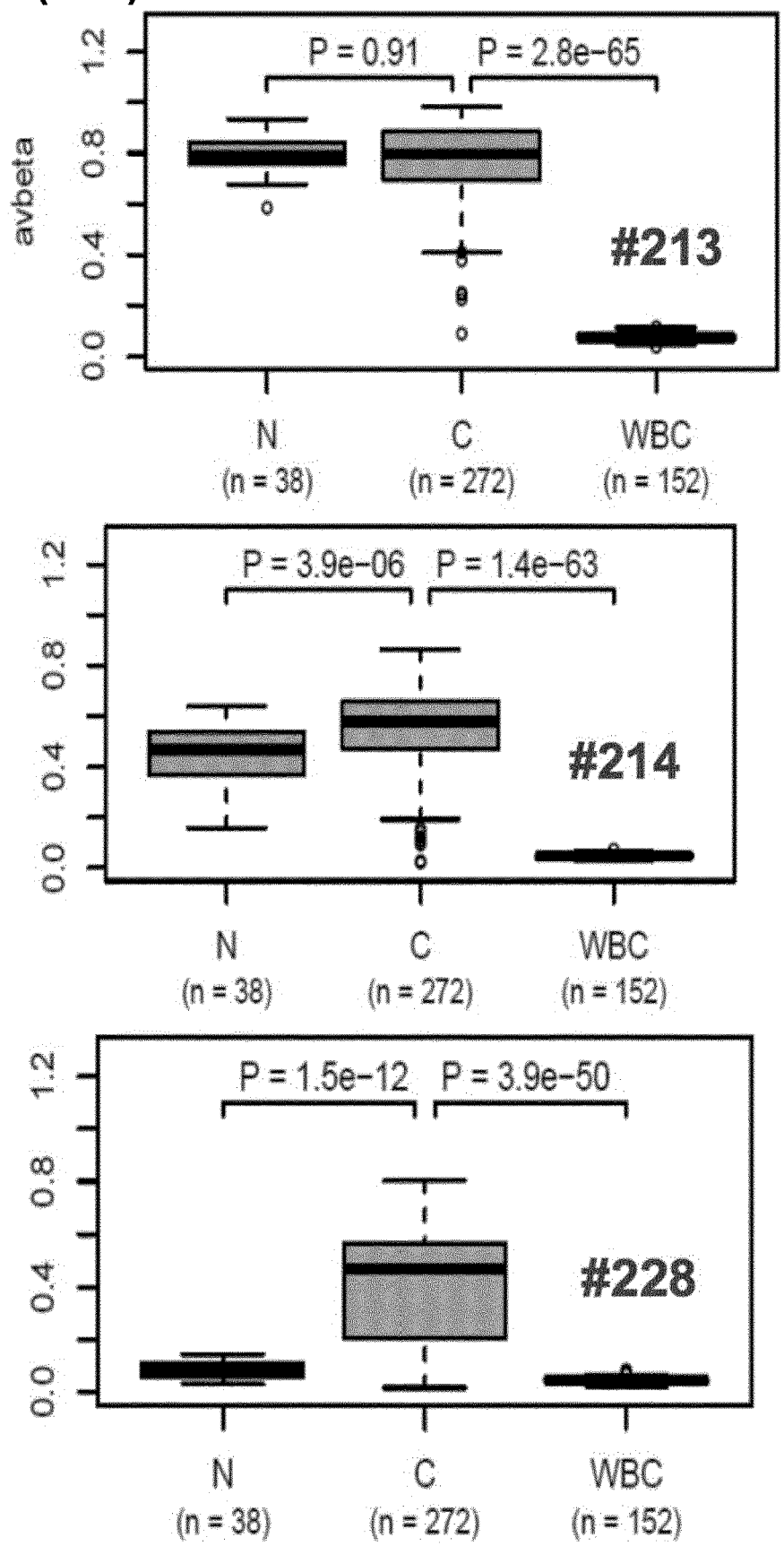
Figure 18:
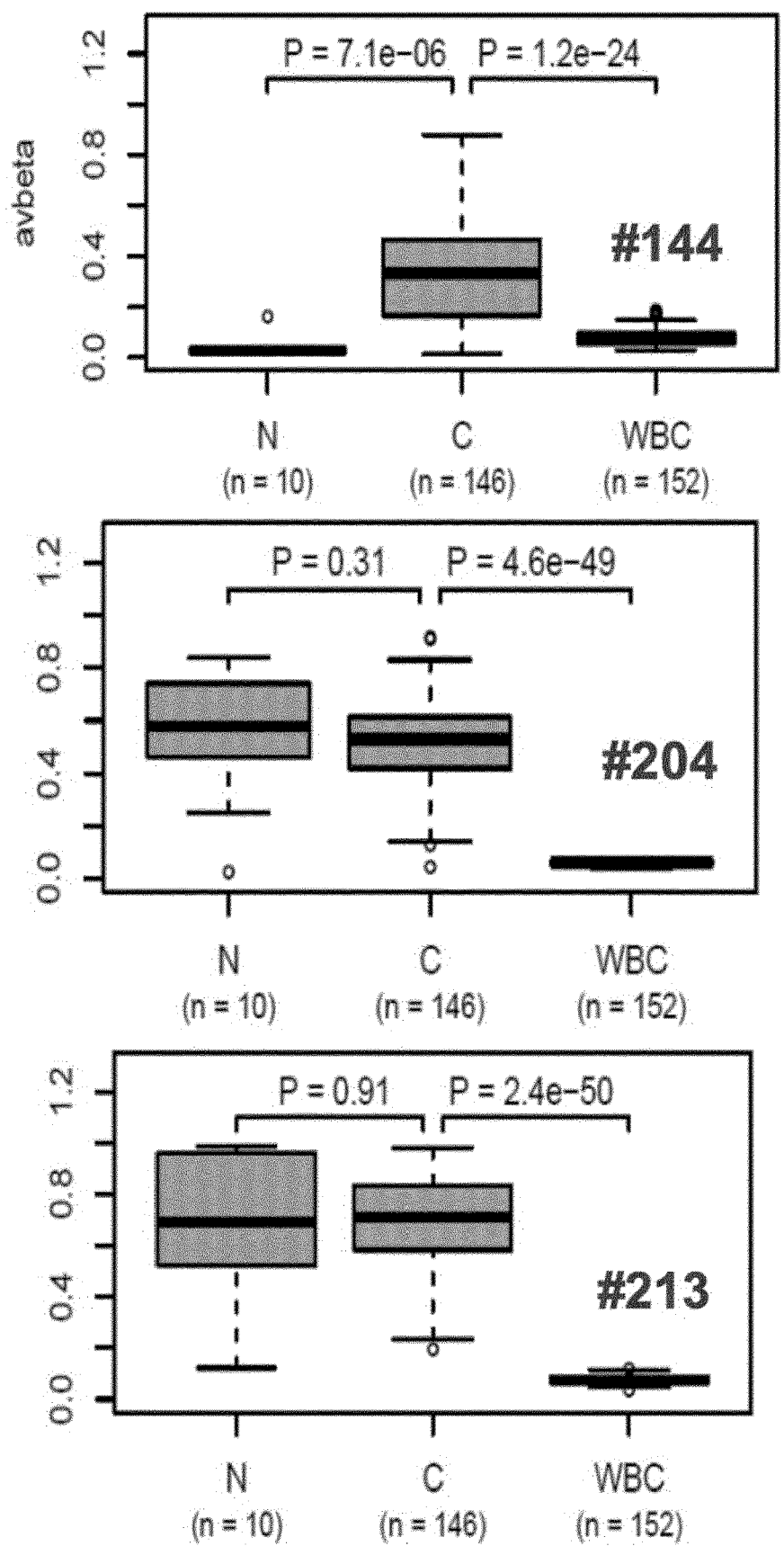
FIG. 18 depicts the magnitude and significance of the association between certain DMRs of the invention and pancreatic cancer. A box-plot of the level of methylation (average beta value "avbeta") for each DMR in DNA isolated from samples of normal (N) tissue, cancerous (C) tissue and white blood cells (WBC) is shown, together with the P-value of a two-tailed Wilcoxon rank sum test.
Figure 18:
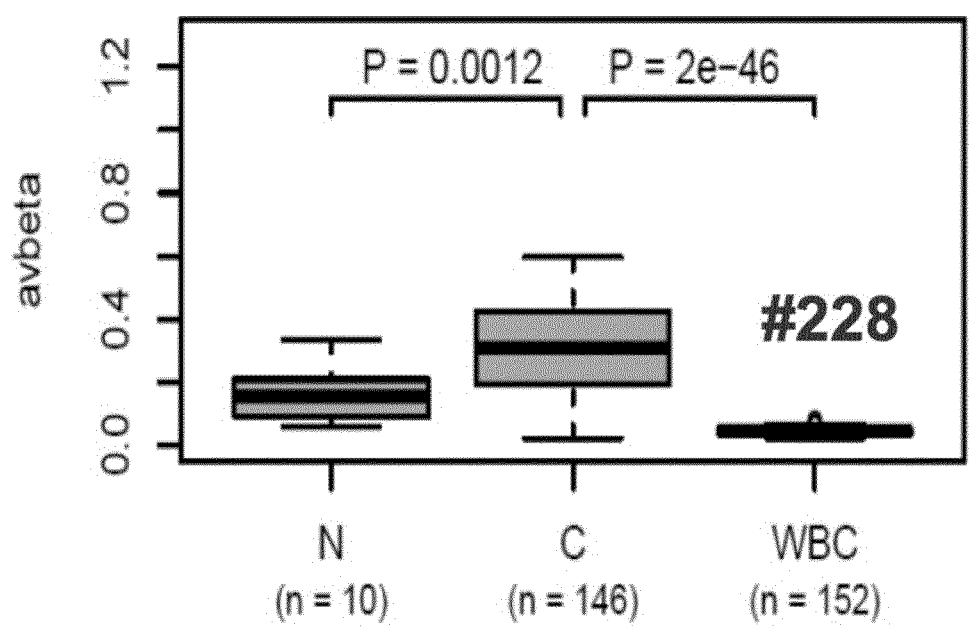
Figure 19:
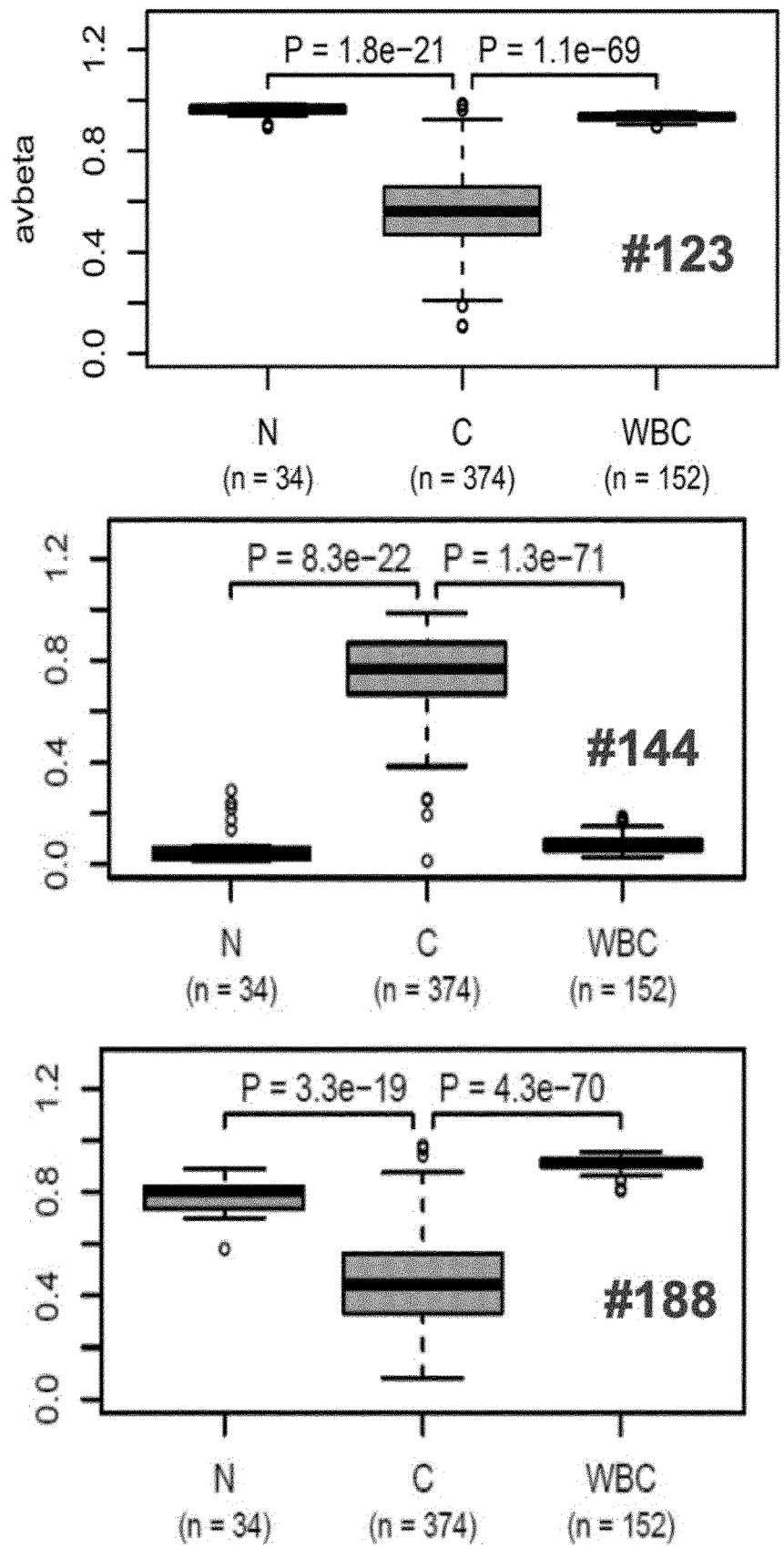
FIG. 19 depicts the magnitude and significance of the association between certain DMRs of the invention and uterine cancer. A box-plot of the level of methylation (average beta value "avbeta") for each DMR in DNA isolated from samples of normal (N) tissue, cancerous (C) tissue and white blood cells (WBC) is shown, together with the P-value of a two-tailed Wilcoxon rank sum test.
Figure 19:
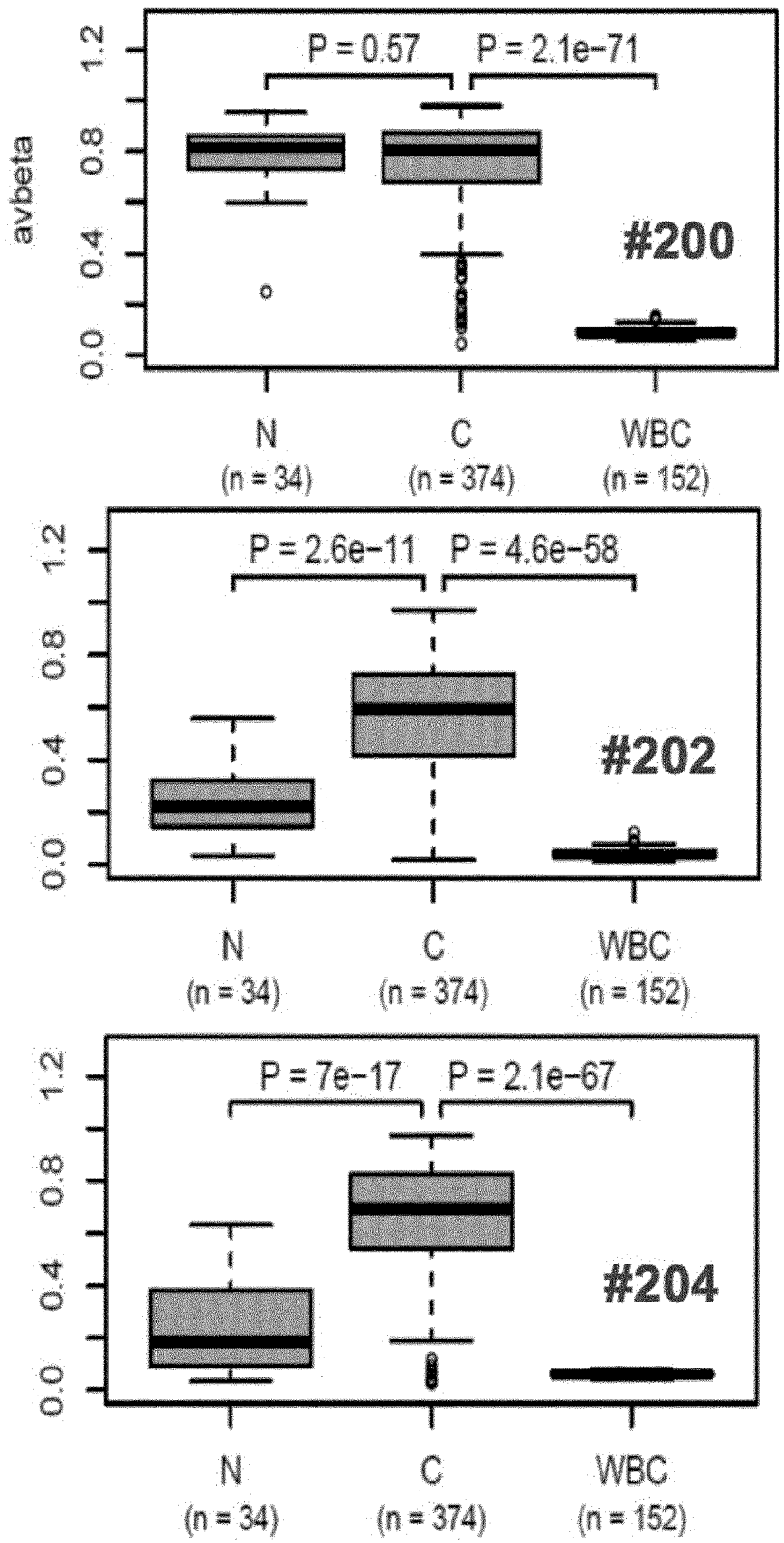
Figure 19:
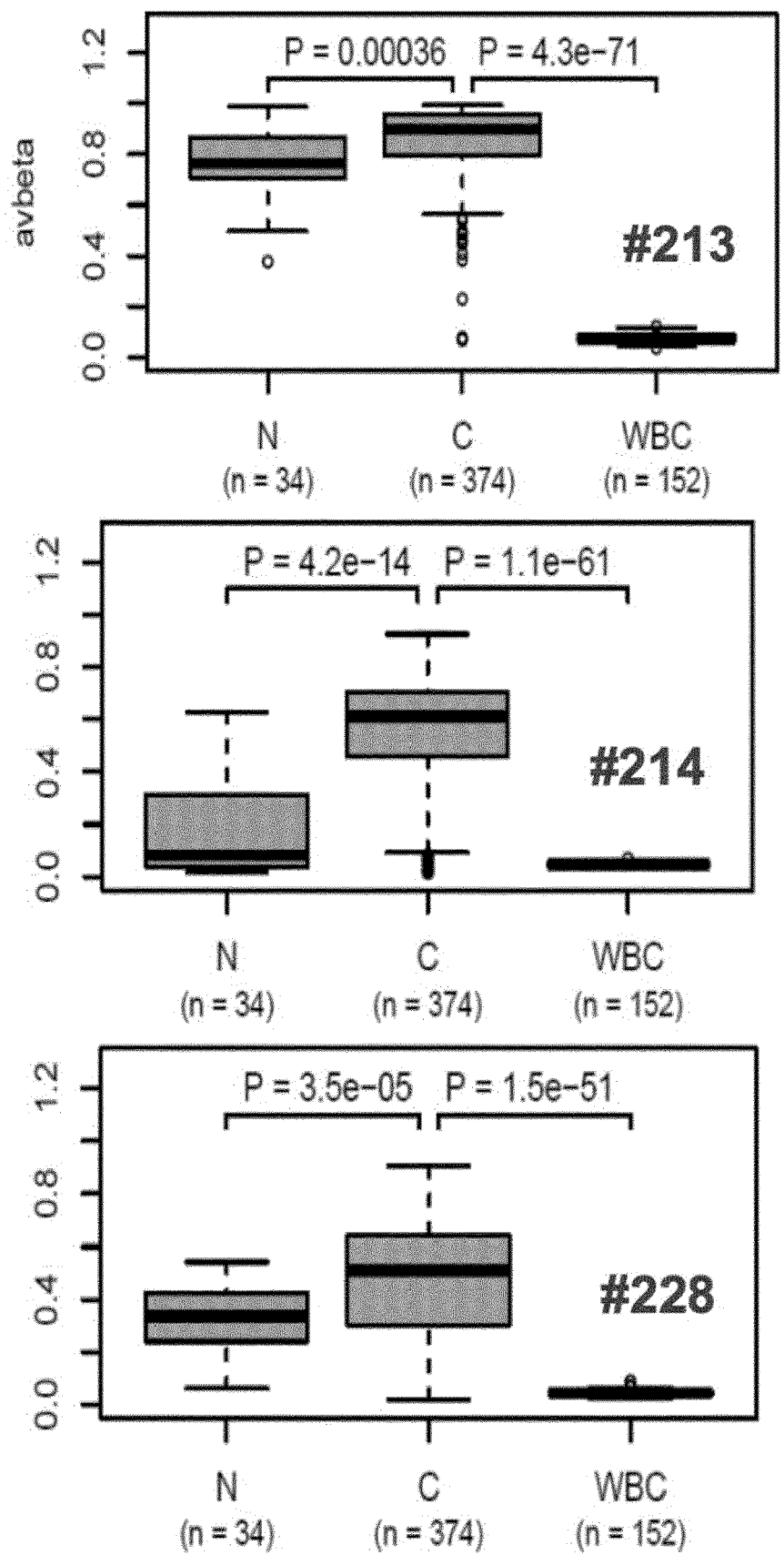
Figure 20:
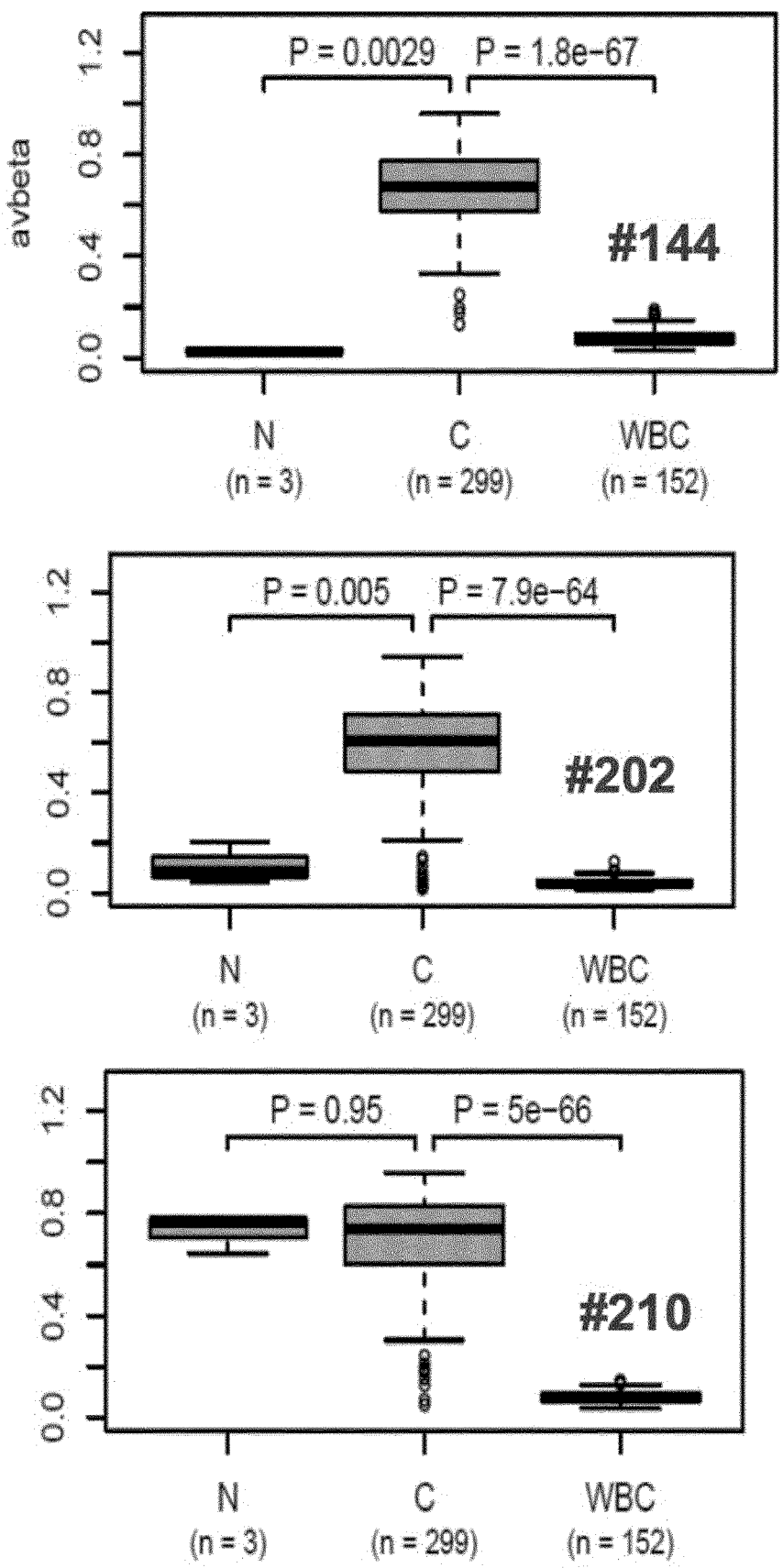
FIG. 20 depicts the magnitude and significance of the association between certain DMRs of the invention and cervical cancer. A box-plot of the level of methylation (average beta value "avbeta") for each DMR in DNA isolated from samples of normal (N) tissue, cancerous (C) tissue and white blood cells (WBC) is shown, together with the P-value of a two-tailed Wilcoxon rank sum test.
Figure 20:
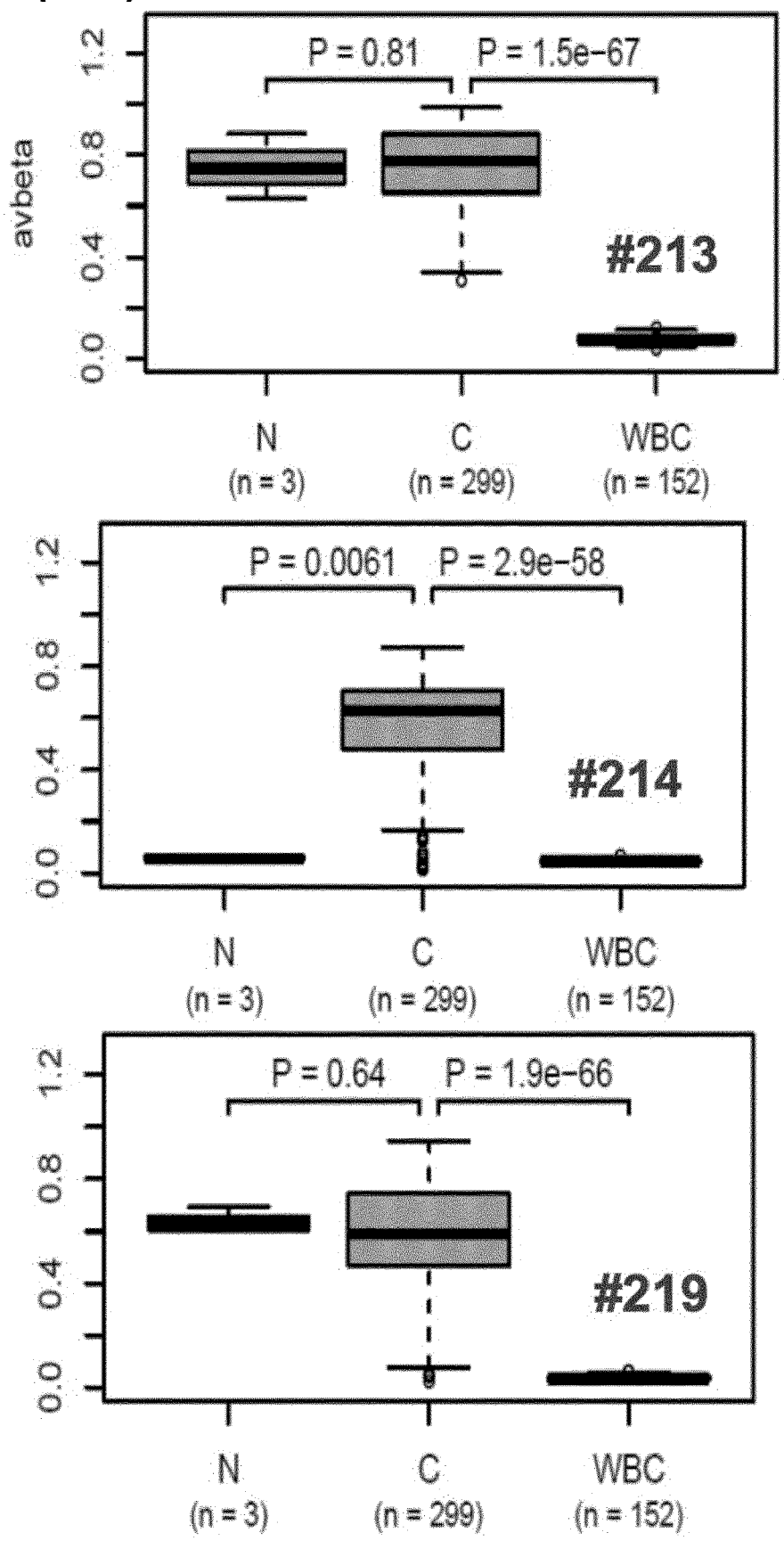
Figure 20:
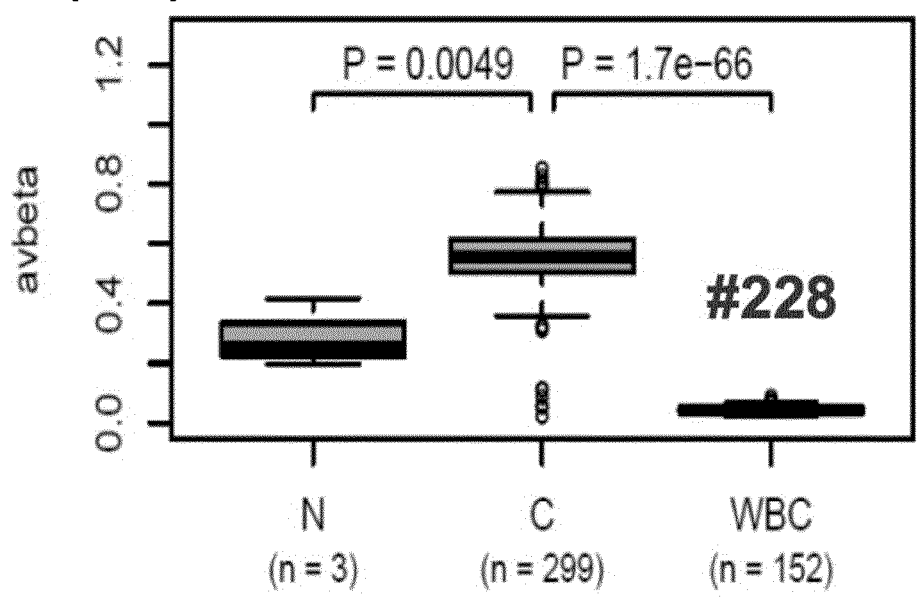
Figure 21:
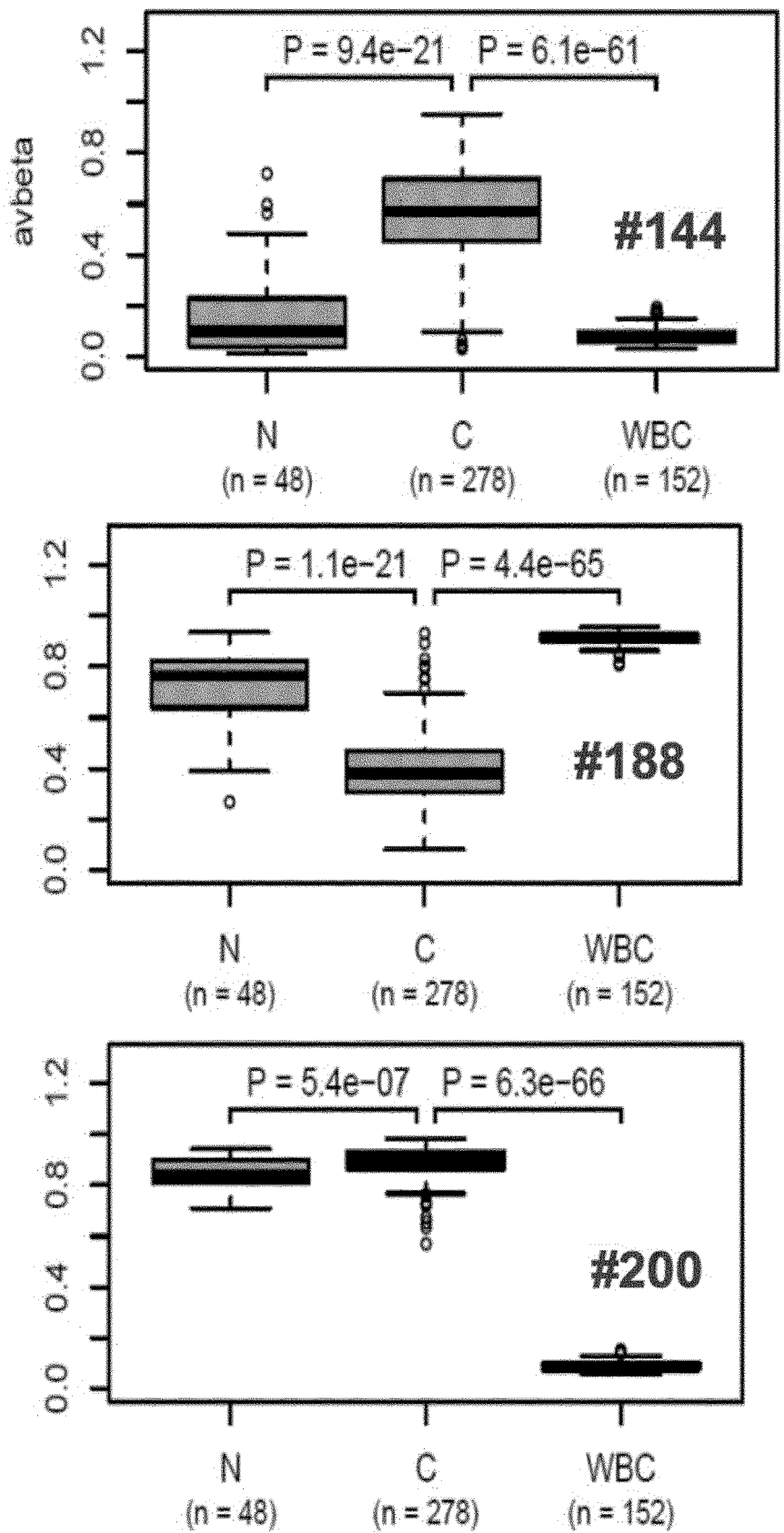
FIG. 21 depicts the magnitude and significance of the association between certain DMRs of the invention and prostate cancer. A box-plot of the level of methylation (average beta value "avbeta") for each DMR in DNA isolated from samples of normal (N) tissue, cancerous (C) tissue and white blood cells (WBC) is shown, together with the P-value of a two-tailed Wilcoxon rank sum test.
Figure 21:
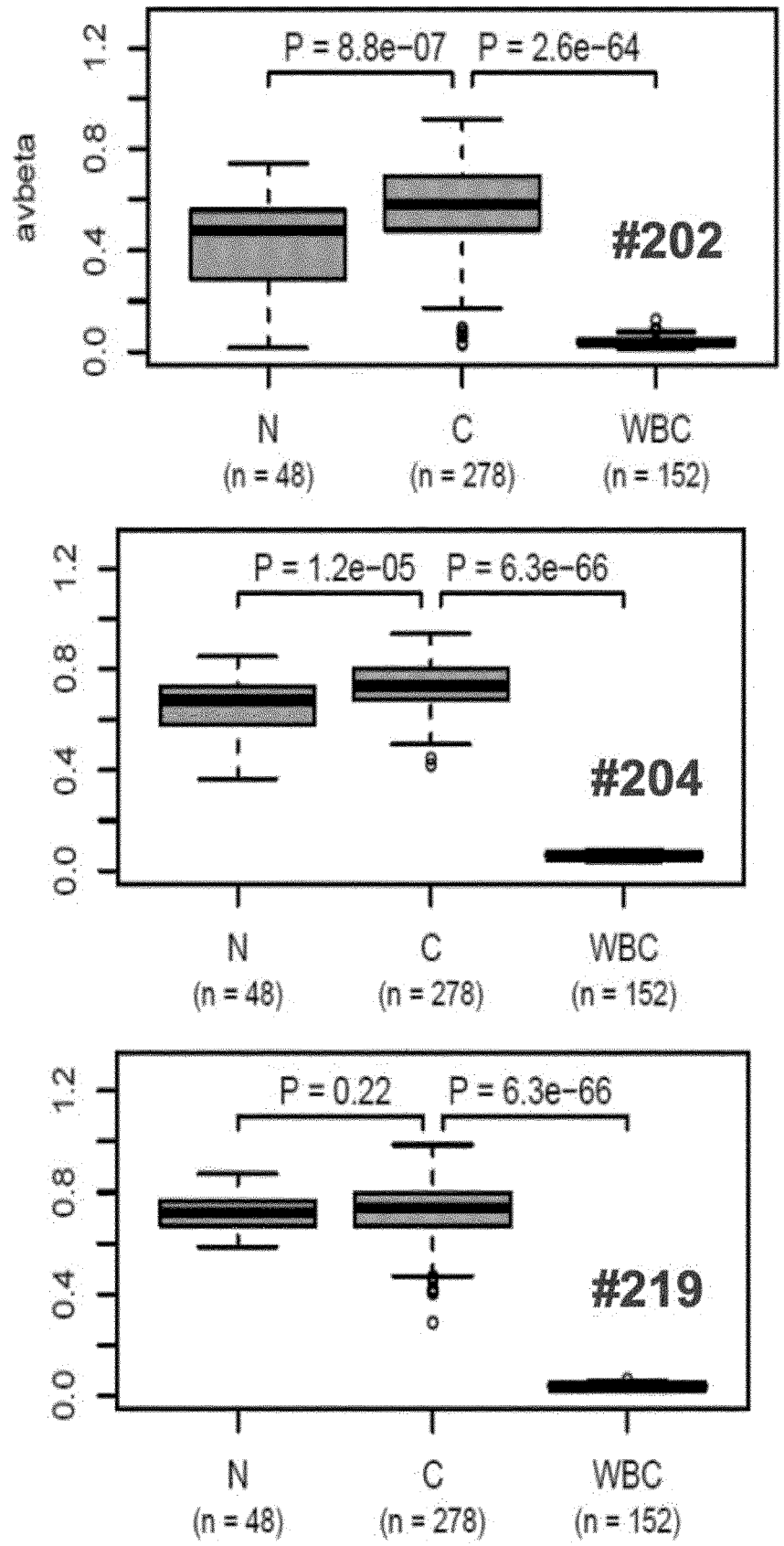
Figure 21:
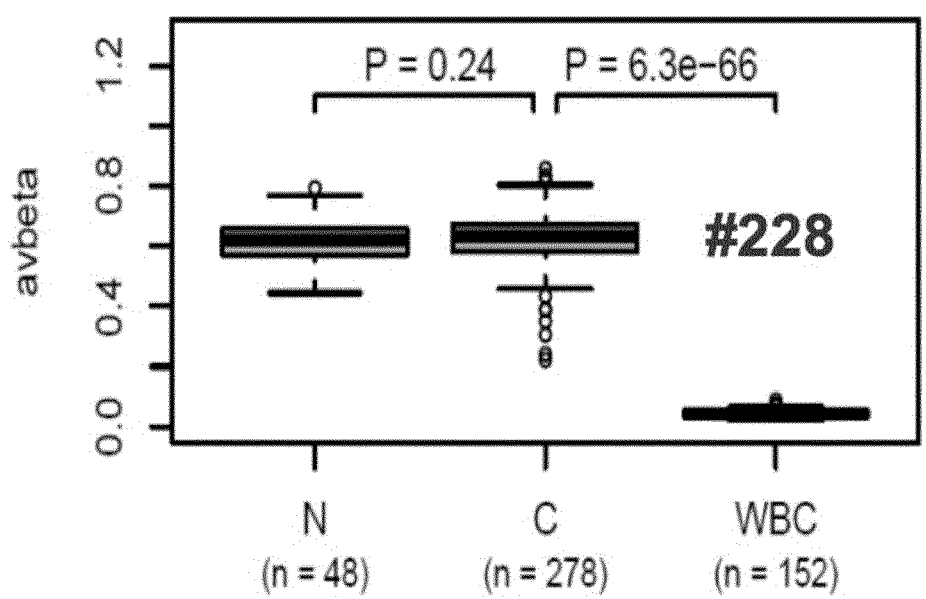

The term "colon cancer" is art recognised, and encompasses any cancer that forms in tissue associated with the colon; in particular those that result in abnormal cells that have the ability to invade or spread to other parts of the body. Aspects or embodiments of the present invention in respect of colon cancer and cell-free DNA are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #123, #144, #188, #202, #204, #210, #213, #214 and #228 (FIG. 17), in particular DMRs selected from the list consisting of: #202 and #213, and preferably a combination that includes at least the two DMRs #202 and #213. Aspects or embodiments of the present invention in respect of colon cancer and DNA of said human individual obtained from a tissue sample are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #123, #144, #188, #204, #210, #214 and #228, and preferably a combination that includes at least two of these DMRs, such as a combination of two DMRs as set forth in Table X6.

In one particular preferred embodiment of the invention, the cancer is colon cancer (and the human individual is a woman or a man, in particular a man) and one of the DMRs is #228, and more preferably another DMR is selected from one or more of the other DMRs of the invention, such as one or more DMRs selected from the list consisting of: #204, #144 and #141. In particular of such embodiments, the sample comprises cell-free DNA of said human individual (eg, cell-free DNA isolated from a plasma or serum sample from such human individual), and the determining step comprises determining, in at least one molecule of said cell-free DNA, the methylation status at one or more of the CpGs located associated with such DMR(s), and wherein, the presence in at least one of said cell-free DNA molecules of one or more of said methylated CpGs indicates the presence of, or a reduced response to therapy against, such cancer in said human individual.

The term "pancreatic cancer" is art recognised, and encompasses any cancer that forms in tissue associated with the pancreas; in particular those that result in abnormal cells that have the ability to invade or spread to other parts of the body. Aspects or embodiments of the present invention in respect of pancreatic cancer and cell-free DNA are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #144, #204, #213 and #228 (FIG. 17), in particular DMRs selected from the list consisting of: #204 and #213, and preferably a combination that includes at least the two DMRs #204 and #213. Aspects or embodiments of the present invention in respect of pancreatic cancer and DNA of said human individual obtained from a tissue sample are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #144 and #228, and preferably a combination that includes at least the two DMRs #144 and #228.

TABLE X6

Preferred pair-combinations of DMRs in respect
of colon cancer and DNA from tissue samples

| | | | | | |
|---|---|---|---|---|---|
| #123 & #144 | #123 & #188 | #123 & #204 | #123 & #210 | #123 & #214 | #123 & #228 |
| | #144 & #188 | #144 & #204 | #144 & #210 | #144 & #214 | #144 & #228 |
| | | #188 & #204 | #188 & #210 | #188 & #214 | #188 & #228 |
| | | | #204 & #210 | #204 & #214 | #204 & #228 |
| | | | | #210 & #214 | #210 & #228 |
| | | | | | #214 & #228 |

In one particular preferred embodiment of the invention, the cancer is pancreatic cancer (and the human individual is a woman or a man) and one of the DMRs is #228, and more preferably another DMR is selected from one or more of the other DMRs of the invention, such as one or more DMRs selected from the list consisting of: #204, #144 and #141. In particular of such embodiments, the sample comprises cell-free DNA of said human individual (eg, cell-free DNA isolated from a plasma or serum sample from such human individual), and the determining step comprises determining, in at least one molecule of said cell-free DNA, the methylation status at one or more of the CpGs located associated with such DMR(s), and wherein, the presence in at least one of said cell-free DNA molecules of one or more of said methylated CpGs indicates the presence of, or a reduced response to therapy against, such cancer in said human individual.

The term "uterine cancer" is art recognised, and encompasses any cancer that forms in tissue associated with the uterus; in particular those that result in abnormal cells that have the ability to invade or spread to other parts of the body. Aspects or embodiments of the present invention in respect of uterine cancer and cell-free DNA are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #123, #144, #188, #200, #202, #204, #213, #214 and #228 (FIG. 17), in particular DMRs selected from the list consisting of: #200 and #213, and preferably a combination that includes at least the two DMRs #200 and #213. Aspects or embodiments of the present invention in respect of uterine cancer and DNA of said human individual obtained from a tissue sample are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #123, #144, #188, #202, #204, #214 and #228, and preferably a combination that includes at least two of these DMRs, such as a combination of two DMRs as set forth in Table X7.

In one particular preferred embodiment of the invention, the cancer is uterine (endometrial) cancer (and the human individual is a woman) and one of the DMRs is #228, and more preferably another DMR is selected from one or more of the other DMRs of the invention, such as one or more DMRs selected from the list consisting of: #204, #144 and #141. In particular of such embodiments, the sample is a sample of vaginal fluid or a cervical smear sample from such woman, and for example comprises cell-free DNA of said woman. Alternatively, the sample comprises cell-free DNA isolated from a plasma or serum sample from such woman. In each case, the determining step can comprise determining, in at least one molecule of said (eg cell-free) DNA, the methylation status at one or more of the CpGs located associated with such DMR(s), and wherein, the presence in at least one of said (eg cell-free) DNA molecules of one or more of said methylated CpGs indicates the presence of, or a reduced response to therapy against, such cancer in said woman.

The term "cervical cancer" is art recognised, and encompasses any cancer that forms in tissue associated with the cervix; in particular those that result in abnormal cells that have the ability to invade or spread to other parts of the body. Aspects or embodiments of the present invention in respect of cervical cancer and cell-free DNA are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #144, #202, #210, #213, #214, #219 and #228 (FIG. 14), in particular DMRs selected from the list consisting of: #210, #213, #219 and #228, and preferably a combination that includes at least two of these DMRs, such as a combination of two DMRs as set forth in Table X8. Aspects or embodiments of the present invention in respect of cervical cancer and DNA of said human individual obtained from a tissue sample are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #144, #202 and #214, and preferably a combination that includes at least two of these DMRs such a combination of two DMRs as set forth in Table X9.

TABLE X7

Preferred pair-combinations of DMRs in respect of uterine cancer and DNA from tissue samples

| | | | | | |
|---|---|---|---|---|---|
| #123 & #144 | #123 & #188 | #123 & #202 | #123 & #204 | #123 & #214 | #123 & #228 |
| | #144 & #188 | #144 & #202 | #144 & #204 | #144 & #214 | #144 & #228 |
| | | #188 & #202 | #188 & #204 | #188 & #214 | #188 & #228 |
| | | | #202 & #204 | #202 & #214 | #202 & #228 |
| | | | | #204 & #214 | #204 & #228 |
| | | | | | #214 & #228 |

TABLE X8

Preferred pair-combinations of DMRs in respect
of cervical cancer and cell-free DNA

| #210 & #213 | #210 & #219 | #210 & #228 |
| | #213 & #219 | #213 & #228 |
| | | #219 & #228 |

TABLE X9

Preferred pair-combinations of DMRs in respect
of cervical cancer and DNA from tissue samples

| #144 & #202 | #144 & #214 |
| | #202 & #214 |

In one particular preferred embodiment of the invention, the cancer is cervical cancer (and the human individual is a woman) and one of the DMRs is #228, and more preferably another DMR is selected from one or more of the other DMRs of the invention, such as one or more DMRs selected from the list consisting of: #204, #144 and #141. In particular of such embodiments, the sample is a sample of vaginal fluid or a cervical smear sample from such woman, and for example comprises cell-free DNA of said woman. Alternatively, the sample comprises cell-free DNA isolated from a plasma or serum sample from such woman. In each case, the determining step can comprise determining, in at least one molecule of said (eg cell-free) DNA, the methylation status at one or more of the CpGs located associated with such DMR(s), and wherein, the presence in at least one of said (eg cell-free) DNA molecules of one or more of said methylated CpGs indicates the presence of, or a reduced response to therapy against, such cancer in said woman.

The term "prostate cancer" is art recognised, and encompasses any cancer that forms in tissue associated with the prostate; in particular those that result in abnormal cells that have the ability to invade or spread to other parts of the body. Aspects or embodiments of the present invention in respect of prostate cancer and cell-free DNA are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #144, #188, #200, #202, #204, #219 and #228 (FIG. 17), in particular DMRs selected from the list consisting of: #219 and #228, and preferably a combination that includes at least the two DMRs #219 and #228. Aspects or embodiments of the present invention in respect of prostate cancer and DNA of said human individual obtained from a tissue sample are particular envisioned for the present invention which makes use of one or more epigenetic markers (eg, one or more methylated CpGs, in particular the related CpGs thereof) located within (or within about 2,000 bp—such as within about 200 bp—5' or 3' of) a nucleic acid sequence comprised in one or more (eg, two, three or four) of the DMRs selected from the list consisting of: #144, #188, #200, #202 and #204, and preferably a combination that includes at least two of these DMRs, such as a combination of two DMRs as set forth in Table X10.

TABLE X10

Preferred pair-combinations of DMRs in respect
of prostate cancer and DNA from tissue samples

| #144 & #188 | #144 & #200 | #144 & #202 | #144 & #204 |
| | #188 & #200 | #188 & #202 | #188 & #204 |
| | | #200 & #202 | #200 & #204 |
| | | | #202 & #204 |

In other certain particular embodiments of the invention, a combination of the cancer and the DMR is one selected from those shown in Table Y1 or Table Y2, in particular any such combination that is marked by "+" or "++" as being preferred or more preferred (respectively) as being a tissue ("T"), a cell-free ("C") or both a tissue and a cell-free ("TIC") DNA marker. Raw data/graphs are not shown, but those combinations showing at least a reasonable difference in magnitude in methylation between cancerous tissue DNA and normal tissue DNA as well as between cancerous tissue DNA and WBC DNA are marked as "T/C"; those showing at least a reasonable difference in magnitude in methylation between cancerous tissue DNA and normal tissue (but not meaningfully between cancerous tissue DNA and WBC DNA) are marked as "T"; while those showing at least a reasonable difference in magnitude in methylation between cancerous tissue DNA and WBC DNA (but not meaningfully between cancerous tissue DNA and normal tissue DNA) are marked as "C". Those combinations of DMR and cancer showing no such meaningful difference in methylation are marked as "NS". The general classification of the utility of each marker/cancer combination as preferred or more preferred is marked as "+" or "++", respectively, and as determined by inspection of the relative magnitudes and significances of each effect.

TABLE Y1

DMR/cancer pair-combinations of particular utility in the present invention

| Cancer/DMR | #123 | #137 | #144 | #148 | #164 | #188 | #200 | #202 | #204 | #210 |
|---|---|---|---|---|---|---|---|---|---|---|
| BLCA | T/C+ | C++ | T/C++ | C | C+ | C+ | C+ | T/C | T/C | C++ |
| BRCA | NS | C++ | T/C++ | C | C+ | T/C+ | C++ | C+ | TC++ | C++ |
| CESC | C | C++ | T/C++ | NS | C+ | C | C++ | C++ | C | C++ |
| COAD | T/C+ | C++ | C++ | C | T/C+ | C++ | C | C++ | C+ | C++ |
| ESCA | T/C | C++ | T/C++ | T | T/C+ | C | C+ | C | C+ | C++ |
| HNSC | T/C | C++ | T/C++ | NS | T/C+ | C | C++ | T/C+ | C+ | C++ |
| KIRC | T/C+ | C++ | T | NS | T | T/C+ | C++ | T/C | T/C | C++ |
| KIRP | T | C++ | T | C | C | C++ | C++ | C | NS | C++ |
| LIHC | T | C++ | T/C++ | C | T/C | C++ | C++ | C | T/C | C++ |
| LSCC | T/C | C++ | T/C++ | T | T/C+ | C+ | C+ | T/C | T/C | T/C+ |
| LUAD | T/C | C++ | T/C++ | T | T/C+ | T/C+ | C++ | T/C | NS | T/C+ |

TABLE Y1-continued

DMR/cancer pair-combinations of particular utility in the present invention

| Cancer/DMR | #123 | #137 | #144 | #148 | #164 | #188 | #200 | #202 | #204 | #210 |
|---|---|---|---|---|---|---|---|---|---|---|
| PAAD | NS | C++ | T/C++ | C | T/C+ | C+ | C+ | NS | C+ | C+ |
| PRAD | T/C+ | C++ | T/C++ | C | T/C+ | T/C+ | C++ | T/C+ | C++ | C |
| READ | T/C++ | C++ | C++ | C | T/C+ | C++ | C | C+ | C+ | C++ |
| SARC | NS | C++ | C | C | C+ | C | C++ | C | C | C++ |
| SKCM | C | C++ | C | C | C+ | C+ | C++ | C | C+ | C* |
| STAD | C+ | C++ | T/C++ | C | C+ | C+ | C++ | C | C | C* |
| THCA | C+ | C++ | C | C | C+ | C | C++ | NS | C+ | C++ |
| UCEC | T/C++ | C++ | T/C++ | T | C++ | T/C+ | C++ | T/C+ | TC++ | C+ |

TABLE Y2

Further DMR/cancer pair-combinations of particular utility in the present invention

| Cancer/DMR | #213 | #214 | #219 | #222 | #223 | #224 | #225 | #226 | #228 |
|---|---|---|---|---|---|---|---|---|---|
| BLCA | C++ | T/C | C+ | C | C+ | C | C | T/C | T/C+ |
| BRCA | C++ | C | C++ | C | C+ | C+ | C | C | C++ |
| CESC | C++ | C | C++ | C | C++ | C+ | C | C | C+ |
| COAD | C++ | C+ | C+ | T | T/C | C+ | C | NS | T/C+ |
| ESCA | C++ | T/C+ | C+ | C | T/C+ | C | C | C | T/C+ |
| HNSC | C++ | T/C+ | C+ | C+ | C+ | C+ | C | NS | C++ |
| KIRC | C++ | T/C | C+ | C | C+ | C++ | C | C | C |
| KIRP | C++ | C | C++ | C+ | C | C++ | C+ | C | T/C |
| LIHC | C++ | C | C | C+ | C+ | C | T | T/C | T/C |
| LSCC | C++ | T/C+ | C+ | T/C | T/C+ | C+ | C | T | T/C+ |
| LUAD | C++ | T/C+ | C+ | C | T/C+ | C+ | C | NS | T/C |
| PAAD | C++ | C | C++ | C | C | C+ | C+ | C | T/C |
| PRAD | C++ | C | C | C+ | C++ | C+ | C++ | NS | C++ |
| READ | C++ | C | C | T | C | C | T/C | NS | C |
| SARC | C++ | NS | C | C | C+ | C++ | NS | NS | NS |
| SKCM | C+ | C | C+ | C | T/C+ | C | NS | C | C |
| STAD | C++ | C | C+ | C | C+ | C+ | C | C | T/C+ |
| THCA | C++ | T | C++ | C++ | C+ | C++ | C++ | C | NS |
| UCEC | C++ | T/C+ | C++ | C++ | C++ | C++ | C | T/C | T/C+ |

Accordingly, in specifically preferred embodiment, the combination of cancer and DMR(s) for use in cell-free DNA embodiments of the invention, are any of those represented by a "C++" or a "T/C++" in Tables Y1 or Table Y2, and the combination of cancer and DMR(s) for use in tissue-sample DNA embodiments of the invention, are any of those represented by a "T/C++". AS will now be apparent to the person of ordinary skill, a plurality of the DMRs of the invention (eg, two, three or four), each having (eg a preferred or more preferred) utility for the same cancer may be used together, and hence such combinations are also envisioned and form other particularly preferred embodiments of the present invention. Therefore, particularly preferred DMRs of the invention include DMR numbers: #137 (showing utility as a cell-free methylation marker in most cancer types), #144 (showing utility as a cell-free and/or tissue methylation maker in many cancers), #188 (showing utility as a cell-free and/or tissue methylation maker in many cancers), #200 (showing utility as a cell-free methylation marker in many cancer types), #210 (showing utility as a cell-free methylation marker in most cancer types), #213 (showing utility as a cell-free methylation marker in many cancer types), #224 (showing utility as a cell-free methylation marker in many cancer types) and #228 (showing utility as a cell-free and/or tissue methylation maker in many cancers).

In a particularly preferred embodiment, a plurality of two or more DMRs of the present invention, where such plurality comprises both DMR #228 and #144, are used as (eg cell-free) methylation markers for a cancer in a human individual, in particular when the cancer is selected from the lists consisting of: (1) breast cancer, lung cancer, colon cancer, pancreatic cancer and ovarian cancer, in each case when the human individual is a woman; or (2) lung cancer, colon cancer and pancreatic cancer, in each case when the human individual is a man. In further preferred of such embodiments, such plurality of DMRs further includes DMR #204 and/or #141. Such embodiments of the invention using a combination of DMRs comprising both DMR #228 and #144 also include those where, when the human individual is a woman, the cancer is not ovarian cancer and/or is not breast cancer and/or is not colon cancer, such as when the human individual is a woman then the cancer is lung cancer and/or pancreatic cancer.

The biological sample to be provided in this aspect of the present invention may be obtained from the human individual (eg, a woan having, suspected of having or being investigated for having, ovarian cancer or any other cancer (other than prostate cancer) analysed herein, or a man having, suspected of having or being investigated for having, any cancer (other than a gynaecological cancer or breast cancer) analysed herein) by any procedure, process or step that the person of ordinary skill will recognise. For example, a biological sample may be obtained by surgery, biopsy, swab, collection of biological fluids etc. The biological sample may be a sample of tissue and/or fluid of the human individual (eg the woman). Examples of a biological fluid include whole blood or a blood fraction (eg, such as plasma or serum). In alternative examples, the sample—from a woman—may be a biological fluid selected from the group consisting of: urine, saliva, sweat, tears, phlegm, beast milk, breast aspirate, vaginal secretion, vaginal wash and colonic wash and cervical smear. In alternative examples, the sample—from a man—may be a biological fluid selected from the group consisting of: urine, saliva, sweat, tears, phlegm, smegma, semen and colonic wash.

In one embodiment, the biological sample may be a liquid biological sample selected from the group consisting of: a blood sample, a plasma sample and a serum sample. In more particular embodiments, the sample is a plasma or serum sample from the human individual (eg the woman or man, as applicable), or is urine from the human individual (eg the woman female or man, as applicable). In certain embodiments, the sample is substantially (or essentially) free from cells, and/or is not a whole blood sample.

In some embodiments, the biological sample is a tissue sample from the human individual, such as a sample of a tumour or a cancer from the human individual. Such tissue sample may be a biopsy sample of the tumour or a cancer such as a needle biopsy samples, or a tumour biopsy sections or an archival sample thereof. Such a tissue sample may comprise living, dead or fixed cells, such as from the tumour or a cancer.

Methods of collecting such biological samples will be known to the person of ordinary skill, in particular the collection of whole blood (eg by needle-puncture of a suitable vein of the woman), and the subsequent preparation of plasma or serum from the whole blood (such as described in the examples hereof). In particular embodiments, the blood may be collected, stored and/or transported in a cell-free DNA blood collection tube, such as one with a formaldehyde-free preservative that stabilises nucleated blood cells. Such stabilisation would be expected to prevent, or reduce, the release of genomic DNA (eg from nucleated blood cells), enhancing the isolation of high-quality cell-free DNA which can be further used in the method or other aspects of the present invention. The use of such tubes in the present invention can, in certain embodiments, reduce the need for immediate plasma preparation. For example, cell-Free DNA is stable for up to 14 days, at room temperature, allowing convenient sample collection, transport and storage over such period. Suitable blood collection tubes include the "Cell-Free DNA BCT®" of Streck Inc, such as their research grade or CE-marked versions of this product.

Accordingly, in certain embodiments, the whole blood collected, for example collected in such a free DNA blood collection tube, may be processed within about 14 days of collection, such as within about 10 days, 7 days, 5 days, 4 days, 3 days or 2 days, or between about 30 mins and 24 hours (such as within about 12 or 8 hours) of collection. Between collection and processing (for example during storage and/or transport) the sample may be kept at ambient (such as room) temperature, or may be maintained at a reduced temperature by refrigeration of use of cooling materials. Suitable reduced temperatures include about 10° C., 4° C. or lower, such as about 0° C., −18° C. or −70° C., or lower such as about −200° C. (as may be provided by storage in liquid nitrogen).

Steps of subsequent processing can include centrifugation or other methods to separate intact cells (such as red and nucleated blood cells) from the biological sample, preparation of plasma or serum from a blood sample and/or extraction of cell-free DNA from the biological. Suitable methods for extraction of cell free DNA, in particular from plasma or serum are described in the examples herein. For example, the QIAamp Circulating Nucleic Acid and/or DNeasy Blood and Tissue extraction product series of Qiagen, as well as automated systems for DNA extraction such as the QiaSymphony (Qiagen), Chemagen 360 (PerkinElmer). The same, analogous or modified procedures may be used to subsequently process other biological fluids, such as urine, tears, breast aspirate or vaginal swabs (or cervical smears), to isolate cell-free DNA therefrom, as too to subsequently process other biological fluids such as urine, saliva, sweat, tears, phlegm, smegma, semen and colonic wash.

The biological sample from the human individual (eg the woman or man, as applicable) comprises, in certain embodiments, cell-free DNA of said human individual. The term "cell-free DNA" (or "cfDNA") is art recognised, and includes the meaning of DNA that is found outside of a cell, such as in a biological fluid (eg blood, or a blood fraction) of a human individual. In particular embodiments, the cell-free DNA may be circulating. "Circulating" is also an art-recognised term, and includes the meaning that an entity or substance (eg cfDNA) is present in, detected or identified in, or isolated from, a circulatory system of the human individual, such as the blood system or the lymphatic system. In particular, when cfDNA is "circulating" it is not located in a cell, and hence may be present in the plasma or serum of blood, or it may be present in the lymph of lymphatic fluid.

The cell-free DNA present in such a biological sample may arise from different sources (ie, tissues or cells) present in or of the human individual (eg the woman or man, as applicable). For example, cfDNA may derive from nucleated (such as white) blood cells and/or other "normal" cells of the body such as dead/dying (or apoptotic/necrotic) epithelial or other cells. Such cfDNA can be deemed "somatic" cfDNA as it is derived from cells that are assumed to comprise a normal genomic complement, genetic and epigenetic make up of the human individual (eg the woman or man, as applicable). In addition to such somatic cfDNA, such a biological sample may contain cfDNA derived from other sources, and hence the total cfDNA present in, or extracted from, the biological sample (such as plasma or serum) may be an admixture of cfDNA derived from two or more different sources, each source providing cfDNA which may have a different genomic complement and/or genetic or epigenetic make up. In the present invention, the determination of the presence or absence (or response to therapy against) of a cancer in the human individual (eg ovarian cancer in a woman) is based on a differential epigenetic make up—as described for the first time herein for the DMRs of the present invention—of (eg cfDNA) derived from cells of the cancer compared to that of the somatic (eg cfDNA) present in the biological sample. The (eg cell free "cf") DNA derived from a tumour (such as an ovarian cancer cell) can be described as (eg circulating) tumour DNA ("tDNA" or "ctDNA" if circulating tumour DNA). In the present invention, the determination of the presence or absence (or response to therapy against) of the cancer (eg ovarian cancer) is based on the (eg single-molecule) analysis of certain epigenetic markers present on the tDNA/ctDNA (as applicable) derived from the cancer (eg ovarian cancer). However, cfDNA present in such a biological sample may contain cfDNA from sources other than, or in additional to, cfDNA derived from the cancer (eg ovarian cancer). For example, cfDNA may comprise an admixture of somatic cfDNA of the human individual (eg a woman), and cfDNA derived from one or more other cancers (or tumorous tissues/cells) that may be present in the human individual (eg for a woman, such as breast cancer). Furthermore, if a woman is pregnant, the cfDNA may comprise cfDNA derived from the foetus and/or the placenta of such foetus (Lo et al 1997, Lancet 350:485), or if the human individual (eg a woman or man, as applicable) has received a tissue, cell or blood transplant/transfusion donated by another individual, the cfDNA of the human individual may comprise DNA derived from the cells of such other individual.

The amount of total cfDNA isolated from such a biological sample, in particular from a blood or blood-fraction sample, may differ from human individual to human individual (eg, from woman to woman) and sample to sample (such as, dependent on the storage, transport, temperature and other environmental conditions the samples is subjected to, as described in the example). For example, between about 0 ng (ie, absence, or essentially absent) and 5000 ng cfDNA per mL of plasma/serum, such as about between about 2 ng/mL or 10 ng/mL and about 2000 or 1000 ng/mL, in particular between about 2 ng/mL or 10 ng/mL and about 500 ng/mL or between about 15 ng/mL or 20 ng/mL or 30 ng/ml or 40 ng/ml or 50 ng/mL and about 500 ng/ml, 400 ng/mL or 300 mg/mL or 250 mg/mL or 200 mg/mL, such as (eg in cases when blood is collected in a free DNA blood collection tube) between about 2 ng/mL or 20 ng/mL and about 500 ng/mL. In any of such embodiments (in particular, when the total cfDNA is at an amount of between about 2 ng/mL or 20 ng/mL and about 500 ng/mL), the cfDNA (such as that derived from ovarian cancer, or another cancer analysed herein) comprises at (or more than) about 0.001%, 0.0025%, 0.005%, 0.0075%, 0.01%, 0.025%, 0.05%, 0.075%, 0.1%, 0.25%, 0.5%, 0.75%, 1%, 2%, 3%, 4%, 5%, 7.5%/0 or 10% of the total cfDNA, such as between about 0.001% and about 10%, or between about 0.1% and about 10%, or between about 0.5% and about 10%, or between about 0.5% and about 5%, or between about 1% and about 5%, and/or the frequency of an epigenetic marker of the present invention (such as one associated with DMR #141, #204, or #228) is at (or more than) about one molecule of the epigenetic marker to about 3, 5, 10, 15, 20, 25, 50, 60, 75, 100, 150, 200, 250, 500, 750, 1000, 1500, 2000, 3000, 4000, 5000, 10000 or more than 10000, such as about 100000 molecules of total cfDNA (or fragments) presenting in or isolated from such biological sample.

Cell-free DNA if present in, or isolated from, a biological sample (such as plasma or serum) is, typically, fragmented. In certain embodiments, the average fragment size of such cfDNA may be between about 50 bp and 5000 bp, for example between about 50 bp and 3000 bp, between about 50 bp and 3000 bp, between about 50 bp and 2000 bp, 50 bp and 2000 bp, such as between about 75 bp and 1000 bp or between about 75 bp and 750 bp, or between about 100 bp and 300 bp, such as between about 150 bp and 200 bp. The average fragment size (and amount/concentration) of cfDNA may be determined by any suitable methodology, as will be apparent to the person of ordinary skill, including by capillary electrophoresis analysis and/or size fractional analysis, such as the Fragment Analyzer and the High Sensitivity Large Fragment Analysis Kit (AATI, USA). Such characterisation can occur prior to the determination step, as its outcome may be used to influence the number of molecules to be analysed and/or the number of those molecules exhibiting the cancer-specific DNAme marker (as described elsewhere herein).

The inventors have identified that, for certain of the DMRs of the present invention, one or more of the CpGs therein have particular relevance for the association of such CpG's/s' methylation status to the presence or absence of, or response to therapy against, one or more certain cancers in a human individual (eg, an ovarian cancer, breast cancer, cervical cancer or uterine cancer in a woman or a prostate cancer in a man, or other certain cancers eg bladder cancer, colon cancer, oesophageal cancer, head and neck cancer, kidney cancer, liver cancer, lung cancer, pancreatic cancer, rectal cancer, sarcoma, skin melanoma, stomach cancer or thyroid cacner in either a woman or a man, as applicable). The identify of those CpGs (each, a "relevant CpG") is underlined in TABLE 1A and TABLE 1B, as applicable, and the genomic position (hg19) of the cytosine (C) of each such relevant CpGs for such DMRs of the present invention is set forth in TABLE 1C.

TABLE 1C

Genome-coordinates of the Cs for each relevant CpGs of the DMRs of the present invention

| DMR# | Genome coordinates (hg19) of the Cs for relevant CpGs | Class |
|---|---|---|
| 141 | chr5: 178004422-178004427-178004442-178004460-178004468-178004471-178004504 | Hyper |
| 204 | chr1: 151810811-151810814-151810816-151810828-151810835-151810841-151810843-151810845-151810852-151810887-151810890- | Hyper |

TABLE 1C-continued

Genome-coordinates of the Cs for each relevant CpGs of the DMRs of the present invention

| DMR# | Genome coordinates (hg19) of the Cs for relevant CpGs | Class |
|---|---|---|
| | 151810893-151810899-151810904-151810907-151810909 | |
| 228 | chr2: 219736312-219736317-219736319-219736335-219736343-219736352-219736361 | Hyper |
| 144 | chr19: 58220440-58220443-58220446-58220460-58220466-58220479-58220482-58220494-58220500-58220513-58220516 | Hyper |
| 123 | chr16: 1271180-1271188-1271192-1271202-1271212-1271229-1271239 | Hypo |
| 129 | chr11: 69054678-69054680-69054700-69054709 | Hypo |
| 137 | chr12: 132896310-132896312-132896333-132896338-132896351-132896361-132896381 | Hypo |
| 148 | chr2: 72359633-72359635-72359648-72359652-72359682 | Hypo |
| 150 | chr7: 156735054-156735067-156735078-156735086-156735093-156735105-156735110-156735116-156735118-156735124-156735140 | Hypo |
| 154 | chr17: 70112177-70112190-70112193-70112209-70112221-70112237 | Hyper |
| 158 | chr16: 74441733-74441743-74441771-74441776-74441787-74441793-74441801 | Hypo |
| 164 | chr4: 174427997-174428007-174428018-174428027 | Hyper |
| 176 | chr6: 119107242-119107244-119107282-119107287 | Hypo |
| 178 | chr19: 13215489-13215495-13215499-13215510-13215521 | Hyper |
| 180 | chr3: 192125900-192125924-192125927-192125938-192125945-192125949 | Hyper |
| 186 | chr22: 21483289-21483317-21483327-21483329-21483332-21483337 | Hypo |
| 188 | chr19: 18497159-18497226-18497233-18497239 | Hypo |
| 190 | chr9: 79629090-79629100-79629103-79629111-79629128-79629130-79629135-79629138 | Hyper |
| 192 | chr12: 75601322-75601325-75601331-75601334-75601361-75601368-75601373-75601379-75601385-75601403-75601408 | Hyper |
| 200 | chr9: 138999208-138999210-138999213-138999217-138999240-138999242-138999264 | Hyper |
| 202 | chr1: 2987558-2987560-2987577-2987579-2987581-2987592-2987598-2987604-2987610-2987627-2987629 | Hyper |
| 208 | chr8: 55467548-55467576-55467581-55467585-55467592-55467606 | Hypo |
| 210 | chr12: 123713553 | Hyper |
| 213 | chr2: 106776975-106776977-106777009-106777015 | Hyper |
| 214 | chr3: 141516291-141516302-141516317 | Hyper |
| 219 | chr16: 30484193-30484218 | Hyper |
| 222 | chr3: 111809470 | Hyper |
| 223 | chr10: 120489294 | Hyper |
| 224 | chr11: 1874070-1874086-1874093 | Hyper |
| 225 | chr7: 142422236 | Hyper |
| 226 | chr1: 3086485-3086487-3086492-3086494-3086496-3086501-3086509 | Hypo |

An epigenetic marker of, or for use in, the present invention may comprise the presence/absence, as applicable, of methylation at a CpG associated with (such as located within) any of the DMRs of the present invention (or within about 2,000 bp—such as within about 200 bp—5' or 3' thereof), and in particular the presence/absence, as applicable, of methylation at one of the relevant CpGs associated with a given DMR of the present invention as set forth in TABLE 1C. However, as set out herein, the determination of the presence or absence of (or response to therapy against) a cancer in a human individual (eg an ovarian cancer in a woman) may be enhanced if, in respect of one or more of such DMRs, the methylation status at a plurality of CpGs for such DMR is determined.

Accordingly, the present invention specifically includes embodiments where the methylation status is determined at a number being two, three, four, five, six, seven, eight, nine, ten, about 12, about 15, about 20, about 25 or more of said CpGs located within said nucleotide sequence and in particular at such number of—or up to the maximum number of—any CpGs (or the relevant CpGs as set forth in TABLE 1C) associated with a given DMR of the present invention. In such embodiments, the presence in at least one of said (eg cell-free) DNA molecules of at least one, up to the respective said number (such as a number between about three and about fifteen) of methylated CpGs or un-methylated CpGs (as applicable) located within one or more of said nucleotide sequences indicates the presence of, or a reduced response to therapy against, the cancer in said human individual (eg an ovarian cancer in said woman).

For example, the present invention includes embodiments where the methylation status is determined at two, three, four, five, six, seven, eight, nine, ten, 11, 12, 13, 14 or 15 CpGs (such as between about four and about ten) located within a hyper-methylated DMR (eg, those set forth in TABLE 1A) of the present invention (or associated therewith, such as within about 2,000 bp—such as within about 200 bp—5' or 3' thereof), and wherein the presence of at least one methylated such CpG associated with such a hyper-methylated DMR of the invention, such as all such CpGs or at least all of the applicable relevant CpGs in such DMR as set forth in TABLE 1C (such as at all two, three, four, five, six, seven, eight, nine, ten, 11, 12, 13, 14 or 15, up to the maximum number of such CpGs associated with said DMR), indicates the presence of, or a reduced response to therapy against, the cancer in said human individual (eg an ovarian cancer in said woman). Preferably, in such embodiments, the presence of methylation at all of the relevant CpGs (see TABLE 1C) for a given hyper-methylated DMR (eg, those set forth in TABLE 1A) indicates the presence of, or a reduced response to therapy against, the cancer in said human individual (eg an ovarian cancer in said woman).

As another example, the present invention also includes embodiments where the methylation status is determined at two, three, four, five, six, seven, eight, nine, ten, 11, 12, 13, 14 or 15 CpGs (such as between about four and about ten) located within a hypo-methylated DMR (eg, those set forth in TABLE 1B) of the present invention (or associated therewith, such as within about 2,000 bp—such as within about 200 bp—5' or 3' thereof), and wherein the absence of at least one methylated such CpG associated with such a hypo-methylated DMR of the invention, such as all such CpGs or at least all of the applicable relevant CpGs in such DMR as set forth in TABLE 1C (such as at all two, three, four, five, six, seven, eight, nine, ten, 11, 12, 13, 14 or 15, up to the maximum number of such CpGs associated with said DMR), indicates the presence of, or a reduced response to therapy against, the cancer in said human individual (eg an ovarian cancer in said woman). Preferably, in such embodiments, the absence of methylation at all of the relevant CpGs (see TABLE 1C) for a given hypo-methylated DMR (eg, those set forth in TABLE 1B) indicates the presence of, or a reduced response to therapy against, the cancer in said human individual (eg an ovarian cancer in said woman).

As will be apparent to the person of ordinary skill, the maximum number of CpGs for which such determination of methylation status may be made will be the number of CpGs located within the sequence that is analysed. For example, for DMR #141 (SEQ ID No. 1), the wild-type sequence shows that 7 CpGs are located therein (of which all 7 are underlined in TABLE 1A, are further identified in TABLE 1C and are the relevant CpGs for such DMR), and hence such number of CpGs would represent a maximum number of CpGs in respect of such sequence for which the methylation status may be determined and hence used to investigate the presence of, or a reduced response to therapy against, the cancer in said human individual (eg an ovarian cancer in said woman).

The status of methylation at any of such CpGs may be determined to be absent (un-methylated) or to be present (methylated), such as in the form of methylcytosine and/or hydroxymethylcytosine and/or formylcytosine, in particular 5-methylcytosine (5mC) or 5-hydroxymethylcytosine (5hmC) or 5-formylcytosine (5fC) (Li & Liu, 2011; Journal of Nucleic Acids, article ID 870726. Ito et al, 2011; Science 333:1300). In one embodiment, the present invention relates to the determination of the 5-methylation and/or 5-hydroxymethylcytosine status at one or more Cs in said CpGs, wherein the presence of one or more 5-methylcytosine and/or 5-hydroxymethylcytosine in the CpGs (in particular, in the relevant CpGs for a DMR, as set out in TABLE 1C) indicates the presence of, or a reduced response to therapy against, the cancer in said human individual (eg an ovarian cancer in said woman). Any of those CpGs investigated which are determined not to comprise 5-methylcytosine, are typically un-methylated cytosine, but in certain embodiments one or more may comprise modifications other than 5-methylcytosine, such as 5hmC or 5fC. Investigation of the respective modification comprised in CpGs is art know, including methylation-sensitive restriction enzyme or bisulphite conversion/analysis (eg for 5mC and/or 5hmC) and reduced bisulphite sequencing (redBS-Seq) (eg, for 5fC), as may be conducted by or products obtained from Cambridge Epigenetix Ltd (UK). Alternatively, single-molecule DNA sequencing/analysis techniques (such as those utilised in the PacBio or Nanopore instruments described elsewhere herein) may be used to determine the status and form of the methylation present at the CpGs that are interrogated as part of the present invention.

As well as the present invention including embodiments were the methylation status at one or more CpGs (in particular, at one or more relevant CpGs) is determined located within a single DMR of the present invention (or associated therewith, such as within about 2,000 bp—such as 200 bp—5' or 3' thereof), for example a DMR selected from the group consisting of #141, #204 and #228 and #144 (SEQ ID NOs.: 1, 2 and 3 and 4, respectively), it specifically envisions other embodiments wherein such CpGs are located within a plurality of DMRs of the present invention (or associated therewith, such as within about 2,000 bp—such as within 200 bp—5' or 3' thereof). Also as described herein, the determination of the presence or absence of (or response to therapy against) the cancer in said human individual (eg an ovarian cancer in a woman) may be enhanced if, in respect of such plurality DMRs, the methylation status of at least one (or more) CpGs of such DMRs is determined, especially those embodiments where in respect of each of such plurality of DMRs, the methylation status of a plurality of CpGs (such as two, three, four, five, six, seven, eight, nine, ten or more than ten, such as 11, 12, 13, 14 or 15, or between about four and about ten), and in particularly of the applicable relevant CpGs for a DMR, is determined.

Accordingly, in certain embodiments of the present invention, the methylation status at one or more CpGs (in particular, of the applicable relevant CpGs) located within a number of two, three, four, five, six, seven, eight, nine, ten or more than ten (such as 11, 12, 13, 14 or 15, or between about four and about ten) of said nucleotide sequences (in particular, within at least two, three or four nucleotide sequences) is determined; wherein, the presence in at least one of said (eg cell-free) DNA molecules of one or more (such as between about four and about ten): (i) methylated such CpGs (eg the relevant CpGs set out in TABLE 1C) located within one or more of said nucleotide sequences of the hyper-methylated DMRs (eg, those of TABLE 1A); and/or (ii) un-methylated such CpGs (eg the relevant CpGs set out in TABLE 1C) located within one or more of said nucleotide sequences of the hypo-methylated DMRs (eg, those of TABLE 1B), indicates the presence of, or a reduced response to therapy, against the cancer in said human individual (eg an ovarian cancer in said woman). In certain of such embodiments, one or more other CpGs within the nucleotide sequence(s) may be either methylated or un-methylated (or their methylation status undetermined), wherein said pattern of methylation can also indicate the presence of (or reduced response to therapy against) the cancer in said human individual (eg ovarian cancer in said woman). For example, one pattern of methylation that indicates the presence of (or reduced response to therapy against) the cancer in said human individual (eg ovarian cancer in said woman) may be for a hyper-methylated DMRs (eg, those of TABLE 1A) that all (or all but one, two or three) of the relevant CpGs set out in TABLE 1C for such DMR are methylated, and that all other CpGs are either methylated or un-methylated (or their methylation status is undetermined); ie that for DMR #228, a pattern of methylation of linked CpGs therein of "X111X111" indicates the presence of (or reduced response to therapy against) the cancer in said human individual (eg ovarian cancer in said woman) (where "1" represents the presence of a methylated CpG and "X" represents the presence of either a methylated or an un-methylated CpG; and the relative position of the non-relevant CpG for #228). In another example, one pattern of methylation that indicates the presence of (or reduced response to therapy against) the cancer in said human individual (eg ovarian cancer in said woman) may be for a hypo-methylated DMRs (eg, those of TABLE 1A) that all (or all but one, two or three) of the relevant CpGs set out in TABLE 1C for such DMR are un-methylated, and that all other CpGs are either methylated or un-methylated (or their methylation status is undetermined). In certain embodiments of the present invention, the pattern of methylation/un-methylation for a given DMR that is associated with the presence of (or reduced response to therapy against) the cancer in said human individual (eg ovarian cancer in said woman) is shown in Table 2B.

The present invention additionally provides for particularly advantageous nucleotide sequences associated with one or more CpGs (in particularly at least one of the applicable relevant CpGs), the methylation status of which is associated with the presence or absence of, or response to therapy against, a cancer in a human individual (eg an ovarian cancer in a woman). As described above, such nucleotide sequences include those selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226; in particular #141 and/or #204 and/or #228 and/or #144 and/or #154 and/or #158 and/or #186 and/or #188 and/or #202, such as preferably #141 and/or #204 and/or #228 (SEQ ID NOs: 1, 2 and 3, respectively), or in certain other embodiments a nucleotide sequence present within about 2,000 bp (such as within about 200 bp) 5' or 3' thereof, and alternatively, in each case, an allelic variant and/or a complementary sequence of any of said nucleotide sequences.

Accordingly, in a particular embodiment, the method of the present invention said nucleotide sequence(s) is/are #141 and/or #204 and/or #228 (SEQ ID NOs: 1, 2 and/or 3); for example, at least one of said nucleotide sequences is #141; or an allelic variant and/or complementary sequence of any of said nucleotide sequences. In an alternative embodiment, the method of the present invention said nucleotide sequence is #144 (SEQ ID NO 4), or an allelic variant and/or complementary sequence of any of said nucleotide sequences; which embodiment may also be include the determination of methylation status at CpGs (in particularly at the applicable relevant CpGs) located in one or more of the nucleotide sequence #141 and/or #204 and/or #228 and/or #144 (SEQ ID NOs: 1, 2 and/or 3 and/or 4). As set out elsewhere, also envisioned are embodiments where the CpGs are located in a nucleotide sequence present within about 2,000 bp (such as within about 200 bp) 5' or 3' of each or any of the respective DMRs. In particular of such embodiments, said nucleotide sequences and the relevant CpGs thereof are, respectively, those set out in TABLE 1D, or an allelic variant and/or complementary sequence of any of said nucleotide sequences.

TABLE 1D

Genomic sequences of the non-primer portion of particular DMRs of the present invention

| DMR# | Marker coordinates (hg19) | Marker genomic sequence (relevant CpGs are underlined)] | Genome coordinates (hg19) of the Cs for relevant CpGs | SEQ ID NO. |
|---|---|---|---|---|
| 141 | chr5:178004422-178004505 | CGCCACGGGAAGGAGGCACACGATTCAGCCCA TGACACCGCCACCTCGGCGTGGTGCTGTAGGG GGAAGCTCAGGCACTCACCG | chr5:178004422-178004442-178004460-178004468-178004471-178004504 | 156 |
| 204 | chr1:151810811-151810917 | CGCCGCGGGCCCCAGGCGCAGCACGCTCTCG CGCGTGGGCCGCAGCTGGCAGCACAGGAAGTC CAGGTGGAAGAGCGGCGGCGTGGGCGGCCCGG CGCGGCGCGGC | chr1:151810811-151810814-151810816-151810828-151810835-151810841-151810843-151810845-151810852-151810887-151810890-151810893-151810899-151810904-151810907-151810909 | 157 |

TABLE 1D-continued

Genomic sequences of the non-primer portion of particular DMRs of the present invention

| DMR# | Marker coordinates (hg19) | Marker genomic sequence (relevant CpGs are underlined)] | Genome coordinates (hg19) of the Cs for relevant CpGs | SEQ ID NO. |
|---|---|---|---|---|
| 228 | chr2:219736301-219736362 | CGGCTGCCAGGCGCCCCGCGGGCGGGCCCCTC CCCGGCCCTCCGGCCTGCCCGGCACCCCG | chr2:219736312-219736317-219736319-219736335-219736343-219736352-219736361 | 158 |
| 144 | chr19:58220438-58220517 | GGCGGCGTCGCCAAGGCTTAGACGCTTTCGTG CAGGAGGGACGACGACTCCCCTCACGCCTTCG TGGCCCCAACTCGGCG | chr19:58220440-58220443-58220446-58220460-58220466-58220479-58220482-58220494-58220500-58220513-58220516 | 159 |

As shown in the examples, a particularly useful test is provided by those embodiments of the present invention in which the methylation status may be determined at one or more CpGs associated with each of a plurality of the DMRs described herein. For example, more than one (such as two, three, four, five, six, seven, eight, nine or ten) of such nucleotides sequence may be investigated for the presence or absence of methylated CpGs located therein. In particular, where at least one methylated CpG (such as a plurality of methylated GpCs)—in particular of the respective relevant CpGs—is determined in any one of the plurality of such nucleotide sequences associated with a hyper-methylated DMR analysed (such as DMR #141, #204, #228 and/or #144), then a determination may be made that the cancer is present in said human individual (eg that the ovarian cancer is present in said woman), or that the cancer in a human individual (eg ovarian cancer in a woman) is not responding to (chemo)therapy. Alternatively, where at least one un-methylated CpG (such as a plurality of un-methylated GpCs)—in particular of the respective relevant CpGs—is determined in any one of the plurality of such nucleotide sequences associated with a hypo-methylated DMR analysed (such as those set forth in TABLE 1B), then a determination may be made that the cancer is present in said human individual (eg that the ovarian cancer is present in said woman), or that the cancer in said human individual (eg ovarian cancer in a woman) is not responding to (chemo) therapy. As will also be understood, the plurality of nucleotide sequences analysed for the presence or absence of methylated CpGs located therein may include at least one nucleotide sequence associated with a hyper-methylated DMR (such as those set forth in TABLE 1A, and in particular DMR #141, #204, #228 and/or #144 as set forth in TABLE 1D) and at least one nucleotide sequence associated with a hypo-methylated DMR (such as those set forth in TABLE 1B), wherein the determination of at least one methylated CpG (such as a plurality of methylated GpCs)—in particular of the respective relevant CpGs—located in said hyper-methylated DMR and/or the determination of at least one un-methylated CpG (such as a plurality of un-methylated GpCs)—in particular of the respective relevant CpGs—located in said hypo-methylated DMR may be used to determine that the cancer is present in said human individual (eg that the ovarian cancer is present in said woman), or that the cancer in a human individual (eg ovarian cancer in a woman) is not responding to (chemo)therapy.

Accordingly, in a particular embodiment of the method of the present invention the methylation status may be determined at one or more of said CpGs located within each of the nucleotide sequences so analysed; wherein, the presence in at least one of said (eg cell-free) DNA molecules of one or more: (i) methylated CpGs (in particular, the applicable relevant CpGs set forth in TABLE 1C) located within any one of said nucleotide sequences associated with the hyper-methylated DMRs (eg as set forth in TABLE 1A); and/or (ii) un-methylated CpGs (in particular, the applicable relevant CpGs set forth in TABLE 1C) located within one or more of said nucleotide sequences associated with the hypo-methylated DMRs (eg as set forth in TABLE 1B), indicates the presence of, or a reduced response to therapy against, a cancer in said human individual (eg an ovarian cancer in said woman). For example, the method includes embodiments where the methylation status of one or more CpGs (in particular, of the applicable relevant CpGs set forth in TABLE 1C) located in each of the nucleotide sequence #141 and #204 and #228 (SEQ ID NOs: 1, 2 and 3)—such as at least one (such as all) of such CpG in each of said sequences—is determined for at least one molecule of said (eg cell-free) DNA, and wherein the presence in at least one of said (eg cell-free) DNA molecules of one or more methylated CpGs located within any one of said nucleotide sequences (such as methylation at all GpCs, or all relevant CpGs, therein, or methylation at all but one, two or three of such GpCs) indicates the presence of, or a reduced response to therapy against, a cancer in said human individual (eg an ovarian cancer in said woman)). As another example, the method includes embodiments where the methylation status of one or more CpGs (in particular, of the applicable relevant CpGs set forth in TABLE 1C) located in each of the nucleotide sequence #228 and #144 (SEQ ID NOs: 3 and 4), and optionally also in one or more of the nucleotide sequences #204 and/or #141 (SEQ ID NOs: 2 and 1, preferably SEQ ID No 2)—such as at least one (such as all) of such CpG in each of said sequences—is determined for at least one molecule of said (eg cell-free) DNA, and wherein the presence in at least one of said (eg cell-free) DNA molecules of one or more methylated CpGs located within any one of said nucleotide sequences (such as methylation at all GpCs, or all relevant CpGs, therein, or methylation at all but one, two or three of such GpCs) indicates the presence of, or a reduced response to therapy against, a cancer in said human individual (eg an ovarian cancer in said woman). In particular of such embodiments, one or more (such as all) of said nucleotide sequences (and the applicable relevant CpGs) are, respectively, those set out in TABLE 1D, or an allelic variant and/or complementary sequence of any of said nucleotide sequences.

One particular feature described in the examples is the presence of patterns of methylation/un-methylation at CpGs associated with the same DMR, in particular at the relevant CpGs for such DMR. Such examples support the assertion that the investigation, analysis and/or determination of such patterns of methylation/un-methylation are particularly useful or advantageous tools for determining presence or absence of, or response to therapy against, a cancer in a human individual (eg an ovarian cancer in a woman). In particular, to provide tests that have a performance that enables them to be used in diagnostic settings; such as having a sensitivity and/or specificity as set out herein. The number of CpGs associated with a given DMR for which the methylation status is determined will depend on the length of nucleotide sequence analysed and the number of CpGs present therein. For a given nucleotide sequence associated with (such as within, or within about 2,000 bp—such as within about 200 bp—5' and/or 3' of) a DMR of the present invention, the number of CpGs for which the methylation status is determined can range from two or more (such as three, four and five, up to the maximum number of CpGs within such nucleotide sequence, and/or up to about nine, ten, 11, 12, 13, 14, 15, 18, about 20, about 25 or about 30. In particular embodiments, the methylation status is determined at a number of between about 5 and about 15 of said CpGs located within the nucleotide sequence(s), and in particular at such number of the relevant CpGs for the nucleotide sequence(s) (eg, as set forth in TABLE 1C). In certain embodiments of the present invention, the number of (eg relevant) CpGs for which the methylation status is determined the pattern of methylation/un-methylation for a given DMR that is associated with the presence of (or reduced response to therapy against) a cancer in said human individual (eg ovarian cancer in said woman) is show in Table 2B.

Accordingly, in certain methods of the present invention, the methylation status may be determined at a number of between about 2 and about 15 (for example, between about four and about ten, such as five, six, seven, eight or nine) of said CpGs (in particular of the relevant CpGs set forth in TABLE 1C) located within said nucleotide sequence(s)—in particular within the nucleotide sequence(s) selected from: #141, #204 and/or #228 (SEQ ID NOs: 1, 2 and/or 3) (or selected from: #228, #144, #204 and/or #141), or an allelic variant and/or complementary sequence thereof; wherein the presence in at least one of said (eg cell-free) DNA molecules of at least said number of methylated CpGs (in particular of methylated relevant CpGs set forth in TABLE 1C) located within any one of said nucleotide sequences indicates the presence of, or a reduced response to therapy against, a cancer in said human individual (eg an ovarian cancer in said woman).

In specific of such embodiments, the methylation status may be determined at about 7 CpGs (in particular, the 7 relevant CpGs) located within nucleotide sequence #141 (SEQ ID NO 1) and/or at about 16 CpGs (in particular, the 16 relevant CpGs) located within nucleotide sequence #204 (SEQ ID NO 2) and/or at about 7 CpGs (in particular, the 7 relevant CpGs) located within nucleotide sequence #228 (SEQ ID NO 3) and/or at about 11 CpGs (in particular, the 11 relevant CpGs) located within nucleotide sequence #144 (SEQ ID NO 4)—for example those CpGs (in particular, the applicable relevant CpGs) located within SEQ ID NOs: 156, 157, 158 and/or 159, respectively—or in each case an allelic variant and/or complementary sequence of any of said nucleotide sequences. In particular embodiments, the methylation status of all CpGs, or at least all of the relevant CpGs, in the given nucleotide sequence may be determined. In one embodiment, the presence of methylation at all of said CpGs in a given nucleotide sequence for the hyper-methylated DMRs #141, #204, #228 and/or #144 can indicate the presence of (or reduced response to therapy against) a cancer in said human individual (eg ovarian cancer in said woman). In other embodiments, the presence of methylation at all but one, two or three of said CpGs in one or more of said nucleotide sequence can indicate the presence of (or reduced response to therapy against) a cancer in said human individual (eg ovarian cancer in said woman). For example, all of the relevant CpGs for DMR #141, #204, #228 and/or #144 may be determined to be methylated, and one or more other CpGs therein they may be either methylated or un-methylated (or their methylation status undetermined), wherein said pattern of methylation can also indicate the presence of (or reduced response to therapy against) a cancer in said human individual (eg ovarian cancer in said woman). In certain embodiments of the present invention, the number of (eg relevant) CpGs for which the methylation status is determined the pattern of methylation/un-methylation for DMR #141, #204, #228 and/or #144 that is associated with the presence of (or reduced response to therapy against) a cancer in said human individual (eg ovarian cancer in said woman) is show in Table 2B.

As will now be apparent to the person of ordinary skill, and as shown in the examples within a clinical setting of ovarian cancer to be superior and/or complementary to a CA125 test (FIGS. 3E and 3F), one particular embodiment of the present invention is based on the analysis and determination of the methylation pattern of three sets of CpGs (in particular, of the applicable relevant CpGs), each set associated with the respective one or three DMRs: #141, #204 and #208 (or the two DMRs: #228 and #144, and optionally also either or both of the DMRs #204 and/or #141); wherein the presence of a (marker) methylation pattern in any one of said DMRs determines the presence or absence of, or response to therapy against, a cancer in a human individual (eg an ovarian cancer in a woman). Therefore, one specific embodiment of the method of the present invention includes where the methylation status is determined at about 7 CpGs (in particular, the 7 relevant CpGs) located within nucleotide sequence #141 (SEQ ID NO 1) and at about 16 CpGs (in particular, the 16 relevant CpGs) located within nucleotide sequence #204 (SEQ ID NO 2) and at about 7 CpGs (in particular, the 7 relevant CpGs)located within nucleotide sequence #228 (SEQ ID NO 3)—for example located within SEQ ID NOs: 156, 157 and/or 158, respectively (or where the methylation status is determined at about the 7 relevant CpGs located within nucleotide sequence #228 (SEQ ID NO 3) and at about the 11 relevant CpGs) located within nucleotide sequence #144 (SEQ ID NO 4), for example located within SEQ ID NOs: 158 and 159, respectively)—or in each case an allelic variant and/or complementary sequence of any of said nucleotide sequences; wherein, the presence in at least one of said (eg cell-free) DNA molecules of at least said number of methylated said CpGs (in particular, said relevant CpGs) located within any one of said nucleotide sequences indicates the presence of, or a reduced response to therapy against, a cancer in said human individual (eg an ovarian cancer in said woman). As described above, in certain of such embodiments other CpGs within such nucleotide sequence may (or may not) be analysed for their methylation status; and if their methylation status is determined then they such CpGs may be determined to be either methylated or un-methylated, and the presence of, or a reduced response to therapy against, a cancer (eg an ovarian cancer) may be determined in said human individual (eg said woman).

For one example of such embodiment, the determination of the presence of methylation (in at least one of said (eg cell-free) DNA molecules, such as more than 10, 20, 50, 100, 500 or 1000, or another number as set out below) at all 7 of the relevant CpGs located within nucleotide sequence #141 (SEQ ID NO 1) indicates the presence of, or a reduced response to therapy against, a cancer in said human individual (eg an ovarian cancer in said woman), regardless of the methylation status of any other CpG therein and/or regardless of the methylation status of CpGs located within nucleotide sequence #204 (SEQ ID NO 2) or nucleotide sequence #228 (SEQ ID NO 3) or nucleotide sequence #144 (SEQ ID NO 4). As a first alternative example of such embodiment, the determination of the presence of methylation (in at least one of said (eg cell-free) DNA molecules, such as more than 10, 20, 50, 100, 500 or 1000, or another number as set out below) at all 16 of the relevant CpGs located within nucleotide sequence #204 (SEQ ID NO 2) indicates the presence of, or a reduced response to therapy against, a cancer in said human individual (eg an ovarian cancer in said woman), regardless of the methylation status of any other CpG therein and/or regardless of the methylation status of CpGs located within nucleotide sequence #141 (SEQ ID NO 1) or nucleotide sequence #228 (SEQ ID NO 3) or nucleotide sequence #144 (SEQ ID NO 4). As a second alternative example of such embodiment, the determination of the presence of methylation (in at least one of said (eg cell-free) DNA molecules, such as more than 10, 20, 50, 100, 500 or 1000, or another number as set out below) at all 7 of the relevant CpGs located within nucleotide sequence #228 (SEQ ID NO 3) or nucleotide sequence #144 (SEQ ID NO 4) indicates the presence of, or a reduced response to therapy against, a cancer in said human individual (eg an ovarian cancer in said woman), regardless of the methylation status of any other CpG therein and/or regardless of the methylation status of CpGs located within nucleotide sequence #141 (SEQ ID NO 1) or nucleotide sequence #204 (SEQ ID NO 2). As will be now be appreciated, in an alternative embodiment, the presence of, or a reduced response to therapy against, a cancer in said human individual (eg an ovarian cancer in said woman) may be also indicated when the presence of methylation is determined at all of the relevant CpGs located within each of nucleotide sequences 141 (SEQ ID NO 1), #204 (SEQ ID NO 2) and #228 (SEQ ID NO 3) (or at all of the relevant CpGs located within each of nucleotide sequences #228 (SEQ ID NO 3) and 144 (SEQ ID NO 4), and optionally also, #204 (SEQ ID NO 2) and/or 141 (SEQ ID NO 1)). In such an alternative embodiment (and as described elsewhere herein), the number of (eg cell-free) DNA molecules in which any of such methylation patterns is determined may be less than if only one of such DMRs is found to have such a methylation pattern. In certain embodiments of the present invention, the number of (eg relevant) CpGs for which the methylation status is determined the pattern of methylation/un-methylation for DMR #141, #204, #228 and/or #144 that is associated with the presence of (or reduced response to therapy against) a cancer in said human individual (eg ovarian cancer in said woman) is show in Table 2B.

In any of the embodiments of the present invention, the biological sample can be further processed, such as comprising a step of isolating (eg cell-free) DNA therefrom. Such isolation can include particular steps of centrifugation (such as density gradient ultracentrifugation, Jonathan et al (2015), J Cancer Prey Curr Res 3:00064), treatment with ionic solutions and/or organic solvents to selectively solubilise/precipitate nucleic acids (such as cell-free DNA), addition of (cell-free DNA) selective binding and separation moieties (such as magnetic beads) and/or filtration or chromatographic steps; and in particular, steps of lysis of sample, absorption to a silica membrane (or column or beads), removal of residual contaminates and/or election of pure nucleic acids, such as cell-free DNA. Other methods of cfDNA isolation can include rapid electrokinetic isolation directly from blood (Sonnenberg et al (2014), Clin Chem 60:500).

Figure 5:
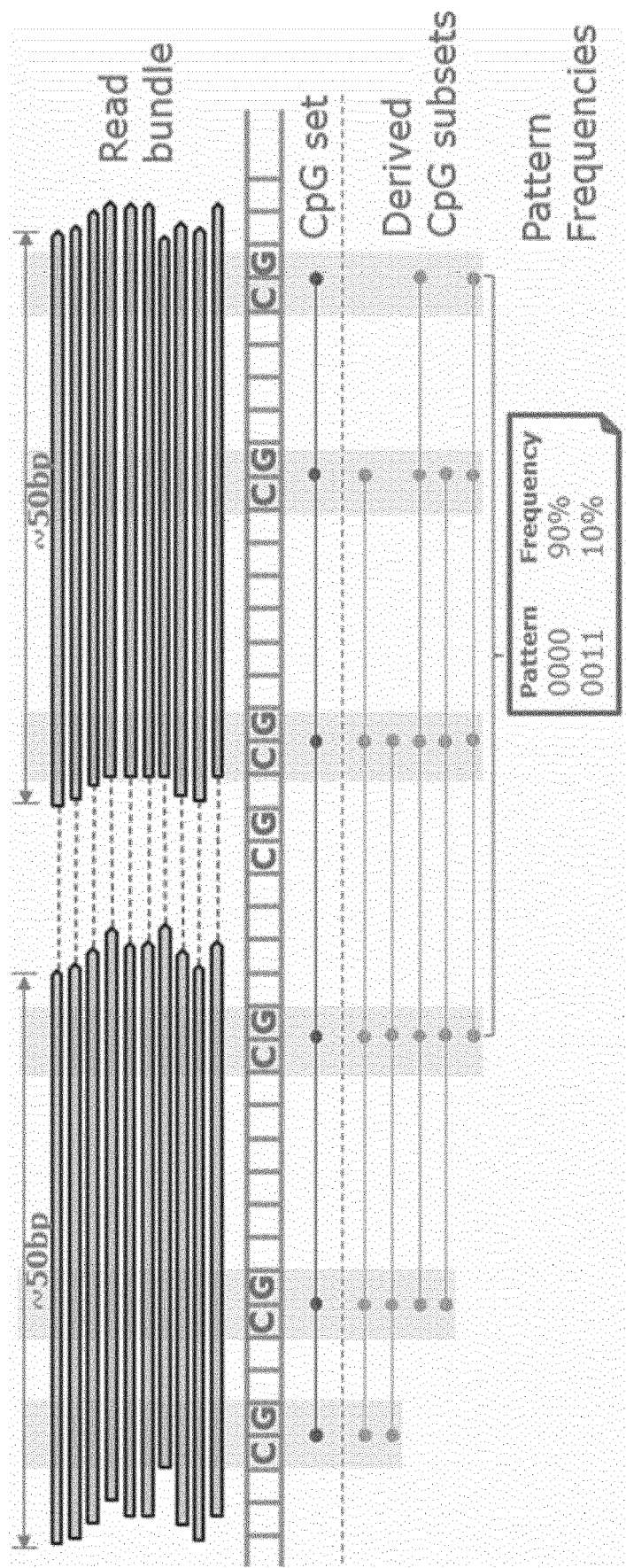

In certain of such embodiments, the biological sample (such as plasma or serum) may be processed to isolate (eg cell-free) DNA generally according to a process as set out in FIG. 5. For example:

Lysing Samples:

Free-circulating nucleic acids in biological fluids are usually bound to proteins or enveloped in vesicles, which may utilise an efficient lysis step in order to release nucleic acids for selective binding to the column (or to Solid Phase Reversible Immobilisation—SPRI—[paramagnetic] beads). Hence, samples may be lysed under highly denaturing conditions at elevated temperatures in the presence of proteinase K and appropriate buffer, such as Buffer ACL from Qiagen (cat. no. 19076), which together provide for inactivation of DNases and RNases and complete release of nucleic acids from bound proteins, lipids, and vesicles.

Adsorption to a Silica Membrane:

Binding conditions can be adjusted by adding an appropriate buffer, such as Buffer ACB (Qiagen) to allow binding of the circulating nucleic acids to the silica membrane. Lysates may then then be transferred onto a separation column (such as the QIAamp Mini column, Qiagen), and circulating nucleic acids adsorbed from a large volume onto the small silica membrane as the lysate is drawn through by vacuum pressure. Appropriate salt and pH conditions can ensure that proteins and other contaminants, which can inhibit PCR and other downstream enzymatic reactions, are not retained on the separation column. A vacuum manifold (e.g., the QIAvac 24 Plus with the QIAvac Connecting System) and a vacuum pump capable of producing a vacuum of −800 to −900 mbar (e.g., QIAGEN Vacuum Pump) may be used for the protocol. A vacuum regulator can be used for easy monitoring of vacuum pressures and convenient vacuum release.

Removal of Residual Contaminants:

Nucleic acids remain bound to the membrane, while contaminants can be efficiently washed away during a plurality of wash steps, such as 2 or 3 wash steps. In a single step, highly pure circulating nucleic acids can be eluted in an appropriate buffer (such as in Buffer AVE, Qiagen), equilibrated to room temperature.

Elution of Pure Nucleic Acids:

Elution can be performed using Buffer AVE. The elution volume may be 50 ul (or greater, such as 100 ul or 150 ul). If higher nucleic acid concentrations are required, the elution volume can be reduced, such as by using 20 ul (or 50 ul). Low elution volume leads to highly concentrated nucleic acid eluates. For downstream applications that use small starting volumes (e.g., some PCR and RT-PCR assays), a more concentrated eluate may increase assay sensitivity. For downstream applications that use a larger starting volume, the elution volume can be increased up to 150 ul. However, an increase in elution volume can decrease the concentration of nucleic acids in the eluate. Eluted nucleic acids can collected in 1.5 ml microcentrifuge tubes or in microtitre plates. If the purified circulating nucleic acids are to be stored for up to 24 hours, they can be stored at 2-8° C.; and/or for storage longer than 24 hours at −15 to −30° C.

In certain embodiments of the present invention, the (eg cell-free) DNA may be subjected to an agent that differentially modifies said DNA based on the methylation status of one or more of the CpGs. Such a modification can facilitate the detection of differences in the methylation status. However, as described elsewhere herein, methods are available to detect differences in the methylation status of CpGs without use of such a modifying agent.

Accordingly, the present invention also includes those embodiments of the method that include a step of treating said DNA with an agent that differentially modifies said DNA based on the methylation status of one or more CpGs located within. Such agents will be known to the person of ordinary skill and include the use of one or more methylation sensitive restriction enzyme and/or of a bisulphite-based reaction. The use of bisulphite or methylation-sensitive restriction enzymes to study differential methylation will be well known to the person of ordinary skill, who may apply teachings of standard texts or adaptation of published methods such as Poon et al (2002), Nygren et al (2010) or Yegnasubramanian et al (2006, Nuc Acid Res 34:e19).

A methylation sensitive is a restriction enzyme that is sensitive to the DNA methylation states. Cleavage of such a restriction enzyme's recognition sequence may be blocked, or impaired, when a particular base in the enzyme's recognition site is modified, eg methylated. In particular embodiments of all aspects of the invention, the agent comprises a methylation-sensitive restriction enzyme, such as a methylation-sensitive restriction enzyme disclosed herein; including such embodiments that comprise two, three, four, five or more of such methylation-sensitive restriction enzymes. In particular embodiments, the reagent agent comprises: at least one methylation sensitive enzyme; at least one methylation sensitive restriction enzyme; and/or an agent selected from the group consisting of: AatII, AciI, AclI, AfeI, AgeI, AgeI-HF, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, Kasl, MluI, NaeI, NarI, NgoMIV, NotI, NotI-HF, NruI, Nt.BsmAI, Nt.CviPII, PaeR7I, PluTI, PmlI, PvuI, PvuI-HF, RsrII, SacII, SalI, SalI-HF, SfoI, SgrAI, SmaI, SnaBI, TspMI and ZraI. In particular embodiments, said reagent is one selected from the group consisting of: BstUI, HhaI and HpaII.

Treatment of DNA with an agent comprising bisulphite (bisulfite) converts un-methylated cytosine residues to uracil, but leaves 5-methylcytosine residues unaffected. Thus, bisulphite treatment introduces specific changes in the DNA sequence that depend on the methylation status of individual cytosine residues, yielding single nucleotide resolution information about the methylation status of a segment of DNA. Various analyses can be performed on the altered sequence to retrieve this information, including the use of PCR primers and/or probes and/or sequencing that can distinguish between such singe-nucleotide changes. As described above, other agents that may uses in methods to determine methylation at CpGs include oxidative bisulphite (eg for analysis of 5hmC).

Bisulphite modification may be conducted using eg the EZ-96 DNA methylation kit (Zymo Research), and/or may include the steps of adding an effective amount of a bisulphite reagent to each sample, and incubating (eg in the dark) at about 50° C. for 12-16 hours (e.g., using a thermal cycler). After such incubation, prior to analysis, a step of incubating the sample at 0-4° C. (e.g., on ice or using a thermal cycler) for 10 minutes may be included.

In particular embodiments of the present invention, said agent may be bisulphite and said determining step may comprise the detection of at least one bisulphite-converted cytosine (such as one in a CpG) within one or more of the nucleotide sequences selected from the group consisting of a sequence produced or producible following bisulphite conversion of a sequence comprised within a DMR selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226; such as a sequence consisting of at least about 10 contiguous bases (preferably at least about 15 contiguous bases for any SEQ ID other than SEQ ID NO: 58) comprised in a sequence selected from the group consisting of SEQ ID NOs (see TABLE 2A): 32, 33, 34, 35, 36, 37, 38, 39, 40, 41, 42, 43, 44, 45, 46, 47, 48, 49, 50, 51, 52, 53, 54, 55, 56, 57, 58, 59, 60, 61 and 62 (such as SEQ ID NO: 32, 33, 34 and/or 35, or in particular of SEQ ID NOs: 32 and 33 and 34, optionally also 35), or an allelic variant and/or complementary sequence of any of said nucleotide sequences. In particular embodiments, said number of contiguous bases is at least about 16, 18, 20, 22, 24, 26, 28, 30, 35, 40, 45, 50, 55, 60, 65, 70, 75, 80, 85, 90, 95, 100, 110, 120, 10, 140, 150 or 160 bases, such as between about 80 and about 160, such as between about 100 and about 160, in each case, independently, up to the maximum number of bases within the sequence selected from said group; wherein one or more of the bases identified by "Y" therein is a U or T (in particular, of a C within a CpG, such as of a relevant CpG of a hypo-methylated DMR) and, preferably, where one or more of another of the bases identified by "Y" therein is a C (in particular, of a C within a CpG, such as of a relevant CpG of a hyper-methylated DMR), or an allelic variant and/or complementary sequence of any of said nucleotide sequences. In particular embodiments, two, three, four, five, six, seven, eight, nine, ten or more than ten of the bases identified by "Y" therein is a U or T (preferably T), such as all of the bases identified by "Y" therein is a U or T (preferably T), or all but one, two, three, four, five, six, seven, eight, nine, ten or more than ten of the bases identified by "Y" therein is a U or T (preferably T), in particular where such other one, two, three, four, five, six, seven, eight, nine, ten or more than ten of the bases identified by another "Y" is a C within a CpG, such as of a relevant CpG of a hyper-methylated DMR).

In particular of such embodiments, the method of the present invention may also include those wherein said agent is bisulphite and said determining step comprises the detection of at least one (non-natural) bisulphite-converted cytosine within a nucleotide sequence having a length of at least about 15 bp comprised in a bisulphite conversion of a sequence comprised within DMR #141 and/or #204 and/or #228 and/or #144 (SEQ ID NOs: 32, 33 and/or 34 and/or 25, respectively), wherein one or more of the bases identified by "Y" therein is a U or T and, preferably, where one or more of the bases identified by "Y" (in particular, those within a CpG, such as one or more (or all) of a relevant CpG) therein is a C, or an allelic variant and/or complementary sequence of any of said nucleotide sequences. Such a nucleotide sequence may be at least about 16 bp, 18 bp, 20 bp, 25 bp, 30 bp, 35 bp, 40 bp, 45 bp, 50 bp, 55 bp, 60 bp or 70 bp, for example up to about 90 bp, 100 bp or 150 bp, such as between about 100 bp and about 160 bp.

In particular embodiments, the sequence detected may be one comprised in a bisulphite conversion of a sequence comprised within DMR #141 and/or #204 and/or #228 and/or #144 (SEQ ID NOs: 32, 33, 34 and/or 35, respectively), such as SEQ ID NOs: 32 or 33 or 34, (or SEQ ID NOs: 34 and 35) wherein all (or all but one, two, three, four or five) of the cytosines of CpGs located (in particular of the relevant CpG) in the analysed sequence are detected as a C (ie, such cytosines are determined to be methylated) and all other cytosines located in the analysed sequence (in particular, the cytosines not of a CpG therein) are detected a U or T (ie, such other cytosines/CpGs are determined to be un-methylated).

As will now be apparent, such a detected BS converted sequence will be a non-natural sequence, as any un-methylated cytosine (such as one outside a CpG) will have been converted to U by the bisulphite treatment, and detected as either a U or a T.

In other certain embodiments of the present invention, the methylation status of the one or more the CpGs present in the (eg cell-free) DNA may be determined without use of an agent that differentially modifies said DNA based on such methylation. For example, single molecule sequencing/analysis of DNA may be used to determine such methylation status. Examples of such technologies include those utilised in the: (1) PacBio instruments (Pacific Biosciences) that use Single Molecule, Real-Time (SMRT) sequencing, based on zero-mode waveguides (ZMWs) and phospholinked nucleotides. ZMWs allow light to illuminate only the bottom of a well in which a DNA polymerase/template complex is immobilized. Phospholinked nucleotides allow observation of the immobilized complex as the DNA polymerase produces a completely natural DNA strand. Such instruments can be used for the direct detection of epigenetic modifications (Mol Genetics & Genomics, 2016; 291:1491); and (2) Nanopore instruments (Oxford Nanopore) that use nanopored membranes to detect variations in current flow, characteristic to the base/modified-base, as single strands of DNA pass through such nanopore (Nature 467:190). Accordingly, in certain embodiments of the present invention the methylation status at said one or more CpGs is determined using single molecule DNA sequencing or analysis, such as by SMRT or nanopore sequencing.

Analysis of the (eg cell-free) DNA present or isolated from the biological sample may, in some embodiments, be subjected to an amplification process, for example prior to or as part of the step of determining the methylation status of the one or more CpGs associated with the DMR.

Accordingly, certain embodiments of the present invention may include a method that also comprises a step of amplifying one or more regions of said (eg cell-free) DNA to produce DNA prior to or as part of said determining step, and preferably after any optional step of treating with said agent. If more than one region of (eg cell-free) DNA is to be amplified, this may occur as a multiplex or pool (eg, conducted in a single mixed reaction), or each region may be amplified separately and/or individually, with the possibility that such independent amplified regions are subsequently mixed or pooled so enable pooled and/or multiplex analysis thereon. As will be apparent, any regions of DNA so amplified, in particular those amplified in in-vitro processes, will be synthetic (of in-vitro produced) DNA molecules.

Amplification of regions of (eg cell-free) DNA may occur by any suitable method, including polymerase chain reaction (PCR) and rolling circle amplification. Those embodiments of the present invention that comprise PCR amplification can further comprises specific steps that are related to the practice of PCR, such as any of those described herein, or in particular the steps of: (A) providing a reaction mixture comprising a double-stranded target DNA, a pair of primers (for example, a pair of primers disclosed herein) designed to amplify a region of such DNA (such as a DMR as described herein) wherein the first primer is complementary to a sequence on the first strand of the target DNA and the second primer is complementary to a sequence on the second strand of the target DNA, Taq polymerase, and a plurality of free nucleotides comprising adenine, thymine, cytosine and guanine; (B) heating the reaction mixture to a first predetermined temperature for a first predetermined time to separate the strands of the target DNA from each other; (C) cooling the reaction mixture to a second predetermined temperature for a second predetermined time under conditions to allow the first and second primers to hybridise with their complementary sequences on the first and second strands of the target DNA, and to allow the Taq polymerase to extend the primers; and (D) repeating steps (B) and (C) at least 20 times. The person of ordinary skill will readily be able to design such PCR primers for use in the method of the invention, for example by use of primer design algorithms and programs such as Clone Manager Professional 9 (Sci-Ed Software), Vector NTI (Life Technologies), or web-based tools such as those found from www.ncbi.nlm.nih.gov/tools/primer-blast/or molbiol-tools.ca/PCR.htm.

In embodiments utilising amplification of regions of (eg cell-free) DNA, include those wherein said amplified region(s) comprises at least one of the nucleotide sequences to be analysed for the methylation status of one or more CpGs; such as the methylation status at a plurality of CpGs (in particular of the relevant CpGs) associated in any of DMRs of the present invention; in particular DMR #141, #204 and/or #228 (or DMR #228, #144, #204 and/or #141).

Any amplified region may also comprise other sequences, such as (non-natural) synthetic sequences that are used to identify the source (eg sample/woman) and/or the reaction. Such "molecular barcoding" is art-known.

In particular embodiments, said amplification may comprise the use of the primer-pair(s) for the respective nucleotide sequence(s) as independently selected from the group of primer-pairs set forth in each row of TABLE 3. For example, for that embodiment of the present invention utilising the DMRs #141, #204 and #228 (or DMR #228 and #144, and optionally also #204 and/or #141), the applicable regions of (eg cell-free) DNA may be amplified with the primers comprising (eg, consisting of) the sequences set forth in SEQ ID NOs 94 and 125; 95 and 126; and 96 and 127, respectively (or 97 and 128 for DMR #144). In particular embodiments, for any of said primers comprising a Y, such primer may be a mixture of (degenerate) primers wherein the base at each Y is either a C or a T; and for those of said primers comprising a R, such primer may be a mixture of (degenerate) primers wherein the base at each R is either a G or an A.

Analysis of the methylation status of the CpGs within the nucleotide sequence of interests (such as associated with or located within a DMR of the present invention) can be conducted by any suitable methodology. For example, the present invention includes those method wherein the methylation status of said CpGs is determined by a technology selected from the group consisting of: methylation specific PCR/MethylLight (eg, via use of real-time quantitative PCR), Epityper, nucleic acid chip-hybridisation, nucleic acid mass-spectrometry, xMAP (Luminex) Methylated DNA immunoprecipitation (MeDIP, in which methylated DNA fragments are isolated/enriched via an antibody raised against 5-methylcytosine (5mC)), Raindance (and other droplet digital PCR methodology—ddPCR) and nucleic acid sequencing, preferably, (single) strand sequencing, nanopore sequencing, bisulphite sequencing, such as targeted bisulphite sequencing. Sequencing (such targeted bisulphite sequencing) may be conducted to enable ultra-high coverage. Also envisioned are embodiments wherein said determination step may be conducted as a pool and/or essentially simultaneously when in respect of two, three, four or more of said nucleotide sequences. As described above, the present in invention include embodiments where the methylation status at said one or more CpGs may be determined using single molecule DNA sequencing or analysis, such as by SMRT or nanopore sequencing.

It will be apparent to the person of ordinary skill that bisulphite-modified DNA methylation sites may be detected using eg methylation-specific PCR (such as using primers and/or probes that selectively bind to the bisulphite-modified sequences) and/or by the subsequent use of restriction enzymes the recognition site of which is created upon such bisulphite-modification. Methylation-specific PCR ("MSP") is described by Herman et al (U56200756, EP0954608 and related family members); and a further development of MSP using probe-based PCR (known as "MethylLight") is described by Laird et al (U56331393, EP1185695 and related family members).

Alternative methods of detecting differences in sequences that have been converted by bisulphite-modification include mass-spectrometry methodologies (eg MASS-Array of Sequenom) or bead-chip technologies such as the Infinium MethylationEPIC Array or Infinium HumanMethylation450 BeadChip technologies of Illumina.

In certain of said embodiments, the methylation status of said CpGs may be determined by bisulphite sequencing, such as by single-read and/or high coverage bisulphite sequencing, such as described in the examples.

As described in the example, one advantage of the present invention is that the analysis of cancer-specific DNAme patterns from tDNA (eg ctDNA) is that a greater dynamic range can be achieved than with alternative tests, such as CA125 for OC. The dynamic range desired for such a DNAme pattern-based test for a cancer (eg ovarian cancer) is related to the number of molecules of said (eg cell-free) DNA (and/or amplified DNA) that are analysed in the method. For example, the more such molecules are investigated for the presence (or absence) of the cancer-specific epigenetic markers, the greater the dynamic range can be achieved; such as the detection of cancer-specific markers in very rarely found tDNA (eg ctDNA) molecules present in the total DNA (or cfDNA, as applicable) of the human individual.

Accordingly, in certain embodiments, the method of the present invention includes those when the methylation status of said CpG(s) is determined in multiple molecules of said (eg cell-free) DNA and/or amplified DNA representing each of said nucleotide sequences.

As will be appreciated, the detection of more than one molecule carrying the cancer-specific DNAme marker would increase the confidence in the determination of the presence of (or reduced response to therapy against) the cancer (eg ovarian cancer) that has been returned by the test. Accordingly, in particular of such embodiments, the method can include where the presence in at least a plurality of said (eg cell-free) DNA molecules of one or more methylated or methylated (as applicable) CpGs located (in particular, the relevant CpGs) within one or more of said nucleotide sequences indicates the presence of, or a reduced response to therapy against, a cancer in said human individual (eg an ovarian cancer in said woman). In such embodiments, the plurality of (eg cell-free) DNA molecules with one or more of said methylated or methylated (as applicable) CpGs located may be a number that is at least 2, 3, 4, 5, 6, 7, 18, 9 or 10, or at least about 15, 20, 25, 30, 35, 40, 45, 50, 55, 60, 70, 80, 90, 100, 125, 150, 175 or 200, or a greater number such as greater than about 500, 1,000, 5,000, 7,500, 1,000, 2,500, 5,000 or greater than 5,000 molecules.

To achieve the desired performance characteristics of the test (such as in terms of sensitivity, specificity and/or dynamic range), a greater number of total (eg cell-free) DNA molecules may need to be analysed than the number of those exhibiting the cancer-specific DNAme marker (ie, one or more methylated or un-methylated—as applicable—CpGs). For example, in particular embodiments of the present invention, the methylation status of said CpG(s) is determined in a number of molecules of said (eg cell-free) DNA and/or amplified DNA representing each of said nucleotide sequences selected from the group consisting of at least about: 1,000, 5,000, 10,000, 50,000, 100,000, 200,000, 500,000, 1,000,000, 1,500,000, 2,000,000, 2,500,000, 3,000,000, 3,500,000, 4,000,000 and 5,000,000 molecules, or more than 5,000,000 molecules.

The total number of DNA molecules to be analysed and/or that number of which, when exhibiting the cancer-specific DNAme marker, determines the presence of (or reduced response to therapy against) a cancer (eg ovarian cancer), can differ from test to test, sample to sample, woman to woman, man to man or population to population. For example, particular such numbers may apply when the human individual (eg woman) carries a typical amount of or proportion of tDNA (eg ctDNA) and total DNA (eg cfDNA), and another when she/he, or the sample obtained from her/him, is atypical in response of total/tDNA (eg total/ctDNA) quality or amount/ratio.

Accordingly, the method of the present invention includes those embodiments wherein a fraction or ratio of, or an absolute number of, (eg cell-free) DNA molecules in said sample having said methylated or un-methylated (as applicable) CpG(s) located within said nucleotide sequence(s) is estimated. To aid the process of determining the presence or absence of, or response to therapy against, a cancer in a human individual (eg an ovarian cancer in a woman), the present invention also includes certain embodiments comprising a step of comparing said fraction or ratio with a standard or cut-off value. For example, if the measured fraction or ratio is greater than such standard or cut-off value, then the test is interpreted to indicate the presence of a cancer in said human individual (eg an ovarian cancer in said woman); or it is interpreted to indicate a reduced response to a therapy against a cancer in said human individual (eg an ovarian cancer in said woman), such as persistence of the cancer (eg OC) or no response of such cancer (eg OC to such therapy). Exemplary standard or cut-off values for such fraction or ratio of cancer-specific patterns/markers for certain of the DMRs of the present invention include about 0.0008 for DMR #141 and/or about 0.00003 for DMR #204 and/or about 0.00001 for DMR #228.

As described above, improved performance of the test of the present invention is achieved by various means; including by the analysis of the methylation status of multiple CpGs (eg a particular DNAme marker pattern) associated with multiple DMRs and/or the analysis of multiple (eg cell-free) DNA molecules for such multiple CpGs at such multiple DMRs. Hence, an excess over a standard or cut-off value for the number of DNAme marker patterns found at any of the multiple DMRs can be a particularly advantageous embodiment for the test of the present invention. Accordingly, the test of the present invention includes those particular embodiments wherein a fraction or ratio of (eg cell-free) DNA molecules with said methylated or un-methylated (as applicable) CpG(s) present in each of said nucleotide sequence(s) is estimated and compared to a respective standard or cut-off value; wherein any one of such fraction or ratios being greater than its respective standard or cut-off value indicates the presence of, or a reduced response to therapy against, a cancer in said human individual (eg an ovarian cancer in said woman). For example, if the methylation status of CpGs located in each of DMRs #141 and #208 and #228 is determined in a test of the present invention, and the fraction or ratios of a SEQ ID No 63 at DMR #141 is greater than about 0.0008 or the fraction or ratios of a SEQ ID No 64 at DMR #204 is greater than about 0.00003 or the fraction or ratios of a SEQ ID No 65 at DMR #228 is greater than about 0.00001, then the presence of (or reduced response to therapy again) the cancer is determined for the human individual (eg ovarian cancer is determined for the woman). Alternatively, the use of multiple DMRs would enable a decision rule to be applied that takes into account the multiple DMRs by using a different cut-off for some markers depending on how many markers are positive for existing cut-off values in a single sample. Generally, for example, lower individual cut-offs can be applied the more DMRs that are found to give a positive result. Another example could be to define a "hyperplane" of cut-off values in N-dimensional space (N=number of markers measured), and for any combination of marker values, it can be determined if they fall "below" (=positive) or "above" (=negative) the hyperplane. Finally, a logistic regression model could be applied that determines, for any combination of marker values, the likelihood of the outcome to be positive. Accordingly, the invention also includes embodiments that may incorporate such analysis approaches when two or more of the DMRs of the invention are utilised.

As described herein, the present invention also provides advantages in that the standard or cut-off value used in respect of a particular DNAme marker can be adapted, for example in response to desired characteristics of the test or in response to the characteristics of the cfDNA isolated of the human individual (eg the woman).

Accordingly, certain embodiments of the test of the present invention include those where said standard or cut-off value(s) is/are modified for a given sample based on one or more of the following factors: (i) the amount or concentration of total (eg cell-free) DNA present in said sample; and/or (ii) a baseline value of said fraction or ratio previously determined for said woman; and/or; (iii) a value of said fraction or ratio determined from multiple samples from a population of women representative of said woman; and/or (iv) the specificity and/or sensitivity and/or dynamic range desired for said method of determination. In particular embodiments applied to cfDNA, said standard or cut-off value(s) may be increased when cfDNA blood collection tubes such as Streck Tubes, are used. For example, in such embodiments, the applicable said standard or cut-off value(s) may be increased by a factor of about 2, 5, 10, 20, 50, 100, 200, 500 or 1000, or by a factor that is greater than 1000.

In particular of such embodiments, the standard or cut-off value may be reduced for a given sample that has an amount and/or concentration and/or quality of total (eg cell-free) DNA present in said sample that is greater than a standard or cut-off value. Suitable methods for the inspection, estimation or determination of amount and/or concentration and/or quality of total (eg cell-free) DNA include those described elsewhere herein. For example, if the quality of the total DNA (eg cfDNA) of the human individual is lower than expected (such as a higher average fragment size than as described herein), and/or if the total DNA (eg cfDNA) amount is higher (in each case indicating that somatic DNA may have been released from eg WBCs during sample collection, transport, storage and/or processing), then the standard or cut-off value used for the respective fraction or ration for the DNAme marker can be reduced. This allows for more possibility to adapt the test to the individual situation or woman (or man) taking the test.

As a further embodiment of the test, it may be practiced multiple times on a given woman or man, such as 2, 3, 4, 5, 6, 7, 8, 9, 10, about 15, about 20 or more than about 20 times (such as about 50 times). Such a repeated test can enhance the (early) detection of a cancer in the human individual (eg ovarian cancer in the woman) and/or the long-term response to therapy against (or monitoring of) the cancer (eg ovarian cancer). Accordingly, the test may include those embodiments when it is practiced on multiple samples; wherein each sample is collected from the same woman or man at different time points. For example, said multiple samples are collected from said woman or man with an interval between them selected from the group consisting of about: 2 days, 3 days, 4 days, 5 days, 7 days, 10, days, 14 days, 21 days, 24 days, 3 weeks, 4 weeks, 5 weeks, 6 weeks, 6, weeks, 8 weeks, 3 months, 4 months, 5 months, 6 months, 8 months, 12 months, 18 months, 2 years, 3 years and 5 years.

In certain of such embodiments, it may be that the test of the present invention is conducted as part of a routine screen of one or more women or men, such as part of an annual screen for the presence or absence of a cancer (eg ovarian cancer for women). For certain women or men (or groups thereof), the period of repeat testing may be shorter. For example, women in high risk groups for OC or breast cancer (such as those with BRAC 1/2 positive/and/or a family history of ovarian cancer and/or belonging to certain subpopulations eg Ashkenazi women) may be tested more frequently, for example every 6, 3, 2, or 1 month. Furthermore, those women or men for which a cancer (eg ovarian cancer for a woman) has already been diagnosed (and perhaps already treated with chemotherapy) may be repeat-tested using the present invention at a frequency of about every 6, 3, 2, 1 month, or even more frequently such as once about every two weeks or about every week.

As has been shown for the CA125-based ROCA test for OC, a deviation or change from an earlier patient-specific standard or cut-off value can provide a further enhanced test for a cancer (eg ovarian cancer). Accordingly, for those embodiments of the present invention where a woman is tested multiple times, the presence of, or a reduced response to therapy against, a cancer in a human individual (eg an ovarian cancer in a woman) is indicated by—in comparison to a previous sample of said woman or man—the presence of, or an increase in the absolute number of, or an increase in the fraction or ratio of, (eg cell-free) DNA molecules in said sample having said methylated or un-methylated (as applicable) CpG(s) located within said nucleotide sequence(s).

As shown by the examples herein, the test of the present invention can be used in combination with other tests for cancer (eg ovarian cancer), in particular with those which reduced (or no) overlap of false positives and/or false negatives to the test of the present invention. Exemplary such tests for eg OC, including those based on CA-125, HE4, transthyretin, apolipoprotein A1, beta-2-microglobin and transferrin (such as ROCA, ROMA and OVA1) are described in more detail elsewhere herein.

Accordingly, in certain embodiments of the present invention, one or more additional steps may be conducted in respect of such other tests for ovarian cancer. In particular, one optional an additional step may comprise that of determining (eg by an in-vitro procedure), from a blood sample from said woman human individual, the amount present therein of one or more proteins independently selected from the group consisting of: CA-125, HE4, transthyretin, apolipoprotein A1, beta-2-microglobin and transferrin; wherein, either or both of: (i) the presence in at least one of said (eg cell-free) DNA molecules of one or more methylated or un-methylated (as applicable) CpGs located within one or more of said nucleotide sequences (such as by an excess of any one of the DNAme marker patterns of the present invention being in excess of a standard or cut-off value); or (ii) an amount of said protein(s) present in said blood sample is greater than a standard or cut-off value for such amount or protein; indicates the presence of, or a reduced response to therapy against, an ovarian cancer in said woman. As will be appreciated, such additional step related to the other test for the cancer (eg ovarian cancer) may be conducted either before or after conducting the DNAme-based aspects of the test. Indeed, the conduct of one (or other) of the tests may be dependent on the outcome of the first, for example to provide additional sensitivity and/or sensitivity to the other all determination, test or diagnosis.

In such embodiments for OC, the protein may be determined by a ROCA, a ROMA and/or an OVA1 diagnostic test.

As described elsewhere herein, the test of the present invention may be applied to different types of the cancer (eg ovarian cancer). For example, in certain embodiments the present invention applied to OC, the ovarian cancer may be an invasive ovarian cancer, such as an invasive epithelial ovarian cancer; in particular one selected from the group consisting of: high grade serious (HGS), endometroid, cell-cell and mucinous ovarian cancers. In alternative embodiments, the cancer may be peritoneal cancer or Fallopian tube cancer.

In particular, the test of the present invention may be used (or useful) for distinguishing the presence of ovarian cancer (such as one described elsewhere herein) from the presence of a benign pelvic mass in a woman.

In other embodiments, the test of the present invention may be used (or useful) for determining the response of a human individual (eg a woman) suffering from a cancer (eg ovarian cancer) to a therapy comprising chemotherapeutic agent(s) against said cancer (eg ovarian cancer) (such as one described elsewhere herein). For example, such a test may be conducted to predict the risk of death of said woman or man, in particular from risk of death by the cancer (eg ovarian cancer for a woman) that is not responding to (chemo)therapy.

In certain of such embodiments, the test of the present invention may be practiced on said woman or man after one, two, three, four and/or five cycles of said (chemo)therapy.

And in further such embodiments, said sample may be obtained from said woman or man within a period after completion of said cycle or (chemo)therapy that is selected from the group consisting of about: 2 hours, 4 hours, 6 hours, 12 hours, 18 hours, 24 hours, 36 hours, 48 hours, 3 days, 4 days, 5 days, 6, days, 7 days, 8 days, 10 days, 12 days, 14 days, 16, days, 18 days, 21 days, 24 days, 4 weeks, 5 weeks, 6 weeks, and 8 weeks.

In particular such embodiments, it may be that a short-lived increase in the ratio or fraction of the DNAme marker is observed shortly after said (chemo)therapy. Without being bound by theory, this may arise due to death/lysis of cancer cells in response to the (chemo)therapy and their shedding of ctDNA into the blood stream of the woman or man. Accordingly, the test of the present invention may include the monitoring of such short lived (eg for 1, 2, 3, 5, 7, or 14 days) increase in DNAme marker(s) as an indication of (initial) response/success of the (chemo)therapy. The test may then be repeated to monitor the reduction of the DNAme marker(s) in cfDNA after such increases, and whether the ratio or fraction of the DNAme marker increases at a later time (indicating a reduced response to therapy against, and/or the recurrence of, the cancer (eg ovarian cancer).

In such embodiments of the present invention, said therapy includes one or more chemotherapeutic agent(s), such as those one that is used and/or is approved (eg, by the European Medicines Agency in Europe and/or by the Food and Drug Administration in the US) for the treatment of a cancer, in particular for the treatment of a cancer analysed herein (eg ovarian cancer). In alternative such embodiments, the chemotherapeutic agent may be one in development on the date hereof, or in the future. Examples of such chemotherapeutic agent include one or more independently selected from the group consisting of: a platinum-based antineoplastic (such as carboplatin, cisplatin, oxaliplatin, nedplatin, picoplatin or satraplatin) and a taxane (such paclitaxel or docetaxel). In particular, the chemotherapeutic agent may be one selected from the group consisting of: carboplatin, paclitaxel, docetaxel, cisplatin, liposomal doxorubicin, gemcita bine, tra bectedin, etoposide, cyclophospha mide an a ngiogenesis inhibitor (such as bevacizumab) and a PARP inhibitor (such as olaparib). Other PARP inhibitors in development include: veliparib (ABT-888) from Abbot, MK4827 from Merck, AG-014699 of Pfizer and Iniparib (BSI-201) of Sanofi-Aventis. Other angiogenesis inhibitors in development include aflibercept, AMG386, cediranib, sorafenib, sunitinib and pazopanib. Antibody-drug conjugates in development include T-DM1, IMGN388, lorvotuzumab mertansine, AN-152, S1(dsFv)-PE38, BIIB015, SAR566658, VB6-845, Thio Hu3A5-VC-MMAE, CDX-014, MEDI-547, SGN-75 and MDX-1203. In particular embodiments, the chemotherapeutic agents may be carboplatin, cisplatin, paclitaxel or docetaxel, or may be combination therapies thereof.

A particular form of (chemo)therapy that may be used in the treatment of a cancer (eg ovarian cancer), and one following which the test may be conducted, is neoadjuvant (chemo)therapy ("NACT").

One particular advantage of the test of the present invention is that it can provide individual-specific therapeutic options. For example, in certain embodiments of the test of the present invention, if said woman or man is determined to respond to (for example, has responded to) said (chemo) therapy, then said woman or man may be designated as being eligible for tumour de-baulking surgery. As will be recognised, if a woman or man is determined to respond to such chemotherapy then tumour de-baulking surgery is an intervention that could prove life-saving. In contrast, if a woman or man is determined to not respond to said (chemo) therapy, then said woman or man may not be suitable for such invasive tumour de-baulking surgery. However, in such embodiments, she/he may be designated as eligible for therapy with one or more second-line chemotherapeutic agent(s) against said cancer (eg ovarian cancer for a woman). The response to therapy with such second-line chemotherapeutic agent(s) may also be determined using a test of the present invention, and if such second-line chemotherapy leads to a response (such as determined sooner by a test of the present invention), then such woman or man may then be designated as being eligible for tumour de-baulking surgery.

Said second-line (chemo)therapy includes one or more chemotherapeutic agent(s) independently selected from the group consisting of: carboplatin, paclitaxel (such as alone, and as a weekly treatment), docetaxel, cisplatin, liposomal doxorubicin, gemcitabine, trabectedin, etoposide, cyclophosphamide, an angiogenesis inhibitor (such as bevacizumab) and a PARP inhibitor (such as olaparib), or any of those chemotherapeutic agent(s) described above. The second line chemotherapeutic agent may, in same embodiments, be the same as that used in said first therapy; but in such alternative embodiment said (same) subsequent chemotherapeutic agent is used at a different dosage, different administration route, different treatment regimen and/or in combination therapy together with other treatment modalities. For example, carboplatin in combination with paclitaxel is commonly used as first line therapy, and carboplatin (alone) may be used as the second line therapy, such as if the patient is relapse-free for 12 months.

In this way, the test of the present invention provides a faster and more accurate test for determining their response to (chemo)therapy against a cancer (eg ovarian cancer), such that the most appropriate, or additional, therapeutic interventions can be made; ultimately increasing the success of treatment for the cancer (eg ovarian cancer), an increase in progression free survival, overall survival and/or quality of life (such as may be measured by pain suffered or reported and/or pain-killer use).

In a first related aspect, the invention relates to a method of determining the methylation status at one or more CpGs of (eg cell-free) DNA comprising the steps:
Providing a biological sample, said sample comprising (eg cell-free) DNA; and
Determining, in at least one molecule of said (eg cell-free) DNA, the methylation status at one or more CpGs (such as one or more relevant CpGs) located within one or more of nucleotide sequences,
wherein, said one or more of the nucleotide sequences are independently selected from the group consisting of: SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and 31 (for example, within one or more of the nucleotide sequences comprised in one or more of the respective DMRs of the present invention independently selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226), or a nucleotide sequence present within about 2,000 bp (such as within about 200 bp) 5' or 3' thereof, or an allelic variant and/or complementary sequence of any of said nucleotide sequences.

In a second related aspect, the invention relates to a method of detecting one or more: (i) methylated CpGs associated with (such as located within) one or more of the hyper-methylated DMRs of the present invention; and/or (ii) un-methylated CpGs associated with (such as located within) one or more of the hypo-methylated DMRs of the present invention, in each case comprised in at least one molecule of (eg cell-free) DNA of a woman or man comprising the steps:
Providing a biological sample, said sample comprising (eg cell-free) DNA of said woman or man; and
Determining, in at least one molecule of said (eg cell-free) DNA, the methylation status at one or more CpGs (such as one or more relevant CpGs) located within one or more of the nucleotide sequences independently selected from the group consisting of: SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and 31 (for example, within one or more of the nucleotide sequences comprised in one or more of the respective DMRs of the present invention independently selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226), or a nucleotide sequence present within about 2,000 bp (such as within about 200 bp 5' or 3') thereof, or an allelic variant and/or complementary sequence of any of said nucleotide sequences,
wherein, the presence in at least one of said (eg cell-free) DNA molecules of one or more: (i) methylated CpGs associated with (such as located within) one or more of the hyper-methylated DMRs of the present invention (eg, as identified in TABLE 1A), for example associated with (such as located within) one or more of said nucleotide sequences independently selected from: SEQ ID NOs: 1, 2, 3, 4, 10, 12, 14, 15, 18, 19, 20, 21, 23, 24, 25, 26, 27, 28, 29 and 30; thereby detects said methylated CpG(s) in the (eg cell-free) DNA of said woman or man; and/or (ii) un-methylated CpGs associated with (such as located within) one or more of the hypo-methylated DMRs of the present invention (eg, as identified in TABLE 1B), for example associated with (such as located within) one or more of said nucleotide sequences independently selected from: SEQ ID NOs: 5, 6, 7, 8, 9, 11, 13, 16, 17, 22 and 31; thereby detects said un-methylated CpG(s) in the (eg cell-free) DNA of said woman or man.

In a third related aspect, the invention relates to a method of diagnosing and treating a woman or man having a cancer (eg an ovarian cancer for a woman) comprising the steps:
Providing a biological sample from said woman or man, said sample comprising (eg cell-free) DNA of said woman or man;
Detecting, in at least one molecule of said (eg cell-free) DNA, whether one or more methylated or un-methylated CpGs (such as one or more relevant CpGs) is located within one or more of the nucleotide sequences independently selected from the group consisting of: SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and 31 (for example, within one or more of the nucleotide sequences comprised in one or more of the respective DMRs of the present invention independently selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226), or a nucleotide sequence present within about 2,000 bp (such as within about 200 bp) 5' or 3' thereof, or an allelic variant and/or complementary sequence of any of said nucleotide sequences;
Diagnosing the woman or man with the cancer (eg with an ovarian cancer for a woman), such as a cancer (eg an ovarian cancer for a woman) that does not respond to a first therapy, when one or more of: (i) said methylated CpGs associated with (such as located within) one or more of the hyper-methylated DMRs of the present invention (eg, as identified in TABLE 1A), for example associated with (such as located within) one or more of said nucleotide sequences independently selected from: SEQ ID NOs: 1, 2, 3, 4, 10, 12, 14, 15, 18, 19, 20, 21, 23, 24, 25, 26, 27, 28, 29 and 30 is detected; and/or (ii) un-methylated CpGs associated with (such as located within) one or more of the hypo-methylated DMRs of the present invention (eg, as identified in TABLE 1B), for example associated with (such as located within) one or more of said nucleotide sequences independently selected from: SEQ ID NOs: 5, 6, 7, 8, 9, 11, 13, 16, 17, 22 and 31 is detected; and Treating said diagnosed woman or man by:
Administering, or recommending administration of, an effective amount of a chemotherapeutic agent to a woman or man diagnosed as having a cancer (eg an ovarian cancer for a woman), such as one that does not respond to the first therapy; or
Conducting, or recommending the conduct of, tumour debaulking surgery to a woman or man diagnosed as having a cancer (eg an ovarian cancer for a woman) that does respond to the first therapy.

In such related aspect, the chemotherapeutic agent and/or the first therapy may be one as described elsewhere herein.

In certain embodiments of such related aspect(s), the methylation status of said CpG(s) may be determined according to one or more of the corresponding embodiments of the other aspects of the present invention; including for example, that said (eg cell-free) DNA of the woman or man may be subjected to an agent that differentially modifies said DNA based on the methylation status of one or more of the CpGs, and/or that the methylation status of the one or more the CpGs is determined without use of such an agent (such as, by single molecule sequencing/analysis of DNA). In certain embodiments of such related aspect(s), the methylation status of said CpG(s) may be determined by the detection of a nucleic acid of the third aspect, such as the detection of a (eg non-natural) nucleic acid comprising at least about 15 contiguous bases comprised in SEQ ID No. 32, 33, 34 and/or 35.

In further certain embodiments of such related aspect(s), the/a biological sample may be collected and/or further processed according to one or more of the corresponding embodiments of the other aspects of the present invention. For example, the biological sample may be obtained from a woman or man having or suspected of having a cancer (eg ovarian cancer for a woman), or suspected to not have responded to therapy against the cancer (eg ovarian cancer). In any such embodiments, the biological sample may be, or may be obtained by, any of the corresponding embodiments of the other aspects of the present invention.

In further of such embodiments, the method of detecting said methylated or un-methylated (as applicable) CpG(s) (in particular, one or more relevant CpGs) may comprise the step of determining the presence or absence of, or response to therapy against, a cancer in said human individual (eg an ovarian cancer in said woman), wherein the detection in at least one of said (eg cell-free) DNA molecules of one or more methylated un-methylated (as applicable) said CpGs located within one or more of said nucleotide sequences indicates the presence of, or a reduced response to therapy against, the cancer in said human individual (eg an ovarian cancer in said woman).

In a second aspect, the invention relates to a chemotherapeutic agent for use in a method of therapy of a cancer in human individual (eg ovarian cancer in a woman), wherein said chemotherapeutic agent is administered to a woman or man (as applicable) within about three months of said woman or man having been predicted and/or determined, using a method of the first aspect, to not respond to a therapy against the cancer (eg ovarian cancer for a woman).

In a related second aspect, the invention also relates to a method of treating a cancer (eg ovarian cancer), comprising administering an effective amount of a chemotherapeutic agent is administered to a woman or man within about three months of said woman or man having been predicted and/or determined, using a method of the first aspect, to not respond to a therapy against the cancer (eg ovarian cancer for a woman).

In certain embodiments of such second aspect, the chemotherapeutic agent is one that is used and/or is approved (eg, by the European Medicines Agency in Europe and/or by the Food and Drug Administration in the US) for the treatment of a cancer, in particular for the treatment of ovarian cancer or any other cancer analysised herein. Examples of such chemotherapeutic agent include one or more independently selected from the group consisting of: carboplatin, paclitaxel, docetaxel, cisplatin, liposomal doxorubicin, gemcitabine, trabectedin, etoposide, cyclophosphamide an angiogenesis inhibitor (such as bevacizumab) and a PARP inhibitor (such as olaparib). In other embodiments, the chemotherapeutic agent may be any one of those described elsewhere herein.

In any embodiments of such second aspect, the chemotherapeutic agent is administered to said woman or man within about 3 months, or about 70, 56, 53, 49, 46, 42, 39, 35, 32, 28, 25, 21, 18, 14, 13, 12, 11, 10, 9, 8, 7, 6, 5, 4, 3, or 2 days or less, such as within about 24, 20, 18, 15, 12, 10, 8, 6, 5, 4, 3 or 2 hours, or within about 1 hour, of said prediction and/or determination. Also envisioned by the present invention, is that such chemotherapeutic agents can be used in combination formulations and/or combination treatment regimens with another chemotherapeutic agent, other pharmaceutical agents and/or medical intervention such as radiation treatment or surgery.

A chemotherapeutic agent may be administered to said woman or man by the applicable or conventional mode of administration, such as intravenously, intramuscularly, intradermally, orally.

In such second aspect, said prediction and/or determination is made using a method of the first aspect. That is, an embodiment of such method of the invention may be practiced, such as to determine or to predict (eg by an increased likelihood) that said woman or man has not responded (or will not respond) to a first therapy against the cancer (eg ovarian cancer for a woman) she/he is suffering from; or that she/he has not responded (or will not respond) completely, sufficiently and/or within a predetermined period of time (such as about 12 months, 6 months, 4 months, 3 months, 2 months, or about 4 weeks or 2 weeks, or about 1 week).

A first therapy against the cancer (eg ovarian cancer) may be surgery, such as tumour de-baulking surgery, or it may be treatment with a chemotherapeutic agent such as one described above. Whilst in one embodiment, the subsequent chemotherapeutic agent used after said prediction and/or determination is different to a chemotherapeutic agent used for said first therapy, in another aspect said subsequent chemotherapeutic agent is the same as that used in said first therapy; but in such alternative embodiment said (same) subsequent chemotherapeutic agent is used at a different dosage, different administration route, different treatment regimen and/or in combination therapy together with other treatment modalities.

In the context of the invention, an effective amount of a chemotherapeutic agent can be any one that will elicit the biological, physiological, pharmacological, therapeutic or medical response of the woman or man that is being sought by the pharmacologist, pharmacist, medical doctor, or other clinician, eg, lessening of the effects/symptoms of the ovarian cancer.

In a third aspect, the invention relates to a nucleic acid comprising a nucleic acid sequence consisting of at least about 10 contiguous bases (preferably at least about 15 contiguous bases for any DMR other than DMR #222) comprised in a particular (eg non-natural) sequence derived from one selected from the group consisting of one set out in TABLE 1A, TABLE 1B or TABLE 2A (for example, a sequence consisting of at least about 10 contiguous bases (preferably at least about 15 contiguous bases for any DMR other than DMR #222) comprised in a sequence producible by (such as produced following) bisulphite conversion of a sequence comprised within a DMR selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226; such as a sequence consisting of at least about 10 contiguous bases (preferably at least about 15 contiguous bases for any SEQ ID other than SEQ ID: NO:58) comprised in a sequence selected from the group consisting of: SEQ ID NOs: 32, 33, 34, 35, 36, 37, 38, 39, 40, 41, 42, 43, 44, 45, 46, 47, 48, 49, 50, 51, 52, 53, 54, 55, 56, 57, 58, 59, 60, 61 and 62 (such as SEQ ID NO: 32, 33, 34 and/or 35), or an allelic variant and/or complementary sequence of any of said nucleotide sequences. In particular embodiments, said number of contiguous bases is at least about 16, 18, 20, 22, 24, 26, 28, 30, 35, 40, 45, 50, 55, 60, 65, 70, 75, 80, 85, 90, 95, 100, 110, 120, 10, 140, 150 or 160 bases, such as between about 80 and about 160, such as between about 100 and about 160, in each case, independently, up to the maximum number of bases within the sequence selected from said group.

TABLE 2A

DMR-correspondence and possible sequences of the bisulphite-converted DMRs of the present invention

| DMR# | Bisulphite-converted amplicon sequence (all CpGs are underlined) | SEQ ID NO. |
|---|---|---|
| 141 | TATTYGGAGGTTTAGGGGTGAGGATTTYGTTAYGGGAAGGAGGTATAYGATTTAGTTTATGATATYG TTATTTYGGYGTGGTGTTGTAGGGGGAAGTTTAGGTATTTATYGAGGATAGGATTYGGGGAATTYGT TG | 32 |
| 204 | GATATTYGGTGGAGAGTYGTAGTTGTTYGTYGYGGGGTTTTAGGYGTAGTAYGTTTTYGYGYGTGGG TYGTAGTTGGTAGTATAGGAAGTTTAGGTGGAAGAGYGGYGGYGTGGGYGGTTYGGYGYGGYGYGGY GAGTGYGGGTTGGTATYGGT | 33 |
| 228 | GTTTTATGGGYGAGTTGTTGTAGTGYGGTTGTTAGGYGTTTYGYGGGYGGGTTTTTTTTYGGTTTTT YGGTTTGTTYGGTATTTTYGGATTTTTTGGTTTYGYGGGTTTTT | 34 |
| 144 | TTTAGGTTTGAYGTGGGTTTTTTAGGGYGGYGTYGTTAAGGTTTAGAYGTTTTYGTGTAGGAGGGAY GAYGATTTTTTTAYGTTTTYGTGGTTTTAATTYGGYGTTTTGTTATTTTTGATTYGGTGAATATAT TTTAGA | 35 |
| 123 | GYGAAGTAGGAGTAGTTGTYGGGTTTTAYGAGTTTTYGTTYGTTTTGGTTYGGGTTTTTTYGAGTTT TGTTATTAGTYGAGGTTGTGYGGGTAATTGGGTTAGTTTTTYGTTAGGAGAGA | 36 |
| 129 | AATTTTGTTGAGTGAGTTTATAAATAGGGTATAATYGAGAYGYGGGAATGTTTGGGTYGTYGYGTAG TTATYGGGTAGGGTYGTTTTTTTTTGTGGGTTAGTAAAAAYGGTGTTAAGTGA | 37 |
| 137 | ATTTYGTTATATATATAGTTGTATTYGGTATAATAYGYGGTTATAGGTTATTTTAGGTYGTTTYGGG TGTTTTTTTYGTAGTTTTAYGTAGATAGAAGATATTTTTYGGGTTTGGGTGTTTAGTTTTTYG | 38 |
| 148 | GAGGTAATGGAAGYGGTTATTTTTGTTTTYGTTTYGYGTTTGGTTGAAGYGATYGGGGTYGAATAYG TTTAYGTTTTTGAATAYGGGYGTTGTGTTATGGGTGTTTYGGATGTTATATAT | 39 |
| 150 | GYGGGTATTTGTAGTTTTAGTTATTYGGGAGGTTGAGGYGGGAGAATGGYGTGAATTYGGGAGGYGG AGTTTGTAGYGAGTYGAGATYGYGTTATYGTATTTTAGTTTGGGYGATAGAGYGAGATTTYGTTTAA AAA | 40 |
| 154 | TTTTYGGAGTTYGGAGTTTAGGTTAGTGGTAGTYGATTTAGTTTTYGAGATTTTTTTAYGTYGTTTT AAAATTAAAAYGGAGTTTAATAYGAAGTTGGGTGAAGTYGTAGTTTGTAGGAGTTAGGGAGATGYGT TTT | 41 |
| 158 | GATTTGTTTTAAAAAAGAAAAAAATAGGGTYGGGYGYGGTGGTTTAYGTTTGTTATTTTAGTATTT TGGGAGGTYGAGGYGGGTGGATTAYGAGGTYGGGAGATYGATATTATTTTGGGTAATAYGGTGAAAT TT | 42 |
| 164 | GATTYGYGAGGTTTTTAGTAGTTTATTTYGGGAYGGYGGTGTTTAGTTTAGTTTAGGGTAATTGGG TTTTTTGAGAGTTYGATTTTTATYGGTTTGGGAGYGAGTGGTTYGAGTTTAGATGTTGGGAATYGTY GTTT | 43 |
| 176 | TAATTTATTTTTTTATTAAATTGTATGAAGAAGGTYGGGYGYGGTGGTTTAYGTTTGTAATTTTAGT ATTTTGGGAGGTYGAGGYGGGYGGATTAYGAGGTTAGGAGATYGAGATTAYGGTGAAATTTYGTTTT TATT | 44 |

TABLE 2A-continued

DMR-correspondence and possible sequences of the bisulphite-converted DMRs of the present invention

| DMR# | Bisulphite-converted amplicon sequence (all CpGs are underlined) | SEQ ID NO. |
|---|---|---|
| 178 | GGTAGGAGYGTTTTATTATGYGTAAGTTYGTGGTTTGGAGAGYGTTGAAGGTGGGAGGGGGAAGAGG GGTAGAATTTTYGYGGGAGYGAGYGTATAGTTGTYGTTTYGTGGTYGTTTGGGAATYGTTGGTTTY GGTTTTGG | 45 |
| 180 | TTGTAGAAGYGTATTTTGTTGAATATTTYGAGGAYGTGTTTTTYGTATAGGGAGYGTTYGTTTTTGT TGGGGTTGGAGYGGYGTTTGGAGGTYGATATTYGGTYGTTGTTGGATTTTTTYGTTTGTYGTTTTTG T | 46 |
| 186 | YGTGTTAGTTAGGATGGTTTYGATTTTTTGATTTYGTGATTAGTTYGTTTYGGTTTTTTAAAGTGTT GGGATTAAAGGYGTGAGTTATYGYGTYGGGTYGAGATTTTGTTTTAAAAAAAAAAGGTTTGGGTTGT GGTATTTTGGGA | 47 |
| 188 | AGAGTTGTATTTYGAAGATTTTAGATTTYGAGAGTTGYGGAAAYGTTAYGAGGATTTGTTAATTAGG TTGYGGGTTAATTAGAGTTGGGAAGATTYGAATATYGATTTYGTTTYGGTTTTTGTAGTTYGGATAT TTAYGTT | 48 |
| 190 | GTTAGAYGAGAGTTTGGGGTTAATGTYGAGGTGGAGYGAYGTTGGTAYGGTAATTTTGAGTTTGYGY GGTTYGGYGTTATTTTTTGGTTTTTYGTTGTTGGTTGGATTT | 49 |
| 192 | YGGTAGGTTATTTAGTAGTAGGGTTTTAYGTYGGTTTYGTYGATGTTTTAGAAGGTTAGTTTTTTTT YGAAGAGYGGTTYGTATAYGTTTGYGGGGTAGTGTAGTTTGTYGGTGYGGTAGTAATTGAGTATATA GGYGAAGAYG | 50 |
| 200 | AATTAGTTTAGTAATYGGYGATTTTAAGYGYGGYGATYGTAAAGGGAGTGTTTGTTTATTYGYGTTT GAAAGTAGATTTTTTTTTYGGTAGGAATATAGGATTTATTTGTTAGTGG | 51 |
| 202 | GTGYGAATAAGATYGGGYGTTTYGTYGTYGAYGYGAAGGGGTTGTTTGTGYGYGGYGTTGYGGGTTT TTYGYGYGTGGGGTGTGYGTGTGYGTGTTYGGGTTYGGTTTTGTGTGTGTATYGYGGGTTTGTTTAG AGTYGGGATTATYG | 52 |
| 208 | ATATTAATTTTGTTYGGGTAYGGTGGTTTAYGTTTGTAATTTTAGTATTTTGGGAGGTYGAGGYGGG YGGATTAYGAGGTTAGGAGATYGAGATTATTTTGGYGAATATGGTGAAATTTYG | 53 |
| 210 | TGTATATAGATTATTGTAGGATTATTTTTTGTGTTTTTAAAATTTTTTTTTTYGTTTTATTTTAT ATATTTTTTGTTTTTATAATTTT | 54 |
| 213 | TYGTTYGGGAATGGGAATATAGTTTATATATGGGAAAAYGYGGTGTAGGGAGAAAATTAATTTAGTGA GGAGYGGAGGYGTAGGATTGTGGAGTGTGTATTYGG | 55 |
| 214 | TTGTTTAAAGGYGTAGAGGAGTAGTTGGGAAYGAGAATAAAGYGGTTAGGTTTTTTYGGAGGAAGG AAGGAGAGAGTTTTAGGAAATAGTTGA | 56 |
| 219 | GGATGAAGGATTTTTGTATTATTGTGATGGTTATGGYGTTGTTGTTTGGGTTTTTTTTTTYGGTAG GTAAGGGAGGAGGTAGGGGAAGGGATATGTGTTT | 57 |
| 222 | TAGGTTATAGGAAGAGGTATTTTTTATAGATGAYGGTTGTAAAATTTTAAGTTGAGTTTTTTTAGGA AGT | 58 |
| 223 | AAGAGAGAGTGGTTGATAATTAGTAGAGAGAGGTTTTTAATTTAYGGAAGTGTTTGTAATATAATTT TTTTGTATATTAGTTGT | 59 |
| 224 | GGTTTTTTTTTYGAGTTATGAAGAGTTGTTTGYGGTTATTTTGGTTTTYGTATTTYGTTTTTGTTA TTTTAGGTTTTTGTAATTTGTTTAAYGTTT | 60 |
| 225 | GAAGTTTGATATTTTTGGTTTTAAATATTGTTTGGTTATAATAYGATATTTAGGGATAGATATTTTT TATGTATAGTAAGTTGTGG | 61 |
| 226 | GGGGGGATTGTYGTTAATTTATTGTTTAATGATYGYGGTTYGYGYGTTTYGAGTAATYGGGTGATGT ATGTGGATTGTGTATATTTYGTGG | 62 |

Each Y, independently either C or T/U

In certain embodiments of such aspect, one or more of the bases identified by "Y" in such sequences of contiguous bases is a U or T (preferably, a T). As will now be apparent to the person of ordinary skill, such sequences (ie, those comprising a U and/or a T at one or more bases identified by "Y") are non-natural sequence as the sequence is produced following conversion of a cytosine in a natural sequence by bisulphite. In particular of such embodiments, such a nucleic acid of the present invention comprising two, three, four, five, six, seven, eight, nine or ten (up to the maximum number of "Ys" present in such sequence of contiguous bases) Us and/or Ts; and in more particular of such embodiments, such a nucleic acids may comprise at least one, two, three, four, five, six, seven, eight, nine, ten or more than ten (up to the maximum number of CpGs present in such sequence of contiguous bases) Cs at any of the bases identified by "Y" therein, such as those "Ys" within CpGs (such as relevant CpGs) located in such sequence of contiguous bases. In particular embodiments, two, three, four, five, six, seven, eight, nine, ten or more than ten of the bases identified by "Y" therein may be a U or T (preferably, a T), such as all of the bases identified by "Y" therein may be a U or T (preferably, a T), or all but one, two, three, four or five of the bases identified by "Y" therein is a U or T (preferably, a T) and preferably all other Y's therein (in particular, those in CpGs) may be Cs.

In other embodiments, such a nucleic acid of the invention comprises a nucleic acid sequence consisting of said number of contiguous bases—for example, at least about 10 contiguous bases (preferably at least about 15 contiguous bases for any SEQ ID other than SEQ ID: NO:89)—comprised in a particular (non-natural) sequence selected from the group consisting of those set forth in TABLE 2B: SEQ ID NOs: 63, 64, 65, 66, 67, 68, 69, 70, 71, 72, 73, 74, 75, 76, 77, 78, 79, 80, 81, 82, 83, 84, 85, 86, 87, 88, 89, 90, 91, 92 and 93 (such as SEQ ID NO: 63, 64, 65 and/or 66, or SEQ ID NOs: 63 and 64 and 65, or SEQ ID Nos 65 and 66, and optionally 54 and/or 53), and in particular of such embodiments, said nucleic acid comprises a sequence selected from said group, or in each case an allelic variant and/or complementary sequence of any of said nucleotide sequences. As will be apparent, typically a bisulphite converted [un-methylated] cytosine would be detected as a T, particularly after an amplification (such as a PCR) step. However, certain detection technologies (for example, those able to detect single molecules) may be able to directly detect a bisulphite converted (un-methylated) cytosine as a U. Accordingly, the sequences of TABLE 2B are also envisioned to encompass the analogous sequences where, instead of a T representing a bisulphite converted (un-methylated) cytosine, such T is instead a U. The location of such Ts (eg, C in the genome sequence outside of CpGs) will readily be identifiable by the person of ordinary skill by comparison of the sequences presented in this TABLE 2B to the corresponding genomic sequence presented in TABLE 1A or TABLE 1B, as applicable.

TABLE 2B

Particular patterns of epigenetic markers associated with the presence of ovarian cancer detected by particular (non-natural) sequences of the DMRs of the present invention

| DMR # | Marker coordinates (hg19) | Detected sequence for marker (relevant CpGs are underlined) | Total No. of CpGs | No. of relevant CpGs | OC specific pattern of methylation | SEQ ID NO. |
|---|---|---|---|---|---|---|
| 141 | chr5:178004422-178004505 | CGTTACGGGAAGGAGGTATACGATTTAGTTTATGATATCGTTATTTCGGCGTGGTGTTGTAGGGGGAAGTTTAGGTATTTATCG | 7 | 7 | 1111111 | 63 |
| 204 | chr1:151810811-151810917 | CGTCGCGGGGTTTTAGGCGTAGTACGTTTTCGCGCGTGGGTCGTAGTTGGTAGTATAGGAAGTTTAGGTGGAAGAGCGGCGGCGTGGGCGGTTCGCGCGGYGYGGT | 18 | 16 | 1111111111111111XX | 64 |
| 228 | chr2:219736301-219736362 | YGGTTGTTAGGCGTTTCGCGGGYGGGTTTTTTTCGGTTTTTCGGTTTGTTCGGTATTTTCG | 9 | 7 | X111X1111 | 65 |
| 144 | chr19:58220438-58220517 | GGCGGCGTCGTTAAGGTTTAGACGTTTTCGTGTAGGAGGGACGACGATTTTTTTTACGTTTTCGTGGTTTTAATTCGGCG | 11 | 11 | 11111111111 | 66 |
| 123 | chr16:1271180-1271240 | TGAGTTTTTGTTTGTTTTGGTTTGGGTTTTTTTTGAGTTTTGTTATTAGTTGAGGTTGTGTG | 7 | 7 | 0000000 | 67 |
| 129 | chr11:69054672-69054732 | TYGAGATGTGGGAATGTTTGGGTYGTYGTGTAGTTATTGGGTAGGGTYGTTTTTTTTTGTG | 8 | 4 | X00XX00X | 68 |
| 137 | chr12:132896310-132896382 | TGTGGTTATAGGTTATTTTAGGTTGTTTGGGTGTTTTTTTTGTAGTTTTATGTAGATAGAAGATATTTTTTG | 7 | 7 | 0000000 | 69 |
| 148 | chr2:72359624-72359687 | TTTTYGTTTTGTGTTTGGTTGAAGTGATTGGGGTYGAATAYGTTTAYGTTTTTGAATATGGGYG | 10 | 5 | X0000XXX0X | 70 |
| 150 | chr7:156735054-156735141 | TGGGAGGTTGAGGTGGGAGAATGGTGTGAATTTGGGAGGTGGAGTTTGTAGTGAGTTGAGATTGTGTTATTGTATTTTAGTTTGGGTG | 11 | 11 | 00000000000 | 71 |
| 154 | chr17:70112163-70112238 | GTYGATTTAGTTTTCGAGATTTTTTTACGTCGTTTTAAAATTAAAACGGAGTTTAATACGAAGTTGGGTGAAGTCG | 7 | 6 | X111111 | 72 |

TABLE 2B-continued

Particular patterns of epigenetic markers associated with the presence of ovarian cancer detected by particular (non-natural) sequences of the DMRs of the present invention

| DMR # | Marker coordinates (hg19) | Detected sequence for marker (relevant CpGs are underlined) | Total No. of CpGs | No. of relevant CpGs | OC specific pattern of methylation | SEQ ID NO. |
|---|---|---|---|---|---|---|
| 158 | chr16:74441727-74441802 | YGGGYGTGGTGGTTTATGTTT GTTATTTTAGTATTTTGGGAG GTTGAGGTGGGTGGATTATGA GGTTGGGAGATTG | 9 | 7 | XX0000000 | 73 |
| 164 | chr4:174427946-174428028 | YGGGAYGGYGGTGTTTAGTTT AGTTTAGGGTAATTGGGTTTT TTGAGAGTTCGATTTTTATCG GTTTGGGAGCGAGTGGTTCG | 7 | 4 | XXX1111 | 74 |
| 176 | chr6:119107238-119107313 | YGGGTGTGGTGGTTTAYGTTT GTAATTTTAGTATTTTGGGAG GTTGAGGTGGGYGGATTAYGA GGTTAGGAGATYG | 9 | 4 | X00X00XXX | 75 |
| 178 | chr19:13215437-13215527 | YGTGGTTTGGAGAGYGTTGAA GGTGGGAGGGGAAGAGGGGT AGAATTTTYGCGGGAGCGAGC GTATAGTTGTCGTTTYGTGGT CGTTTYG | 10 | 5 | XXX1111X1X | 76 |
| 180 | chr3:192125880-192125950 | YGTGTTTTTYGTATAGGGAGC GTTYGTTTTTGTTGGGGTTGG AGCGCGTTTGGAGGTCGATA TTCGGTCG | 9 | 6 | XX1X11111 | 77 |
| 186 | chr22:21483273-21483360 | YGTGATTAGTTYGTTTTGGTT TTTTAAAGTGTTGGGATTAAA GGTGTGAGTTATTGTGTTGGG TTGAGATTTGTTTTAAAAAA AAAA | 8 | 6 | XX000000 | 78 |
| 188 | chr19:18497159-18497245 | TGAGAGTTGYGGAAAYGTTAY GAGGATTTGTTAATTAGGTTG YGGGTTAATTAGAGTTGGGAA GATTTGAATATTGATTTTGTT TYG | 9 | 4 | 0XXXX000X | 79 |
| 190 | chr9:79629090-79629145 | CGAGGTGGAGCGACGTTGGTA CGGTAATTTTGAGTTTGCGCG GTTCGGCGTTATTT | 8 | 8 | 11111111 | 80 |
| 192 | chr12:75601322-75601409 | CGTCGGTTTCGTCGATGTTTT AGAAGGTTAGTTTTTTTTCGA AGAGCGGTTCGTATACGTTTG CGGGGTAGTGTAGTTTGTCGG TGCG | 11 | 11 | 11111111111 | 81 |
| 200 | chr9:138999208-138999265 | CGCGGCGATCGTAAAGGGAGT GTTTGTTTATTCGCGTTTGAA AGTAGATTTTTTTCG | 7 | 7 | 1111111 | 82 |
| 202 | chr1:2987530-2987630 | YGTYGTYGAYGYGAAGGGGTT GTTTGTGCGCGGYGTTGYGGG TTTTTCGCGCGTGGGGTGTGC GTGTGCGTGTTCGGGTTCGGT TTTGTGTGTGTATCGCG | 18 | 11 | XXXXX11XX111111111 | 83 |
| 208 | chr8:55467547-55467607 | ATGTTTGTAATTTTAGTATTT TGGGAGGTTGAGGTGGGTGGA TTATGAGGTTAGGAGATTG | 6 | 6 | 000000 | 84 |
| 210 | chr12:123713533-123713562 | TTTTTAAAATTTTTTTTTTC GTTTTATTT | 1 | 1 | 1 | 85 |
| 213 | chr2:106776970-106777018 | GAAAACGCGGTGTAGGGAGAA AATTAATTTAGTGAGGAGCGG AGGCGTA | 4 | 4 | 1111 | 86 |
| 214 | chr3:141516288-141516321 | GAACGAGAATAAAGCGGTTAG GTTTTTTTCGGAG | 3 | 3 | 111 | 87 |

TABLE 2B-continued

Particular patterns of epigenetic markers associated with the presence of ovarian cancer detected by particular (non-natural) sequences of the DMRs of the present invention

| DMR # | Marker coordinates (hg19) | Detected sequence for marker (relevant CpGs are underlined) | Total No. of CpGs | No. of relevant CpGs | OC specific pattern of methylation | SEQ ID NO. |
|---|---|---|---|---|---|---|
| 219 | chr16:30484192-30484232 | GCGTTGTTGTTTGGGTTTTTT TTTTTCGGTAGGTAAGGGAG | 2 | 2 | 11 | 88 |
| 222 | chr3:111809469-111809474 | NNACGGTTNN | 1 | 1 | 1 | 89 |
| 223 | chr10:120489276-120489298 | AGAGAGGTTTTTAATTTACGG AA | 1 | 1 | 1 | 90 |
| 224 | chr11:1874066-1874099 | TTTGCGGTTATTTTGGTTTTC GTATTTCGTTTTT | 3 | 3 | 111 | 91 |
| 225 | chr7:142422227-142422245 | GTTATAATACGATATTTAG | 1 | 1 | 1 | 92 |
| 226 | chr1:3086483-3086511 | ATTGTGGTTTGTGTGTTTTGA GTAATTGG | 7 | 7 | 0000000 | 93 |

In sequences, each Y, independently, C or T/U
In methylation pattern, each independently: 1 = methylation, 0 = un-methylation and X = either methylation or un-methylation In a fourth aspect, the invention relates to a nucleic acid probe that is complementary to the particular (eg non-natural) sequence of a nucleic acid of the third aspect, preferably wherein said nucleic acid probe is labelled.

In certain of such embodiments, the label is a detectable moiety such as detectable fluorescent moiety. Examples of suitable fluorescent moieties include, but are not limited to, 6-carboxyfluorescein (6-FAM), VIC, HEX, Cy3, Cy5, TAMRA, JOE, TET, ROX, R-phycoerythrin, fluorescein, rhodamin, Alexa, or Texas Red. Said nucleic acid probe may further comprise enhancers and/or quencher molecules Iowa Black FQ, ZEN, Iowa Black RQ TAMRA, Eclipse, BHQ-1.

Such a nucleic acid probe has utility to detect the nucleic acid of the invention to which it is complementary, such as in the/a method of the first aspect of the invention, such as by hybridisation (and detection thereof) between said probe and its complementary nucleic acid of the invention.

In particular embodiments of said aspect, a nucleic acid probe of the present invention differential may bind to its complementary nucleic acid of the invention depending on the methylation status of one or more CpCs within said nucleic acid sequence. For example, a nucleic acid probe may be designed to bind only (or preferably) to: (i) a nucleic acid used in the method of the present invention when an un-methylated cytosine in a CpG has been converted to U or T (following bisulphite treatment of an un-methylated such CpG); compared to (ii) a nucleic acid used in the method of the present invention when said cytosine has not been converted following bisulphite treatment (ie, when such CpG comprises 5-methylcytosine). As will now be apparent to the person of ordinary skill, such specifically (or preferentially) for binding/hybridisation nucleic acid probes may be designed using routine methodology following the disclosure of the complementary sequences herein; and will readily be usable in array based and/or PCR-based detection technology, such as MethylLight, MSP, or BeadChip (eg Illumina Epic arrays).

In a fifth aspect, the invention relates to a PCR primer pair for amplifying a nucleic acid sequence consisting of at least 10 contiguous bases (such as the number of contiguous bases described elsewhere herein, and preferably at least 15 contiguous bases for any SEQ ID other than SEQ ID NO:58) comprised in a sequence selected from the group consisting of: SEQ ID NOs: 32, 33, 34, 35, 36, 37, 38, 39, 40, 41, 42, 43, 44, 45, 46, 47, 48, 49, 50, 51, 52, 53, 54, 55, 56, 57, 58, 59, 60, 61 and 62 (such as SEQ ID NO: 32, 33, 34 and/or 35), or a nucleotide sequence present within about 2,000 bp (such as within about 200 bp) 5' or 3' thereof, or an allelic variant and/or complementary sequence of any of said nucleotide sequences.

In certain embodiments of such aspect, at least one primer of said pair may include a sequence corresponding to at least one (eg non-natural) bisulphite-converted CpG; such a primer pair having particular utility in amplifying (eg by PCR amplification) bisulphite converted sequences. Indeed, in other embodiments, the primer pair may be a degenerate primer pair such that two version of at least one of said primer pair are present such that both the bisulphite-converted CpG (ie the CpG is un-methylated and converted to U/T) and the non-converted CpG (ie the CpG comprises 5-methylcytosine and remains as C) are amplified/detected.

In particular embodiments, a primer pair of the present invention is one selected from the group primer-pairs set forth in each row of TABLE 3.

TABLE 3

Particular primer pairs and predicted amplicon size

| DMR# | Primer sequence 1 | SEQ ID NO. | Primer sequence 2 | SEQ ID NO. | Amplicon size |
|---|---|---|---|---|---|
| 141 | TATTYGGAGGTTTAGGGGTGAGGATTT | 94 | CAACRAATTCCCCRAATCCTATCCT | 125 | 136 bp |

TABLE 3-continued

Particular primer pairs and predicted amplicon size

| DMR# | Primer sequence 1 | SEQ ID NO. | Primer sequence 2 | SEQ ID NO. | Amplicon size |
|---|---|---|---|---|---|
| 204 | GATATTYGGTGGAGAGTYGTAGTTGTT | 95 | ACCRATACCAACCCRCACTC | 126 | 154 bp |
| 228 | GTTTTATGGGYGAGTTGTTGTAGTG | 96 | AAAAACCCRCRAAACCAAAAAATC | 127 | 111 bp |
| 144 | TTTAGGTTTGAYGTGGGTTTTTTAG | 97 | TCTAAAATATATTCACCRAATCAAAAATAACAAAA | 128 | 140 bp |
| 123 | GYGAAGTAGGAGTAGTTGTYGGGTTTTA | 98 | TCTCTCCTAACRAAAAACTAACCCAATTACC | 129 | 120 bp |
| 129 | AATTTTGTTGAGTGAGTTTATAAATAGGGTATAA | 99 | TCACTTAACACCRTTTTTACTAACC | 130 | 120 bp |
| 137 | ATTTYGTTATATATATAGTTGTATTYGGTATAATA | 100 | CRAAAAACTAAACACCCAAACC | 131 | 130 bp |
| 148 | GAGGTAATGGAAGYGGTTATTTTTG | 101 | ATATATAACATCCRAAACACCCATAACACAA | 132 | 120 bp |
| 150 | GYGGGTATTTGTAGTTTTAGTTATT | 102 | TTTTTAAACRAAATCTCRCTCTAT | 133 | 137 bp |
| 154 | TTTTYGGAGTTYGGAGTTTAGGTTAGTGGTA | 103 | AAAACRCATCTCCCTAACTCCTACAAACTA | 134 | 137 bp |
| 158 | GATTTTGTTTTAAAAAAGAAAAAAATAGGGT | 104 | AAATTTCACCRTATTACCCAAAATAATAT | 135 | 136 bp |
| 164 | GATTYGYGAGGTTTTTTAGTAGTTTATTT | 105 | AAACRACRATTCCCAACATCTAAACT | 136 | 138 bp |
| 176 | TAATTTATTTTTTATTAAATTGTATGAAGAAGGT | 106 | AATAAAAACRAAATTTCACCRTAATCT | 137 | 138 bp |
| 178 | GGTAGGAGYGTTTTATTATGYGTAAGTT | 107 | CCAAAACCRAAACCAACRATTCC | 138 | 142 bp |
| 180 | TTGTAGAAGYGTATTTTGTTGAATATTTYGAGGA | 108 | ACAAAAACRACAAACRAAAAAATCCAACAA | 139 | 135 bp |
| 186 | YGTGTTAGTTAGGATGGTTTYGATTTTTTGATTT | 109 | TCCCAAAATACCACAACCCAAACC | 140 | 146 bp |
| 188 | AGAGTTGTATTTYGAAGATTTTAGATTT | 110 | AACRTAAATATCCRAACTACAAAAAC | 141 | 141 bp |
| 190 | GTTAGAYGAGAGTTTGGGGTTAATGT | 111 | AAATCCAACCAACAACRAAAAACCAAA | 142 | 109 bp |
| 192 | YGGTAGGTTATTTAGTAGTAGGGTTTTA | 112 | CRTCTTCRCCTATATACTCAATTACTAC | 143 | 144 bp |
| 200 | AATTAGTTTAGTAATYGGYGATTTTAAG | 113 | CCACTAACAAATAAATCCTATATTCCTAC | 144 | 115 bp |
| 202 | GTGYGAATAAGATYGGGYGTTT | 114 | CRATAATCCCRACTCTAAACAAACC | 145 | 148 bp |
| 208 | ATATTAATTTTGTTYGGGTAYGGTGGTTT | 115 | CRAAATTTCACCATATTCRCCAAAATAATCT | 146 | 121 bp |
| 210 | GGAGTTGTAAAAAATAAAGGAATATGTG | 116 | TACATACAAATTACTATAAAACCATTTCCTATAC | 147 | 92 bp |
| 213 | TYGTTYGGGAATGGGAATATAGTTATATATGG | 117 | CCRAATACACACTCCACAATCC | 148 | 103 bp |
| 214 | TTGTTTAAAGGYGTAGAGGAGTAGTTGG | 118 | TCAACTATTTCCTAAAACTCTCTCCTTCCTTC | 149 | 94 bp |
| 219 | GGATGAAGGATTTTGTATTATTGTGATGGTTATG | 119 | AAACACATATCCCTTCCCCTACCTC | 150 | 101 bp |

TABLE 3-continued

Particular primer pairs and predicted amplicon size

| DMR# | Primer sequence 1 | SEQ ID NO. | Primer sequence 2 | SEQ ID NO. | Amplicon size |
|---|---|---|---|---|---|
| 222 | TAGGTTATAGGAAGAGGTATTTTTATAGATG | 120 | ACTTCCTAAAAAAACTCAACTTAAAATTTTAC | 151 | 70 bp |
| 223 | AAGAGAGAGTGGTTGATAATTAGTAG | 121 | ACAACTAATATACAAAAAAATTATATTACAAACAC | 152 | 84 bp |
| 224 | GGTTTTTTTTTYGAGTTATGAAGAGTTG | 122 | AAACRTTAAACAAATTACAAAAACCTAAAATAAC | 153 | 97 bp |
| 225 | GAAGTTTGATATTTTTGGTTTTAAATATTGTTTG | 123 | CCACAACTTACTATACATAAAAAATATCTATCC | 154 | 86 bp |
| 226 | GGGGGGATTGTYGTTAATTTATTGTTTAATG | 124 | CCACRAAATATACACAATCCACATACATCAC | 155 | 91 bp |

Each Y, independently, C or T; each R, independently, G or A

In a sixth aspect, the invention relates to a plurality of nucleic acids comprising least two, three, four, five, six, seven, eight, nine, ten or more (such as about 12, 15, 20, 25 or 30) nucleic acid sequences of the third aspect and/or of the nucleic acid probes of the fourth aspect and/or of the PCR primer pairs of the fifth aspect (for example, such PCR primers for amplifying at least 15 contiguous bases of SEQ ID NO: 32, 33, 34 and/or 35, in particular at least 3 pairs of primers for amplifying at least 15 contiguous bases of at least SEQ ID NO: 32, 33 and 34, or SEQ ID NO: 34 and 35, and optionally and 33 and/or 32).

In certain embodiments of such aspect, said plurality of nucleic acids may be in any form that is applicable to the practice of the invention (or its storage or preparation), such as in the form of an admixture or an array. For example, such arrays may comprise a microtitire plate or a hybridisation chip.

As will now be apparent to the person of ordinary skill, any of such nucleic acids (including the probes and/or PCR primer pairs) of the present invention may be synthetic (ie, synthesised by chemical and/or enzymatic means/methods practiced in-vitro), and/or may be isolated and/or are not natural occurring or are used or present in a non-natural composition or mixture. Furthermore, any of the methods of the present invention may produce (and hence a composition or any nucleic acid of the present invention may comprise) an in-vitro-produced nucleic acid molecule, such as a DNA product of a PCR reaction (eg a "PCR product"). One or more of such in-vitro-produced nucleic acid molecules may be non-natural because they comprise a nucleotide primer and/or probe that includes at least one non-natural substituted base, detectable label or bases, such a nucleic acid molecule having been generated by polymerase extension (or partial nuclease digestion) or bisulphite or enzymatic conversion of such nucleic acid (eg a labelled primer and/or probe), and hence providing at least a fraction of such nucleic acid molecules that include a non-natural base or detectable label, such that even though the nucleic acid sequence of the nucleic acid molecules may otherwise comprise a naturally occurring sequence (or fragment thereof), such an in-vitro-produced nucleic acid molecule is non-natural by virtue of (at least) the non-natural base and/or detectable label that it includes.

In a seventh aspect, the invention relates to a kit (for example, one for determining the presence or absence of, or response to therapy against, a cancer in a human individual (eg an ovarian cancer in a woman)), such as a kit of parts comprising two or more separate compartments, holders, vessels or containers (eg each holding a different component of the kit), wherein said kit comprises:
  two, three, four, five, six, seven, eight, nine, ten or more (such as about 12, 15, 20, 25 or 30) nucleic acid sequences of the third aspect and/or of the nucleic acid probes of the fourth aspect and/or of the PCR primer pairs of the fifth aspect (for example, such PCR primers for amplifying at least 15 contiguous bases of SEQ ID NOs: 32, 33, 34 and/or 35, in particular at least 3 pairs of primers for amplifying at least 15 contiguous bases of at least SEQ ID NO: 32, 33 and 34, or SEQ ID NO: 34 and 35, and optionally 33 and/or 32) and/or the population of nucleic acids of the sixth aspect; and
optionally, said kit further comprising:
  (i) a printed manual or computer readable memory comprising instructions to use said synthetic nucleic acid sequence(s), labelled nucleic acid probe(s) and/or population of nucleic acids to practice a method of the first aspect and/or to produce or detect the nucleic acid sequence(s) of the third aspect; and/or
  (ii) one or more other item, component or reagent useful for the practice of a method of the first aspect and and/or the production or detection of the nucleic acid sequence(s) of third aspect, including any such item, component or reagent disclosed herein and/or useful for such practice, production or detection.

In certain embodiments said kit further comprises one or more additional components. For example, such a kit may comprise one or more (such as two, three, four, all) of the following:
  means to collect and/or store a biological sample, such as blood, to be taken from said human individual (eg woman or man), preferably wherein said means is a blood collection tube; and/or
  means to extract DNA, preferably cell-free DNA, from the sample to be taken from said human individual woman or man), preferably wherein said means is a cell-free DNA extraction kit; and/or
  an agent to differentially modify DNA based on the methylation status of one or more CpGs located within said DNA, preferably wherein said agent is bisulphite; and/or
  one or more reagents to detect a nucleic acid sequence, preferably for detecting the sequence of a bisulphite-converted nucleotide sequence; and/or a printed manual or computer readable memory comprising instructions to identify, obtain and/or use one or more of said means, agent or reagent(s) in the context of a method of the first aspect.

In some embodiments, any method of the invention may be a computer-implemented method, or one that is assisted or supported by a computer. In some embodiments, information reflecting the determination, detection, presence or absence of one or more methylated or un-methylated (as applicable) CpGs located within one or more of said nucleotide sequences comprised in at least one molecule of (eg cell-free) DNA of a woman or man in a sample is obtained by at least one processor, and/or information reflecting the determination, detection, presence or absence of one or more methylated CpGs located within one or more of said nucleotide sequences comprised in at least one molecule of (eg cell-free) DNA of a woman or man in a sample is provided in user readable format by another processor. The one or more processors may be coupled to random access memory operating under control of or in conjunction with a computer operating system. The processors may be included in one or more servers, clusters, or other computers or hardware resources, or may be implemented using cloud-based resources. The operating system may be, for example, a distribution of the Linux™ operating system, the Unix™ operating system, or other open-source or proprietary operating system or platform. Processors may communicate with data storage devices, such as a database stored on a hard drive or drive array, to access or store program instructions other data. Processors may further communicate via a network interface, which in turn may communicate via the one or more networks, such as the Internet or other public or private networks, such that a query or other request may be received from a client, or other device or service. In some embodiments, the computer-implemented method (or the one that is assisted or supported by a computer) of detecting the determination, detection, presence or absence of one or more methylated CpGs located within one or more of said nucleotide sequences comprised in at least one molecule of (eg cell-free) DNA of a woman or man in a sample may be provided as a kit.

In an eighth aspect, the invention relates to a to a computer program product comprising: a computer readable medium encoded with a plurality of instructions for controlling a computing system to perform and/or manage an operation for determining the presence or absence of, or response to therapy against, a cancer in a human individual (eg an ovarian cancer in a woman), from a biological sample from said human individual (eg said woman), said sample comprising (eg cell-free) DNA of said human individual (eg a woman or man), and determining, in at least one molecule of said (eg cell-free) DNA, the methylation status at one or more CpGs located within one or more nucleotide sequences in accordance with a method of the first aspect; said operation comprising the steps of:

receiving a first signal representing the number of molecules of said (eg cell-free) DNA comprising one or more methylated or un-methylated CpGs (such as relevant CpGs) located within one or more of the nucleotide sequences independently selected from the group consisting of: SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and 31 (for example, within one or more of the nucleotide sequences comprised in one or more of the respective DMRs of the present invention independently selected from the group consisting of DMR #: #141, #204, #228, #144, #123, #129, #137, #148, #150, #154, #158, #164, #176, #178, #180, #186, #188, #190, #192, #200, #202, #208, #210, #213, #214, #219, #222, #223, #224, #225 and #226), or a nucleotide sequence present within 200 bp 5' or 3' thereof, or an allelic variant and/or complementary sequence of any of said nucleotide sequences; and determining a classification of the presence or absence of, or response to therapy against, the cancer in said human individual (eg an ovarian cancer in said woman) based on their being at least one molecules of said (eg cell-free) DNA comprising one or more: (i) said methylated CpGs associated with (such as located within) one or more of the hyper-methylated DMRs of the present invention (eg, as identified in TABLE 1A), for example associated with (such as located within) one or more of said nucleotide sequences independently selected from: SEQ ID NOs: 1, 2, 3, 4, 10, 12, 14, 15, 18, 19, 20, 21, 23, 24, 25, 26, 27, 28, 29 and 30; and/or (ii) said un-methylated CpGs associated with (such as located within) one or more of the hypo-methylated DMRs of the present invention (eg, as identified in TABLE 1B), for example associated with (such as located within) one or more of said nucleotide sequences independently selected from: SEQ ID NOs: 5, 6, 7, 8, 9, 11, 13, 16, 17, 22 and 31.

In certain embodiments of a computer program product of the present invention the operation further comprises steps of: receiving a second signal representing the number of molecules of said (eg cell-free) DNA comprising said nucleotide sequence(s); and estimating a fraction or ratio of molecules of said (eg cell-free) DNA comprising one or more methylated or un-methylated (as applicable) CpGs located within one or more of the nucleotide sequences within all of said nucleotide sequence(s).

In particular embodiments of the computer program product of the present invention, said classification is determined by comparing said a fraction or ratio to a standard or cut-off value; such as a standard or cut-off value described elsewhere herein. Such an embodiment has particular utility where different populations of women or men (such as patient stratification; or even individualised therapy) is desired. The establishment of the applicable standard or cut-off value for each population of women or men will be apparent to the person of ordinary skill, such as by the collection and analysis of data from a statistically meaningful number of women or men within the desired population, and/or stratification of sub-populations from large population studies. In particular of such embodiments, the computer program may comprise, or the cut-off values may be calculated by, a machine-learning algorithm that is trained on the DMR-based data generated from samples from, for example, women with OC vs. control samples, for example, the (sub)populations of women described herein and/or from samples from other (sub)populations such as UKCTOCS, by using any number and combination of the methylation patterns/DMRs as described herein. In other embodiments, eg when applied to cfDNA, the standard or cut-off value may be modified based on the amount of total DNA present in a sample (for example, if increased such as by contamination from genomic DNA leaking from WBCs) and/or if the average sample size of the extracted DNA is increased (for example, a fragment size of greater than about 1000 bp), which can also indicate contamination from genomic DNA. By way of none limiting examples, such a standard or cut-off value may be reduced by factor, such as by a factor of 2, 3, 4, 5, 6, 8 or 10 (in particular, by a factor of 3) if the DNA extracted from one or more samples used in a study or test exhibits characteristics (such as those described herein) of contamination from genomic DNA.

In other particular embodiments, the computer program product of the present invention may be for an operation that further comprises the steps of: receiving a third signal representing: (i) the amount or concentration of total (eg cell-free) DNA present in said sample; and/or (ii) a baseline value of said fraction or ratio previously determined for said woman or man; and modifying said standard or cut-off value for a given sample based on said third signal. As will now be apparent to the person of ordinary skill, such patient-specific modification of the standard or cut-off value can provide increased personalisation of detection (such as by an increase in specificity and/or sensitivity for individual women or man), analogously to that provided by the ROCA test.

The computer program product of the present invention may include embodiments wherein said first signal, and optional second signal, is determined from nucleotide sequence and/or methylation status information of a plurality of said molecules of said (eg cell-free) DNA and/or amplified DNA representing each of said nucleotide sequences, preferably wherein said plurality is a number selected from the group consisting of at least about: 50, 100, 1,000, 5,000, 10,000, 50,000, 100,000, 200,000, 500,000, 1,000,000, 1,500,000, 2,000,000, 2,500,000, 3,000,000, 3,500,000, 4,000,000 and 5,000,000 molecules, or more than 5,000,000 molecules. In particular of such embodiments, said operation may further comprise the steps of: for each of said molecule's sequence and/or methylation status information, determining if said molecule comprises none, one or more: (i) methylated CpGs associated with (such as located within) one or more of the hyper-methylated DMRs of the present invention (eg, as identified in TABLE 1A), for example associated with (such as located within) one or more of said nucleotide sequences independently selected from: SEQ ID NOs: 1, 2, 3, 4, 10, 12, 14, 15, 18, 19, 20, 21, 23, 24, 25, 26, 27, 28, 29 and 30, or a nucleotide sequence present within about 2,000 bp (such as 200 bp) 5' or 3' thereof, or an allelic variant and/or complementary sequence of any of said nucleotide sequences; and/or (ii) un-methylated CpGs associated with (such as located within) one or more of the hypo-methylated DMRs of the present invention (eg, as identified in TABLE 1B), for example associated with (such as located within) one or more of said nucleotide sequences independently selected from: SEQ ID NOs: 5, 6, 7, 8, 9, 11, 13, 16, 17, 22 and 31, or a nucleotide sequence present within about 2,000 bp (such as 200 bp) 5' or 3' thereof, or an allelic variant and/or complementary sequence of any of said nucleotide sequences; and calculating said first signal, and optional second signal, based on said determination for all or a portion of said plurality of molecules. In certain embodiments, the number of said (eg cell-free) DNA and/or amplified DNA molecules to be analysed may be predetermined. For example, depending on the expected stage of the cancer (eg ovarian cancer), age or general (or specific) health of the woman or man, or the total number of (eg cell-free) DNA found in the biological sample of the woman or man, the said number may be of the higher (eg, greater than about 100,000, 500,000, 1,000,000, 1,500,000 or 2,000,000) or lower (eg less than about 100,000, 500,000, 1,000,000, 1,500,000 or 2,000,000) regions of said range. The number of DNA molecules analysed can be modified, predetermined and/or selected for reasons such as to achieve a particular sensitivity and/or specificity of the test; or may be increased for a second or subsequent test conducted for a woman or man who has had a borderline result for a previous test or where said woman or man may desire increased sensitivity and/or specificity (ie confidence of the test result) before making a decision on further therapy.

The ability to increase the number of said DNA molecules analysed is one particular advantage of the test of the present invention, as it enables the dynamic range of the test to be increased (eg, to that desired), including to a dynamic range that is greater than alternative (eg protein-based) tests for a cancer (eg OC) such as those based on the CA125 for OC.

In further embodiments of the computer program product of the present invention for OC, said operation may further comprise the steps of:
receiving a signal representing the amount present, in a sample of blood taken from said woman, of one or more proteins independently selected from the group consisting of: CA-125, HE4, transthyretin, apolipoprotein A1, beta-2-microglobin and transferrin; and
comparing said a fraction or ratio to a standard or cut-off value for said protein; and
determining a classification of the presence or absence of, or response to therapy against, an ovarian cancer in said woman based on their being either of (i) at least one molecules of said (eg cell-free) DNA comprising one or more of said methylated or un-methylated (as applicable) CpGs located within one or more of said nucleotide sequences; and/or (ii) an amount of said protein(s) present in said blood sample is greater than said standard or cut-off value for such amount or protein.

As will be known to gynecological oncologists, each (or certain combinations) of said proteins are associated with and used for the diagnosis of ovarian cancer. Accordingly, the present invention envisions that it is used in combination with such protein-based diagnostic tests. In particular, and as set out elsewhere herein, the combination of the test of the present invention shows independent sensitivity and/or specificity to CA125 (and/or other protein-based tests). Importantly, in the data presented below, there was no overlap between the DNAme-false positives and the CA125-false positives for OC. Therefore, the application of a test of the present invention to OC with one or more of such (independent) protein-based diagnostic tests would be particularly advantageous to women in that such a combination would provide greater confidence in the result of such a combined test; for example that their (combination) result was not a false positive or false negative; ie that they have been correctly diagnosed for: (i) the presence of ovarian cancer (such as HGS ovarian cancer; or one that is not responding, or has not responded, to chemotherapy treatment), or (ii) the absence of ovarian cancer (such as having a benign pelvic mass), or the absence of HGS ovarian cancer (or having an ovarian cancer that is responding, or has responded, to chemotherapy treatment).

A number of such protein-based tests for ovarian cancer are used, including those which have been validated in clinical trials and are commercially available. In particular, suitable protein-based tests that may be used in combination with the test of the present invention for OC include tests for CA125 (in particular when conducted in a routine manner for each woman, such as in the ROCA® test of Abcodia Ltd. Refs. 6, 7) and/or HE4 (such as the ELEXSYS®/COBAS® versions thereof of Roche Diagnostics), as well as when CA125 and HE4 are used in a combined test (such as the ROMA—Risk of Ovarian Malignancy Algorithm—test. Moore et al, 2009; Gynecological Oncology 112:49. Malkasian et al, 1988; Am J Obstet Gynecol 159:341) and/or when CA125 is used in a test that also involves other proteins including transthyretin, apolipoprotein A1, beta-2-microglobin and/or transferrin (such as in the OVA1 test of Aspira Labs. Ueland et al, 2009: Obstet Gynecol 117:1289. Ware Miller et al, 2011; Obstet Gynecol 117:1298).

In other embodiments, the test of the present invention is used in combination with other DNA-based diagnostic tests for the cancer (eg ovarian cancer). For example for OC, other gynecological cancers and breast cancers, determination of a woman's germline mutational status of BRCA1 and/or BRCA2 gene or any other high risk genes including but not limited to RAD51, PALB2, ATM, BRIP1, CHEK2, PTEN, CDH1. Also envisioned for such other DNA-based diagnostic tests for the cancer (eg ovarian cancer), are those tests which may include the analysis of one or more single-nucleotide polymorphisms (SNPs) that are associated with the cancer (eg OC). In other embodiments, the test of the present invention is used in combination with epidemiological-based models for the cancer (eg ovarian cancer), such as those which use various combinations of family history, and for women (and espically for gylnocological and breast cancers) number of lifetime ovulatory cycles (eg a function of period taking oral contraceptive pill, number of pregnancies and time of breastfeeding), as well as body mass index and hormone replacement therapy use.

Any of such other diagnostic tests for a cancer (eg ovarian cancer) may be used to identify a sub-population of women or men who are at a higher/highest risk of developingthe cancer (eg ovarian cancer for women), and as described above, can be used to "artificially increase" the prevalence of the cancer, (eg OC) (ie, only in that identified group at highest risk). In such sub-populations, then the specificity of the inventive test can be lower without a major impact on the rate of false positives.

In another aspect, the present invention also relates to a use of a nucleic acid sequences of the third aspect of the present invention and/or a labeled nucleic acid probes of the fourth aspect of the present invention and/or a PCR primer pair of the fifth aspect of the present invention (for example, such PCR primers for amplifying at least 15 contiguous bases of SEQ ID NO: 32, 33, 34 and/or 35, in particular at least 3 pairs of primers for amplifying at least 15 contiguous bases of at least SEQ ID NO: 32, 33 and 34 or SEQ ID NO: 34 and 35, and optionally 33 and/or 32) and/or a plurality of nucleic acids of the sixth aspect of the present invention and/or a kit of the seventh aspect of the present invention and/or a computer program product of the eighth aspect of the present invention, in each case for determining (such in-vitro, including in an in-vitro diagnostic test) the presence or absence of, or response to therapy against, a cancer in a human individual (eg an ovarian cancer in a woman). It being envisioned that all embodiments set forth herein for other aspects are also encompassed within this use of the present invention.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Terms as set forth herein are generally to be understood by their common meaning unless indicated otherwise. Where the term "comprising" or "comprising of" is used herein, it does not exclude other elements. For the purposes of the present invention, the term "consisting of" is considered to be a particular embodiment of the term "comprising of". If hereinafter a group is defined to comprise at least a certain number of embodiments, this is also to be understood to disclose a group that consists of all and/or only of these embodiments. Where used herein, "and/or" is to be taken as specific disclosure of each of the two specified features or components with or without the other. For example, "A and/or B" is to be taken as specific disclosure of each of (i) A, (ii) B and (iii) A and B, just as if each is set out individually herein. Analogously, the terms "in particular", "particular" or "certain" (and the like), when used in the context of any embodiment of the present invention, in each case is to be interpreted as a non limiting example of just one (or more) possible such embodiment(s) amongst others, and not that such "particular" or "certain" embodiment is the only one envisioned by the present invention. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated. The terms "of the [present] invention", "in accordance with the [present] invention", or "according to the [present] invention" as used herein are intended to refer to all aspects and embodiments of the invention described and/or claimed herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety; provided that In case of conflict, the present specification, including definitions, will control.

In view of the above, it will be appreciated that the present invention also relates to the following numbered itemised embodiments:

Item 1. A method of determining the presence or absence of, or response to therapy against, an ovarian cancer in a woman, said method comprising the steps:
providing a biological sample from said woman, said sample comprising cell-free DNA of said woman; and
determining, in at least one molecule of said cell-free DNA, the methylation status at one or more CpGs located within one or more of the nucleotide sequences independently selected from the group consisting of: SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and 31, or a nucleotide sequence present within about 2,000 bp (such as within about 200 bp) 5' or 3' thereof, or an allelic variant and/or complementary sequence of said nucleotide sequence(s),
wherein, the presence in at least one of said cell-free DNA molecules of one or more: (i) methylated CpGs associated with (such as located within) one or more of said nucleotide sequences independently selected from: SEQ ID NOs: 1, 2, 3, 4, 10, 12, 14, 15, 18, 19, 20, 21, 23, 24, 25, 26, 27, 28, 29 and 30; and/or (ii) un-methylated CpGs associated with (such as located within) one or more of said nucleotide sequences independently selected from: SEQ ID NOs: 5, 6, 7, 8, 9, 11, 13, 16, 17, 22 and 31, indicates the presence of, or a reduced response to therapy against, an ovarian cancer in said woman;

preferably wherein said biological sample is liquid biological sample selected from the group consisting of: a blood sample, a plasma sample and a serum sample.

Item 2. The method of item 1, wherein said CpGs for a given nucleotide sequence are identifiable by a genome position for the cysteine thereof, independently selected from the list of genome positions corresponding to said nucleotide sequence set forth in TABLE 1C.

Item 3. The method of item 1 or 2, wherein the presence in at least one of said cell-free DNA molecules of one or more pattern of methylation and/or un-methylation as set forth in TABLE 2B for the respective nucleotide sequence(s), indicates the presence of, or a reduced response to therapy against, an ovarian cancer in said woman.

Item 4. The method of any one of items 1 to 3, wherein said nucleotide sequence(s) is/are associated with DMR(s) #141 and/or #204 and/or #228 (eg, SEQ ID NOs: 1, 2, 3 and/or 4), or an allelic variant and/or complementary sequence of said nucleotide sequence(s).

Item 5. The method of item 4, wherein the methylation status is determined at one or more of said CpGs located within each of said three nucleotide sequences; wherein, the presence in at least one of said cell-free DNA molecules of one or more methylated CpGs, and/or of one or more pattern of methylation and/or un-methylation as set forth in TABLE 2B for the respective nucleotide sequence(s), located within any one of said nucleotide sequences indicates the presence of, or a reduced response to therapy against, an ovarian cancer in said woman.

Item 6. The method of item 5, wherein the methylation status is determined at about 7 CpGs located within nucleotide sequence SEQ ID NO 1 and at about 16 to 18 CpGs located within nucleotide sequence SEQ ID NO 2 and about 7 to 9 CpGs located within nucleotide sequence SEQ ID NO 3; wherein, the presence in at least one of said cell-free DNA molecules of at least said number of methylated said CpGs, and/or of one or more pattern of methylation and/or un-methylation as set forth in TABLE 2B for the respective nucleotide sequence(s), located within any one of said nucleotide sequences indicates the presence of, or a reduced response to therapy against, an ovarian cancer in said woman.

Item 7. The method of any one of items 1 to 6, comprising the step of treating said cell-free DNA with an agent that differentially modifies said cell-free DNA based on the methylation status of one or more CpGs located within; preferably a methylation sensitive restriction enzyme and/or bisulphite;

preferably wherein said agent is bisulphite and said determining step comprises the detection of at least one bisulphite-converted un-methylated cytosine within one or more of the nucleotide sequences independently selected from those set forth in TABLE 2A (eg, independently selected the group consisting of: SEQ ID NOs 32, 33, 34, 35, 36, 37, 38, 39, 40, 41, 42, 43, 44, 45, 46, 47, 48, 49, 50, 51, 52, 53, 54, 55, 56, 57, 58, 59, 60, 61 and 62), wherein one or more of the bases identified by "Y" therein is a U or T and, preferably, where one or more of the bases identified by "Y" in a CpG therein is a C, or an allelic variant and/or complementary sequence of said nucleotide sequence(s).

Item 8. The method of item 7, wherein said agent is bisulphite and said determining step comprises the detection of at least one bisulphite-converted un-methylated cytosine within a nucleotide sequence having a length of at least 15 bp (such as at least 50 bp) comprised in SEQ ID NO 32 and/or SEQ ID NO 33 and/or SEQ ID NO 34, wherein one or more of the bases identified by "Y" therein is a U or T and, preferably, where one or more of the bases identified by "Y" in a CpG therein is a C, or an allelic variant and/or complementary sequence of said nucleotide sequence(s).

Item 9. The method of any one of items 1 to 8, wherein the methylation status of said CpG(s) is determined in multiple molecules of said cell-free DNA and/or amplified DNA representing each of said nucleotide sequences; preferably wherein:

(a) the presence in at least a plurality of said cell-free DNA molecules of one or more methylated and/or un-methylated CpGs (as applicable), and/or the presence in at least a plurality of said cell-free DNA molecules of one or more pattern of methylation and/or un-methylation as set forth in TABLE 2B for the respective nucleotide sequence(s), located within one or more of said nucleotide sequences, indicates the presence of, or a reduced response to therapy against, an ovarian cancer in said woman; and/or (b) said plurality of cell-free DNA molecules with one or more of said methylated and/or un-methylated CpGs (as applicable), and/or the presence in at least a plurality of said cell-free DNA molecules of one or more pattern of methylation and/or un-methylation as set forth in TABLE 2B for the respective nucleotide sequence(s), located is at least 2, 3, 4, 5, 6, 7, 18, 9 or 10, or at least about 15, 20, 25, 30, 35, 40, 45, 50, 55, 60, 70, 80, 90, 100, 125, 150, 175 or 200, or a greater number such as greater than about 500, 1,000, 5,000, 7,500, 1,000, 2,500, 5,000 or greater than 5,000 molecules; and/or (c) the methylation status of said CpG(s) is determined in a number of molecules of said cell-free DNA and/or amplified DNA representing each of said nucleotide sequences selected from the group consisting of at least about: 1,000, 5,000, 10,000, 50,000, 100,000, 200,000, 500,000, 1,000,000, 1,500,000, 2,000,000, 2,500,000, 3,000,000, 3,500,000, 4,000,000 and 5,000,000 molecules, or more than 5,000,000 molecules.

Item 10. The method of item 9, wherein a fraction or ratio of, or an absolute number of, cell-free DNA molecules in said sample having said methylated and/or un-methylated CpG(s) (as applicable) located within said nucleotide sequence(s), and/or having said pattern of methylation and/or un-methylation as set forth in TABLE 2B for the respective nucleotide sequence(s), is estimated.

Item 11. The method of item 10, further comprising a step of comparing said fraction or ratio with a standard or cut-off value; wherein a fraction or ratio greater than the standard or cut-off value indicates the presence of or a reduced response to therapy against, an ovarian cancer in said woman;

preferably wherein said standard or cut-off value(s) is/are modified for a given sample based on:
the amount or concentration of total cell-free DNA present in said sample; and/or
a baseline value of said fraction or ratio previously determined for said woman; and/or a value of said fraction or ratio determined from multiple samples from a population of women representative of said woman; and/or the specificity and/or sensitivity desired for said method of determination;

more preferably wherein said standard or cut-off value is/are reduced fora given sample that has an amount or concentration of total cell-free DNA present in said sample that is greater than a standard or cut-off value.

Item 12. A nucleic acid comprising at least 10 (preferable at least about 15, such as at least 50, for any SEQ ID other than SEQ ID NO:58) contiguous bases comprised in a sequence selected from the group consisting of: SEQ ID NOs 32, 33, 34, 35, 36, 37, 38, 39, 40, 41, 42, 43, 44, 45, 46, 47, 48, 49, 50, 51, 52, 53, 54, 55, 56, 57, 58, 59, 60, 61 and 62, wherein said nucleic acid sequence includes one or more of the bases identified by "Y" therein is a U or T and, preferably, where one or more of the bases identified by "Y" therein is a C, or an allelic variant and/or complementary sequence of said nucleotide sequence;

preferably wherein said nucleic acid sequence comprises at least 15, (such as at least 50) contiguous bases comprised in a sequence of SEQ ID NOs 32, SEQ ID NOs 33 or SEQ ID NOs 34, wherein said nucleic acid sequence includes one or more of the bases identified by "Y" therein is a U or T and, preferably, where one or more of the bases identified by "Y" therein is a C, or an allelic variant and/or complementary sequence of said nucleotide sequence; and more preferably wherein said nucleic acid sequence is comprised in a sequence as set forth in TABLE 2B (eg, a sequence selected from the group consisting of: SEQ ID NOs 63, 64, 65, 66, 67, 68, 69, 70, 71, 72, 73, 74, 75, 76, 77, 78, 79, 80, 81, 82, 83, 84, 85, 86, 87, 88, 89, 90, 91, 92 and 93.

Item 13. A nucleic acid primer pair for amplifying a nucleic acid sequence consisting of at least 10 (preferable at least about 15, such as at least 50, for any SEQ ID other than SEQ ID NO: 89) contiguous bases comprised in a sequence selected from the group consisting of: SEQ ID NOs: SEQ ID NOs 63, 64, 65, 66, 67, 68, 69, 70, 71, 72, 73, 74, 75, 76, 77, 78, 79, 80, 81, 82, 83, 84, 85, 86, 87, 88, 89, 90, 91, 92 and 93, or a nucleotide sequence present within about 2,000 bp (such as within about 200 bp) 5' or 3' thereof, or an allelic variant and/or complementary sequence said nucleotide sequence(s);

preferably wherein:

(a) at least one primer of said pair includes a sequence corresponding to at least one bisulphite-converted CpG present in said nucleotide sequence(s); and/or (b) said primer pair is selected from the group of primer-pairs set forth in each row of TABLE 3.

Item 14. A kit, preferably for determining the presence or absence of, or response to therapy against, an ovarian cancer in a woman, said kit comprising:

one or more nucleic acid sequences of item 12 and/or primer pairs of item 13; and optionally, said kit further comprising:

(i) a printed manual or computer readable memory comprising instructions to use said nucleic acid sequence(s) and/or primer pair(s) to practice a method of any one of items 1 to 11 and/or to produce or detect the nucleic acid sequence(s) of item 12; and/or (ii) one or more other item, component or reagent useful for the practice of a method of any one of items 1 to 11 and and/or the production or detection of the nucleic acid sequence(s) of item 12, including any such item, component or reagent disclosed herein useful for such practice, production or detection.

Item 15. A computer program product comprising: a computer readable medium encoded with a plurality of instructions for controlling a computing system to perform and/or manage an operation for determining the presence or absence of, or response to therapy against, an ovarian cancer in a woman, from a biological sample from said woman, said sample comprising cell-free DNA of said woman, and determining, in at least one molecule of said cell-free DNA, the methylation status at one or more CpGs located within one or more nucleotide sequences in accordance with a method as set forth in any one of items 1 to 11; said operation comprising the steps of:

receiving a first signal representing the number of molecules of said cell-free DNA comprising one or more methylated and/or un-methylated CpGs (as applicable), and/or comprising one or more pattern of methylation and/or un-methylation as set forth in TABLE 2B for the respective nucleotide sequence(s), located within one or more of the nucleotide sequences independently selected from the group consisting of: SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and 31, or a nucleotide sequence present within about 2,000 bp (such as within about 200 bp) 5' or 3' thereof, or an allelic variant and/or complementary sequence of said nucleotide sequence(s); and determining a classification of the presence or absence of, or response to therapy against, an ovarian cancer in said woman based on their being at least one molecules of said cell-free DNA comprising one or more said methylated and/or un-methylated CpGs (as applicable), and/or comprising one or more said pattern of methylation and/or un-methylation, located within one or more of said nucleotide sequences;

preferably wherein said operation further comprises the steps of:

receiving a second signal representing the number of molecules of said cell-free DNA comprising said nucleotide sequence(s); and estimating a fraction or ratio of molecules of said cell-free DNA comprising one or more said methylated and/or un-methylated CpGs (as applicable), and/or comprising one or more said pattern of methylation or un-methylation, located within one or more of the nucleotide sequences within all of said nucleotide sequences; and more preferably wherein said classification is determined by comparing said a fraction or ratio to a standard or cut-off value.

Certain aspects and embodiments of the invention will now be illustrated by way of examples and with reference to the description, figures and tables set out herein. Such examples of the Methods, Results, Supplementary Information, Discussion, conclusions and other uses or aspects of the present invention are representative only, and should not be taken to limit the scope of the present invention to only such representative examples. Furthermore, any embodiments, text or other descriptions found in such examples are also to encompassed and considered as part of the description of the present invention.

Methods:

Patients and Sample Collection:

We have used a total of 703 tissue and 251 serum samples in seven sets (FIG. 1). For Serum Sets 1-3 and the NACT Serum Set, women attending the hospitals in London and Prague were invited, consented and 20-40 mL blood obtained (VACUETTE® Z Serum Sep Clot Activator tubes, Cat 455071, Greiner Bio One International GmbH), centrifuged at 3,000 rpm for 10 minutes with serum stored at −80° C. Serum CA125 was analysed for the validation sets using the CA125 Cobas immunoassay platform (Roche Diagnostics, Burgess Hill, UK). For detailed information see the Supplementary Information.

Additionally, a seventh validation set may be provided from the UK Collaborative Trial of Ovarian Cancer Screening (UKCTOCS) (Refs. 6, 7, 22). For example, all women (among those in the control arm) who donated serum samples at recruitment and developed invasive epithelial OC within two years of recruitment and the corresponding age and centre matched women who did not develop ovarian cancer within five years of recruitment can be analysed. Blood samples from all UKCTOCS volunteers can be spun down for serum separation after being couriered at room temperature to a central laboratory, and aliquoted and stored in liquid nitrogen vapour phase until thawing and analysed such as described herein; even if only 1 mL of serum per UKCTOCS volunteer may be available.

Isolation and Bisulphite Modification of DNA:

DNA was isolated from tissue and serum samples at GATC Biotech (Constance, Germany). Tissue DNA was quantified using NanoDrop and Qubit (both Thermo Fisher Scientific, USA); the size was assessed by agarose gel electrophoresis. Serum DNA was quantified using the Fragment Analyzer and the High Sensitivity Large Fragment Analysis Kit (AATI, USA). DNA was bisulfite converted at GATC Biotech.

DNAme Analysis in Tissue:

Genome wide methylation analysis was performed either by the Illumina Infinium Human Methylation 450K beadchip array (Illumina Inc USA, WG-314-1003) as previously described (Refs. 24, 25) or using Reduced Representation Bisulfite Sequencing (RRBS) at GATC Biotech. For the 450 k methylation data we developed a pipeline in order to select the most promising cancer-specific differentially methylated regions (DMRs) that are most likely to fulfil the strict specificity criteria of a serum based test (see Supplementary Information).

For RRBS, DNA was digested by the restriction endonuclease MspI that is specific for the CpG containing motif CCGG; a size selection of the library provides an enhanced coverage for the CpG-rich regions including CpG islands, promoters and enhancer elements (Refs. 26, 27). The digested DNA was adapter ligated, bisulfite modified and PCR amplified. The libraries were sequenced on Illumina's HiSeq 2500 with 50 bp or 100 bp paired-end mode. Using Genedata Expressionist® for Genomic Profiling v9.1, we have established a bioinformatics pipeline for the detection of cancer specific DMRs. The most promising DMRs have been taken forward for the development and validation of serum based clinical assays (see Supplementary Information).

Targeted Ultra-High Coverage Bisulphite Sequencing of Serum DNA:

Targeted bisulfite sequencing libraries were prepared at GATC Biotech. In brief, bisulfite modification was performed with 1 mL serum equivalent. Modified DNA was used to test up to three different markers using a two-step PCR approach. Ultra-high coverage sequencing was performed on Illumina's MiSeq or HiSeq 2500 with 75 bp or 125 bp paired-end mode (see Supplementary Information).

Statistical/Data Analyses:

For DMR discovery the data analysis pipelines are described within the respective sections in the Supplementary Information. In brief, Genedata Expressionist® for Genomic Profiling was used to map reads to human genome version hg19, identify regions with tumor specific methylation patterns, quantify the occurrence of those patterns, and calculate relative pattern frequencies per sample. Pattern frequencies were calculated as number of reads containing the pattern divided by total reads covering the pattern region. The 95% CI intervals for sensitivity and specificity have been calculated according to the efficient-score method (Ref. 28). Differences in pattern frequencies or coverage have been analysed using Mann Whitney U test.

Results:

Study Design:

The samples, techniques and purpose of the three phases of the study—marker discovery, assay development and test validation—are summarized in FIG. 1.

Figure 2:
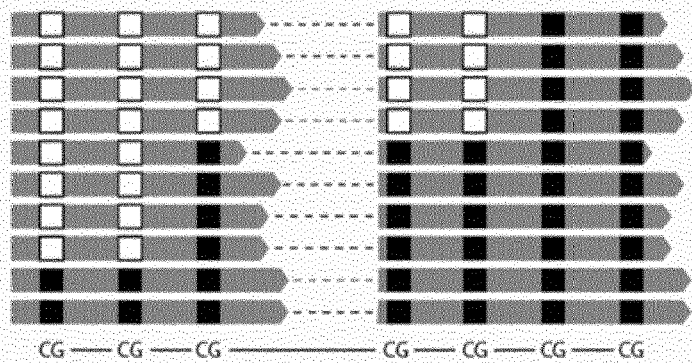
Figure 2:
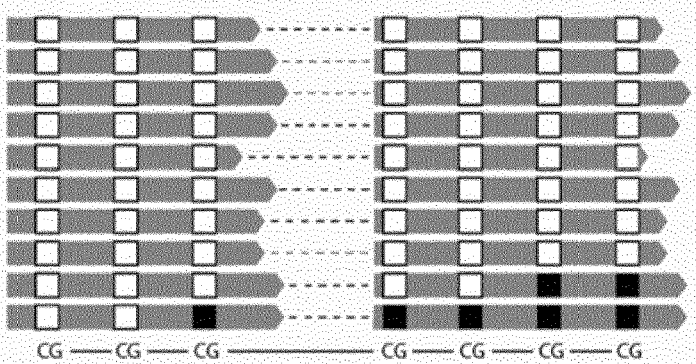
Figure 2:
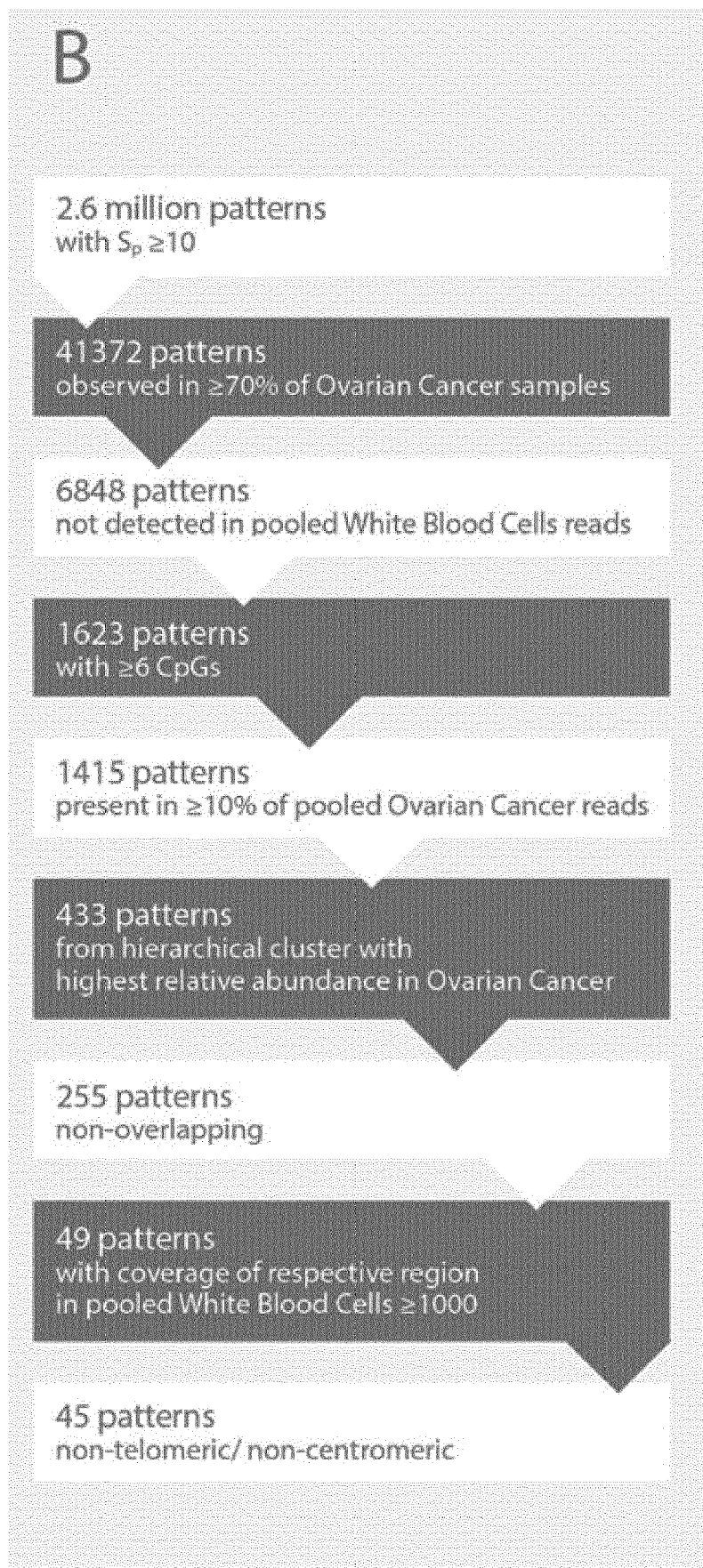
Figure 2:
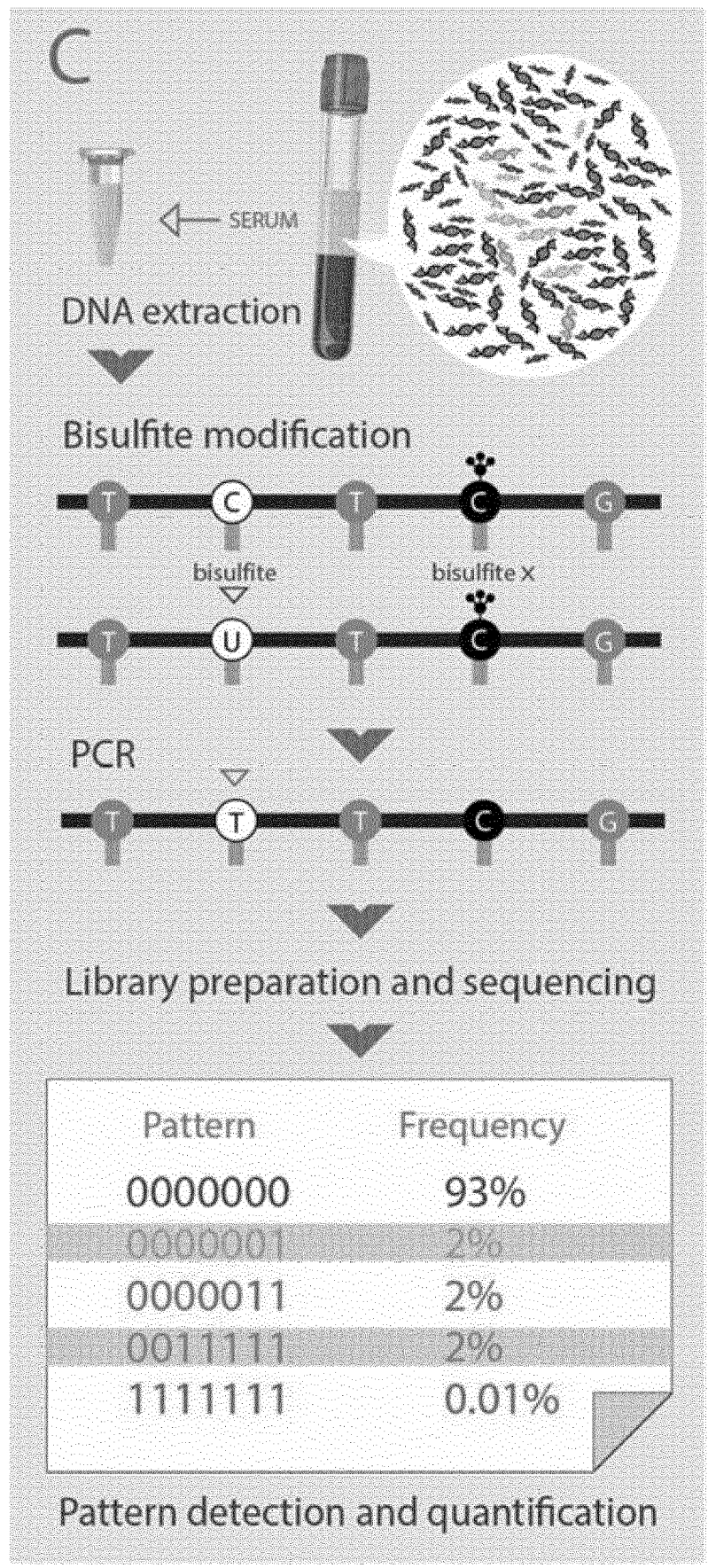
Figure 6:
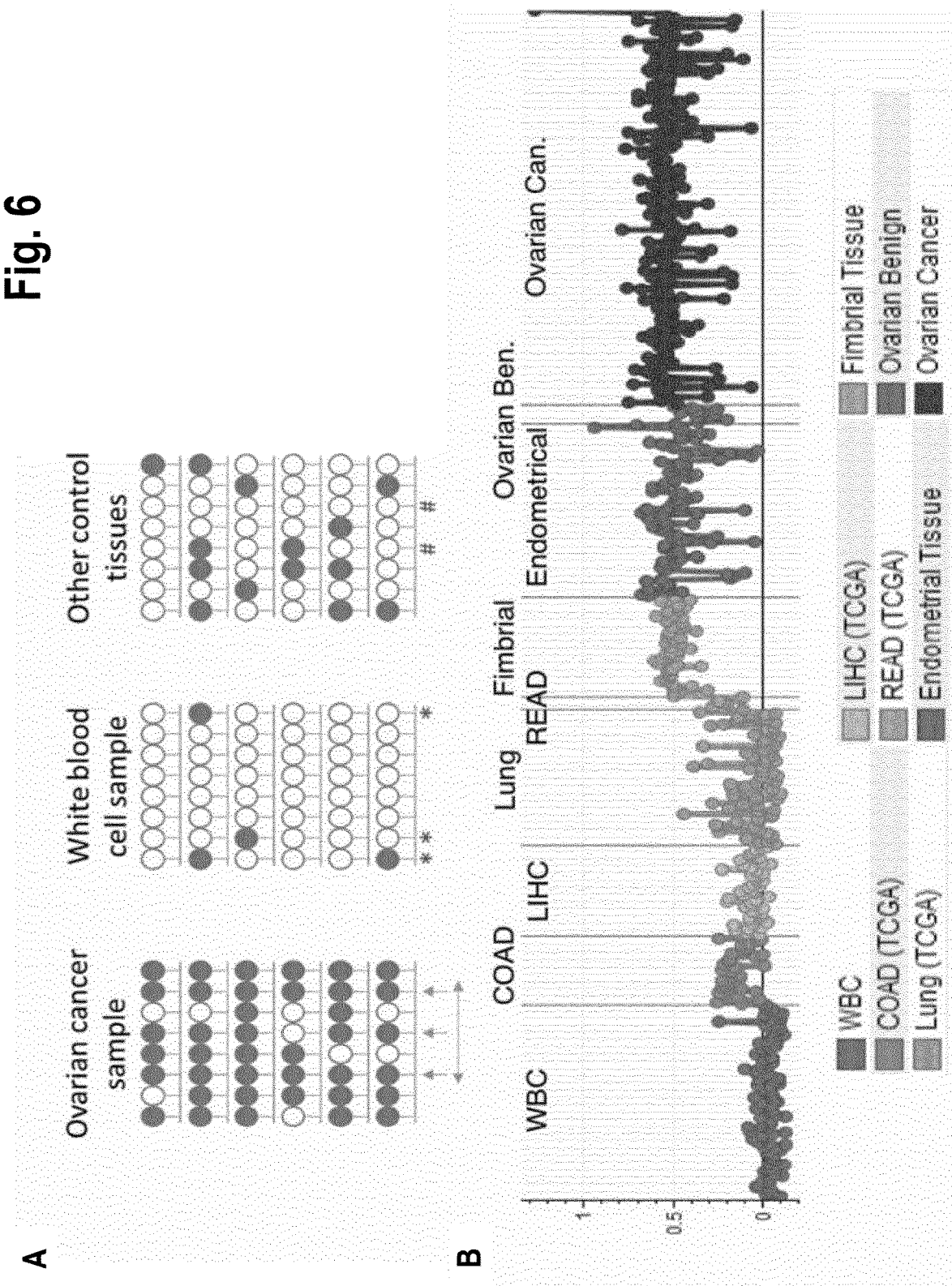
Figure 7:
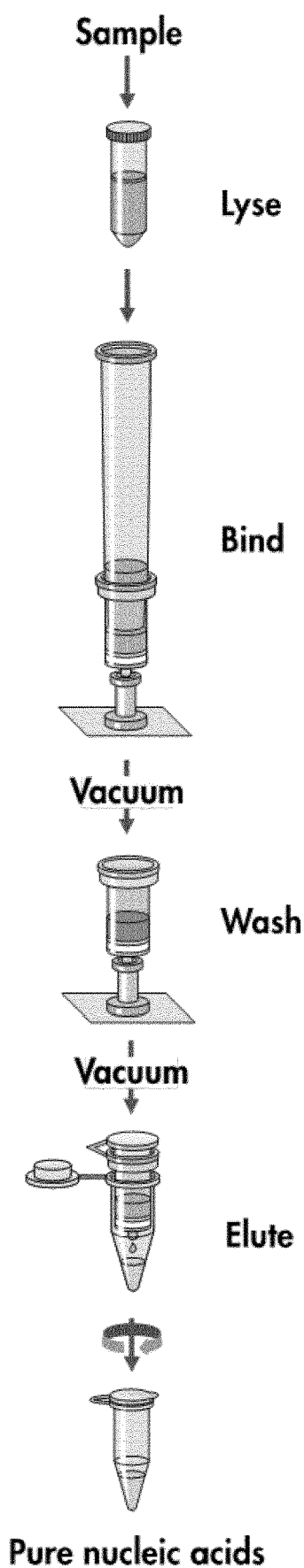

DNA Methylation Marker Discovery in Tissue:

We have used two independent epigenome-wide approaches in order to discover DMRs which have the potential for diagnosing ovarian cancer with high sensitivity and specificity. (1) Illumina Infinium Human Methylation450 BeadChip Array (450K) technology was used to interrogate the methylation status of 485,000 genomic sites in 218 ovarian cancer (Ref. 28) and 438 control samples (FIG. 1; see also Supplementary Information). A set of 19 high scoring and ranking DMRs were selected for targeted-BS based serum assay development. FIG. 6 shows an example of a selected top DMR (reaction #228). (2) Using RRBS, we first determined the methylation pattern frequencies in relevant genomic regions in different tissues. The algorithm that we have developed scans the whole genome and identifies regions that contain at least 10 aligned paired-end reads. These read bundles are split into smaller regions of interest which contain at least 4 CpGs in a stretch of, at most, 100 base pairs (bp). For each region and tissue/sample the absolute frequency (number of supporting reads) for all observed methylation patterns was determined (FIG. 2A). This led to tens of millions of patterns per tissue/sample. The patterns were filtered in a multi-step procedure to identify the methylation patterns which specifically occur in tumour samples. In order to increase sensitivity and specificity, respectively, of our pattern discovery procedure, we pooled reads from different tumour or white blood cell (WBC) samples, respectively, and scored patterns based on over-representation within tumour tissue. The results were summarized in the specificity score Sp, which reflects the cancer specificity of the patterns. After applying a cut-off of Sp 10, 2.6 million patterns for OC remained and were further filtered according to the various criteria demonstrated in FIG. 2B (and Supplementary Information).

For the filtered unique cancer specific patterns for OC identified in the Array (n=19) and RRBS (n=45) approach, respectively, bisulfite sequencing primers have been designed and technically validated, eventually leading to 31 candidate markers, The genome coordinates (hg19) and genomic sequence of each DMR is shown in TABLE 1A and TABLE 1B, and the possible bisulphite-converted sequences thereof (where "Y" symbolises either a C or a U/T, preferably a C or a T) are shown in TABLE 2A (with CpGs—sites of possible 5-methylcytosine—shown underlined).

Figure 8:
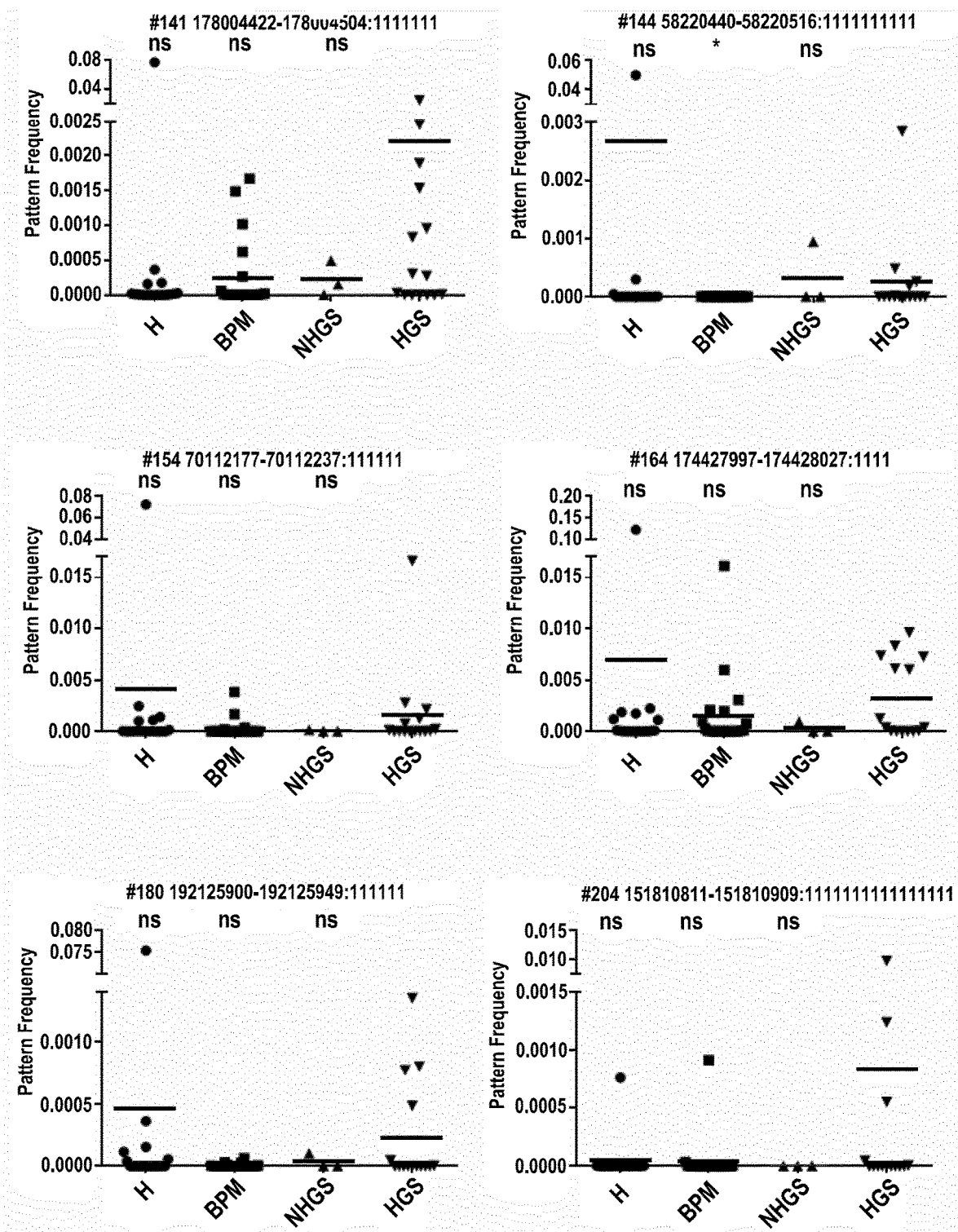
Figure 9:
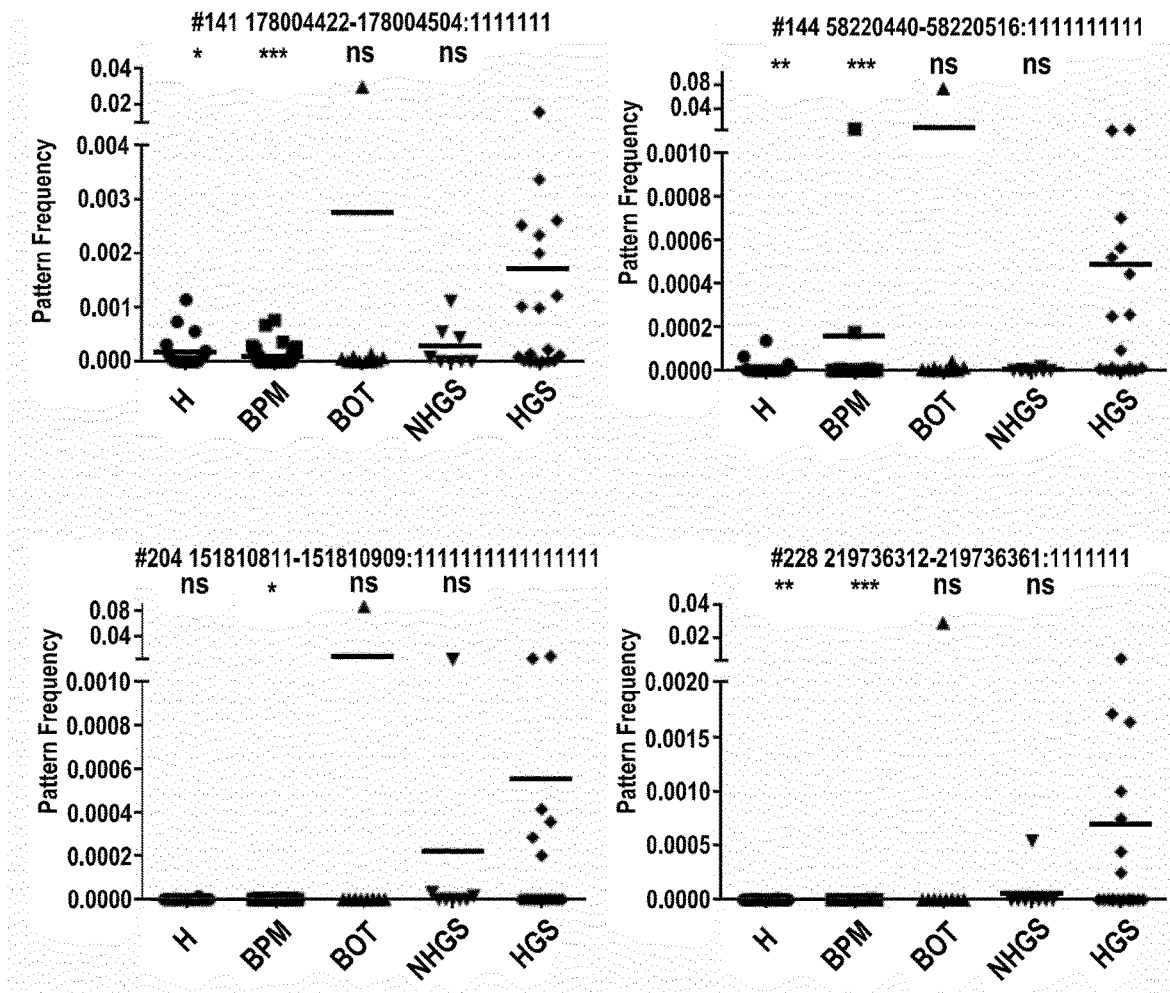

Serum DNAme Assay Establishment:

We used ultra-deep BS sequencing (FIG. 2C) to develop serum assays for the 31 candidate regions in 59 serum samples from Set 1 (FIG. 1 and Supplementary Information and FIG. 8). Based on sensitivity and specificity, nine markers have been selected for further validation in Set 2 (n=92). In Sets 1&2 combined, the specificity/sensitivity of the top four candidate markers (FIG. 9) referred to Regions #141, #144, #204 and #228 (#228 was only analysed in Set 2) to discriminate HGS OC from healthy women or those with a benign pelvic mass at pattern frequency thresholds of 0.0008, 0.0001, 0.0001 and 0.0001 was 95.7%/42.4%, 93.5%/48.5%, 100%/25.0% and 100%/36.8%, respectively. Interestingly region #144 has already been defined as a promising cell-free DNA marker for cancer, in particular ovarian cancer (Refs. 30, 31). The combination of Regions #141, #204 and #228 (at least one of these regions with a pattern frequency above the aforementioned threshold) resulted in a 98.1% specificity and a 63.2% sensitivity. These regions are linked to genes COL23A1, C2CD4D and WNT6, respectively.

Figure 3:
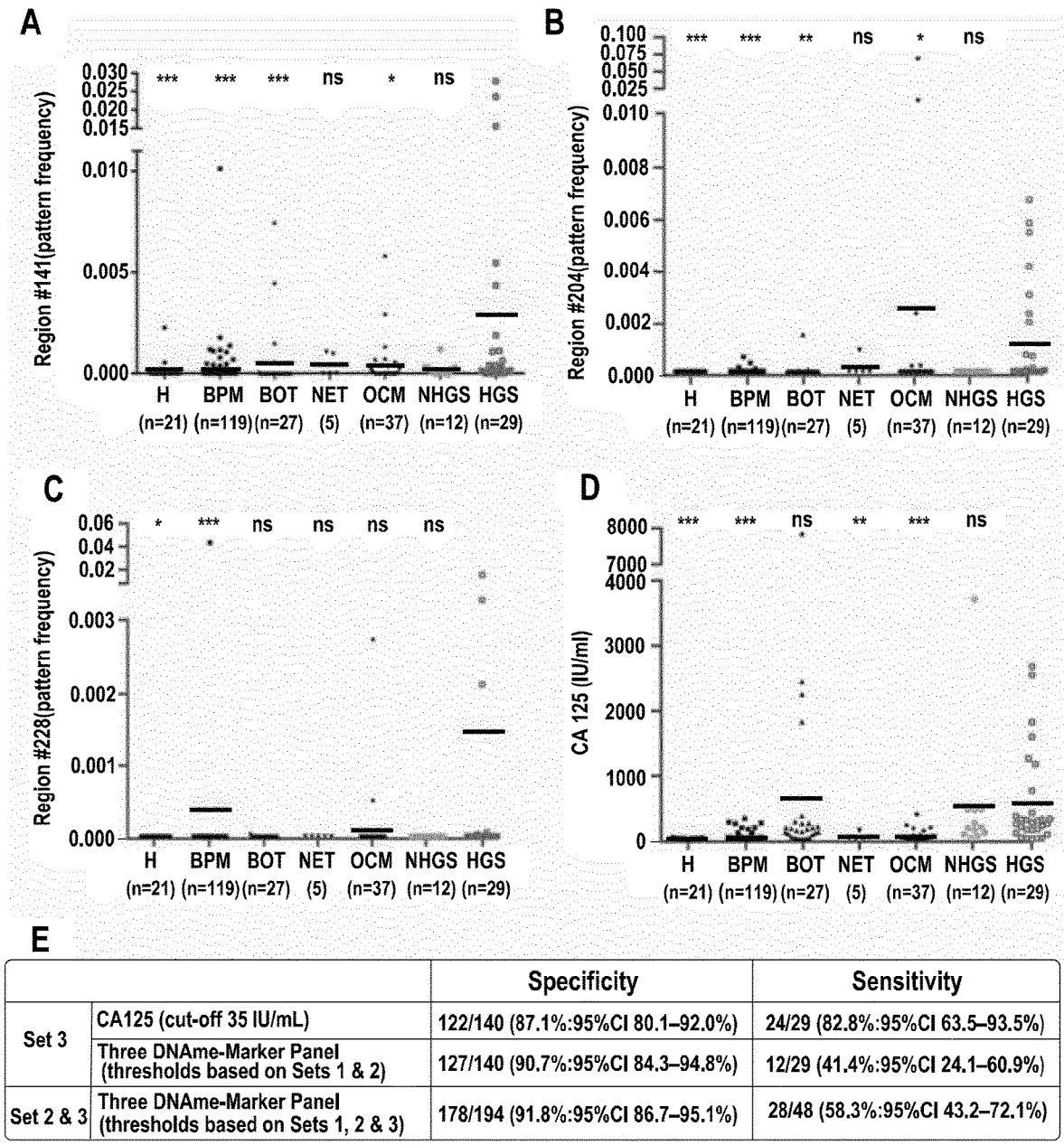
Figure 10:
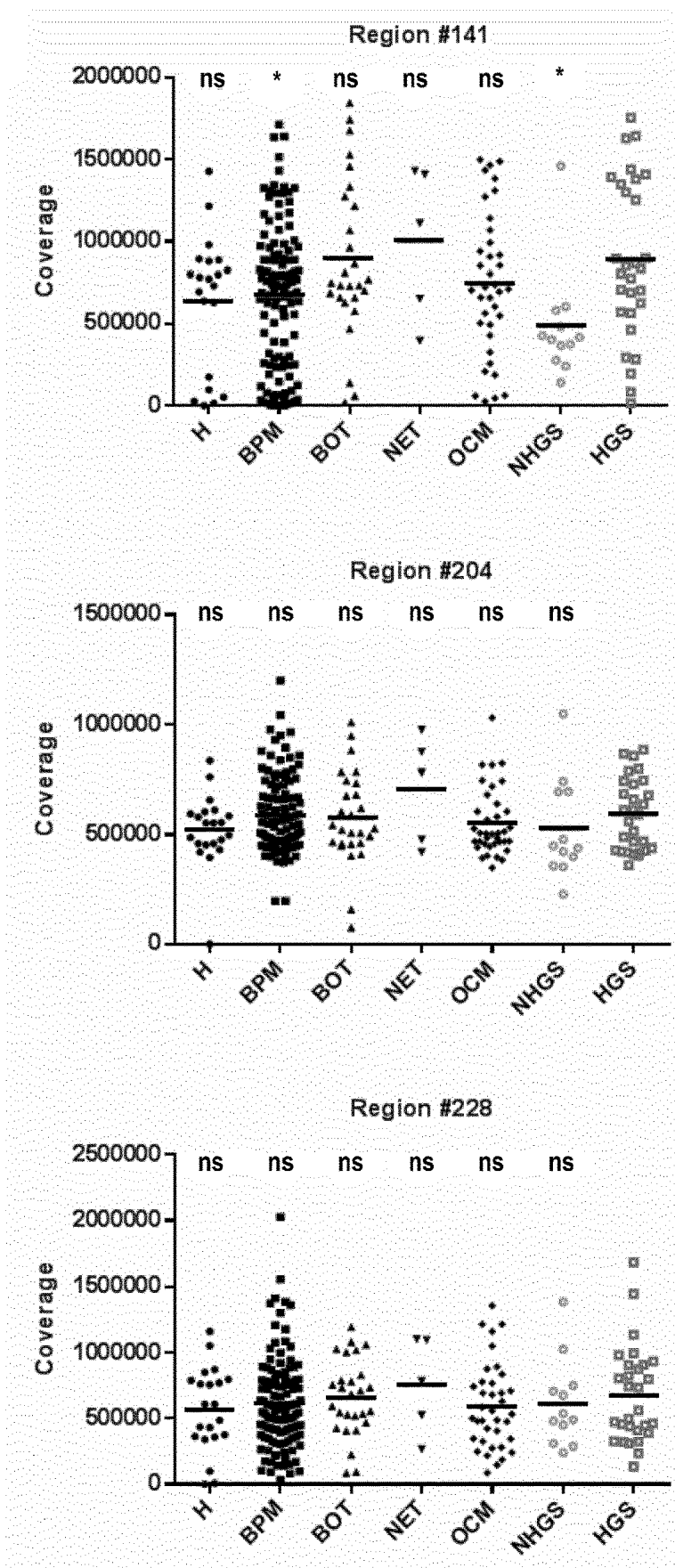
Figure 11:
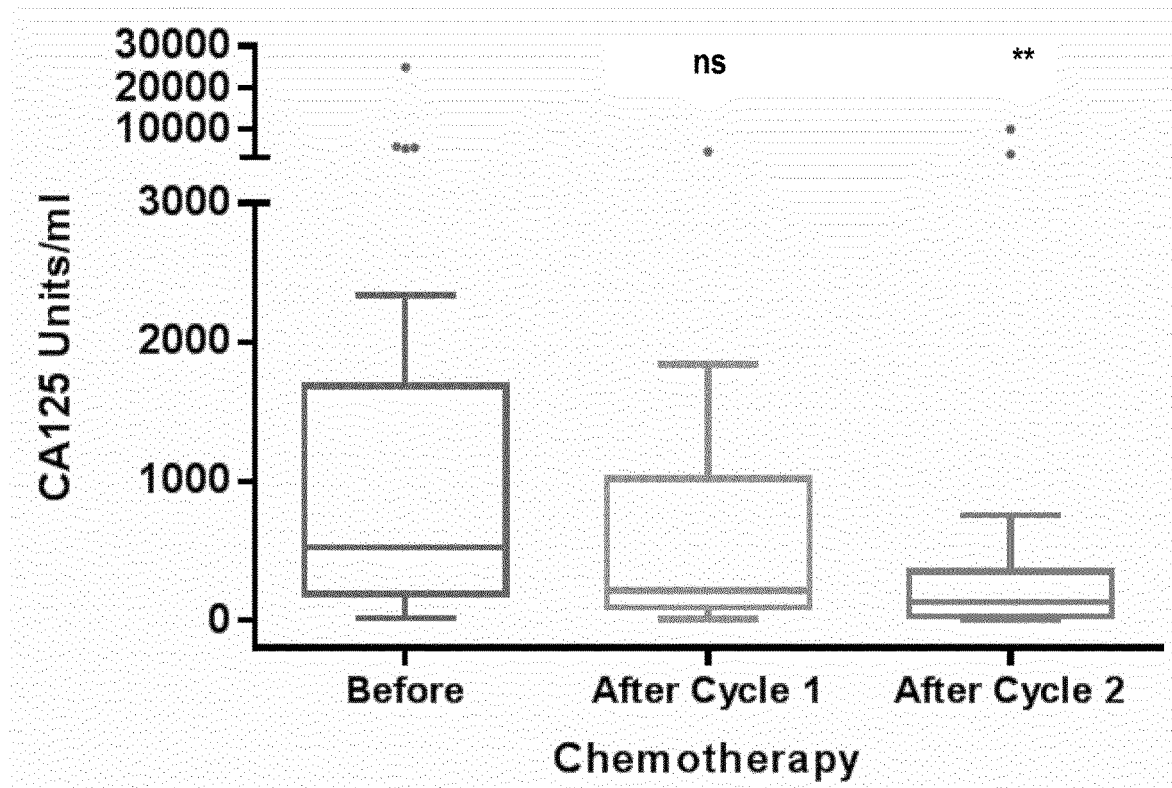
Figure 12:
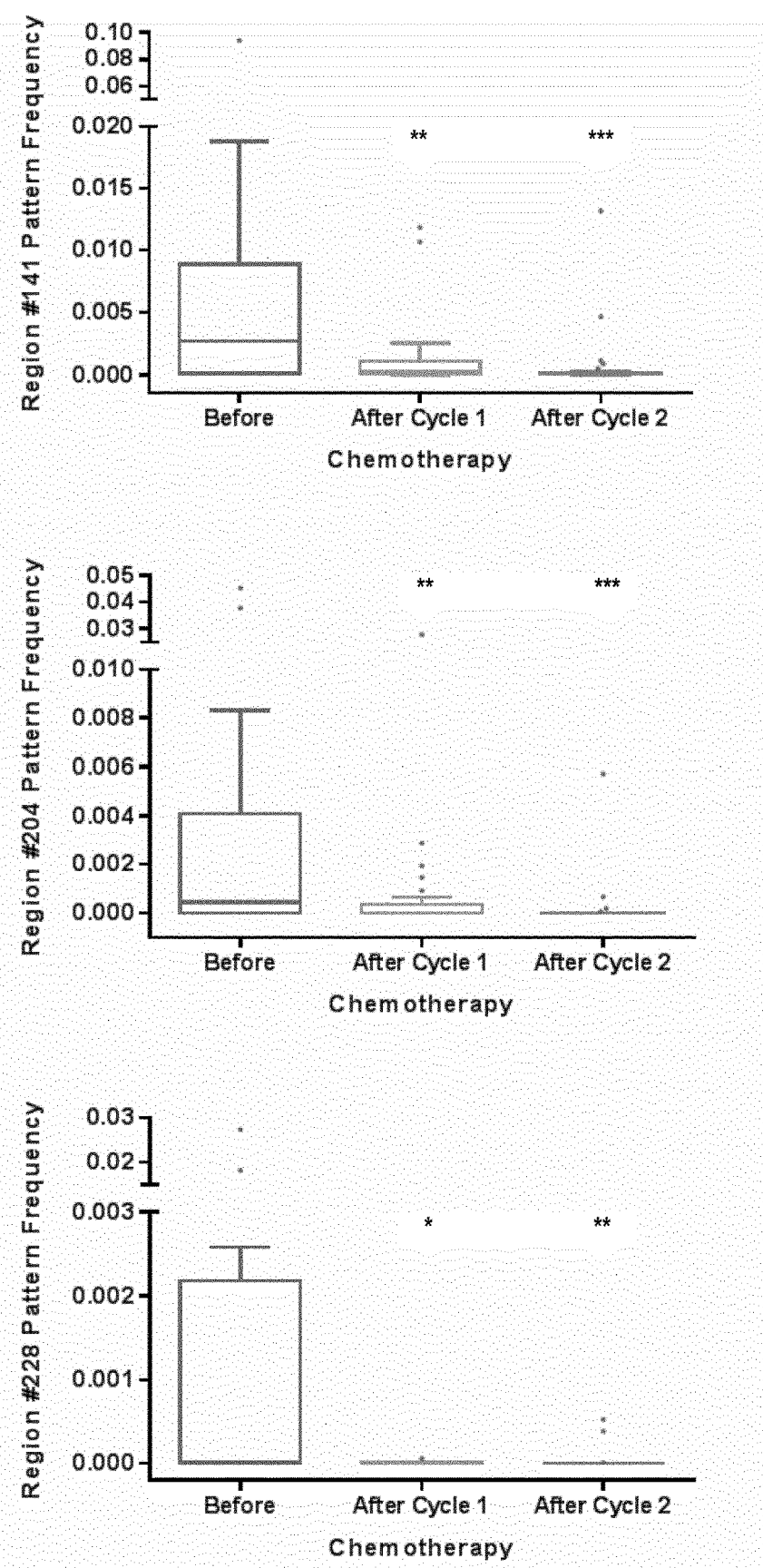
Figure 13:
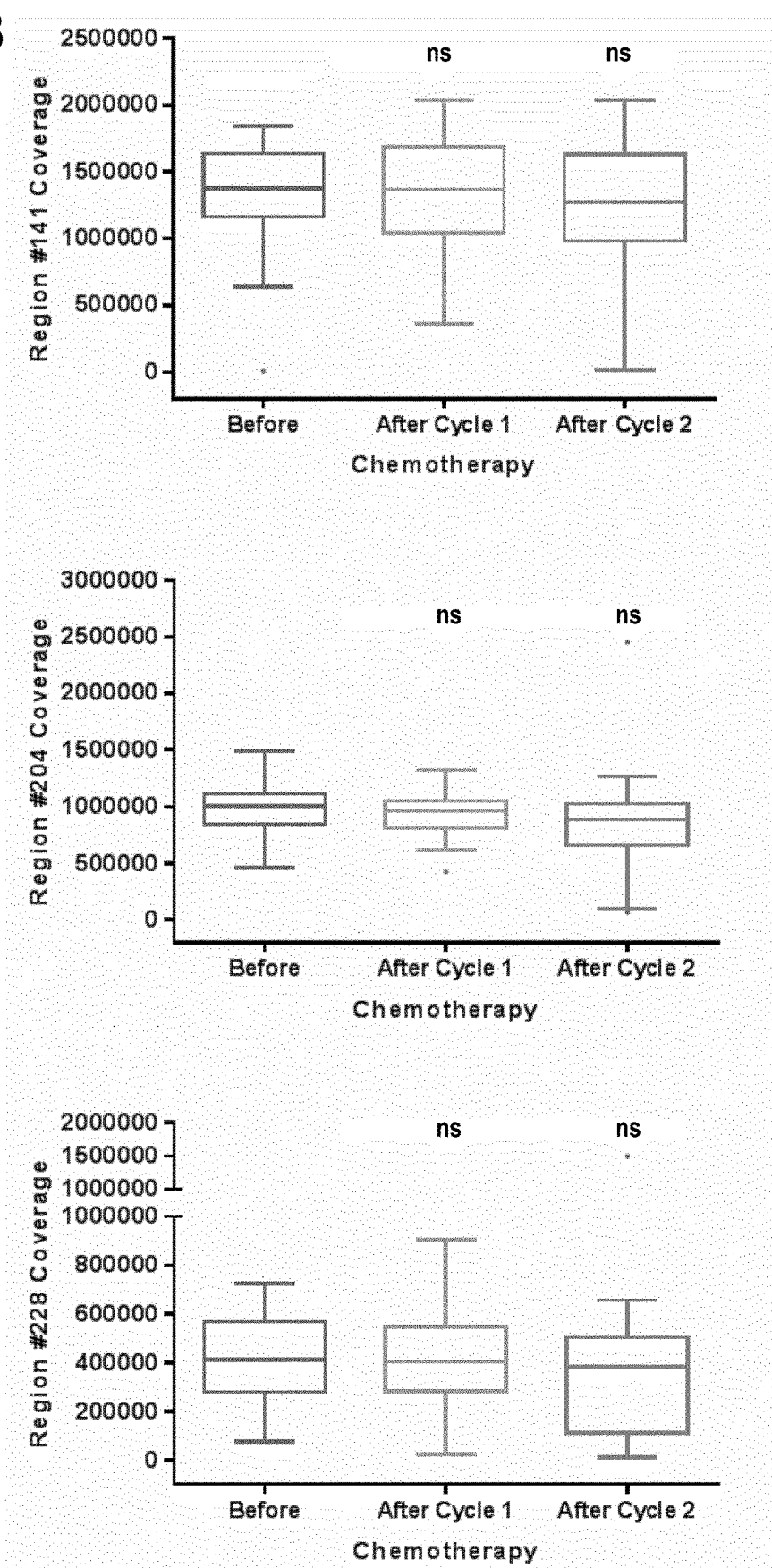

Clinical Validation of the Serum DNAme Assay:

We validated the combination of the three markers in Set 3 (FIG. 3A-C) alongside the CA125 serum marker (FIG. 3D). The average coverage (i.e. DNA strands read by the sequencer for each sample and region) is >500,000 (FIG. 10). Applying the above indicated cut-off thresholds for the three DNAme markers and 35 IU/mL for serum CA125 led to specificities of 90.7% and 87.1% and sensitivities of 41.4% and 82.8%, respectively (FIG. 3E). Due to the fact that Reaction #228 was only analysed in Set 2, we combined Set 2 and Set 3 in order to redefine the thresholds. Whereas for #141 the threshold of 0.0008 remained unchanged, for #204 and #228 we further lowered the pattern frequency threshold to 0.00003 and 0.00001, respectively, leading to a specificity and sensitivity now of 91.8% and 58.3%, respectively (FIG. 3E). Importantly, there was no overlap between the DNAme- and CA125-false positive controls (FIG. 3F).

Figure 4:
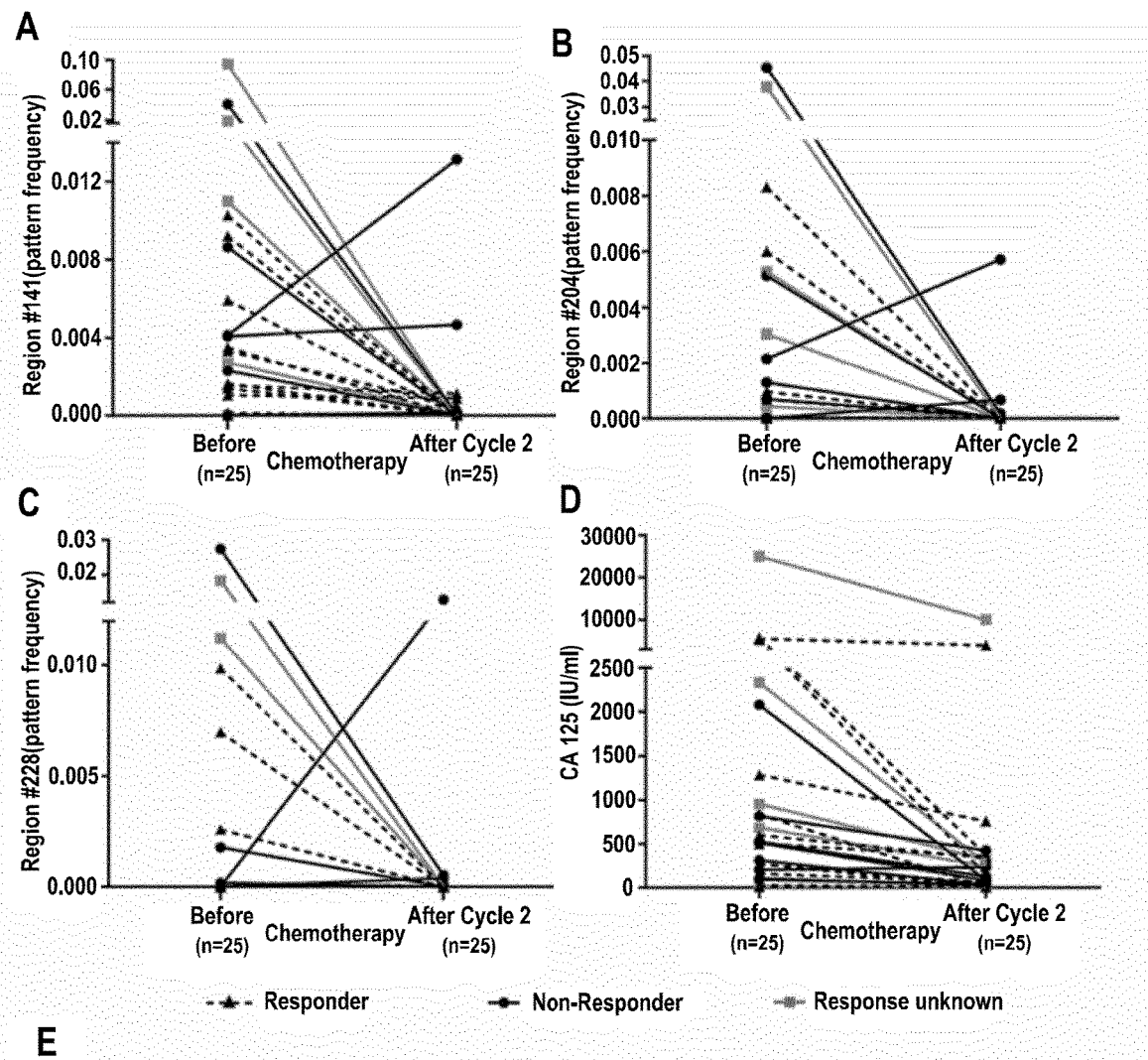

Serum DNAme to Predict Response to Platinum-Based Neoadjuvant Chemotherapy:

We recruited 25 ovarian cancer patients who received carboplatin-based neoadjuvant chemotherapy. Compared with the pre-treatment sample, all three DNAme markers dropped substantially and more dramatically compared to CA125 after one and two cycles (FIG. 4A-D and FIGS. 11, 12, 13). Whereas CA125 dynamics was not able to discriminate chemotherapy-responders from non-responders (FIG. 4E and Supplementary Information), serum DNAme dynamics (i.e. serum DNAme as defined in Set 2&3, before as compared to after two cycles) correctly identified 78% and 86% of responders and non-responders (Fisher's exact test p=0.04) overall and 78% and 100% amongst those women who were left without residual disease after interval debulking surgery (Fisher's exact test p=0.007) (FIG. 4E).

Serum DNAme for Early Diagnosis of Ovarian Cancer:

In order to judge whether our marker panel is able to diagnose ovarian cancer early, samples predating OC diagnosis by up to 2 years (cases) and matched controls can be used from the control (no screening)—arm of the UKC-TOCS cohort. As at the time of their collection, UKCTOCS samples were not obtained, treated or stored with the analysis cell-free DNA in mind. Hence, it is to be expected that upon DNA extraction it will be found that either or both the amount of DNA/mL serum as well as the average DNA fragment size may be higher (such as dramatically higher) in UKCTOCS samples compared with the other samples used in this study. As has been previously observed and proposed (Anjum et al, 2014, Genome Med 6:47), without being bound by theory, such effect may be due to DNA from WBCs leaking into the serum during the 24-48 hour blood sample transport time—in particular in the warm season). This "contaminating" high quality [genomic rather than tumour] DNA would not only dilute the cancer signal but also skew the target sequence amplification towards WBC DNA. In order to adjust for these factors, an a priori decision may be made to reduce the threshold for the three regions by a factor, such as by a factor of 3, and/or to split the analyses in samples above (high) and below (low) the median amount of DNA.

Such adjustments can enable the three DNAme-marker panel to yet further confirm its validation above and its utility for the early detection of ovarian cancer. Indeed, it can then be used to identify cases with a specificity of over 70%, 80%, or 90% (such as between about 70% and 80% or between about 80% and 90%) and a sensitivity of over 45% 50%, 55% or 60% (such as between about 50% and 55% or between about 55% and 60%) [indeed, the sensitivity may be even higher in CA125 negative (<35U/mL) samples] in samples with a lower than median amount of DNA and may remain literally unchanged within two years between sample collection and cancer diagnosis. Given the greater dynamic range of DNAme panel test and the results above, it can have higher sensitivity but lower specificity compared to that of CA125 using a cut-off of 35U/ml in the early detection of ovarian cancer, and/or to have no overlap of false positives. The DNAme panel has higher sensitivity but lower specificity compared to that of CA125 using a cut-off of 35U/ml in the early detection of ovarian cancer.

Supplementary Information:

Subjects and Sample Collection:

We analysed a total of 6 sets as detailed in FIG. 1:

1. Array-Set: Ovarian cancer samples (Refs. 51, S2), WBC samples (Ref. S3) and Fallopian Tube samples (Ref. S4) have been described before. Ten benign pelvic tumours (2× endometriosis-ovarian cyst, 1× fibroma, 2× papillary serous cystadenoma, 1× mucinous cystadenoma, 2× serous cystadenoma, 1× mucinous cystadenoma with Brenner tumour and 1 dermoid cyst), 96 endometrial samples (Ref. 51) (Haukeland University Hospital, Bergen, 52 patients with primary and metastatic samples equalling 87, 8× benign endometrial (all hyperplasia) & 1 cell line) and 170 samples (38 colon (COAD controls), 50 liver (LIHC controls), 75 lung (LUSC and LUAD controls), 7 rectum (READ controls) from the publically available The Cancer Genome Atlas (TCGA) repository were analysed.

2. RRBS Set: 11 prospectively collected invasive epithelial ovarian cancer samples (high grade serous n=8, low grade serous n=1, endometrioid n=1, mean age=54.7 years), one benign tumour (papillary serous cystadenoma, age=86 years), 18 normal tissue samples (normal breast n=7 and normal ovarian n=11, mean age=60.2 years), two normal endometrial tissues mean age=68, and twenty three white blood cell samples (breast cancer patients n=10 & ovarian cancer patients n=13 [11 of which match corresponding OC tissue samples, 1 matches corresponding normal endometrial sample and 1 matches normal ovarian sample], mean age=57.8) were assessed by RRBS.

All samples of the RRBS Set were collected prospectively at the University College London Hospital in London (University College London Hospital, 235 Euston Rd, Fitzrovia, London NW1 2BU) and at the Charles University Hospital in Prague (Gynecological Oncology Center, Department of Obstetrics and Gynecology, Charles University in Prague, First Faculty of Medicine and General University Hospital, Prague, Apolinarska 18128 00 Prague 2, Czech Republic). The study was approved by the local research ethics committees: UCL/UCLH Biobank for Studying Health & Disease NC09.13) and the ethics committee of the General University Hospital, Prague approval No.: 22/13 GRANT—7. RP—EPI-FEM-CARE respectively. All patients provided written informed consent.

3. Serum Set 1: Serum samples from the following volunteers have been collected (at the time of diagnosis, prior to treatment):
   Healthy volunteers (n=19, mean age 41.1 years).
   Women with benign pelvic masses (n=22, mean age 41.3 years) with the following histologies: endometriosis (n=6), fibroids (n=5), hydrosalpinx (n=1), serous cystadenoma (n=5) and mucinous cystadenoma (n=5).
   Patients with ovarian cancers (n=18, mean age 62.2 years): endometrioid (n=2) and clear cell (n=1) and high grade serous (n=15) ovarian cancers; 10 and 8 women had a stage I/II and stage III/IV ovarian cancer, respectively.

All samples of Serum Set 1 were collected prospectively at the University College London Hospital in London and at the Charles University Hospital in Prague. The study was approved by the local research ethics committees: UCL/UCLH Biobank for Studying Health & Disease (NC09.13) and the ethics committee of the General University Hospital, Prague approval No.: 22/13 GRANT—7. RP—EPI-FEM-CARE respectively. All patients provided written informed consent.

4. Serum Set 2: Serum samples from the following volunteers have been collected (at the time of diagnosis, prior to treatment):
   Healthy volunteers (n=20, mean age 42.8 years).
   Women with benign pelvic masses (n=34, mean age 40.0 years) with the following histologies: endometriosis (n=7), fibroids (n=8), pelvic inflammatory disease or pelvic abscess (n=9), serous cystadenoma (n=5) and mucinous cystadenoma (n=5).
   Patients with borderline ovarian tumors (n=11, mean age 47.3 years): mucinous (n=6) and serous (n=5) borderline tumor.
   Patients with ovarian cancers (n=27, mean age 62.9 years): endometrioid (n=3) and clear cell (n=3), mucinous (n=2) and high grade serous (n=19) ovarian cancers; 10 and 17 women had a stage I/II and stage III/IV ovarian cancer, respectively.

All samples of Serum Set 2 were collected prospectively at the University College London Hospital in London and at the Charles University Hospital in Prague. The study was approved by the local research ethics committees: UCL/UCLH Biobank for Studying Health & Disease NC09.13) and the ethics committee of the General University Hospital, Prague approval No.: 22/13 GRANT—7. RP—EPI-FEM-CARE respectively. All patients provided written informed consent.

5. Serum Set 3: Serum samples from the following volunteers have been collected (at the time of diagnosis, prior to treatment):
   Healthy volunteers (n=21, mean age 50.8 years).
   Women with benign pelvic masses (n=119, mean age 41.4 years) with the following histologies: endometriosis (n=21), fibroids (n=21), pelvic inflammatory disease or pelvic abscess (n=7), serous cystadenoma (n=20), mucinous cystadenoma (n=20) and dermoid cysts (n=29).
   Patients with borderline ovarian tumors (n=27, mean age 57.1 years): mucinous (n=7) and serous (n=20) borderline tumor.
   Patients with non-epithelial tumors (n=5, mean age 55.8 years): granulosa cell tumors.
   Patients with non-ovarian cancers (n=37, mean age 58.3 years): cervical (n=10), endometrial (n=20) and colorectal (n=7) cancers.
   Patients with ovarian cancers (n=41, mean age 59.6 years): endometrioid (n=3) and clear cell (n=5), mucinous (n=4) and high grade serous (n=29) ovarian cancers; 16 and 25 women had a stage I/II and stage III/IV ovarian cancer, respectively.

All samples of Serum Set 3 were collected prospectively at the University College London Hospital in London and at the Charles University Hospital in Prague; CA125 analysis was performed using the CA125 Cobas immunoassay and platform (Roche Diagnostics, Burgess Hill, UK). The study was approved by the local research ethics committees. The study was approved by the local research ethics committees: UCL/UCLH Biobank for Studying Health & Disease (NC09.13) and the ethics committee of the General University Hospital, Prague approval No.: 22/13 GRANT—7. RP—EPI-FEM-CARE respectively. All patients provided written informed consent.

Of note: For the Serum Sets 1-3 which have been prospectively collected within EpiFemCare there is a substantial age difference between women who presented with benign pelvic masses and women who presented with ovarian cancer. We were completely aware of this as the main purpose was to benchmark DNAme markers against CA125 and to assess whether CA125 false positive controls are also DNAme-false positive. The main source of false positivity are endometriosis, pelvic inflammatory disease and fibroids—all conditions which are substantially more prevalent (or occur exclusively) in premenopausal (i.e. younger women) whereas ovarian cancer is far more prevalent in older women.

6. NACT ("Neoadjuvant Chemotherapy") Set: Patients (n=25) at the Gynaecological Oncology Centre in Prague deemed not to be suitable for up-front surgery have been recruited. The average age was 62.8 years. High grade serous ovarian cancers were the most prevalent histology (n=23) and the remaining two patients had clear cell ovarian cancers. Twenty-four patients received Carboplatin-Paclitaxel combination chemotherapy and one patient received Carboplatin only. All but two patients had interval debulking surgery. Among the 23 patients, 14 had no residual disease, 5 had macroscopic residual disease and 4 had microscopic residual disease (i.e. tumor reaches the edge of at least one of the resected specimens—according to TNM classification). Twelve patients were deemed to be platinum-sensitive (no recurrence within 6 months after successful completion of neoadjuvant and adjuvant chemotherapy and interval debulking surgery) and eight patients were deemed to be platinum-refractory (n=2, no response to chemotherapy or progression on chemotherapy) or platinum-resistant (n=6, recurrence within 6 months after successful completion of neoadjuvant and adjuvant chemotherapy and interval debulking surgery). For 5 patients no data were available on platinum-sensitivity.

All serum samples of the NACT Set were collected prospectively at the Charles University Hospital in Prague. Each patient provided three samples at the following time-points:
   At the time of histological diagnosis, prior to chemotherapy.
   Three weeks after the first cycle of chemotherapy (immediately prior to the second cycle).
   Three weeks after the second cycle of chemotherapy (immediately prior to the third cycle).

CA125 analysis on the NACT Set was performed using the CA125 Cobas immunoassay and platform (Roche Diagnostics, Burgess Hill, UK). The study was approved by the local research ethics committees: UCL/UCLH Biobank for Studying Health & Disease (NC09.13) and the ethics committee of the General University Hospital, Prague approval No.: 22/13 GRANT—7. RP—EPI-FEM-CARE respectively. All patients provided written informed consent. Eighteen and seven patients presented with a stage IIIC and IV ovarian cancer respectively.

In addition to these six sets, a seventh set could be used to provide further confirmation on the validation of the present assay provided by the other sets. Such a seventh set could comprise samples from the UKCTOCS collection. For example, among those women who were randomised into the control arm of UKCTOCS between 2001 and 2005, the subset of such women who developed an invasive epithelial ovarian cancer within 2 years of serum sample donation and had at least 4 mL of non-haemolysed serum available, and such number of women stratified into those women which developed a high grade serous, mucinous, endometrioid, clear cell, carcinosarcoma or a carcinoma not otherwise specified, respectively. The average age at sample donation can be calculated in years; as can the number of such women, the number of women who were diagnosed within one year and those who were diagnosed between 1-2 years after sample donation, as well as the respective number of women who were diagnosed with a stage I/II and stage III/IV cancer, respectively. For each of the such cases, three women who did not develop any cancer within the first five years after recruitment can be matched with regards to age at recruitment, centre and month of recruitment (controls).

DNA Methylation Analyses in Tissue Samples:

DNA isolation: DNA was isolated from tissue samples using the Qiagen DNeasy Blood and Tissue Kit (Qiagen Ltd, UK, 69506) and 600 ng was bisulfite converted using the Zymo methylation Kits (Zymo Research Inc, USA, D5004/8).

Illumina Infinium Human Methylation450 BeadChip Array data analysis: Genome wide methylation analysis was performed using the Illumina Infinium Methylation 450K beadchip (Illumina Inc USA, WG-314-1003). The raw data processing and quality control was performed in R/Bioconductor (versions 2.15.0/2.11) (Ref. S5) using minfi (Ref. S6) and BMIQ (Ref. S7) packages. Identification of differentially methylated regions (DMRs) was carried out using Genedata Expressionist® for Genomic Profiling as described below.

To correct for the individual probe to probe variation in the affinity/sensitivity to unnmethylated vs. methylated DNA we used fully methylated (SssI treated) and unmethylated (whole genome amplified; WGA) genomic DNA from WBC samples of different individuals. These technical controls were used for both filtering out probes that do not show sufficient specificity (i.e. cannot discriminate between methylated vs. unmethylated state) and to perform array-wide recalibration of the biological sample data to normalize for the probe to probe variation in background and dynamic range, respectively. The removal of the non-specific probes was achieved by doing a T-test with SssI vs WGA samples (using M-values) and removing the probe sets that have p-value <0.01 and effect size below <5 i.e. cannot discriminate between fully methylated and unmethylated DNA. The normalization was done for each sample individually for each probe set with the formula $M_{true}=(M_{measured}-M_{WGA})(M_{SssI}-M_{WGA})$; $M_{SssI}$ and $M_{WGA}$ values used were average (arithmetic mean) values of the respective sample groups. For the downstream analyses the individual sample SssI and WGA data were also normalized with the same formula. This leads to efficient removal of background noise from the probe to probe variation and increases the power to detect homogenously methylated or unmethylated genomic regions. T-test and normalization were performed in Genedata Expressionist® for Genomic Profiling software.

The control sample set was selected to identify DMRs that are cancer specific and would also be specific in a serum based clinical assay. Therefore, in addition to the ovarian (including Fallopian Tube and endometrium) control tissues we used a large panel of tissues that are likely to shed DNA into the serum [i.e. white blood cells (WBCs), lung, liver, rectum and colon], with WBCs being the most abundant source of normal germline DNA in serum samples. Two statistical approaches were used to identify DMRs from the 450K data: (1) a statistical test to identify single probes showing differential methylation between ovarian cancer and WBC samples, and (2) a sliding window ANOVA approach that scans the whole genome and identifies sets of neighboring probes (Ranges) showing correlated methylation differences between ovarian cancer and WBC samples. Only the DMRs showing no methylation in WBCs were considered for downstream analysis steps. The identified DMRs where ranked and scored based on the following criteria: (1) Differences in methylation levels between ovarian cancer and the control tissues (with WBC difference being emphasized). (2) Feasibility of designing a clinical assay (number of CpGs in the region to allow designing an assay with sufficient sensitivity/specificity). (3) For ranges only: Reliability of the DMRs (number of probes within the Range).

In the sliding window approach, the algorithm performs a pooling of all features in a given sliding window (120 bp) before it calculates an ANOVA p-value between sample groups. The pooling increases statistical robustness and also results in smoother ANOVA p-Values. The smoothed ANOVA p-Values are then used to detect regions containing one or more p-values exceeding the given Maximum P-Value threshold (1e-5). If a gap of more than 1000 bp is detected between similar methylation differences, two different regions are reported. Note, that the algorithm also reports single probes showing significant methylation difference (if no neighbouring similar methylation difference is present), but groups of probes with similar profile do get lower p-values and are therefore preferentially reported. The sliding window approach was used for OC vs WBC samples to detect cancer DMRs (using normalized M-values) and arithmetic mean M-values of the probes per detected DMR (here after referred as "Range") were reported for all the relevant samples for downstream analysis. The Range discovery was performed in Genedata Expressionist® for Genomic Profiling v8.0 software. The Ranges varied in size between 1 and 45432 bp, with average (arithmetic mean) size being 368 bp. The Ranges showing methylation in WBC were removed by a T-test with WBC vs. WGA samples (p-value <1e-6 and/or directed effect >0.15; i.e. M(WBC) >M(WGA)+0.15). Next, a T-test for OC vs WBC was used and Ranges showing significant difference (p-value <1e-6) and difference (directed effect) of WBC upper quartile vs OC lower quartile >0.15 were selected as differentially methylated regions. For different control tissue samples the methylation values were calculated for the same OC vs WBC Ranges (arithmetic mean M-values of the probes per detected DMR).

For ranking of the DMRs the effect sizes of methylation of cancer samples versus different relevant controls tissues were calculated. In addition to "direct" control tissues (fimbrial/endometrial/benign ovarian tissues) also large tissues with high turnover (liver, lung, rectum and colon) were included; data were download from TCGA data portal (https://tcga-data.nci.nih.gov/tcga/) as level 3 data as detP filtered beta-values; data normalization was carried out as described above. The effect sizes were always calculated with cancer lower quartile vs control tissue upper quartile values (based on SssI/WGA normalized M-values).

Two different scoring methods were used for the effect sizes. In Method 1 the OC vs WBC effect size gets the weight 6×, and all the control tissue 1/4×. In Method 2 the OC vs WBC effect size gets the weight 6×, and all the control tissue 1×. The Method 2 takes more into account the data from all the control tissues whereas Method 1 maximises the effect of the difference between WBC and cancers samples. However, for both methods only DMRs prefiltered for low methylation in WBCs were used (as described above). The final scores are the sum of the tissue scores and the feasibility and confidence scores (see next paragraph). If data were not available for a certain probe for a certain tissue (i.e. was filtered out due to high detection p-value), the score for the tissue was 0.

For further ranking of the DMRs feasibility (for designing a functional clinical assay) and confidence (for ranges) scores were calculated. The feasibility score is based on number of CpG dinucleotides within (or close by; +/−60 bp) a probe/range. If the number of CpGs is <5, the score is −0.5, if the number of CpGs is between 5 and 9 the score is 0 and if the number of CpGs is >=10 the score is 0.5. The number of CpGs per range was calculated using EMBOSS cpgreport tool in Galaxy (Refs. S8-S10) using the range genomic coordinates as input. The confidence score for ranges is 0.5 if 2 or more probes are within the range, if only one probe the score is 0.

Reduced Representation Bisulfite Sequencing (RRBS):
RRBS:
RRBS libraries were prepared by GATC Biotech AG using INVIEW RRBS-Seq according to proprietary SOPs. In brief, DNA was digested with the restriction endonuclease MspI that is specific for the CpG containing motif CCGG; a subsequent size selection provides enhanced coverage for the CpG-rich regions including CpG islands, promoters and enhancer elements (Refs. S11, S12). The digested DNA is then adapter ligated, bisulfite modified and PCR-amplified. The libraries were sequenced on Illumina's HiSeq 2500 with 50 bp or 100 bp paired-end mode.

After sequencing raw data was trimmed using Trimmomatic (0.32) to remove adapter sequences and low quality bases at the beginning and end of reads. Subsequently, reads were trimmed with TrimGalore (0.3.3) to remove cytosines derived from library preparation which must not be included in the methylation analysis. Read pairs were mapped to the human genome (hg19) in Genedata Expressionist® for Genomic Profiling 8.0 applying Bisulfite Mapper based on BOWTIE v2.1.0 (Ref. S13) with the settings - -no-discordant - -reorder -p 8 - -end-to-end - -no-mixed -D 50 -k 2 - -fr - -norc -X 400 -I 0 - -phred33. Further analysis was done using Genedata Expressionist® for Genomic Profiling v9.1.

Computation of RRBS-Determined Methylation Pattern Frequencies:

In order to allow the sensitive detection of methylation patterns with low abundance, the read data available for each sample type (e.g. breast cancer, ovarian cancer and white blood cells) were pooled across patients and sequencing runs. Candidate genomic regions for methylation pattern analysis were defined based on bundles of at least 10 paired-end reads covering at least 4 consecutive CpG sites which are located within a genomic range of at most 150 bp. As illustrated in FIG. 5, our algorithm first determines sets of consecutive CpG sites of maximum size, from which multiple potentially overlapping subsets are derived, which still meet the selection criteria. CpG sites located in the gap between the mate reads are ignored. For each derived set of CpG sites, the absolute and relative frequencies of all methylation patterns observed in the corresponding reads are determined. The methylation patterns are represented in terms of binary strings in which the methylation state of each CpG site is denoted by 1 if methylated or 0 if unmethylated. The algorithm for selecting candidate regions and calculating methylation pattern frequencies was implemented in our software platform Genedata Expressionist® for Genomic Profiling.

Procedure for the Selection of Tumour-Specific RRBS-Determined Methylation Patterns:

In order to ensure that the pattern exclusively occurs in tumour samples, all patterns present in white blood cells were excluded. A score for assessing the relevance of each pattern was determined by integrating multiple subordinate scores which quantitatively capture desired properties of candidate biomarker patterns. First, for each pattern a Tumour Specificity Score Sp=DL·TP·TE·AF was calculated, which consists of the four components Dilution Factor DL, Tumour Prevalence TP, Tumour Enrichment Factor TE and Avoiding Factor AF. The formal definitions of the score components are given in the following:

$$DL_{WBC} = \frac{\#\text{total reads}}{\#\text{reads with pattern}} * \frac{1}{10^3}$$

$$TP_{tumor} = \frac{\#\text{reads with pattern in tumor}}{\#\text{total reads in tumor}} * 10$$

$$TE_{tumor} = \frac{\#\text{observed reads with pattern in tumor}}{\#\text{expected reads with pattern in tumor}}$$

$$AF_{WBC} = \frac{\#\text{expected reads with pattern in } WBC}{\#\text{observed reads with pattern in } WBC}$$

The Dilution Factor DL and Tumour Prevalence TP favour patterns which are supported by a high proportion of reads in tumour and low proportion of reads in WBC, respectively. A pattern observed in 1 out of 10 reads in tumour and in 1 out of 1000 reads in WBC scores 1 for both factors. The Tumour Enrichment Factor TE and Avoiding Factor AF were included to assess the overrepresentation of the pattern in tumour samples and its underrepresentation in WBC samples, respectively, relative to an expected number of pattern reads which is based on the observed overall methylation level in those tissues. In order to estimate the number of expected reads supporting the pattern, the methylation frequencies are calculated for each CpG site individually. Next, the number of expected reads with a specific pattern is calculated as the product of the relative frequencies of the tumour specific methylation states observed for each CpG site in the pattern times the number of reads stretching across the pattern. A TE>1 indicates that a pattern is more frequent in tumour than expected when randomly distributing the observed methylation levels across reads. Besides favouring tumour specificity our scoring procedure was also designed to make patterns with high variance of the highest priority (i.e., patterns for which a high number of transitions in the methylation state is observed between consecutive CpG sites). Such patterns may be a product of the epigenetic reprogramming of tumour cells and in order to account for the potentially increased biological relevance of these patterns another score component was introduced. The normalized variance $V_P$ of a pattern p is defined as the pattern variance divided by the maximum variance, i.e., the pattern length minus 1. The scores for the tumour specificity $S_P$ and pattern variance $V_P$ were combined in the tumor-specific variance score $SV_P=V_P \cdot \log(S_P)$. In order to facilitate the ranking of each candidate genomic region r based on the relevance of patterns $p_1, \ldots, p_N$ observed in the region the aggregation score $AS_r$ was calculated based on the following formula:

$$AS_r = \sum_{i=1}^{n} \frac{1}{i} SV_{P_i}$$

The aggregation score $AS_r$ corresponds to a weighted sum of the tumour-specific variance scores of the observed patterns. The weighting was included since an ordinary sum would introduce a bias towards regions, in which a high number of patterns have been observed due to a high read coverage and/or high CpG site density. All of the presented statistics for assessing the relevance of methylation patterns and genomic regions were implemented in Genedata Expressionist® for Genomic Profiling and R, respectively.

DNA Methylation Analyses in Serum Samples:

Serum Separation:

For Serum Sets 1-3 and the NACT Serum Set, women attending the hospitals in London and Prague have been invited, consented and 20-40 mL blood has been obtained (VACUETTE® Z Serum Sep Clot Activator tubes, Cat 455071, Greiner Bio One International GmbH), centrifuged at 3,000 rpm for 10 minutes and serum collected and stored at −80° C. We have applied non-stringent measures (i.e. allowed for up to 12 hours between blood draw and centrifugation) purposely in order to mimic the situation of UKCTOCS samples which could be used to compare the results presented herein, which samples had been sent from the recruiting centre to UCL within 24-48 hours before centrifugation.

Serum DNA Isolation and Bisulfite Modification:

DNA was isolated using the DNeasy Blood and Tissue Kit (Qiagen Ltd, UK, 69506) at GATC Biotech (Constance, Germany). Serum DNA was quantified using the Fragment Analyzer and the High Sensitivity Large Fragment Analysis Kit (AATI, USA). DNA was bisulfite converted using the EZ-96 DNA Methylation Kit (Zymo Research Inc, USA, D5004/8) at GATC Biotech.

Targeted Ultra-High Coverage Bisulfite Sequencing:

Targeted bisulfite sequencing was performed at GATC. To this end, a two-step PCR approach was used similar to the recently published BisPCR2 (Ref. S14). Bisulfite modification was performed with 1 mL serum equivalent. For each batch of samples, positive and non-template controls were processed in parallel. Bisulfite converted DNA was used to test up to three different markers using automated workflows. After bisulfite modification the target regions were amplified using primers carrying the target specific sequence and a linker sequence. Amplicons were purified and quantified. All amplicons of the same sample were pooled equimolarly. In a second PCR, primers specific to the linker region were used to add sequences necessary for the sequencing and multiplexing of samples. Libraries were purified and quality controlled. Sequencing was performed on Illumina's MiSeq or HiSeq 2500 with 75 bp or 125 bp paired-end mode. Trimming of adapter sequences and low quality bases was performed with Trimmomatic as described for the RRBS data.

Assessment of RRBS-Determined Methylation Pattern Frequency in Serum DNA:

After sequencing, raw data were trimmed using Trimmomatic (0.32) to remove adapter sequences and low quality bases at the beginning and end of reads. Subsequently, reads were trimmed with TrimGalore (0.3.3) to remove cytosines derived from library preparation which must not be included in the methylation analysis. Further analysis was done using Genedata Expressionist® for Genomic Profiling 9.1. Read pairs were mapped to the human genome (hg19) applying Bisulfite Mapper based on BOWTIE v2.2.5 (13) with the settings - -no-discordant -p 8 - -norc - -reorder -D 50 - -fr - -end-to-end -X 500 -I 0 - -phred33 -k 2 - -no-mixed. Coverage was calculated per sample and target region using Numeric Data Feature Quantification activity by calculating the arithmetic mean of the coverage in each region. As part of the data quality control, efficiency of the bisulfite conversion was estimated in each sample by quantifying the methylation levels of CpHpG and CpHpH sites (where H is Any Nucleotide Except G), with minimum coverage of 10, within the target regions. The median bisulfite conversion efficiency was 99.4%, with efficiency for no sample being lower than 97.7%. Methylation pattern frequencies in serum samples for target regions were determined as described above. Relative pattern frequencies were calculated by dividing the number of reads containing the pattern by the total number of reads covering the pattern region.

Discussion

Circulating tumour DNA analysis—using cancer—specific DNAme markers and/or patterns of the present invention—shows independent sensitivity/specificity to that of CA125 and has a greater dynamic range correlating with changes in tumour burden and response to treatment.

Consistent with published data (Ref. 8), CA125 change after 2 cycles of chemotherapy was not able to indicate responsiveness to chemotherapy (in this case carboplatin alone or in combination with paclitaxel). The fact that serum DNAme-dynamics—as analysed using a method of the present invention—correctly identified 7/9 and 6/7 neoadjuvant chemotherapy responders and non-responders, respectively, provides a proof of principle and a basis for prospective clinical trials to individualise pre-operative systemic treatment in advanced ovarian cancer.

In healthy individuals, cell-free DNA is present at concentrations between 0 and 100 ng/mL and an average of 30 ng/mL (Ref. 32). DNA derived from tumour cells is shorter than that from non-malignant cells in the plasma of cancer patients (Ref. 33). One problem to be solved is the development of DNAme based markers (and an assay) for ovarian cancer detection, in particular early detection of ovarian cancer. Samples available in order to carry out this task are from large population based screening studies. For example, the largest of such studies being UKCTOCS. Serum samples from 100,000 women need to be collected in order to secure sufficient numbers (i.e. between 40-50) of women who develop ovarian cancer within 2 years of sample donation. Within the UKCTOCS setting whole blood samples were couriered to the central laboratory with median time to spin of 22 hours. Prospectively collected blood samples were spun down between 2-12 hours after collection in order to mimic the collection-setting typically used for large studies like UKCTOCS. It is expected for such an analysis of UKCTOCS samples that, and as has been already seen for other prospectively collected sets including UKCTOCS (Anjum et al, 2014), samples from such prospectively collected sets contain higher than average amounts of cell-free DNA and fragments being longer on average. Both factors are likely to reflect the leakage of WBC DNA into serum. Despite these complicating factors the three-DNAme marker panel can outperform CA125 in detecting ovarian cancer, also for detecting ovarian cancer early.

False CA125-positivity can usually be explained by a CA125 producing benign condition (Ref. 34). The fact that in Serum Set 3 there was no overlap at all between false CA125 and false DNAme positive samples indicates that the DNAme-false positivity is largely triggered by technical artefacts as a result of extremely low thresholds down to a pattern frequency of 0.000003 (i.e. 3 cancer patterns in the background of 1.000.000 DNA fragments with a non-cancer pattern).

Based on the UKCTOCS prevalence screen (Ref. 23), the Risk of Ovarian Cancer Algorithm (ROCA) identified 0.65% of women at an elevated risk of which 13% (42/327) have eventually been diagnosed after having been assessed by ultrasound, additional imaging and clinical assessment. Applying the three-marker DNAme test of the present invention with a conservative estimate of specificity and sensitivity of 90% and 60%, respectively, in ROCA-elevated risk women would immediately enable diagnosis and treatment of the 0.05% of women within a population with an ovarian cancer with a positive predictive value of 44% (i.e. only 2.3 operations are necessary to diagnose/treat 1 ovarian cancer patient).

At the UKCTOCS prevalence screen (Ref. 22), the Risk of Ovarian Cancer Algorithm (ROCA) identified elevated risk in 0.65% of women of whom 13% (42/327) were diagnosed after repeat CA125 testing, ultrasound, additional imaging and clinical assessment. Applying the three-marker DNAme test of the present invention with a conservative estimate (i.e. excessive background DNA will not be an issue in prospective samples) of specificity and sensitivity of 90% and 60%, as a second line test to ROCA-elevated risk women could substantially decrease time to diagnosis in at least half the women with ovarian cancer.

Overall and for the first time, the present invention provides serum DNAme markers and assays (and other means and methods) that can diagnose ovarian cancers (or are useful for such diagnosis), and it is likely that they are able to detect/diagnose OC up to two years in advance of conventional methods of diagnosis, and are able to individualise ovarian cancer treatment. The recent advance of purpose-made blood collection tubes (such as those from Streck as described above) that stabilise circulating DNA and prevent leakage of DNA from blood cells (Ref. 35) will facilitate clinical implementation of DNAme pattern detection in cell free DNA as a clinical tool in cancer medicine.

Certain (Other) Cancers:

The inventors were surprised to find that one or more of the DMRs of the present invention showed a massive difference in methylation between DNA isolated from cancer tissue and DNA isolated from white bloods cells (WBC) from non-cancer human individuals, and indeed certain of these markers even shown such a difference in methylation between DNA isolated from cancer tissue and DNA isolated from (corresponding) normal tissue.

FIGS. 14 to 21 show the average beta value (an estimate of methylation level, based on a ratio of intensities between methylated and unmethylated alleles (Du et al, 2010; BMC Bioinformatics, 11:587)) for given DMRs of the invention analysed in DNA isolated from cancerous (C) tissues and white blood cells (WBC) as well as DNA isolated from normal (N) tissue that corresponds to the cancerous tissue. P-values show the hugely significant difference in methylation level at these DMRs between cancerous and WBC DNA. A total of 19 markers were tested over 20 cancer entities, giving a total of 380 separate tests; so even after correction of signification for such multiple tests (eg, by the Bonferroni procedure), the P-values of these difference remain highly significant, with most being even smaller than even 10e-50).

The 19 DMRs of the present invention included in this analysis were DMRs: #123, #137, #144, #148, #164, #188, #200, #202, #204, #210, #213, #214, #219, #222, #223, #224, #225, #226 and #228, and the 20 cancer entities were: Ovarian cancer (OC), Bladder Urothelial Carcinoma (BLCA), Breast invasive carcinoma (BRCA), Cervical squamous cell carcinoma and endocervical adenocarcinoma (CESC), Colon adenocarcinoma (COAD), Oesophageal carcinoma (ESCA), Head and Neck squamous cell carcinoma (HNSC), Kidney renal clear cell carcinoma (KIRC), Kidney renal papillary cell carcinoma (KIRP), Liver hepatocellular carcinoma (LIHC), Lung squamous cell carcinoma (LSCC), Lung adenocarcinoma (LUAD), Pancreatic adenocarcinoma (PAAD), Prostate adenocarcinoma (PRAD), Rectum adenocarcinoma (READ), Sarcoma (SARC), Skin Cutaneous Melanoma (SKCM), Stomach adenocarcinoma (STAD), Thyroid carcinoma (THCA) and Uterine Corpus Endometrial Carcinoma (UCEC)

The cancers that are, in particular, most associated with the DMRs of the invention comprise the following entities: breast cancer (BRCA), lung cancer (eg lung adenocarcinoma (LUAD) and lung squamous cell carcinoma (LSCC)), colon cancer (COAD), pancreatic cancer (PMD), uterine cancer (UCEC), cervical cancer (CESC) and prostate cancer (PRAD) (FIGS. 14 to 21). Accordingly, as well as having relevance for ovarian cancer, the applicable such DMRs (as shown in the respective figure, or as set out in more detail elsewhere herein)—either alone or in combination—can be used in methods of the present invention to determine the presence or absence of, or response to therapy against, such other cancers in a human individual; which human individual is a woman (eg for breast cancer, uterine cancer or cervical cancer, is a man (eg for prostate cancer) or may be either a woman or a man (eg for lung cancer, colorectal cancer or pancreatic cancer).

In particular, given the highly significant difference between the methylation level (eg, average beta value) of each of such DMR in DNA isolated from WBC compare to DNA isolated from the cancerous tissue, it is of particular relevance for such DMRs to have utility as markers for detection of DNA released by cancerous issues into the bloodstream of the human individual; ie as ctDNA. This utility can be explained because (and as explained in more detail elsewhere herein) the largest fraction of cell-free DNA present in the bloodstream originates from WBC, but tumour cells also (eg, because of their increased turnover) release their DNA into the circulatory system and can be detected as ctDNA, eg amongst the cell-free DNA isolated from serum or plasma. As those DMRs of the invention shown in FIGS. 14 to 19 exhibit a highly significant difference in methylation between DNA isolated from cancerous (C) tissue and white blood cells (WBC), they therefore represent DMRs that can be used to detect (eg, early) the presence of the applicable cancer in a biological sample from said human individual that comprises cell-free DNA of said human individual. Elsewhere herein (eg in the analysis of OC in woman), it has been demonstrated that the DMRs of the present invention, when present on DNA originating from cancerous tissue, can be detected in cell-free DNA.

Of particular relevance and surprise, are those DMRs of the present invention that show such a significant difference in methylation (eg, average beta value) between DNA isolated from cancerous (C) tissue and white blood cells (WBC), but that show no (or little or reduced) difference in methylation between normal (N) and cancerous (C) tissue. Despite there being no (or little) difference in methylation at these DMRs in DNA isolated from normal (N) tissue compared to cancerous (C) tissue, there was still a significant difference in their methylation in DNA isolated from WBC of non-cancer human individuals; ie the normal tissue in such non-cancer patients was not detectable as cell-free DNA in such non-cancer human individuals. Accordingly, the DMRs showing such a methylation pattern are of particular utility to detect (eg early) the differentially methylated DNA originating from tumour cells that would be expected to be shed into the circulation of cancer patients and hence be detectable as ctDNA from eg serum or plasma of such patients, analogous to the examples and clinical trials described for OC in women. For example, DMR #228 can be used to detect (eg early) the presence of, inter alia, a prostate or pancreatic cancer in a human individual (such as a man) by the presence of differentially methylated (in these cases, hyper-methylated) CpGs associated with such DMR within cell-free DNA (eg, cell-free DNA isolated from the serum or plasma of a human individual (such as a man) suspected of suffering from such cancer.

Correspondingly, those DMRs of the present invention that show such a significant difference in methylation (eg, average beta value) between DNA isolated from cancerous (C) tissue and normal (N) tissue (WBC) are of particular utility to detect cancerous tissue present in a tissue sample taken from a human individual suspected of suffering from such cancer. For example, DMR #144 can be used to detect (eg early) the presence of a prostate or pancreatic cancer in an individual (such as a man) by the presence of differentially methylated (in these cases, hyper-methylated) CpGs associated with such DMR within cell-free DNA isolated from a tissue biopsy from a human individual (such as a man) suspected of suffering from such cancer.

Indeed, DMR #144 shows a significantly higher level of methylation in DNA isolated from tumour/cancer tissues (C) compared to DNA isolated from normal tissues (N) and/or WBC in all cancer types analysed herein, as well as a high magnitude of difference in such methylation in virtually all of such cancers except in kidney cancer (graphs not shown). As such, DMR #144 is a particularly preferred DMR for use herein as a (eg cfDNA) methylation marker for (eg early) detection/diagnosis of one or more of these cancers. However, despite DMR #144 showing a high magnitude of difference between DNA isolated from tumour tissues (C) compared to DNA isolated from WBC in colon cancer, DMR #144 also shows relatively high methylation in DNA isolated from normal (N) colon tissue (see FIG. 17), and similarly for DNA from normal compared to cancerous rectal tissue (graph not shown). As a consequence, DMR #144 may show a higher false positive rate—ie lower specificity—(eg in pattern frequency of methylated CpGs) as a cfDNA marker, and this may be reflected by the relatively high (compared to DMRs #228, #204 and #141) pattern frequency for DMR #144 seen in non-cancer serum cases (see FIGS. 8 and 9). A screening/diagnostic test for cancer with high specificity is extremely important because low specificity leads to high false positive rates and low positive predictive value, and hence a lot of individuals would have to undergo further additional unnecessary tests and potentially invasive (and risky/unnecessary) procedures. Therefore, in order to increase the specificity without losing sensitivity of a screening/diagnostic test for the early detection of one or more of these cancers from cfDNA (eg isolated from plasma or serum), an analysis of methylation at DMR #144 can be combined with an analysis of methylation at one or more other DMR of the invention. It has been surprisingly found by the present inventor(s) that DMR #228 not only has particular utility as a cfDNA methylation marker for the early detection of these same cancers, but that DMR #228 shows a relatively low methylation level in DNA isolated from normal (N) colon tissue compared to cancerous (C) colon tissue (see FIG. 17), and also a correspondingly low methylation level in normal rectal tissue (graph not shown). Accordingly, the non-overlapping nature of methylation level in normal tissue from both the colon and the rectum between DMRs #144 and #228 means that a screening/diagnostic test for the early detection of one or more of these cancers (in particular for colon or rectal cancer) from cfDNA (eg isolated from plasma or serum) based on the analysis of methylation at DMR #144 and at DMR #228 would have particular utility, and is a preferred combination of DMRs for use in the various aspects of the present invention. Indeed, the test parameters of such a test (using both DMR #144 and DMR #228) may be yet enhanced—eg by further increasing its specificity without losing (or even increasing) its sensitivity—by additionally analysing methylation at one or more further DMRs of the present invention, in particular at DMR #204 and/or #141.

The difference in methylation (eg, average beta value) between DNA isolated from cancerous (C) ovarian tissue and normal (N) ovarian tissue was highly significant for each DMR of the invention (P-values ranging from 7.2e-36 for DMR #148 to those smaller than this, even as small as 1.5e-60, for all other DMRs), with a difference in mean average beta values between ovarian cancer tissue and normal tissue ranging from over 0.1 (DMRs #148 and #123) to over 0.4 for all other DMRs; including for DMRs #144, #204 and #228, and with a direction of difference corresponding to the hyper-methylation or hypo-methylation class of the marker, ie WBC DNA showed significantly increased methylation at hypo-methylated DMRs #123, #137, #148, #188 and #226 compared to DNA from ovarian cancer tissue, and all other (hyper-methylated) DMRs showed significantly increased methylation in DNA isolated from ovarian cancer tissue compared to WBC DNA (data not shown).

DNA isolated from WBC samples were analysed for methylation using the Illumina Infinium Human Methylation 450K beadchip array (Illumina Inc USA, WG-314-1003)—as described above—at 19 of the DMRs of the present invention that have at least one CpG described herein present/detectable on such 450K beadchip array. Data on methylation for each of such DMRs in the various cancer entities was obtained from The Cancer Genome Atlas (TCGA) public data repository, and the average beta value for such DMR in each such sample/data set used to compare and determine a significance of difference between cancerous (C) and normal (N) tissue, as well as the WBC data described herein. P-values shown are from a two-tailed Wilcoxon rank sum test.

Note: The work leading to this invention has received funding from the European Union Seventh Framework Programme (FP7/2007-2013) under Grant Agreement Number 305428 (Project EpiFemCare).

REFERENCES

1. Hennessy B T, Coleman R L, Markman M. Ovarian cancer. Lancet 2009; 374(9698):1371-1382.

2. Bowtell D D, Bohm S, Ahmed A A et al. Rethinking ovarian cancer II: reducing mortality from high-grade serous ovarian cancer. Nat Rev Cancer 2015; 15(11):668-679.
3. Bast R C, Jr., Klug T L, St J E et al. A radioimmunoassay using a monoclonal antibody to monitor the course of epithelial ovarian cancer. N Engl J Med 1983; 309(15): 883-887.
4. Buys S S, Partridge E, Black A et al. Effect of screening on ovarian cancer mortality: the Prostate, Lung, Colorectal and Ovarian (PLCO) Cancer Screening Randomized Controlled Trial. JAMA 2011; 305(22):2295-2303.
5. Cramer D W, Bast R C, Jr., Berg C D et al. Ovarian cancer biomarker performance in prostate, lung, colorectal, and ovarian cancer screening trial specimens. Cancer Prev Res (Phila) 2011; 4(3):365-374.
6. Jacobs I J, Menon U, Ryan A et al. Ovarian cancer screening and mortality in the UK Collaborative Trial of Ovarian Cancer Screening (UKCTOCS): a randomised controlled trial. Lancet 2016; 387(10022):945-956.
7. Menon U, Ryan A, Kalsi J et al. Risk Algorithm Using Serial Biomarker Measurements Doubles the Number of Screen-Detected Cancers Compared With a Single-Threshold Rule in the United Kingdom Collaborative Trial of Ovarian Cancer Screening. J Clin Oncol 2015; 33(18):2062-2071.
8. Vallius T, Hynninen J, Auranen A et al. Serum H E4 and CA125 as predictors of response and outcome during neoadjuvant chemotherapy of advanced high-grade serous ovarian cancer. Tumour Biol 2014; 35(12):12389-12395.
9. Dawson S J, Tsui D W, Murtaza M et al. Analysis of circulating tumor DNA to monitor metastatic breast cancer. N Engl J Med 2013; 368(13):1199-1209.
10. Murtaza M, Dawson S J, Tsui D W et al. Non-invasive analysis of acquired resistance to cancer therapy by sequencing of plasma DNA. Nature 2013; 497(7447): 108-112.
11. Wang Y, Springer S, Mulvey C L et al. Detection of somatic mutations and HPV in the saliva and plasma of patients with head and neck squamous cell carcinomas. Sci Transl Med 2015; 7(293):293ra104.
12. Siravegna G, Mussolin B, Buscarino M et al. Clonal evolution and resistance to EGFR blockade in the blood of colorectal cancer patients. Nat Med 2015; 21(7):827.
13. Bettegowda C, Sausen M, Leary R J et al. Detection of circulating tumor DNA in early- and late-stage human malignancies. Sci Transl Med 2014; 6(224):224ra24.
14. Lanman R B, Mortimer S A, Zill O A et al. Analytical and Clinical Validation of a Digital Sequencing Panel for Quantitative, Highly Accurate Evaluation of Cell-Free Circulating Tumor DNA. PLoS One 2015; 10(10): e0140712.
15. Sun K, Jiang P, Chan K C et al. Plasma DNA tissue mapping by genome-wide methylation sequencing for noninvasive prenatal, cancer, and transplantation assessments. Proc Natl Acad Sci USA 2015; 112(40):E5503-E5512.
16. Pepe M S, Feng Z, Janes H, Bossuyt P M, Potter J D. Pivotal evaluation of the accuracy of a biomarker used for classification or prediction: standards for study design. J Natl Cancer Inst 2008; 100(20):1432-1438.
17. Baylin S B, Jones P A. A decade of exploring the cancer epigenome—biological and translational implications. Nat Rev Cancer 2011; 11(10):726-734.
18. Forshew T, Murtaza M, Parkinson C et al. Noninvasive identification and monitoring of cancer mutations by targeted deep sequencing of plasma DNA. Sci Transl Med 2012; 4(136):136ra68.
19. Leary R J, Sausen M, Kinde I et al. Detection of chromosomal alterations in the circulation of cancer patients with whole-genome sequencing. Sci Transl Med 2012; 4(162):162ra154.
20. Wittenberger T, Sleigh S, Reisel D et al. DNA methylation markers for early detection of women's cancer: promise and challenges. Epigenomics 2014; 6(3):311-327.
21. Potter N T, Hurban P, White M N et al. Validation of a real-time PCR-based qualitative assay for the detection of methylated SEPT9 DNA in human plasma. Clin Chem 2014; 60(9):1183-1191.
22. Norton M E, Jacobsson B, Swamy G K et al. Cell-free DNA analysis for noninvasive examination of trisomy. N Engl J Med 2015; 372(17):1589-1597.
23. Menon U, Gentry-Maharaj A, Hallett R et al. Sensitivity and specificity of multimodal and ultrasound screening for ovarian cancer, and stage distribution of detected cancers: results of the prevalence screen of the UK Collaborative Trial of Ovarian Cancer Screening (UKCTOCS). Lancet Oncol 2009; 10(4):327-340.
24. Teschendorff A E, Yang Z, Wong A et al. Correlation of Smoking-Associated DNA Methylation Changes in Buccal Cells With DNA Methylation Changes in Epithelial Cancer. Jama Oncol 2015; 1(4):476-485.
25. Teschendorff A E, Lee S H, Jones A et al. HOTAIR and its surrogate DNA methylation signature indicate carboplatin resistance in ovarian cancer. Genome Med 2015; 7(1):108.
26. Gu H, Smith Z D, Bock C, Boyle P, Gnirke A, Meissner A. Preparation of reduced representation bisulfite sequencing libraries for genome-scale DNA methylation profiling. Nat Protoc 2011; 6(4):468-481.
27. Lee Y K, Jin S, Duan S et al. Improved reduced representation bisulfite sequencing for epigenomic profiling of clinical samples. Biol Proced Online 2014; 16(1):1.
28. Newcombe R G. Two-sided confidence intervals for the single proportion: comparison of seven methods. Stat Med 1998; 17(8):857-872.
29. Bartlett T E, Jones A, Goode E L et al. Intra-Gene DNA Methylation Variability Is a Clinically Independent Prognostic Marker in Women's Cancers. PLoS One 2015; 10(12):e0143178.
30. Sanchez-Vega F, Gotea V, Petrykowska H M et al. Recurrent patterns of DNA methylation in the ZNF154, CASP8, and VHL promoters across a wide spectrum of human solid epithelial tumors and cancer cell lines. Epigenetics 2013; 8(12):1355-1372.
31. Margolin G, Petrykowska H M, Jameel N, Bell D W, Young A C, Elnitski L. Robust Detection of DNA Hypermethylation of ZNF154 as a Pan-Cancer Locus with in Silico Modeling for Blood-Based Diagnostic Development. J Mol Diagn 2016; 18(2):283-298.
32. Gormally E, Caboux E, Vineis P, Hainaut P. Circulating free DNA in plasma or serum as biomarker of carcinogenesis: practical aspects and biological significance. Mutat Res 2007; 635(2-3):105-117.
33. Jiang P, Lo Y M. The Long and Short of Circulating Cell-Free DNA and the Ins and Outs of Molecular Diagnostics. Trends Genet 2016; 32(6):360-371.

34. Hirsch M, Duffy J, Davis C J, Nieves P M, Khan K S. Diagnostic accuracy of cancer antigen 125 for endometriosis: a systematic review and meta-analysis. BJOG 2016.
35. Kang Q, Henry N L, Paoletti C et al. Comparative analysis of circulating tumor DNA stability In KEDTA, Streck, and CellSave blood collection tubes. Clin Biochem 2016.
51. Bartlett T E, Jones A, Goode E L, Fridley B L, Cunningham J M, Berns E M et al. Intra-Gene DNA Methylation Variability Is a Clinically Independent Prognostic Marker in Women's Cancers. PLoS One 2015; 10(12): e0143178.
S2. Teschendorff A E, Lee S H, Jones A, Fiegl H, Kalwa M, Wagner W et al. HOTAIR and its surrogate DNA methylation signature indicate carboplatin resistance in ovarian cancer. Genome Med 2015; 7(1):108.
S3. Teschendorff A E, Yang Z, Wong A, Pipinikas C P, Jiao Y, Jones A et al. Correlation of Smoking-Associated DNA Methylation Changes in Buccal Cells With DNA Methylation Changes in Epithelial Cancer. Jama Oncol 2015 July; 1(4):476-85.
S4. Bartlett T E, Chindera K, McDermott J, Breeze C E, Cooke W R, Jones A et al. Epigenetic reprogramming of fallopian tube fimbriae in BRCA mutation carriers defines early ovarian cancer evolution. Nat Commun 2016; 7:11620.
S5. Gentleman R C, Carey V J, Bates D M, Bolstad B, Dettling M, Dudoit S et al. Bioconductor: open software development for computational biology and bioinformatics. Genome Biol 2004; 5(10):R80.
S6. Aryee M J, Jaffe A E, Corrada-Bravo H, Ladd-Acosta C, Feinberg A P, Hansen K D et al. Minfi: a flexible and comprehensive Bioconductor package for the analysis of Infinium DNA methylation microarrays. Bioinformatics 2014 May 15; 30(10):1363-9.
S7. Teschendorff A E, Marabita F, Lechner M, Bartlett T, Tegner J, Gomez-Cabrero D et al. A beta-mixture quantile normalization method for correcting probe design bias in Illumina Infinium 450 k DNA methylation data. Bioinformatics 2013 Jan. 15; 29(2):189-96.
S8. Dedeurwaerder S, Defrance M, Calonne E, Denis H, Sotiriou C, Fuks F. Evaluation of the Infinium Methylation 450K technology. Epigenomics 2011 December; 3(6):771-84.
S9 Goecks J, Nekrutenko A, Taylor J. Galaxy: a comprehensive approach for supporting accessible, reproducible, and transparent computational research in the life sciences. Genome Biol 2010; 11(8):R86.
S10. Giardine B, Riemer C, Hardison R C, Burhans R, Elnitski L, Shah P et al. Galaxy: a platform for interactive large-scale genome analysis. Genome Res 2005 October; 15(10):1451-5.
S11. Gu H, Smith Z D, Bock C, Boyle P, Gnirke A, Meissner A. Preparation of reduced representation bisulfite sequencing libraries for genome-scale DNA methylation profiling. Nat Protoc 2011 April; 6(4):468-81.
S12. Lee Y K, Jin S, Duan S, Lim Y C, Ng D P, Lin X M et al. Improved reduced representation bisulfite sequencing for epigenomic profiling of clinical samples. Biol Proced Online 2014; 16(1):1.
S13. Chen P Y, Cokus S J, Pellegrini M. BS Seeker: precise mapping for bisulfite sequencing. BMC Bioinformatics 2010; 11:203.
S14. Bernstein D L, Kameswaran V, Le Lay J E, Sheaffer K L, Kaestner K H. The BisPCR(2) method for targeted bisulfite sequencing. Epigenetics Chromatin 2015; 8:27.

---

The invention claimed is:

1. A method of determining the presence of a cancer in a human individual, said method comprising:
   providing a serum or plasma sample from said human individual, said sample comprising cell-free DNA;
   determining, in at least one molecule of said cell-free DNA, the methylation status at 16 CpGs located at positions 28, 31, 33, 45, 52, 58, 60, 62, 69, 104, 107, 110, 116, 121, 124 and 126 within the nucleotide sequence of SEQ ID NO: 2 or a 100% complementary sequence to said nucleotide sequence;
   determining the presence of cancer in said human individual when at least one molecule of said cell-free DNA is methylated at each of said 16 CpGs; and
   treating the cancer in said human individual by (i) administering a chemotherapeutic agent selected from the group consisting of paclitaxel, docetaxel, cisplatin, liposomal doxorubicin, gemcitabine, trabectedin, etoposide, cyclophosphamide, an angiogenesis inhibitor and a PARP inhibitor, or (ii) by performing tumor de-baulking surgery;
   wherein (a) when the human individual is a woman the cancer is selected from the group consisting of: breast cancer, lung squamous cell carcinoma, colon cancer, pancreatic cancer, uterine (endometrial) cancer, and ovarian cancer; or (b) when the human individual is a man the cancer is selected from the group consisting of: lung squamous cell carcinoma, colon cancer, pancreatic cancer and prostate cancer.

2. The method of claim 1, further comprising determining the methylation status at CpGs located in at least one nucleotide sequence selected from SEQ ID NOs: 1, 3, 4, and a 100% complementary sequence of said nucleotide sequence(s).

3. The method of claim 1, further comprising the step of treating said cell-free DNA with an agent that differentially modifies said cell-free DNA based on the methylation status of the CpGs.

4. The method of claim 3, wherein said agent is bisulfite.

5. The method of claim 1, wherein the methylation status of said CpGs is determined in multiple molecules of said cell-free DNA.

6. The method of claim 5, wherein a fraction or ratio of, or an absolute number of, cell-free DNA molecules in said sample having said methylated CpGs located within said nucleotide sequence, and/or having a pattern of methylation for the nucleotide sequence SEQ ID NO: 64, is estimated.

7. The method of claim 1, further comprising using a primer pair for amplifying the nucleic acid sequence consisting of SEQ ID NO 64 or a 100% complementary sequence to said nucleotide sequence.

8. The method of claim 1, wherein treating the cancer in said human individual comprises tumor de-baulking surgery.

9. The method of claim 1, wherein the human individual is a woman and the cancer is selected from the group consisting of: breast cancer, uterine (endometrial) cancer, and ovarian cancer.

10. The method of claim 9, wherein the cancer is ovarian cancer.

11. A method of treating cancer in a human individual previously treated with carboplatin comprising: administering a chemotherapeutic agent to said human individual previously treated with carboplatin within about 3 months of said human individual having been determined to have a reduced response to a carboplatin therapy by a method comprising:
   providing a serum or plasma sample from said human individual, said sample comprising cell-free DNA;
   determining, in at least one molecule of said cell-free DNA, the methylation status at 16 CpGs located at positions 28, 31, 33, 45, 52, 58, 60, 62, 69, 104, 107, 110, 116, 121, 124 and 126 within the nucleotide sequence of SEQ ID NO: 2 or a 100% complementary sequence to said nucleotide sequence;
   determining that said human individual will have a reduced response to carboplatin therapy when at least one molecule of said cell-free DNA is methylated at each of the 16 CpGs;
   wherein: (a) when the human individual is a woman the cancer is selected from the group consisting of: breast cancer, lung squamous cell carcinoma, colon cancer, pancreatic cancer, uterine (endometrial) cancer, and ovarian cancer; or (b) when the human individual is a man the cancer is selected from the group consisting of: lung squamous cell carcinoma, colon cancer, pancreatic cancer and prostate cancer; and
   wherein the chemotherapeutic agent is selected from the group consisting of: paclitaxel, docetaxel, cisplatin, liposomal doxorubicin, gemcitabine, trabectedin, etoposide, cyclophosphamide, an angiogenesis inhibitor and a PARP inhibitor.

12. The method of claim 11, further comprising the step of treating said cell-free DNA with an agent that differentially modifies said cell-free DNA based on the methylation status of the CpGs.

13. The method of claim 12, wherein said agent is bisulfite.

14. The method of claim 11, wherein the methylation status of said CpGs is determined in multiple molecules of said cell-free DNA.

15. The method of claim 14, wherein a fraction or ratio of, or an absolute number of, cell-free DNA molecules in said sample having said methylated CpGs located within said nucleotide sequence, and/or having a pattern of methylation for the nucleotide sequence SEQ ID NO: 64, is estimated.

16. The method of claim 11, wherein the carboplatin is carboplatin-based neoadjuvant chemotherapy.

17. The method of claim 11, wherein the human individual is a woman and the cancer is selected from the group consisting of: breast cancer, uterine (endometrial) cancer, and ovarian cancer.

18. The method of claim 17, wherein the cancer is ovarian cancer.

* * * * *